United States Patent
Sun et al.

(10) Patent No.: US 9,346,852 B2
(45) Date of Patent: May 24, 2016

(54) SUBSTITUTED ADIPIC ACID AMIDES AND USES THEREOF

(75) Inventors: Chongqing Sun, East Windsor, NJ (US); William R. Ewing, Yardley, PA (US); Scott A. Bolton, Newtown, PA (US); Zhengxiang Gu, Princeton, NJ (US); Yanting Huang, Pennington, NJ (US); Natesan Murugesan, Princeton Junction, NJ (US); Yeheng Zhu, Stockton, NJ (US)

(73) Assignee: Bristol-Myers Scuibb Company, Princeton, NJ (US)

( * ) Notice: Subject to any disclaimer, the term of this patent is extended or adjusted under 35 U.S.C. 154(b) by 333 days.

(21) Appl. No.: 14/005,018

(22) PCT Filed: Mar. 13, 2012

(86) PCT No.: PCT/US2012/028900
§ 371 (c)(1),
(2), (4) Date: Sep. 13, 2013

(87) PCT Pub. No.: WO2012/125622
PCT Pub. Date: Sep. 20, 2012

(65) Prior Publication Data
US 2013/0345123 A1 Dec. 26, 2013

Related U.S. Application Data

(60) Provisional application No. 61/452,324, filed on Mar. 14, 2011.

(51) Int. Cl.
| | |
|---|---|
| C07D 471/04 | (2006.01) |
| C07D 487/04 | (2006.01) |
| C07D 495/04 | (2006.01) |
| C07K 5/078 | (2006.01) |
| A61K 45/06 | (2006.01) |
| A61K 31/554 | (2006.01) |
| A61K 38/05 | (2006.01) |
| C07D 513/04 | (2006.01) |
| C07D 519/00 | (2006.01) |

(52) U.S. Cl.
CPC .......... *C07K 5/06139* (2013.01); *A61K 31/554* (2013.01); *A61K 38/05* (2013.01); *A61K 45/06* (2013.01); *C07D 471/04* (2013.01); *C07D 487/04* (2013.01); *C07D 495/04* (2013.01); *C07D 513/04* (2013.01); *C07D 519/00* (2013.01)

(58) Field of Classification Search
CPC ... C07D 471/04; C07D 487/04; C07D 495/04
See application file for complete search history.

(56) References Cited

FOREIGN PATENT DOCUMENTS

WO    WO 2006/091506    8/2006

*Primary Examiner* — Bruck Kifle
(74) *Attorney, Agent, or Firm* — Elliott Korsen

(57) ABSTRACT

The present invention provides compounds of Formula (I), or a pharmaceutically acceptable salt thereof, wherein A is a five to eight membered monocyclic or a nine to twelve membered bicyclic heterocyclic ring, as further defined herein; Y is S, $CH_2$, or CH; Z is CH or N; $R^7$ and $R^9$ are hydrogen or $(C_1-C_6)$alkyl; $R^2$ is $(C_1-C_6)$alkoxy, OH, CN, $(C_1-C_6)$alkyl, halogen, or $CF_3$; r and s are 0, 1, or 2; and $R^1$ and $R^3$ are as further defined herein. These compounds are agonists, partial agonists and/or modulators of the NPY4 receptor and may be used for the treatment and prophylaxis of obesity, food intake, and other diseases and conditions modulated by the NPY4 receptor.

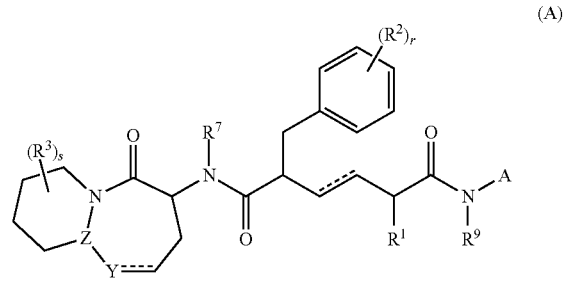

(A)

13 Claims, No Drawings

SUBSTITUTED ADIPIC ACID AMIDES AND USES THEREOF

FIELD OF THE INVENTION

The present invention provides substituted adipic acid amides and analogues thereof, which are agonists, partial agonists or modulators of the NPY4 receptor, compositions containing the compounds, and methods of using them, for example, for the treatment of obesity, to control appetite, feeding, food intake, energy expenditure, caloric intake, gastric motility, diabetes and other related conditions.

BACKGROUND OF THE INVENTION

Obesity and its associated disorders are common and very serious public health problems in the United States and throughout the world. Upper body obesity is the strongest risk factor known for type 2 diabetes mellitus and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia.

Obesity reduces life-span and carries a serious risk of the co-morbidities listed above, as well disorders such as infections, varicose veins, acanthosis nigricans, eczema, exercise intolerance, insulin resistance, hypertension hypercholesterolemia, cholelithiasis, orthopedic injury, and thromboembolic disease (Rissanen et al., *Br. Med. J.* 301:835-837 (1990)). Obesity is also a risk factor for the group of conditions called insulin resistance syndrome, or "Syndrome X" and metabolic syndrome. The worldwide medical cost of obesity and associated disorders is enormous.

Obesity remains a poorly treatable, chronic, essentially intractable metabolic disorder. Accordingly, a need exists for new therapies useful in weight reduction and/or weight maintenance in a subject. Such therapies would lead to a profound beneficial effect on the subject's health.

The present invention provides methods and compositions useful in the control, treatment, and prevention of obesity and obesity-related conditions, disorders, and diseases, such as those referenced above.

Neuropeptide Y (NPY), peptide YY (PYY), and pancreatic peptide (PP) are members of the PP family characterized by a 36-amino acid sequence with a tyrosine amide at the carboxy-terminus and six conserved C-terminal amino acids.

NPY is a wide spread neuropeptide with multiple actions in various parts of both central and peripheral nervous systems, acting through a number of different receptor subtypes in man such as Y1, Y2, Y4 and Y5. There are four well-established types of PP-fold peptide receptors in man, Y1, Y2, Y4 and Y5, which all recognize NPY1-36 and PYY1-36 with similar affinity. Affinity studies suggest that the Y4 receptors bind PP with a subnanomolar affinity corresponding to the concentrations found in plasma, whereas NPY and PYY are recognized with much lower affinity.

The NPY receptors are responsible for many diverse physiologic actions including feeding regulation, energy homeostasis, locomotion, seizure, thermoregulation, circadian rhythms, anxiety, cardio-respiratory function, and fertility. PYY(3-36), a major circulating form of PYY corresponding to residues 3-36 of PYY, interacts with at least three NPY receptor subtypes (NPY1, NPY2, and NPY5), and PP interacts with the NPY1, NPY4 and NPY5 receptors. See Balasubramaniam et al., "Neuropeptide Y (NPY) $Y_4$ Receptor Selective Agonists Based on NPY(32-36): Development of an Anorectic $Y_4$ Receptor Selective Agonist with Picomolar Affinity", *J. Med. Chem.*, 49:2661-2665 (2006).

PP is known to play an important role in the control of food intake and long term energy balance. Sainsbury et al., "Y4 Receptors and Pancreatic Polypeptide Regulate Food Intake via Hypothalamic Orexin and Brain-derived Neurotropic Factor Dependent Pathways", *Neuropeptides*, 44:261-268 (2010). PP-fold peptides and analogs of these have been investigated for use in treating obesity and associated diseases, including for example, Prader Willi's syndrome, based on the demonstrated effect of PP levels in animal models and in man. It has been shown since the mid seventies that PP affects food intake in rodents. Evidence from rodent studies has shown that PP is in fact a powerful and efficient anorexigenic peptide when administered peripherally, influencing food intake, energy metabolism, and body weight. See, e.g., Asakawa et al., "Characterization of the Effect of Pancreatic Polypeptide in the Regulation of Energy Balance", *Gastroenterology*, 124:1325-1336 (2003).

Additionally, obese humans have shown low basal levels of PP and PYY as well as lower meal responses of these peptides. In 1993, it was reported that infusion of PP in obese patients with Prader Willi's syndrome decreased food intake. In 2003, this finding was confirmed by infusion of PP in normal human subjects where a long lasting suppression of appetite and reduced food intake over 24 hours was observed. See Batterham et al., "Pancreatic Polypeptide Reduces Appetite and Food Intake in Humans", *J. Clin. Endocrinol. Metab.*, 88:3989-3992 (2003). Further clinical studies have since demonstrated a dose-dependent correlation between PP levels in humans and food intake. See, e.g., Jesudason et al., "Low-dose Pancreatic Polypeptide Inhibits Food Intake in Man", *J. Nutrition*, 97:426-429 (2007); and Schmidt et al., "A Role for Pancreatic Polypeptide in the Regulation of Gastric Emptying and Short Term Metabolic Control", *J. Clin. Endocrinol. Metab.*, 90(9):5241-5246 (2005).

Additionally, it has been shown that PP has no effect on appetite or food intake in Y4 knock out animals. See Lin et al., "Critical Role of Arcuate Y Receptors and the Melanocortin System in Pancreatic Polypeptide-Induced Reduction in Food Intake in Mice", *PloS ONE*, 4(12):1-10 (December 2009). This demonstrates that the PP dose-dependent effect on food intake is mediated through the Y4 receptor.

NPY2 agonists and NPY4 agonists have previously been described as useful in preparations, formulations, pharmaceutical compositions, and administration routes, for treatment of obesity and associated diseases, for example, in U.S. Publication No. 2002/0141985 and PCT Publication No. WO 2005/077094.

For treating conditions responsive to Y4 receptor modulation, such as obesity and intestinal hypersecretion, it would be desirable to use PP-fold peptides or peptide mimics such as small molecules which were specific for the Y4 receptor. In particular, it would be highly desirable to use such agents which are selective for the Y4 receptor over the Y1 receptor, as activation of the Y1 receptor is expected to potentially cause unwanted cardiovascular and renal side effects, such as vasoconstriction and natriuresis. Additionally, Y4 receptors are expressed in specific regions of the brain relative to other Y receptors, such that Y-4 specific compounds may have a greater impact in reducing food intake with fewer side effects, such as nausea. See Lin et al., at p. 9.

Thus, use of selective and efficacious Y4 receptor agonists over Y1 and Y2 receptor agonists would be particularly useful in diseases and conditions susceptible to Y4 receptor activation.

The present invention relates to novel substituted adipic acid amides which have the ability to activate, partially activate and/or modulate the NPY4 receptor. Such compounds are therefore potentially useful for the treatment of obesity, to control appetite, feeding, food intake, energy expenditure, caloric intake, gastric motility, diabetes and other related conditions, including those referenced above and elsewhere herein.

SUMMARY OF THE INVENTION

The present invention provides substituted adipic acid amides, and analogues thereof, which are useful as agonists, partial agonists or modulators of the NPY4 receptor, including stereoisomers, tautomers, pharmaceutically acceptable salts, or solvates thereof.

The present invention also provides pharmaceutical compositions comprising a pharmaceutically acceptable carrier and one or more of the compounds of the present invention or stereoisomers, tautomers, pharmaceutically acceptable salts, or solvates thereof.

The compounds of the invention may be used in the treatment and/or prophylaxis of multiple diseases or disorders associated with the NPY4 receptor, such as obesity, appetite control, feeding behavior, food intake, energy expenditure, caloric intake, gastric motility, Metabolic Syndrome and its component conditions, disorders of glucose metabolism, diabetes and related conditions, microvascular complications associated with diabetes, the macrovascular complications associated with diabetes, cardiovascular diseases, and other maladies.

The compounds of the invention may be used in therapy.

The compounds of the invention may be used for the manufacture of a medicament for the treatment and/or prophylaxis of multiple diseases or disorders associated with the NPY4 receptor.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

According to one embodiment of the invention, a compound is provided having the formula (A),

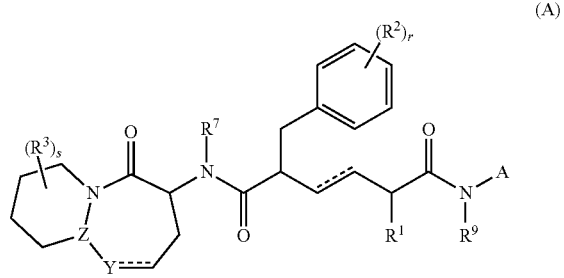

(A)

or a pharmaceutically acceptable salt thereof, wherein:

A is a five- to eight-membered fully or partially saturated monocyclic heterocyclic ring containing from one to two nitrogen atoms and one carbonyl group on the ring; or a nine- to twelve-membered fully saturated or partially saturated bicyclic heterocyclic ring containing one to two nitrogen atoms, optionally one sulfur atom, and one to two carbonyl groups on the ring; wherein when ring A is monocyclic it is optionally substituted with one to two groups $R^{4a}$, and when ring A is bicyclic, it is optionally substituted with one to two groups $R^4$, each independently selected from each other;

each of the bonds denoted as -----, independently of each other, is selected from a single bond and a double bond;

Y is S or $CH_2$ when the bond adjacent Y is a single bond, or Y is CH when the bond adjacent Y (-----) is a double bond;

Z is CH or N, provided that when Z is N, Y is $CH_2$ and the bond adjacent Y is a single bond;

$R^1$ is hydrogen or $(C_1-C_6)$alkyl, wherein the alkyl may be substituted with one or more of halogen, OH, $CONH_2$, $CO_2(C_1-C_6)$alkyl, $(C_1-C_6)$alkoxy, CN, $CF_3$, $CO_2H$, $(C_3-C_6)$cycloalkyl, and/or phenyl, wherein the phenyl substituent may be further substituted with one or more of $OCH_3$, OH, and/or halogen;

$R^2$ is at each occurrence selected from $(C_1-C_6)$alkoxy, OH, CN, $(C_1-C_6)$alkyl, halogen, and $CF_3$;

$R^3$ and $R^4$ are at each occurrence selected independently from CN, $CF_3$, $(C_1-C_3)$alkyl, $(C_2-C_4)$alkenyl, $(C_1-C_4)$alkoxyl, $CO_2(C_1-C_6)$alkyl, oxadiazolyl, $CONH(C_1-C_4)$alkyl, and CONH-thiozolyl; and $R^{4a}$ is selected from $R^4$ and phenyl, wherein said phenyl is optionally further substituted with halogen, $(C_1-C_4)$alkyl, or $(C_1-C_4)$alkoxyl;

$R^7$ and $R^9$, at each occurrence taken independently of each other, are selected from hydrogen and $(C_1-C_6)$alkyl; and r and s are independently 0, 1, or 2.

According to another aspect of the invention, a compound is provided having the formula:

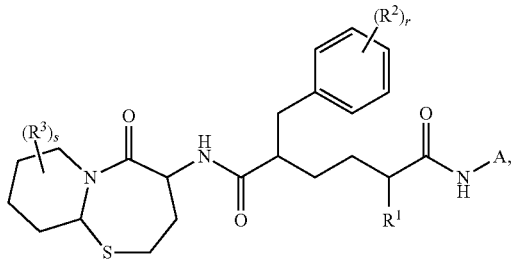

or a pharmaceutically acceptable salt thereof; wherein each of the variables A, $R^1$, $R^2$, $R^3$, r, and s are selected from any of the choices set forth herein for these variables, either above with relation to compounds of formula (A), or below with reference to compounds of formula A.1, A.2, A.3, or A.4, wherein $R^2$ in $R^2$ may be selected from $R^{2a}$ and $R^{2b}$ and $R^3$ may be selected $R^{3a}$ and $R^{3b}$.

According to another aspect of the invention, a compound is provided having the formula:

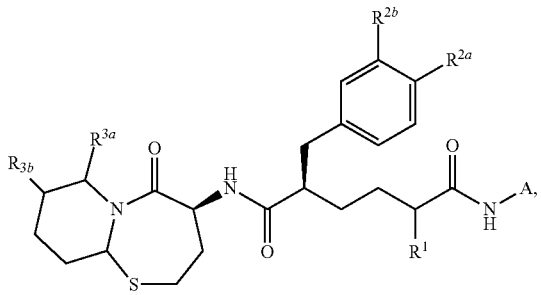

wherein A and $R^1$ are selected from any of the choices set forth herein for said variables, either above with relation to compounds of formula (A), or below with reference to compounds of formula A.1, A.2, A.3, or A.4; and $R^{2a}$ and $R^{2b}$ may be selected from hydrogen, halogen, $(C_1-C_3)$alkyl, and $(C_1-C_4)$alkoxyl, and $R^{3a}$ and $R^{3b}$ may be independently selected from hydrogen, CN, $(C_1-C_4)$alkyl, $CF_3$, and $CO_2(C_1-C_4)$alkyl; or a pharmaceutically acceptable salt thereof.

According to another aspect of the invention, a compound is provided having the formula:

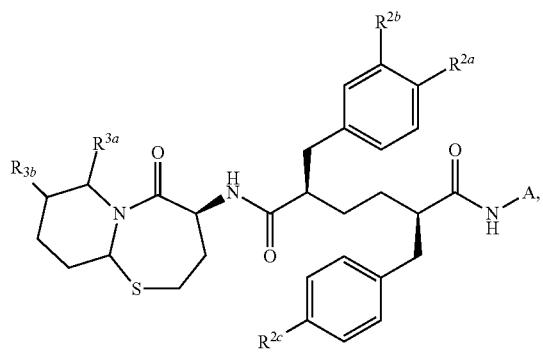

wherein A is selected from any of the choices set forth herein for said variable, either above with relation to compounds of formula (A), or as shown below with reference to compounds of formula A.1, A.2, A.3, or A.4; and $R^{2a}$ and $R^{2b}$ are selected from hydrogen, halogen, $(C_1-C_3)$alkyl, and $(C_1-C_4)$alkoxyl, and $R^{3a}$ and $R^{3b}$ are independently selected from hydrogen, CN, $(C_1-C_4)$alkyl, $CF_3$, and $CO_2(C_1-C_4)$alkyl; and $R^{2c}$ is selected from hydrogen, halogen, $(C_1-C_3)$alkyl, and $(C_1-C_4)$alkoxyl.

According to another aspect of the invention, there is provided compounds according to any of the formulae above containing ring A, wherein the ring A is further defined as:

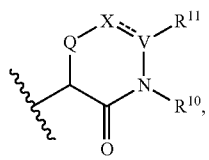

wherein:
Q is $-(CR^5R^6)_m-(CH=CH)_o-(CH_2)_n-$; and
when the bond between X and V is a single bond, X is selected from a bond, S, $CH_2$, or NHC(=O); and when the bond between X and V is a double bond, X is $CR^{12}$;
V is CH or N, provided that when V is N, X is $CH_2$ and the bond between X and V is a single bond; or V can be C, when X is $CR^{12}$ and $R^{11}$ and $R^{12}$ are taken together to form phenyl;
$R^5$ and $R^6$ are independently hydrogen or $(C_1-C_6)$alkyl, or $R^5$ and $R^6$ may be taken together to form a $(C_3-C_5)$cycloalkyl;
$R^{10}$ and $R^{11}$ are selected together with V and X, wherein:
(a) $R^{10}$ and $R^{11}$ are taken together with the atoms to which they are attached to form a 5- or 6-membered heterocyclo containing one or two nitrogen atoms, said heterocycle optionally substituted with one or more of $R^4$, wherein V is N or CH, and X is S, a bond, NHC(=O), or $CH_2$; or
(b) $R^{10}$ is selected from hydrogen, $(C_1-C_4)$alkyl, $(CH_2)_p$-pyridinyl, or $(CH_2)_q$-phenyl, wherein the alkyl optionally may be substituted with $CO_2(C_1-C_2)$alkyl, and the phenyl optionally may be substituted with halogen, $(C_1-C_2)$alkyl, or $(C_1-C_2)$alkoxyl, and wherein V is CH or N; or
(c) $R^{10}$ is hydrogen, V is C, X is $CR^{12}$, and $R^{11}$ and $R^{12}$ are taken together to form phenyl;
m is 1, 2, 3, or 4;
n is 0 or 1;
o is 0 or 1; provided that m, n and o, taken together, are 1 to 4, and provided further that when the bond between X and V is a double bond, either n is 1 or o is 0; and
p and q are independently 0, 1, 2, or 3.

According to another aspect of the invention, there is provided a compound having formula (A.1),

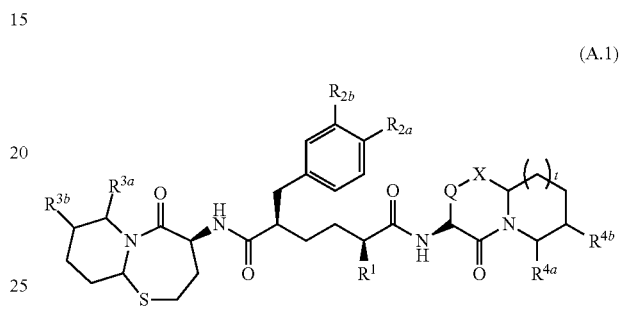

or a pharmaceutically acceptable salt thereof, wherein:
X is a bond, S, or $CH_2$;
$R^{2a}$ and $R^{2b}$ are selected from hydrogen, halogen, $(C_1-C_3)$alkyl, and $(C_1-C_4)$alkoxyl;
$R^{1a}$, $R^{3b}$, $R^{4a}$, and $R^{4b}$ are each independently selected from hydrogen, CN, $CF_3$, $(C_1-C_3)$alkyl, $(C_2-C_4)$alkenyl, $(C_1-C_3)$alkoxyl, $COO(C_1-C_6)$alkyl, oxadiazolyl, $CONH(C_1-C_4)$alkyl, and C(O)NH-thiozolyl; and
t is 0, 1 or 2.

Additionally, in compounds of formula A.1, the variables X, $R^{2a}$, $R^{2b}$, $R^{3a}$, $R^{3b}$, $R^{4a}$, and $R^{4b}$ may be independently selected from any of the other choices set forth for these variables herein.

According to another embodiment of the invention, there is provided a compound having the formula (A.1), above, wherein:
X is S;
Q is $(CR^5R^6)_m$;
$R^1$ is $-CH_2$-phenyl, wherein the phenyl is optionally substituted with one of halogen, $(C_1-C_3)$alkyl, and $(C_1-C_4)$alkoxyl;
$R^{3a}$ and $R^{4a}$ are independently hydrogen or $COOCH_3$;
$R^{3b}$ and $R^{4b}$ are each either hydrogen or $CF_3$;
$R^5$ and $R^6$ are each hydrogen or $CH_3$;
m is 1 or 2 (more preferably 2); and
t is 1.

According to another embodiment, there is provided a compound having the formula A.2,

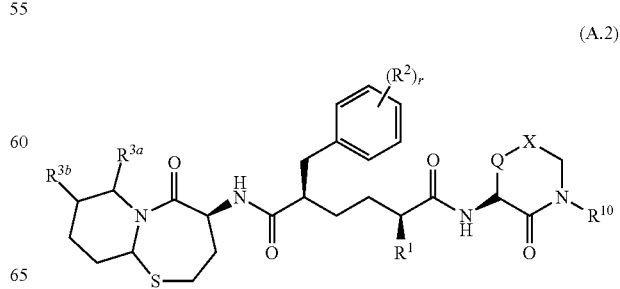

or a pharmaceutically acceptable salt thereof, wherein:

X is a bond or CH$_2$;

R$^2$ is selected from halogen, (C$_1$-C$_3$)alkyl, and (C$_1$-C$_4$)alkoxyl;

R$^{3a}$ and R$^{3b}$ are each independently selected from hydrogen, CN, CF$_3$, (C$_1$-C$_3$)alkyl, (C$_2$-C$_4$)alkenyl, (C$_1$-C$_3$)alkoxyl, CO$_2$(C$_1$-C$_6$)alkyl, oxadiazolyl, CONH(C$_1$-C$_4$)alkyl, and C(O)NH-thiozolyl;

R$^{10}$ is selected from hydrogen, (C$_1$-C$_4$)alkyl, and phenyl, wherein the alkyl optionally may be substituted with CO$_2$(C$_1$-C$_2$)alkyl, and the phenyl optionally may be substituted with halogen, (C$_1$-C$_2$)alkyl, or (C$_1$-C$_2$)alkoxyl; and r is 0 or 1.

According to another embodiment, there is provided a compound having the formula A.2, above, wherein:

R$^1$ is —CH$_2$-phenyl, wherein the phenyl is optionally substituted with one of halogen, (C$_1$-C$_3$)alkyl, or (C$_1$-C$_4$)alkoxyl;

R$^{3a}$ is independently hydrogen or CF$_3$;

R$^{3b}$ is independently hydrogen or CF$_3$; and

R$^{10}$ is phenyl optionally substituted with —OCH$_3$.

According to another embodiment, there is provided a compound having the formula A.3,

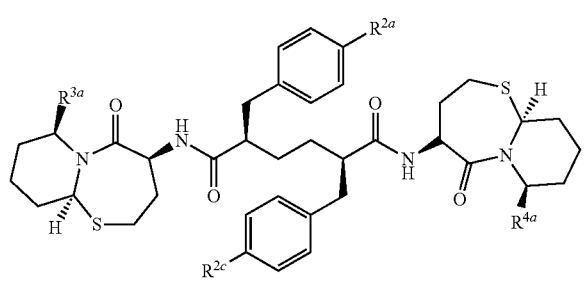

(A.3)

or a pharmaceutically acceptable salt thereof, wherein:

R$^{3a}$ and R$^{4a}$ are each independently hydrogen, CN, CF$_3$, (C$_1$-C$_3$)alkyl, (C$_2$-C$_4$)alkenyl, (C$_1$-C$_3$)alkoxyl, COO(C$_1$-C$_6$)alkyl, oxadiazolyl, CONH(C$_1$-C$_4$)alkyl, or C(O)NH-thiozolyl; and R$^{2a}$ and R$^{2c}$ are each independently hydrogen, OCH$_3$, OH, F, or Cl.

According to another embodiment, there is provided a compound having the formula A.4,

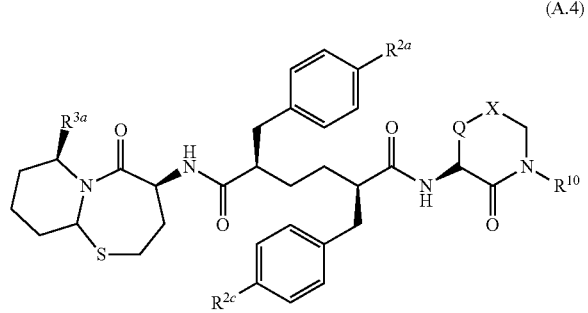

(A.4)

or a pharmaceutically acceptable salt thereof, wherein:

X is a bond or CH$_2$;

R$^{3a}$ is hydrogen, CN, CF$_3$, (C$_1$-C$_3$)alkyl, (C$_2$-C$_4$)alkenyl, (C$_1$-C$_3$)alkoxyl, COO(C$_1$-C$_6$)alkyl, oxadiazolyl, CONH(C$_1$-C$_4$)alkyl, or C(O)NH-thiozolyl; and R$^{2a}$ and R$^{2c}$ are independently hydrogen, OCH$_3$, OH, F, or Cl.

According to another embodiment, there is provided a compound having any one of the formulae defined above, wherein R$^{3a}$ is hydrogen, CN, CF$_3$, CH$_3$, CH$_2$CH$_3$, propylene, or COOCH$_3$; and R$^{10}$ is isobutyl, phenyl, or benzyl, wherein the phenyl or benzyl optionally are substituted ortho with —CH$_3$ or —OCH$_3$.

Alternative Embodiments of the Invention

In another aspect, the present invention provides, a compound of Formula (I):

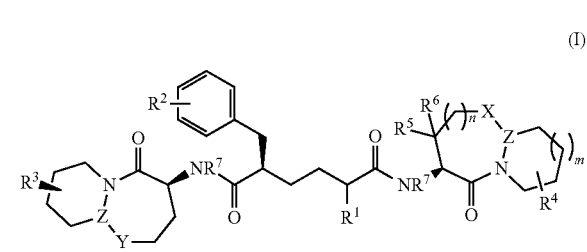

(I)

wherein:

X is CH$_2$, O, or S;

Y is CH$_2$, O, or S;

Z is CH or N;

with the proviso that when Z is N, X and Y are CH$_2$;

R$^1$ is hydrogen, (C$_1$-C$_6$)alkyl, substituted (C$_1$-C$_6$)alkyl, arylalkyl or heteroarylalkyl; wherein the aryl, heteroaryl or alkyl groups can be substituted with one or more halogen, OH, (C$_1$-C$_6$)alkoxy, CN, (C$_1$-C$_6$)alkyl, (C$_3$-C$_6$)cycloalkyl, COOH, COO(C$_1$-C$_6$)alkyl, CONH$_2$ or CF$_3$;

R$^2$ is hydrogen, halogen, OH, (C$_1$-C$_6$)alkoxy, CN, (C$_1$-C$_6$)alkyl or CF$_3$;

R$^3$ and R$^4$ are independently hydrogen, COO(C$_1$-C$_6$)alkyl, CON(R$^7$)$_2$, CONHR$^8$, CN, CH$_2$OH, CH$_2$OCH$_3$, —CF$_3$, CHF$_2$, CH$_2$F, (C$_1$-C$_6$)alkyl, substituted (C$_1$-C$_6$)alkyl, (C$_3$-C$_6$)cycloalkyl, substituted (C$_3$-C$_6$)cycloalkyl, (C$_2$-C$_6$)alkenyl, or a 5- to 10-membered heteroaryl containing 1-4 heteroatoms selected from N, O, and S;

R$^5$ and R$^6$ are independently hydrogen or (C$_1$-C$_6$)alkyl or

R$^5$ and R$^6$ may be taken together to form a (C$_3$-C$_5$)cycloalkyl;

R$^7$ is one or more hydrogen or (C$_1$-C$_6$)alkyl;

R$^8$ is C$_1$-C$_6$)alkyl, aryl or heteroaryl;

m is 0, 1 or 2;

n is 0, 1 or 2;

or a stereoisomer, tautomer, or pharmaceutically acceptable salt thereof.

In another aspect, the invention is directed to a compound of formula II

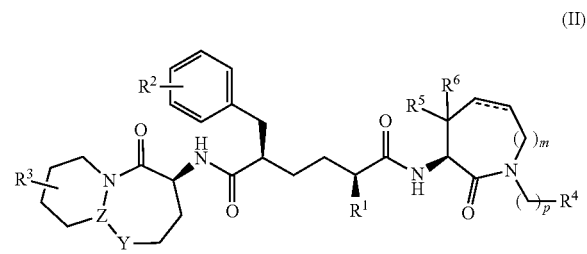

(II)

9 wherein:
Y is $CH_2$, O, or S;
Z is CH or N;
with the proviso that when Z is N, Y is $CH_2$;
the dotted line designates an optional double bond;
$R^1$ is hydrogen, $(C_1-C_6)$alkyl, substituted $(C_1-C_6)$alkyl, arylalkyl or heteroarylalkyl; wherein the aryl, heteroaryl or alkyl groups can be substituted with one or more halogen, OH, $(C_1-C_6)$alkoxy, CN, $(C_1-C_6)$alkyl, $(C_3-C_6)$cycloalkyl, COOH, COO$(C_1-C_6)$alkyl, $CONH_2$ or $CF_3$;
$R^2$ is hydrogen, halogen, OH, CN, $(C_1-C_6)$alkoxy, $(C_1-C_6)$alkyl or $CF_3$;
$R^3$ is hydrogen, COO$(C_1-C_6)$-alkyl, CON$(R^7)_2$, CONHR$^8$, CN, $CH_2OH$, $CH_2OCH_3$, —$CF_3$, $CHF_2$, $CH_2F$, $(C_1-C_6)$alkyl, substituted $(C_1-C_6)$alkyl, $(C_3-C_6)$cycloalkyl, substituted $(C_3-C_6)$cycloalkyl, $(C_2-C_6)$alkenyl or a 5- to 10-membered heteroaryl containing 1-4 heteroatoms selected from N, O, and S;
$R^4$ is $(C_1-C_6)$alkyl, substituted $(C_1-C_6)$alkyl, aryl or heteroaryl wherein the alkyl, aryl or heteroaryl group is optionally substituted with —OH, halogen, $(C_1-C_6)$alkyl or $(C_1-C_6)$alkoxy;
$R^5$ and $R^6$ are independently hydrogen or $(C_1-C_6)$alkyl, or
$R^5$ and $R^6$ may be taken together to form a $(C_3-C_5)$cycloalkyl;
$R^7$ is hydrogen or $(C_1-C_6)$alkyl;
$R^8$ is $C_1-C_6$)alkyl, aryl or heteroaryl,
m is 0, 1 or 2;
n is 0, 1 or 2;
or a stereoisomer, tautomer, or pharmaceutically acceptable salt thereof.

In another aspect, the invention is directed to a compound of formula III

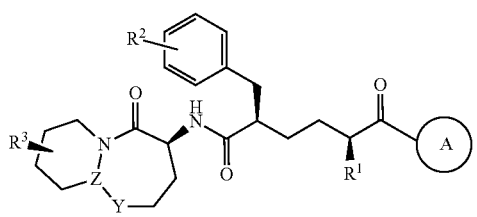

(III)

wherein:
Y is $CH_2$, O, or S;
Z is CH or N;
with the proviso that when Z is N, Y is $CH_2$;
$R^1$ is hydrogen, $(C_1-C_6)$alkyl, substituted $(C_1-C_6)$alkyl, arylalkyl or heteroarylalkyl; wherein the aryl, heteroaryl or alkyl groups can be substituted with one or more halogen, OH, $(C_1-C_6)$alkoxy, CN, $(C_1-C_6)$alkyl, $(C_3-C_6)$cycloalkyl, COOH, COO$(C_1-C_6)$alkyl, $CONH_2$ or $CF_3$;
$R^2$ is hydrogen, halogen, OH, CN, $(C_1-C_6)$alkoxy, $(C_1-C_6)$alkyl or $CF_3$;
$R^3$ is hydrogen, COO$(C_1-C_6)$-alkyl, CON$(R^7)_2$, CONHR$^8$, CN, $CH_2OH$, $CH_2OCH_3$, —$CF_3$, $CHF_2$, $CH_2F$, $(C_1-C_6)$alkyl, substituted $(C_1-C_6)$alkyl, $(C_3-C_6)$cycloalkyl, substituted $(C_3-C_6)$cycloalkyl, $(C_2-C_6)$alkenyl or a 5- to 10-membered heteroaryl containing 1-4 heteroatoms selected from N, O, and S;

10

A is

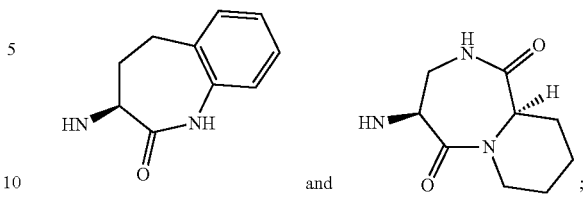

and or a stereoisomer, tautomer, or pharmaceutically acceptable salt thereof.

In another aspect, the invention is directed to a compound of formula I wherein:
X is $CH_2$, O, or S;
Y is $CH_2$ or S;
Z is CH or N;
with the proviso that when Z is N, X and Y are $CH_2$;
$R^1$ is hydrogen, $(C_1-C_6)$-alkyl, substituted $(C_1-C_6)$alkyl or arylalkyl, wherein the aryl or alkyl groups is optionally substituted with one or more halogen, OH, $(C_1-C_6)$-alkoxy, CN, $(C_1-C_6)$-alkyl, $(C_3-C_6)$cycloalkyl, COO$(C_1-C_6)$alkyl, $CONH_2$ or $CF_3$;
$R^2$ is hydrogen, halogen, OH, $(C_1-C_6)$alkoxy, CN, $(C_1-C_6)$-alkyl, or $CF_3$;
$R^3$ and $R^4$ are independently hydrogen, CN, —$CF_3$, $CHF_2$, $CH_2F$, $(C_1-C_6)$alkyl, substituted $(C_1-C_6)$alkyl, $(C_3-C_6)$cycloalkyl, substituted $(C_3-C_6)$cycloalkyl or COO$(C_1-C_6)$alkyl;
$R^5$ and $R^6$ are independently hydrogen or $CH_3$;
m is 0, 1 or 2;
n is 0, 1 or 2;
or a stereoisomer, tautomer, or pharmaceutically acceptable salt thereof.

In another aspect, the invention is directed to a compound of formula I wherein:
Y is S;
Z is CH;
$R^1$ is hydrogen, $(C_1-C_6)$alkyl, substituted $(C_1-C_6)$alkyl or arylalkyl, wherein the aryl or alkyl groups is optionally substituted with one or more halogen, OH, $(C_1-C_6)$-alkoxy, CN, $(C_1-C_6)$-alkyl, $(C_3-C_6)$cycloalkyl, COO$(C_1-C_6)$alkyl, $CONH_2$ or $CF_3$;
$R^2$ is hydrogen, halogen, OH, $(C_1-C_6)$alkoxy, CN or $CF_3$;
$R^3$ and $R^4$ are independently hydrogen, CN, $CF_3$ or COO $(C_1-C_6)$alkyl;
m is 0 or 1;
n is 0 or 1;
or a stereoisomer, tautomer, or pharmaceutically acceptable salt thereof.

In a another aspect, the invention is directed to a compound of formula II wherein:
Y is $CH_2$ or S;
Z is CH;
$R^1$ is hydrogen, $(C_1-C_6)$alkyl, substituted $(C_1-C_6)$alkyl, arylalkyl or heteroarylalkyl; wherein the aryl, heteroaryl or alkyl groups can be substituted with one or more halogen, OH, $(C_1-C_6)$alkoxy, CN, $(C_1-C_6)$alkyl, $(C_3-C_6)$cycloalkyl, COOH, COO$(C_1-C_6)$alkyl, $CONH_2$ or $CF_3$;
$R^2$ is hydrogen, halogen, OH, CN, $(C_1-C_6)$alkoxy, $(C_1-C_6)$alkyl or $CF_3$;
$R^3$ is hydrogen, COO$(C_1-C_6)$alkyl, CN or —$CF_3$;
$R^4$ is aryl wherein the aryl is optionally substituted with —OH, halogen, $(C_1-C_6)$alkyl or $(C_1-C_6)$alkoxyl;
$R^5$ and $R^6$ are independently hydrogen or $CH_3$;
m is 0, 1 or 2;
p is 0;

or a stereoisomer, tautomer, or pharmaceutically acceptable salt thereof.

In another aspect, the invention provides a compound selected from those exemplified or a stereoisomer, tautomer, or pharmaceutically acceptable salt thereof.

II. Other Embodiments of the Invention

In another embodiment, the present invention provides a composition comprising one or more of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and one or more of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of one or more of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention methods provides a pharmaceutical composition for treating diabetes, especially Type II diabetes, which includes the step of administering a therapeutically effective amount of at least one compound according to Formula I alone or in combination with one or more additional anti-diabetic agents to a patient in need of such treatment, wherein the anti-diabetic agent is described herein.

In another embodiment, the present invention provides a pharmaceutical composition further comprising additional therapeutic agent(s). In a preferred embodiment, the present invention provides pharmaceutical composition, wherein the additional therapeutic agent is, for example, a dipeptidyl peptidase-IV (DPP4) inhibitor (for example a member selected from saxagliptin, sitagliptin, vildagliptin and alogliptin).

In another embodiment, the present invention provides a pharmaceutical composition further comprising additional therapeutic agent(s). In a preferred embodiment, the present invention provides pharmaceutical composition, wherein the additional therapeutic agent is, for example, a sodium glucose transport (SGLT) inhibitor (for example, dapagliflozin).

In another embodiment, the present invention provides a method for the treatment and/or prophylaxis of multiple diseases or disorders that have been associated to be treated through the modulation of the NPY4 receptor comprising administering to a patient in need of such treatment and/or prophylaxis a therapeutically effective amount of one or more of the compounds of the present invention, alone, or, optionally, in combination with another compound of the present invention and/or one or more other type of therapeutic agent.

Examples of diseases or disorders that have been associated to be treated through the modulation of the NPY4 receptor according to the present invention include, but are not limited to, gastric motility, obesity and being overweight and conditions in which obesity and being overweight are considered contributory factors. These include bulimia, bulimia nervosa, Syndrome X (Metabolic Syndrome), diabetes, type 2 diabetes mellitus or Non Insulin Dependent Diabetes Mellitus (NIDDM), hyperglycemia, impaired glucose tolerance, insulin resistance, cardiovascular disease, hypertension, atherosclerosis, coronary artery disease, myocardial infarction, peripheral vascular disease, stroke, thromboembolic diseases, hyperlipidemia, hypercholesterolemia, gall bladder disease, osteoarthritis, sleep apnea, reproductive disorders such as polycystic ovarian syndrome, or cancer of the breast, prostate or colon.

In another embodiment, the present invention provides a method for the treatment and/or prophylaxis of obesity, appetite control, food intake, energy expenditure, caloric intake, diabetes, hyperglycemia, gestational diabetes, dyslipidemia, hypertension and cognitive impairment, comprising administering to a patient in need of such treatment and/or prophylaxis a therapeutically effective amount of at least one of the compounds of the present invention, alone, or, optionally, in combination with another compound of the present invention and/or at least one other type of therapeutic agent. Preferably, the second therapeutic agent is an anti-obesity, or an anti-diabetic agent.

In another embodiment, the invention provides a method for decreasing motility of the upper GI tract, e.g., decreasing gastric emptying.

In another embodiment, the present invention provides a compound of the present invention for use in therapy.

In another embodiment, the present invention provides a compound of the present invention for use in therapy for the treatment and/or prophylaxis of multiple diseases or disorders that have been associated to be treated through the modulation of the NPY4 receptor.

In another embodiment, the present invention also provides the use of a compound of the present invention for the manufacture of a medicament for the treatment and/or prophylaxis of multiple diseases or disorders that have been associated to be treated through the modulation of the NPY4 receptor.

In another embodiment, the present invention provides a method for the treatment and/or prophylaxis of multiple diseases or disorders that have been associated to be treated through the modulation of the NPY4 receptor, comprising: administering to a patient in need thereof a therapeutically effective amount of a first and second therapeutic agent, wherein the first therapeutic agent is a compound of the present invention. Preferably, the second therapeutic agent is, for example, dipeptidyl peptidase-IV (DPP4) inhibitor (for example a member selected from saxagliptin, sitagliptin, vildagliptin and alogliptin).

In another embodiment, the present invention provides a method for the treatment and/or prophylaxis of multiple diseases or disorders that have been associated to be treated through the modulation of the NPY4 receptor, comprising: administering to a patient in need thereof a therapeutically effective amount of a first and second therapeutic agent, wherein the first therapeutic agent is a compound of the present invention. Preferably, the second therapeutic agent is, for example, a sodium glucose transport (SGLT) inhibitor (for example, dapagliflozin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders that have been associated to be treated through the modulation of the NPY4 receptor.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Definitions

The following are definitions of terms that may be used in the present specification. The initial definition provided for a group or term herein applies to that group or term throughout the present specification individually or as part of another group, unless otherwise indicated.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

The term "alkyl" refers to straight or branched chain unsubstituted hydrocarbon groups of 1 to 20 carbon atoms, preferably 1 to 6 carbon atoms. The expression "lower alkyl" refers to unsubstituted alkyl groups of 1 to 4 carbon atoms. For example, "$C_1$-$C_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g., $SO_2NH_2$, substituted sulfonamido, nitro, cyano, carboxy, carbamyl, e.g., $CONH_2$, substituted carbamyl e.g., CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or arylalkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively.

The term "arylsulfonylaminocarbonyl" refers to an arylsulfonyl bonded to an aminocarbonyl.

The terms "aryloxyalkyl", "aryloxycarbonyl" or "aryloxyaryl" refer to an aryloxy bonded to an alkyl or substituted alkyl; a carbonyl; or an aryl or substituted aryl, respectively.

The term "arylalkyl" refers to an alkyl or substituted alkyl in which at least one of the hydrogen atoms bonded to at least one of the carbon atoms is replaced with an aryl or substituted aryl. Typical arylalkyls include, but are not limited to, for example, benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl.

The term "arylalkyloxy" refers to an arylalkyl bonded through an oxygen linkage (—O-arylalkyl).

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g., imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocyclic ring. Exemplary groups include cyclopropyl, cyclobutyl, cyclopentyl, cyclohexyl, cycloheptyl, cyclooctyl, cyclodecyl, cyclododecyl, bicycloheptane, bicyclooctane and adamantyl. Exemplary substituents include one or more alkyl groups as described above, or one or more groups described above as alkyl substituents.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocyclo", "heterocyclyl" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl. Examples of heterocycles include, but are not limited to, azetidinyl, pyrrolinyl, piperidinyl, piperazinyl, tetrahydrofuranyl, morpholinyl, dihydropyrrazolyl, dihydro-isoxazolyl. Also included are fused ring and spiro compounds containing, for example, the above heterocycles.

As used herein, the term "heteroaryl", is intended to mean a stable, 5-, 6-, or 7-membered monocyclic or bicyclic or 7-, 8-, 9-, 10-, 11-, 12-, 13-, or 14-membered polycyclic heteroaryl ring that is fully unsaturated, and that contains carbon atoms and 1, 2, 3 or 4 heteroatoms independently selected from the group consisting of N, O and S; and including any polycyclic group in which any of the above-defined heteroaryl rings is fused to a benzene ring or a heterocyclyl ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heteroaryl ring may be attached to its pendant group at any heteroatom or carbon atom that results in a stable structure. The heteroaryl rings described herein may be substituted on carbon or on a nitrogen atom if the resulting compound is stable. A nitrogen in the heteroaryl may optionally be quaternized. Examples of heteroaryls include, but are not limited to, pyridinyl, pyrimidinyl, pyrazinyl, pyridazinyl, furanyl, thienyl, pyrrolyl, pyrazolyl, imidazolyl, indolyl, tetrazolyl, isoxazolyl, oxazolyl, oxadiazolyl, thiadiazolyl, thiazolyl, benzimidazolyl, 1H-indazolyl, benzofuranyl, benzothiofuranyl, benztetrazolyl, benzotriazolyl, benzisoxazolyl, benzoxazolyl, isoquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzene ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzene when the second ring is a carbocycle). The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of bicyclic heterocyclic groups are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydroquinazolinyl.

As used herein, the term "azabicycloalkyl" is intended to mean a stable bicyclic hydrocarbon that includes one nitrogen and optionally another heteroatom chosen from the group of N, O, S. The two fused rings are connected at non adjacent atoms. Examples of azabicycloalkyl groups are, but not limited to, 2-azabicyclo[2.2.1]heptane, 2-azabicyclo[2.2.2]octane, 2-azabicyclo[3.1.1]heptane, 6-azabicyclo[3.1.1]heptane, 8-azabicyclo[3.2.1]octane, 6-azabicyclo[3.2.1]octane, 1,4-diazabicyclo[3.2.1]octane, 6-azabicyclo[3.2.2]nonane.

The term "heteroatoms" shall include oxygen, sulfur and nitrogen.

The term "alkylsulfone" refers to —$R^k S(=O)_2 R^k$, wherein $R^k$ is an alkyl or substituted alkyl.

The term "oxo" refers to the divalent radical =O.

The term "carbamate" refers to the group —$OC(=O)NH_2$.

The term "amide" refers to the group —$C(=O)NH_2$.

The term "sulfonamide" refers to the group —$SO_2NH_2$.

The terms "substituted amide", "substituted sulfonamide", or "substituted carbamate" refer to an amide, sulfonamide, or carbamate, respectively, having at least one hydrogen replaced with a group chosen from alkyl, substituted alkyl, alkenyl, substituted alkenyl, cycloalkyl, and substituted cycloalkyl.

A substituted amide, for example, refers to the group —$C(=O)NR^m R^n$ wherein $R^m$ and $R^n$ are independently selected from H, alkyl, substituted alkyl, alkenyl, substituted alkenyl, cycloalkyl, and substituted cycloalkyl, provided at least one of $R^m$ or $R^n$ is a substituted moiety.

A substituted sulfonamide, for example, refers to the group —$SO_2NR^o R^p$ wherein $R^o$ and $R^p$ are independently selected from alkyl, substituted alkyl, alkenyl, substituted alkenyl, cycloalkyl, and substituted cycloalkyl, provided at least one of $R^o$ or $R^p$ is a substituted moiety.

A substituted carbamate, for example, refers to the group —$OC(=O)NR^q R^r$ wherein $R^q$ and $R^r$ are independently selected from alkyl, substituted alkyl, alkenyl, substituted alkenyl, cycloalkyl, and substituted cycloalkyl, provided at least one of $R^q$ or $R^r$ is a substituted moiety.

The term "ureido" refers to the group —$NHC(=O)NH_2$.

The term "cyano" refers to the group —CN.

The terms "cycloalkylalkyl" or "cycloalkylalkoxy" refer to a cycloalkyl or substituted cycloalkyl bonded to an alkyl or substituted alkyl; or an alkoxy, respectively.

The term "nitro" refers to the group —$N(O)_2$.

The term "thio" refers to the group —SH.

The term "alkylthio" refers to the group —$SR^s$ where $R^s$ is an alkyl, substituted alkyl, cycloalkyl, or substituted cycloalkyl.

The term "thioalkyl" refers to the group —$R^t S$ where $R^t$ is an alkyl, substituted alkyl, cycloalkyl, or substituted cycloalkyl.

The term "alkylsulfonyl" refers to the group —$S(=O)_2 R^u$ where $R^u$ is an alkyl, substituted alkyl, cycloalkyl, or substituted cycloalkyl.

The term "alkylsulfinyl" refers to the group —$S(=O)R^v$ where $R^v$ is an alkyl, substituted alkyl, cycloalkyl, or substituted cycloalkyl.

The term "carboxy" refers to the group —$C(=O)OH$.

The terms "carboxyalkoxy" or "alkoxycarbonylalkoxy" refer to a carboxy, or an alkoxycarbonyl, respectively, bonded to an alkoxy.

The term "alkoxycarbonyl" refers to the group —$C(=O)OR^w$ where $R^w$ is an alkyl, substituted alkyl, cycloalkyl, substituted cycloalkyl, aryl, substituted aryl, heteroaryl, or substituted heteroaryl.

The term "arylalkoxycarbonyl" refers to an aryl or substituted aryl bonded to an alkoxycarbonyl.

The terms "alkylcarbonyloxy" or "arylcarbonyloxy" refer to the group —$OC(=O)R^x$, where $R^x$ is an alkyl or substituted alkyl, or an aryl or substituted aryl, respectively.

The term "carbamoyl" refers to the groups —$OC(=O)NH_2$, —$OC(=O)NHR^x$, and/or —$OC(=O)NR^y R^z$, wherein $R^y$ and $R^z$ are independently selected from alkyl and substituted alkyl.

The group —$NR^6(C=O)R^9$ refers to a group where $R^6$ is selected from hydrogen, lower alkyl and substituted lower alkyl, and $R^9$ is selected from hydrogen, alkyl, substituted alkyl, alkoxy, aminoalkyl, substituted aminoalkyl, alkylamino, substituted alkylamino, aryl and substituted aryl.

The term "carbonyl" refers to a $C(=O)$.

The terms "alkylcarbonyl", "aminocarbonyl", "alkylaminocarbonyl" "aminoalkylcarbonyl", or "arylaminocarbonyl" refer to an alkyl or substituted alkyl; an amino; an alkylamino or substituted alkylamino; an aminoalkyl or substituted aminoalkyl; or an arylamino, respectively, bonded to a carbonyl.

The terms "aminocarbonylaryl" or "aminocarbonylalkyl" refer to an aminocarbonyl bonded to an aryl or substituted aryl; or an alkyl or substituted alkyl, respectively.

The term "sulfonyl" refers to the group $S(=O)_2$.

The term "sulfinyl" refers to an $S(=O)$.

The term "carboxyalkyl" refers to an alkyl or substituted alkyl bonded to a carboxy.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:
a) Bundgaard, H., ed., *Design of Prodrugs,* Elsevier (1985), and Widder, K. et al., eds., *Methods in Enzymology,* 112: 309-396, Academic Press (1985);
b) Bundgaard, H., Chapter 5, "Design and Application of Prodrugs," Krosgaard-Larsen, P. et al., eds., *A Textbook of Drug Design and Development,* pp. 113-191, Harwood Academic Publishers (1991); and
c) Bundgaard, H., *Adv. Drug Deliv. Rev.,* 8:1-38 (1992).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

The term "modulator" refers to a compound that acts at the NPY4 receptor to alter its ability to regulate downstream signaling events. Examples of receptor modulators include agonists, antagonists, partial agonists, inverse agonists, allosteric antagonists and allosteric potentiators as defined in standard pharmacology textbooks (e.g., Ross, E. M. et al., *Goodman and Gilman's The Pharmacological Basis of Therapeutics,* 10th Edition, Chapter 2, pp. 31-43, McGraw Hill (2001)).

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination. "Therapeutically effective amount" is also intended to include an amount of the combination of compounds claimed that is effective to inhibit Trk related diseases and/or conditions. The combination of compounds is preferably a synergistic combination. Synergy, as described, for example, by Chou et al., *Adv. Enzyme Regul.,* 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition, Mack Publishing Company, Easton, Pa. (1985), which is incorporated herein by reference in its entirety.

Utility

The compounds of the present invention can be administered to mammals, preferably humans, for the treatment of a variety of conditions and disorders, including, but not limited to metabolic and eating disorders as well as conditions associated with metabolic disorders (e.g., obesity, diabetes, arteriosclerosis, hypertension, polycystic ovary disease, cardiovascular disease, impaired glucose hemostasis, insulin resistance, hypercholesterolemia, hypertriglyceridemia, choletithiasis, dislipidemic conditions, bulimia nervosa and compulsive eating disorders); gastrointestinal disorders and inflammatory diseases such as inflammatory bowel disease, colitis and/or Crohn's disease.

Dosage Forms

The compounds of the present invention can be administered in oral dosage form The dosage form for said pharmaceutical composition includes such oral dosage forms as granules, powders, tablets, capsules, syrups, emulsions, suspensions, etc. and such non-oral dosage forms as injections (e.g., subcutaneous, intravenous, intramuscular and intraperitoneal injections), drip infusions, external application forms (e.g., nasal spray preparations, transdermal preparations, ointments, etc.), and suppositories (e.g., rectal and vaginal suppositories).

These dosage forms can be manufactured by the per se known technique conventionally used in pharmaceutical procedures. The specific manufacturing procedures are as follows.

To manufacture an oral dosage form, an excipient (e.g., lactose, sucrose, starch, mannitol, etc.), a disintegrator (e.g., calcium carbonate, carboxymethylcellulose calcium, etc.), a binder (e.g., α-starch, gum arabic, carboxymethylcellulose, polyvinylpyrrolidone, hydroxypropylcellulose, etc.), and a lubricant (e.g., talc, magnesium stearate, polyethylene glycol 6000, etc.), for instance, are added to the active component or components and the resulting composition is compressed. Where necessary, the compressed product is coated, by the per se known technique, for masking the taste or for enteric dissolution or sustained release. The coating material that can be used includes, for instance, ethylcellulose, hydroxymethylcellulose, polyoxyethylene glycol, cellulose acetate phthalate, hydroxypropylmethylcellulose phthalate, and EUDRAGIT® (Rohm & Haas, Germany, methacrylic-acrylic copolymer).

Injections can be manufactured typically by the following procedure. The active component or components are dissolved, suspended or emulsified in an aqueous vehicle (e.g., distilled water, physiological saline, Ringer's solution, etc.) or an oily vehicle (e.g., vegetable oil such as olive oil, sesame oil, cottonseed oil, corn oil, etc. or propylene glycol) together with a dispersant, e.g., Tween 80 (Atlas Powder, U.S.A.), HCO 60 (Nikko Chemicals), polyethylene glycol, carboxymethylcellulose, sodium alginate, etc.), a preservative (e.g., methyl p-hydroxybenzoate, propyl p-hydroxybenzoate, benzyl alcohol, chlorobutanol, phenol, etc.), an isotonizing agent (e.g., sodium chloride, glycerol, sorbitol, glucose, inverted sugar, etc.) and other additives. If desired, a solubilizer (e.g., sodium salicylate, sodium acetate, etc.), a stabilizer (e.g., human serum albumin), a soothing agent (e.g., benzalkonium chloride, procaine hydrochloride, etc.) and other additives can also be added.

A dosage form for external application can be manufactured by processing the active component or components into a solid, semi-solid or liquid composition. To manufacture a solid composition, for instance, the active component or components, either as they are or in admixture with an excipient (e.g., lactose, mannitol, starch, microcrystalline cellulose, sucrose, etc.), a thickener (e.g., natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions may optionally contain a pH control agent (e.g., carbonic acid, phosphoric acid, citric acid, hydrochloric acid, sodium hydroxide, etc.), and a preservative (e.g., p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides [e.g., cacao butter, Witepsols (Dinamit-Nobel), etc.], medium-chain fatty acids [e.g., Migriols (Dinamit-Nobel), etc.], vegetable oils (e.g., sesame oil, soybean oil, cotton-seed oil, etc.), etc. The water-soluble base includes, for instance, polyethylene glycols propylene glycol, etc. The hydrophilic base includes, for instance, natural gums, cellulose derivatives, vinyl polymers, and acrylic polymers, etc.

Dosages

The dosage of the pharmaceutical composition of the present invention may be appropriately determined with reference to the dosages recommended for the respective active components and can be selected appropriately according to the recipient, the recipient's age and body weight, current clinical status, administration time, dosage form, method of administration, and combination of the active components, among other factors. For example, the dosage of the insulin sensitivity enhancer for an adult can be selected from the clinical oral dose range of 0.01 to 10 mg/kg body weight (preferably 0.05 to 10 mg/kg body weight, more preferably 0.05 to 5 mg/kg body weight) or the clinical parenteral dose range of 0.005 to 10 mg/kg body weight (preferably 0.01 to 10 mg/kg body weight, more preferably 0.01 to 1 mg/kg body weight). The other active component or components having different modes of action for use in combination can also be used in dose ranges selected by referring to the respective recommended clinical dose ranges.

The proportions of the active components in the pharmaceutical composition of the present invention can be appropriately selected according to the recipient, the recipient's age and body weight, current clinical status, administration time, dosage form, method of administration, and combination of active components, among other factors.

Pharmaceutical Combinations

The present invention includes within its scope pharmaceutical compositions comprising a therapeutically effective amount of at least one of the compounds of Formula I, together with a pharmaceutically acceptable carrier or diluent. Compounds of the present invention can be used alone or in pharmaceutical combinations comprising other suitable therapeutic agents useful in the treatment of the aforementioned disorders including anti-obesity agents, anti-diabetic agents, appetite suppressants, lipid-lowering agents, HDL-raising agents, cognition enhancing agents, agents used to treat neurodegeneration, agents used to treat bowel disorders, anti-inflammatory agents, anti-anxiety agents, and anti-depressants.

The pharmaceutical combinations of the present invention can be formulated in combination, or separately by mixing the respective active components either together or independently with a physiologically acceptable carrier, excipient, binder, diluent, etc. When the active components are formulated independently, the respective formulations can be extemporaneously admixed using a diluent or the like and administered or can be administered independently of each other, either concurrently or at staggered times to the same subject. So, such other therapeutic agent(s) may be administered prior to, simultaneously with, or following the administration of the NPY4 receptor agonist in accordance with the invention.

Examples of suitable anti-obesity agents for use in combination with the compounds of the present invention include melanocortin receptor (MC4R) agonists, cannabinoid receptor modulators, endocannabinoid synthesis modulators, GPR119 agonists, inhibitors of fat absorption, growth hormone secretagogue receptor (GHSR) antagonists, galanin receptor modulators, orexin antagonists, SGLT2 inhibitors, DPP4 inhibitors, triple monoamine reuptake inhibitors, CCK agonists, GLP-1 agonists, and other Pre-proglucagon-derived peptides; NPY1 or NPY5 antagonist, NPY2 modulators, MCHR1 antagonists, corticotropin releasing factor modulators, histamine receptor-3 (H3) modulators, aP2 inhibitors, PPAR gamma modulators, PPAR delta modulators, acetyl-CoA carboxylase (ACC) inhibitors, steroyl Co-A desaturase-1 (SCD-1) inhibitors, 11-β-HSD-1 inhibitors, adiponectin receptor modulators; beta 3 adrenergic agonists, thyroid receptor beta modulators, lipase inhibitors, serotonin receptor agonists, monoamine reuptake inhibitors or releasing agents, anorectic agents, CNTF (ciliary neurotrophic factor), BDNF (brain-derived neurotrophic factor), leptin and leptin receptor modulators, cannabinoid-1 receptor inverse agonists/neutral antagonists, DGAT inhibitors, opiate antagonists, and amylin receptor modulators.

Preferred antiobesity agents include SGLT2 inhibitors, such as those disclosed in U.S. Pat. No. 6,414,126. Most preferred anti-obesity agents include dapagliflozin and lipase inhibitors, such as orlistat, or monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol.

Examples of suitable anti-diabetic agents for use in combination with the compounds of the present invention include: oral antihyperglycemic agents, insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glucokinase inhibitors, glycogen phosphorylase inhibitors, and/or meglitinides, as well as insulin, and/or glucagon-like peptide-1 (GLP-1), GLP-1 agonist, a PTP-1B inhibitor (protein tyrosine phosphatase-1B inhibitor), and/o a histone deacetylase modulator such as a SIRT1 activator.

The compounds of the present invention may be employed in combination with anti-hyperlipidemia agents, or agents used to treat arteriosclerosis. An example of an hypolipidemic agent would be a fibric acid derivatives, bile acid sequestrants, nicotinic acid, aspirin, poly(diallylmethylamine) derivatives, quaternary amine poly(diallyldimethylammonium chloride) and ionenes and other known serum cholesterol lowering agents. Hypolipidemic agents include ACAT inhibitors, an upregulator of LDL receptor activity, and cholesterol absorption inhibitors.

Lipid agent or lipid-modulating agents include cholesteryl transfer protein inhibitors (CETP) The hypolipidemic agent may be an ileal Na$^+$/bile acid cotransporter inhibitor such as disclosed in Drugs of the Future, 24:425-430 (1999). The ATP citrate lyase inhibitor which may be employed in the combination of the invention may include, for example, those disclosed in U.S. Pat. No. 5,447,954.

The other lipid agent also includes a phytoestrogen compounds, a beta-lactam cholesterol absorption inhibitor, a PPAR α-agonist and/or an FXR agonist; an LDL catabolism promoter, a sodium-proton exchange inhibitor; an LDL-receptor inducer or a steroidal glycoside; an anti-oxidant, an antihomocysteine agent, a cholesterol absorption inhibitor, an HMG-CoA synthase inhibitor, or a lanosterol demethylase inhibitor, a sterol regulating element binding protein-I (SREBP-1).

Biological Data

NPY4 cAMP HTRF Agonist Assay

The functionality of the compound at Y4 receptor was analyzed using an inhibitory cAMP assay (CISBIO, HTRF cAMP kit #62AM4PEC) to measure the Gi activation by Y4 agonism.

The human Y4 stable CHO clonal cells were maintained in culture medium (F-12 containing 10% Fetal Bovine Serum, 50 mg/ml GENETICIN®, 100 mg/ml Zeocin). Before the experiment, 5 μL of 1 uM Forskolin (Sigma, # F6886) and 100 uM IBMX (Sigma, # I5879) in PBS buffer were added into 384-well plates (PE, Proxi-plate) that were pre-dotted with 100 mL compounds. The cells were removed from the flasks by Cellstripper, counted and adjusted to $1.0 \times 10^6$ cells/mL in PBS buffer, and added 5 μL/well (5000 cells/well) into the above 384-well plates. The cells were then covered and incubated for 30 minutes at room temperature. After incubation, 5 μL/well of D2-conjugate in HTRF lysis buffer was first added, followed by adding 5 μL/well of anti-cAMP Cryptate in HTRF lysis buffer. The plates were incubated for another 1 hour at room temperature and read on the EnVision Multilabel Plate Reader.

Compounds described herein were tested in the above assay. The following results were obtained.

TABLE 1

| NPY4 cAMP HTRF Agonist Assay EC$_{50}$ (nM) ||
| --- | --- |
| Compound | EC$_{50}$ (nM) |
| Example 1 | 17 |
| Example 4 | 130 |

TABLE 1-continued

NPY4 cAMP HTRF Agonist Assay $EC_{50}$ (nM)

| Compound | $EC_{50}$ (nM) |
|---|---|
| Example 5 | 200 |
| Example 9 | 14 |
| Example 12 | 60 |
| Example 18 | 155 |
| Example 30 | 230 |
| Example 32 | 24 |
| Example 38 | 5 |
| Example 43 | 835 |
| Example 59 | 270 |
| Example 72 | 55 |
| Example 74 | 470 |
| Example 79 | 18 |
| Example 90 | 270 |
| Example 96 | 7 |
| Example 100 | 210 |

III. Methods of Preparation

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

NMM N-methylmorpholine
THF Tetrahydrofuran
rt room temperature
NaHMDS sodium hexamethyldisilazide
$H_2O_2$ hydrogen peroxide
EtOAc ethyl acetate
Hex Hexanes
MeOH Methanol
DCM Dichloromethane
Pd/C palladium on carbon
DMF N,N-dimethylformamide
EDC 1-[3-(dimethylamino)propyl]-3-ethylcarbodiimide hydrochloride
TEA Triethylamine
HOBT 1-hydroxybenzotriazole hydrate
DMAP N,N-dimethylpyridin-4-amine
TMSI trimethylsilyl iodide
TFAA trifluoroacetic anhydride
mmol Millimole
RP reverse phase
$NaHCO_3$ sodium bicarbonate
$Na_2SO_4$ sodium sulfate
$KHSO_4$ potassium hydrogen sulfate
DIPEA di-isopropyl ethylamine
DIC N,N'-diisopropylcarbodiimide The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Compounds of Formula (I) can be prepared as shown in Scheme 1. trans-2-Butene-1,4-dicarboxylic acid A can be reacted with base, e.g., NMM and an activating reagent, such as pivaloyl chloride to form the mixed anhydride. A chiral auxiliary ($X_c$), such as the Evans' auxiliary, can be deprotonated with base, e.g., n-BuLi and reacted with the mixed anhydride to give intermediate B. Intermediate B can be deprotonated with base, e.g., NaHMDS (2 eq) and reacted a substituted benzyl halide C (2 eq) to give bisbenzylated intermediate D. Hydrogenation of the olefin with Pd/C and $H_2$ produces alkane E. The chiral auxiliaries are removed with $H_2O_2$ and LiOH to provide diacid F. Diacid F can be coupled with amine G (2.2 eq) using a base such as DIPEA and a suitable coupling reagent, e.g., EDC and HOBT to give compounds of Formula (I).

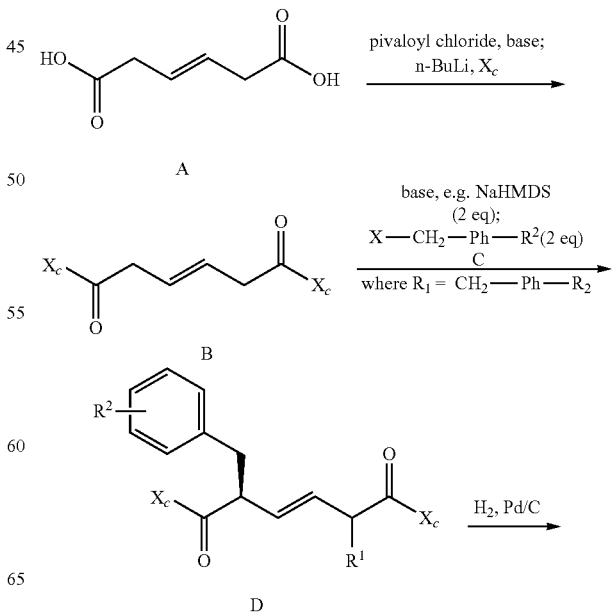

Scheme 1

27
-continued

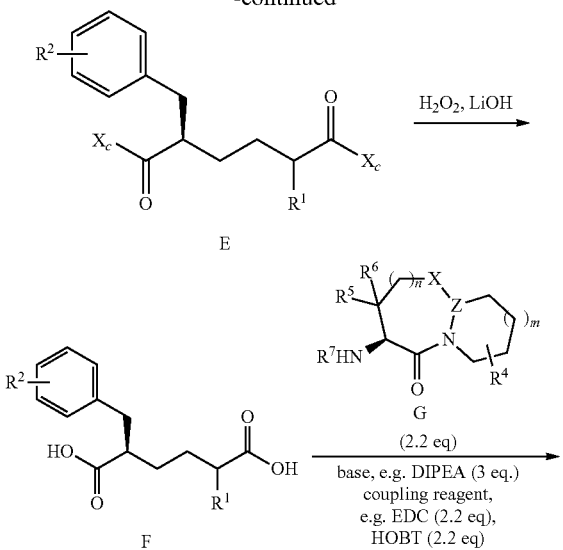

E

28
-continued

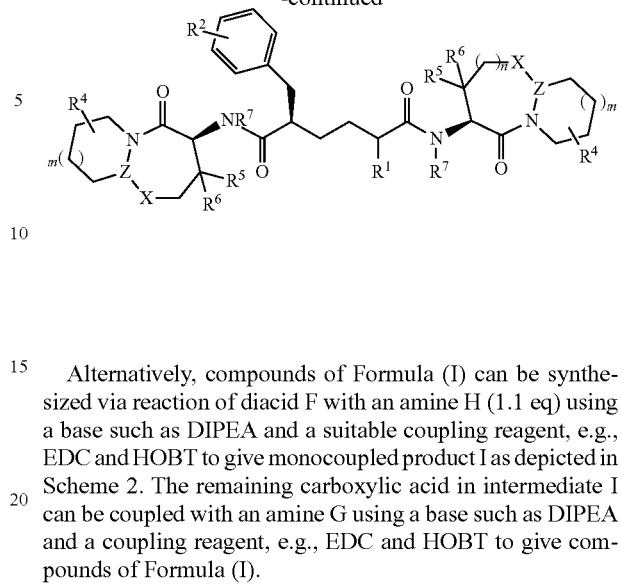

Alternatively, compounds of Formula (I) can be synthesized via reaction of diacid F with an amine H (1.1 eq) using a base such as DIPEA and a suitable coupling reagent, e.g., EDC and HOBT to give monocoupled product I as depicted in Scheme 2. The remaining carboxylic acid in intermediate I can be coupled with an amine G using a base such as DIPEA and a coupling reagent, e.g., EDC and HOBT to give compounds of Formula (I).

Scheme 2

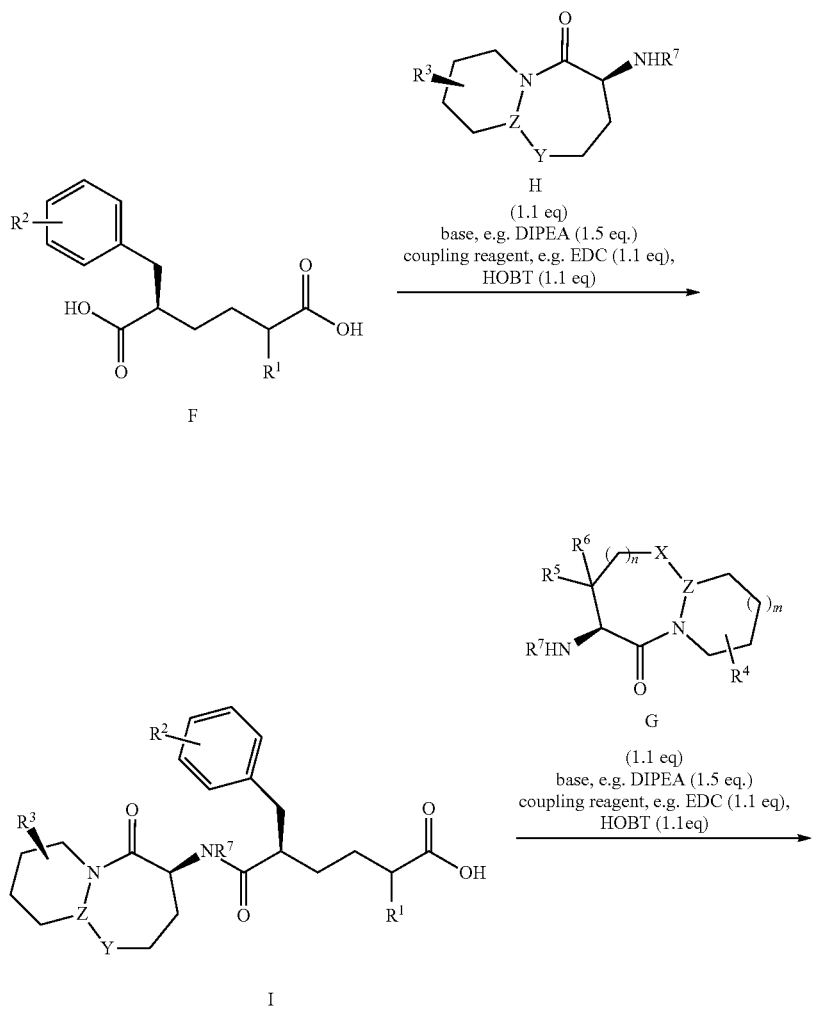

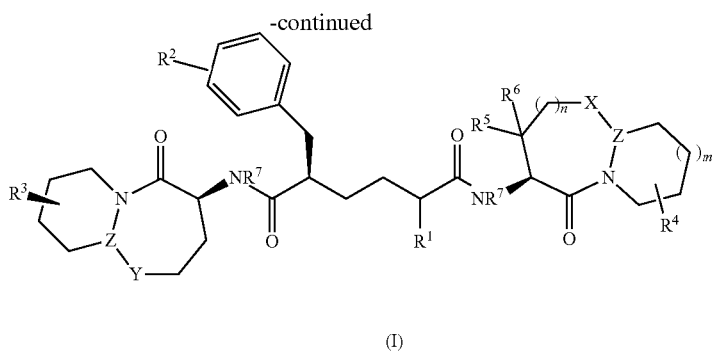

(I)

Compounds of Formula (I) may be synthesized by reaction of intermediate B with a base, e.g., NaHMDS (0.9 eq) followed by a substituted benzyl halide C (0.9 equiv) to give monobenzylated intermediate J as shown in Scheme 3. Monobenzylated intermediate J can be deprotonated with a base, e.g., NaHMDS (1.2 eq) and reacted with a substituted benzyl or allyl halide K to give intermediate D, which can be converted to compounds of Formula (I) according to the sequence depicted in Scheme 1.

(0.9 eq) to give alkylated intermediate L as shown in Scheme 4. Intermediate L can be deprotonated with a base, such as NaHMDS (1.2 eq) and reacted with a substituted benzyl halide C to give intermediate D, which can be transformed to compounds of Formula (I) according to the sequence depicted in Scheme 1.

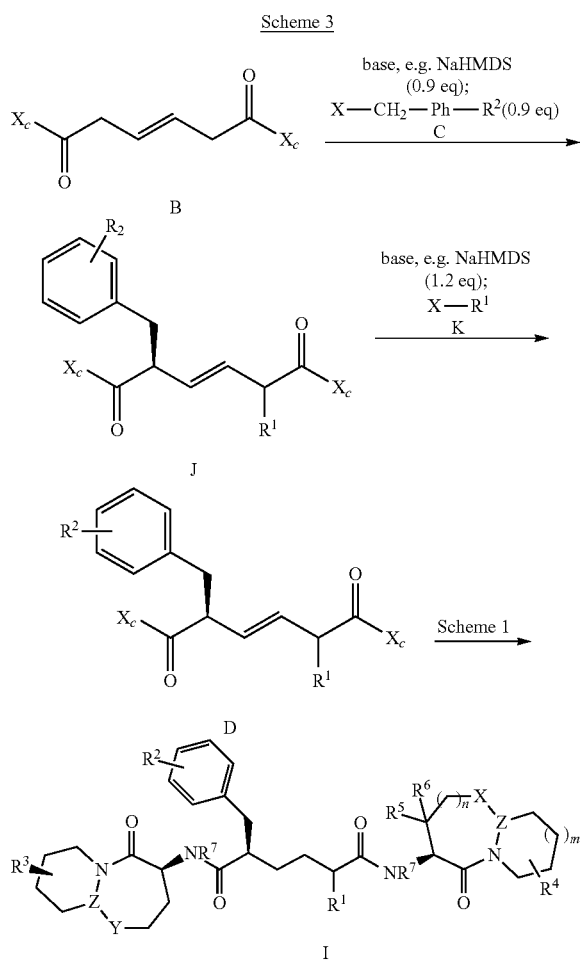

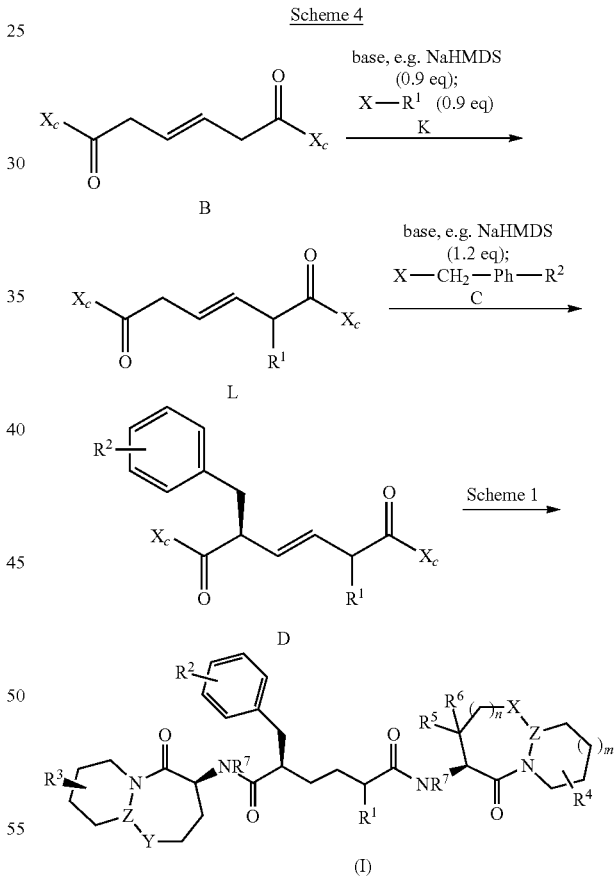

Alternatively, compounds of Formula (I) can be synthesized by reaction of intermediate B with a base, e.g., NaHMDS (0.9 eq) and a substituted benzyl halide or allyl halide K Compounds of Formula (II) can be synthesized via the reaction of intermediate B with a base, e.g., NaHMDS (0.9 eq) followed by a substituted benzyl halide or allyl halide K (0.9) to give monoalkylated intermediate M as depicted in Scheme 5. This intermediate can be deprotonated with a base, such as NaHMDS and reacted with a second substituted benzyl halide or allyl halide C to give the bisalkylated intermediate N. The alkene N is reduced with $H_2$ and Pd/C to give alkane O. The chiral auxiliaries can be removed with $H_2O_2$ and LiOH to provide diacid P. Diacid P can be coupled with an amine Q (1.1 eq) using a base such as DIPEA and a suitable coupling reagent, e.g., EDC and HOBT to give monocoupled product R. The remaining carboxylic acid in intermediate R can be coupled with an amine S using a coupling reagent, e.g., EDC and HOBT to give compounds of Formula (II).
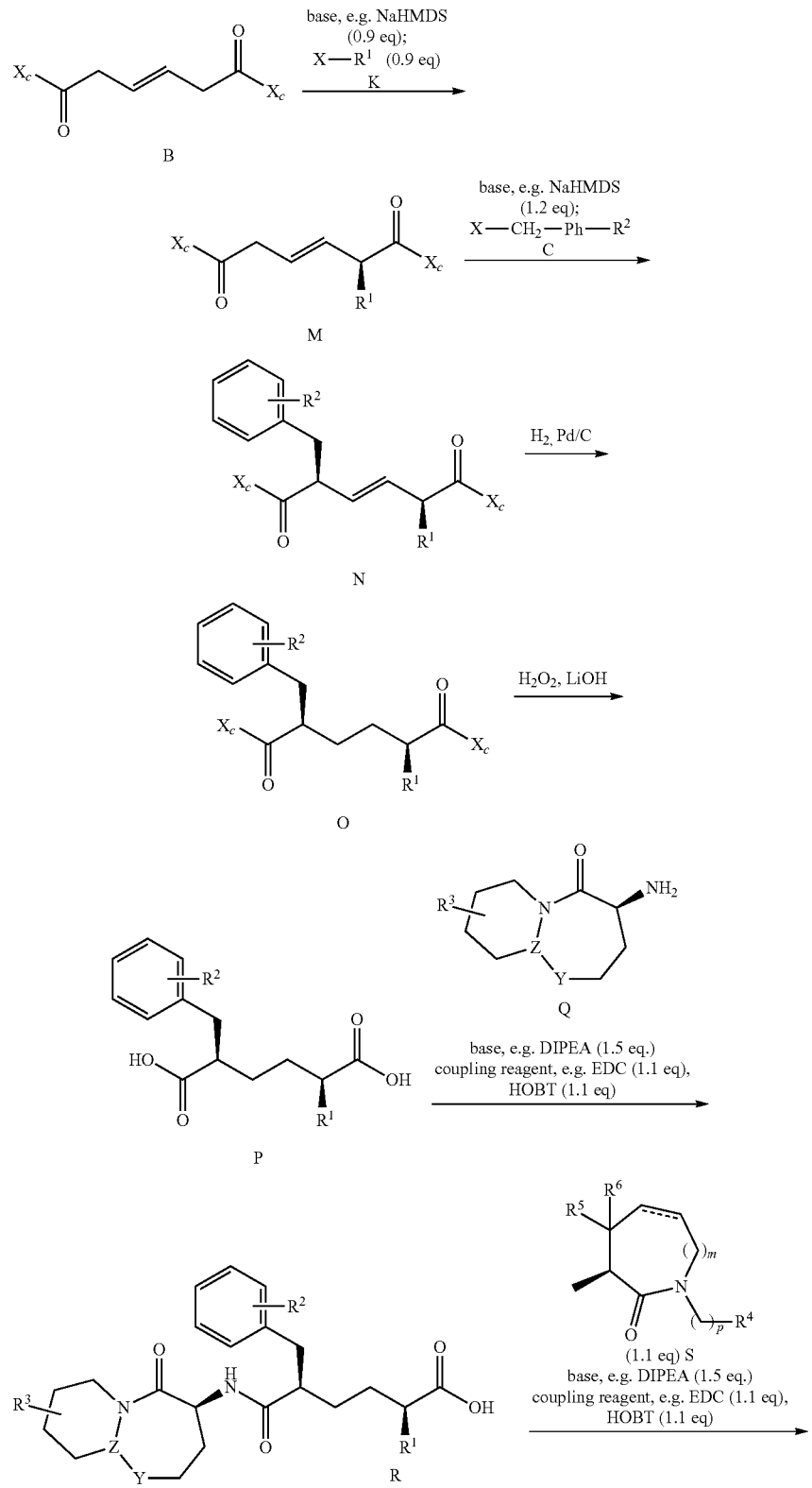
Scheme 5

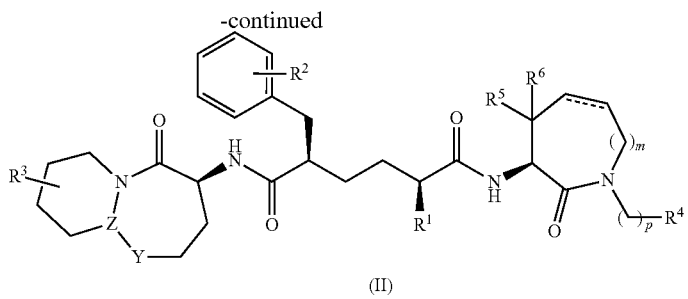

(II)

Alternatively, compounds of Formula (II) can be synthesized from the reaction of intermediate B with base, e.g., NaHMDS (2 eq) and then bisalkylated with a substituted benzyl halide K to afford intermediate O as shown in Scheme 6. Intermediate O can be transformed to compounds of Formula (II) following the methods depicted in Scheme 5. Additionally, the above scheme 5 can be used to prepare compounds of formula (A.5), herein (see Scheme 7), wherein in the last step, the desired amino-substituted ring A (A-NH$_2$), replaces the group

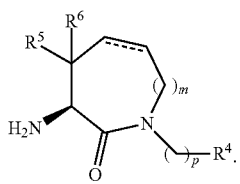

One skilled in the field will appreciate that the alternate intermediates may be used in place of the group Q to introduce variation in the left hand ring, and hydrogenation steps and/or reagents can be eliminated from the schemes to produce molecules will less saturation than those shown, e.g., as in Example 2 below.

Scheme 6

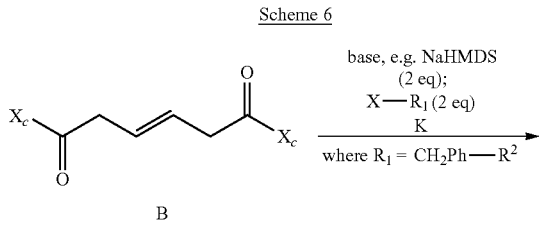

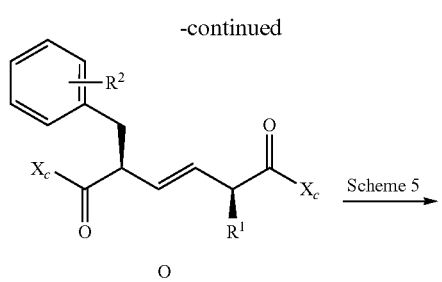

O

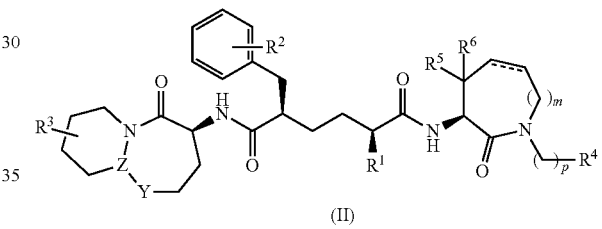

(II)

Compounds of Formula (II) can be synthesized via the reaction of diacid P with a suitable coupling reagent, such as DIC to form the cyclic anhydride T in situ, which can be reacted with amine Q to afford monocoupled product R using a base such as TEA as demonstrated in Scheme 7. Intermediate R can be transformed to compounds of Formula (II) and/or compounds of formula (A.5), following the methods depicted in Scheme 5.

Scheme 7

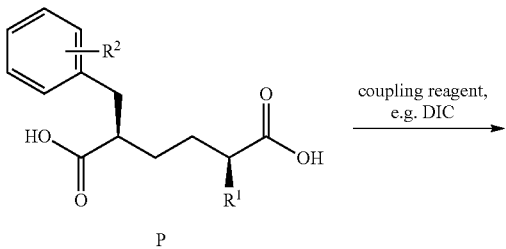

P

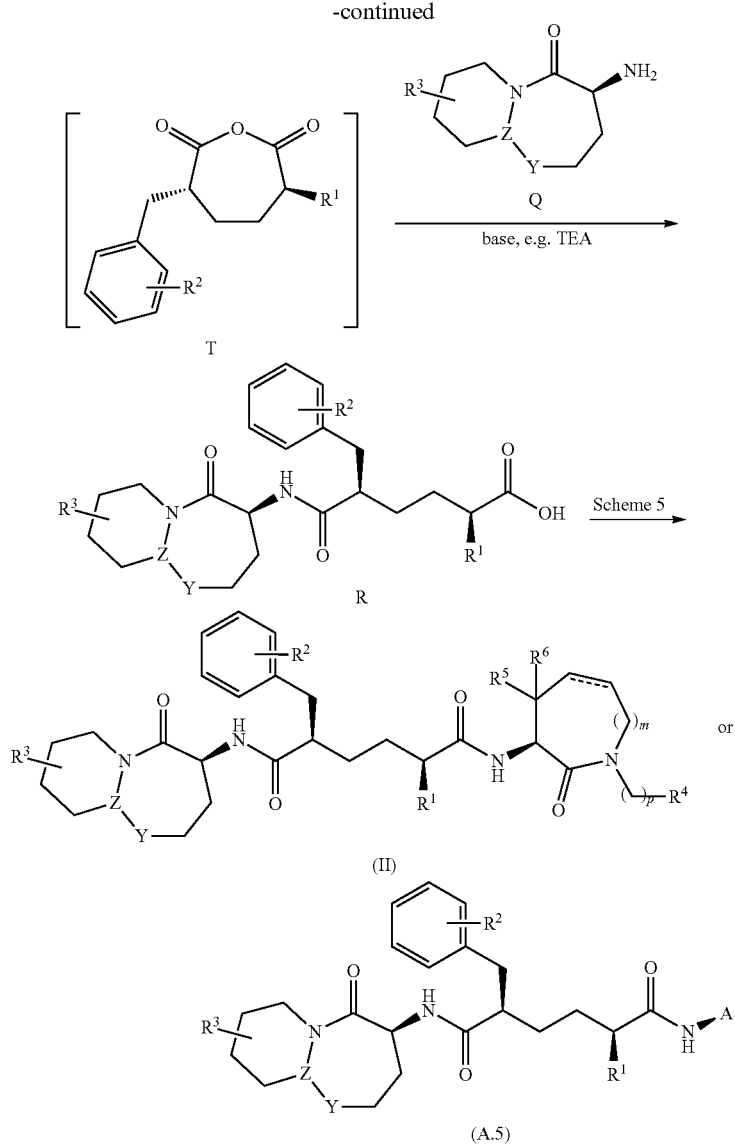

EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

HPLC/MS and Preparatory/Analytical HPLC Methods Employed in Characterization or Purification of Examples Preparatory HPLC Method A was performed on a Shimadzu SCL-10A liquid chromatograph with a linear gradient of 20-100% Solvent B over 10 or 30 minutes, with either a 2 or 5 minute (respectively) hold at 100% Solvent B;
UV visualization at 220 nm;
Column: Axia Luna 5u C18 30×100 mm;
Flow rate: 20 mL/min;
Solvent A: 10% MeOH, 90% Water, 0.1% Trifluoroacetic Acid; and
Solvent B: 90% MeOH, 10% Water, 0.1% Trifluoroacetic Acid.

Preparatory HPLC Method B was performed on a Shimadzu SCL-10A liquid chromatograph with a linear gradient of 0-100% Solvent B over 10 or 30 minutes, with either a 2 or 5 minute (respectively) hold at 100% Solvent B;
UV visualization at 220 nm;
Column: YMC S5 ODS C18 30×100 mm;
Flow rate: 20 mL/min;
Solvent A: 10% MeOH, 90% Water, 0.1% Trifluoroacetic Acid; and
Solvent B: 90% MeOH, 10% Water, 0.1% Trifluoroacetic Acid.

Chiral preparatory HPLC Method A was performed on a Berger MGII SFC liquid chromatograph:
Column: CHIRALPAK® AD-H SFC, 250×21 cm ID, 5 μm
Flow rate: δ 0 mL/min
Mobile Phase: 70/30 $CO_2$/IPA
Detector Wavelength: 210 nm
Injection Volume: 4000 μL Chiral preparatory HPLC Method B was performed on a Berger MGII SFC liquid chromatograph:
Column: CHIRALPAK® IA, 250×21 cm ID, 5 μm
Flow rate: 60 mL/min, 125 bar backpressure
Mobile Phase: 60/40 $CO_2$/MeOH
Detector Wavelength: 210 nm
Injection Volume: 200 μL NMR Employed in Characterization of Examples $^1H$ NMR spectra (unless otherwise noted) were obtained with JEOL or Bruker FOURIER® transform spectrometers operating at 400 MHz or 500 MHz. $^1$H-nOe experiments were performed in some cases for regiochemistry elucidation with a 400 MHz Bruker FOURIER® Transform spectrometer.

Spectral data are reported as chemical shift (multiplicity, number of hydrogens, coupling constants in Hz) and are reported in ppm (δ units) relative to either an internal standard (tetramethyl silane=0 ppm) for $^1$H NMR spectra, or are referenced to the residual solvent peak (2.49 ppm for $CD_3SOCD_2H$, 3.30 ppm for $CD_2HOD$, 1.94 for $CHD_2CN$, 7.26 ppm for $CHCl_3$ 5.32 ppm for $CDHCl_2$).

General Procedures

General Procedure A: Removal of Evans Chiral Auxiliary

A solution of $H_2O_2$ (30% in water, 7 eq) was slowly added to a 0° C. solution of starting material containing an Evans chiral auxiliary (1 eq) in $THF/H_2O$. Lithium hydroxide monohydrate (3.5 eq) was then added. The reaction mixture was stirred at 0° C. for 40 min. After this time, the reaction mixture was quenched by addition of saturated aqueous $Na_2SO_3$ and saturated aqueous $NaHCO_3$. The reaction mixture was then concentrated to remove most of the THF. The mixture was partitioned between EtOAc and water. The aqueous phase was isolated and washed with EtOAc. The aqueous phase was then acidified using aqueous 5 N HCl to pH<2. The cloudy mixture was extracted with EtOAc (2×). The organic extracts were combined, washed with saturated aqueous NaCl, dried over $MgSO_4$ and concentrated to give the desired carboxylic acid.

General Procedure B: Hydrogenation of a Double Bond (Olefin)

To a solution of starting material containing a double bond in MeOH was added 10% Pd/C (5 mol %). The reaction mixture was stirred under an atmosphere of hydrogen (balloon) for 3 hr. After this time, the reaction mixture was filtered through CELITE® and the filtrate was concentrated to give the saturated desired product.

General Procedure C: Monoalkylation of Benzyl, Substituted Benzyl or Allyl Group Onto (E)-1,6-bis ((S)-4-benzyl-2-oxooxazolidin-3-yl)hex-3-ene-1,6-dione A solution of NaHMDS (1.0 M in THF, 0.9 eq) was slowly added dropwise over 5 min to a −78° C. solution of (E)-1,6-bis((S)-4-benzyl-2-oxooxazolidin-3-yl)hex-3-ene-1,6-dione (1 eq) in THF. After the addition, the reaction mixture was allowed to stir for another 15 min at −78° C. and then benzyl bromide, a substituted benzyl bromide, or allyl iodide (0.9 eq) was added dropwise. The reaction temperature was then slowly raised to 0° C. over 1 hr. The reaction mixture was stirred at 0° C. for an additional 1 hr and then was quenched by the addition of saturated aqueous $NH_4Cl$. The resulting mixture was then partitioned between EtOAc and water. The organic phase was isolated, washed with saturated aqueous NaCl, dried over $MgSO_4$, filtered and concentrated. The crude product was purified using silica gel chromatography (ISCO system) eluting with a gradient of 0-100% EtOAc/Hex to give the monoalkylated product.

General Procedure D: Bis-benzylation of (E)-1,6-bis ((S)-4-benzyl-2-oxooxazolidin-3-yl)hex-3-ene-1,6-dione with a benzyl or substituted benzyl halide A solution of NaHMDS (1.0 M in THF, 2 eq) was slowly added dropwise over 5 min to a −78° C. solution of (E)-1,6-bis((S)-4-benzyl-2-oxooxazolidin-3-yl)hex-3-ene-1,6-dione (1 eq) in THF. After the addition, the reaction mixture was allowed to stir for another 15 min at −78° C. and then a solution of benzyl bromide or a substituted benzyl bromide (2 eq) and 1,3-dimethyl-2-imidazolidinone (2 eq) was added dropwise. The reaction mixture was then warmed to 0° C. and stirred for 30 min. The reaction mixture was warmed to rt and stirred at rt for an additional 2.5 hr. After this time, the reaction mixture was quenched by addition of saturated aqueous $NH_4Cl$. The reaction mixture was then partitioned between EtOAc and water. The organic phase was isolated, washed with saturated aqueous NaCl, dried over $MgSO_4$, filtered and concentrated. The crude product was purified using silica gel chromatography (ISCO system) eluting with a gradient of 0-100% EtOAc/Hex to give the bis-benzylated product.

General Procedure E: Benzylation or allylation of a (S,E)-2-benzyl-1,6-bis((S)-4-benzyl-2-oxooxazolidin-3-yl)hex-3-ene-1,6-dione with a substituted benzyl or allyl halide A solution of NaHMDS (1.0 M in THF, 1.2 eq) was added dropwise to a −78° C. solution of (S,E)-2-benzyl-1,6-bis((S)-4-benzyl-2-oxooxazolidin-3-yl)hex-3-ene-1,6-dione in THF. After 45 min at −78° C., allyl bromide (5 eq) or a substituted benzyl halide (5 eq) was added dropwise. After 5 min, the dry ice/acetone bath was replaced by an ice bath. The reaction mixture was stirred at 0° C. for 1 hr and then for an additional 1 hr at rt. The reaction mixture was quenched by the addition of saturated aqueous $NH_4Cl$. The solution was partitioned between EtOAc and water. The organic phase was isolated, dried over $MgSO_4$, filtered and concentrated. The crude product was purified using silica gel chromatography (ISCO system) eluting with a gradient of 0-100% EtOAc/Hex to give the desired product.

General Procedure F: Bis-Amidation of a Substituted Adipic Acid

To a mixture of a substituted adipic acid (1 eq), an amine (2.2 eq) and DMF was added DIPEA (3 eq), EDC (2.2 eq) and HOBT (2.2 eq). The reaction was stirred at rt overnight. After this time, the reaction mixture was partitioned between EtOAc and water. The layers were separated and the organic phase was washed with aqueous 0.5 N HCl, saturated $NaHCO_3$, and saturated aqueous NaCl. The organic solution was then dried over $MgSO_4$, filtered and concentrated. The crude product was purified by RP prep-HPLC (Method A). Fractions containing the product were concentrated to give the bis-amide.

General Procedure G: Mono-Amidation of a Substituted Adipic Acid

To a solution of a substituted adipic acid (1 eq) in a mixture of DCM and DMF (6:1) was added EDC (1 eq) in portions.

The reaction mixture was then stirred at rt for 24 hr. The reaction mixture was concentrated to remove the DCM. Then an amine or amine salt (1.05 eq) was added to the DMF solution followed by TEA (1.05 eq or 2.1 eq for amine salt). The reaction mixture was left to stir at rt for 3 hr. The reaction mixture was partitioned between a 1:2 ratio of EtOAc and 5% aqueous $KHSO_4$. The organic phase was isolated, washed with saturated aqueous NaCl, dried over $MgSO_4$, filtered and concentrated. The crude product was purified using silica gel chromatography to give the mono-amide.

General Procedure H: Amidation of a Substituted Mono-Amidated Adipic Acid

To a mixture of a substituted mono-amidated adipic acid (1 eq), an amine (1.1 eq) and DMF was added DIPEA (1.5 eq), EDC (1.1 eq) and HOBT (1.1 eq). The reaction was stirred at rt overnight. After this time, the reaction mixture was partitioned between EtOAc and water. The layers were separated and the organic phase was washed with aqueous 0.5 N HCl, saturated $NaHCO_3$, and saturated aqueous NaCl. The organic solution was then dried over $MgSO_4$, filtered and concentrated. The crude product was purified by RP prep-HPLC (Method A). Fractions containing the product were concentrated to give the bis-amide.

Intermediate 1: (E)-1,6-Bis((S)-4-benzyl-2-oxooxazolidin-3-yl)hex-3-ene-1,6-dione

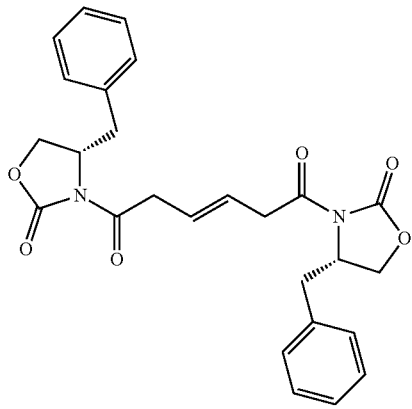 [SMILES: O=C(C/C=C/CC(=O)N1C(=O)OC[C@@H]1Cc1ccccc1)N1C(=O)OC[C@@H]1Cc1ccccc1]

Pivaloyl chloride (6.73 gm, 55.8 mmol) was slowly added to a solution of (E)-hex-3-enedioic acid (4.00 gm, 27.8 mmol) and NMM (5.64 gm, 55.8 mmol) in THF (100 mL) at 0° C. The ice bath was removed and the mixture was allowed warm to rt. After 30 min the mixture was cooled back down to 0° C. In a separate vessel, a solution of n-BuLi (2.5 M in hexanes, 22.2 mL, 55.5 mmol) was slowly added to a −78° C. solution of (S)-4-benzyloxazolidin-2-one (Evans chiral auxiliary) (9.84 gm, 55.5 mmol) in THF (100 mL). The mixture was allowed to stir at −78° C. for 45 min. The mixture containing the activated di-acid was cooled to −78° C. and then cannulated into the mixture containing the lithiated Evans chiral auxiliary. Upon addition the reaction mixture turned reddish in color. The dry ice/acetone bath was removed and the mixture was allowed to warm to rt. After 2 hr at rt, the reaction mixture was quenched by addition of saturated aqueous $NH_4Cl$ (50 mL). The mixture was partitioned between water and a small amount of EtOAc. The aqueous phase was isolated and extracted with EtOAc. All organic phases were combined, washed with saturated aqueous NaCl, dried over $MgSO_4$ and concentrated. The crude product was purified using silica gel chromatography (ISCO system) eluting with a gradient of 0-10% MeOH/DCM to give (E)-1,6-bis((S)-4-benzyl-2-oxooxazolidin-3-yl)hex-3-ene-1,6-dione (3.06 g, 6.62 mmol, 23.8% yield) as a white solid.

Intermediate 2: (E)-Hex-3-enedioyl dichloride

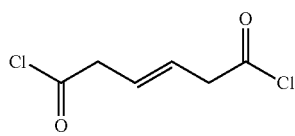

Thionyl chloride (827 gm, 222 mmol) was added to a reaction vessel containing trans-2-butene-1,4-dicarboxylic acid (8.00 gm, 55.5 mmol). The mixture was then heated at 95° C. for 5 hr. After this time, the reaction mixture was cooled to rt and then was concentrated. The residue was dried under reduced pressure (vacuum pump) to give (E)-hex-3-enedioyl dichloride (10.0 gm, 55.2 mmol, 100% yield) as a red oil.

Intermediate 3: (2R,5R)-2,5-Dibenzylhexanedioic acid

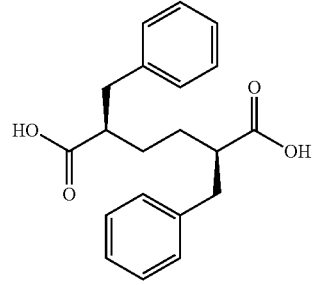 [SMILES: O=C(O)[C@H](CC[C@H](Cc1ccccc1)C(=O)O)Cc1ccccc1]

A: (2S,5S,E)-2,5-Dibenzyl-1,6-bis((S)-4-benzyl-2-oxooxazolidin-3-yl)hex-3-ene-1,6-dione

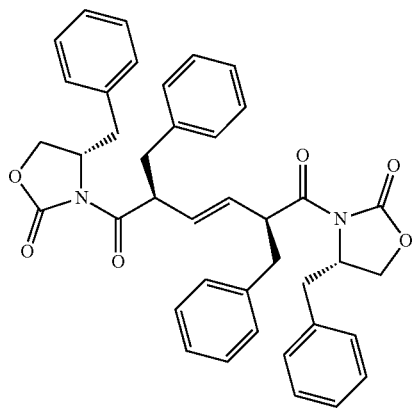 [SMILES: O=C1OC[C@H](Cc2ccccc2)N1C(=O)[C@H](/C=C/[C@H](Cc1ccccc1)C(=O)N1C(=O)OC[C@@H]1Cc1ccccc1)Cc1ccccc1]

(2S,5S,E)-2,5-Dibenzyl-1,6-bis((S)-4-benzyl-2-oxooxazolidin-3-yl)hex-3-ene-1,6-dione was synthesized as described in General Procedure D using benzyl bromide (1.62 gm, 9.46 mmol) followed by chiral separation using chiral preparatory HPLC (Method A) to give a white solid (500 mg, 0.777 mmol, 14.4% yield).

B: (2R,5R)-2,5-Dibenzyl-1,6-bis((S)-4-benzyl-2-oxooxazolidin-3-yl)hexane-1,6-dione A: (S,E)-2-Benzyl-1,6-bis((S)-4-benzyl-2-oxooxazolidin-3-yl)hex-3-ene-1,6-dione

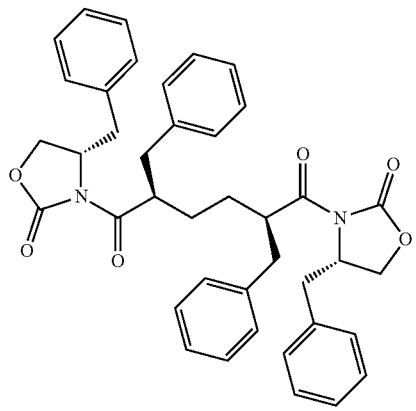 [SMILES: O=C1OC[C@H](Cc2ccccc2)N1C(=O)[C@H](CC[C@H](Cc1ccccc1)C(=O)N1C(=O)OC[C@@H]1Cc1ccccc1)Cc1ccccc1]

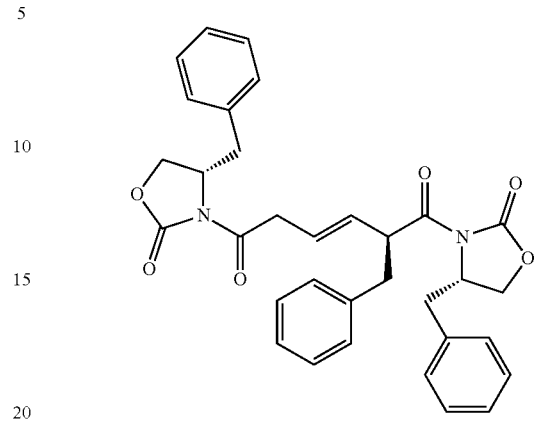

(2R,5R)-2,5-Dibenzyl-1,6-bis((S)-4-benzyl-2-oxooxazolidin-3-yl)hexane-1,6-dione was synthesized as described in General Procedure B using (2S,5S,E)-2,5-dibenzyl-1,6-bis((S)-4-benzyl-2-oxooxazolidin-3-yl)hex-3-ene-1,6-dione (11.9 gm, 19.5 mmol) to give a white solid (11.9 gm, 18.5 mmol, 100% yield).

(R)-2-Benzyl-1,6-bis((S)-4-benzyl-2-oxooxazolidin-3-yl)hexane-1,6-dione was synthesized as described in General Procedure C using benzyl bromide (971 mg, 5.68 mmol) to give a white solid (471 mg, 0.852 mmol, 11.3% yield).

B: (R)-2-Benzyl-1,6-bis((S)-4-benzyl-2-oxooxazolidin-3-yl)hexane-1,6-dione

C: (2R,5R)-2,5-Dibenzylhexanedioic acid

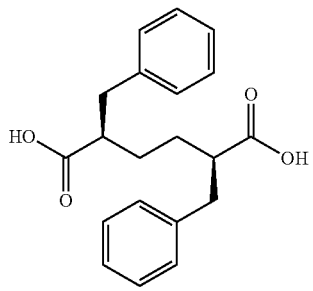 [SMILES: O=C(O)[C@H](CC[C@H](Cc1ccccc1)C(=O)O)Cc1ccccc1]

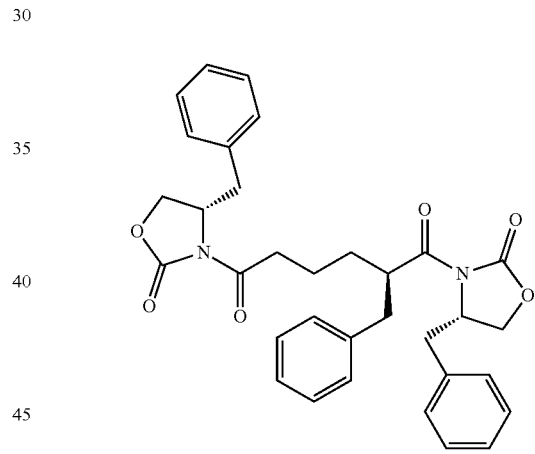

(2R,5R)-2,5-Dibenzylhexanedioic acid was synthesized as described in General Procedure A using (2R,5R)-2,5-dibenzyl-1,6-bis((S)-4-benzyl-2-oxooxazolidin-3-yl)hexane-1,6-dione (11.9 gm, 18.5 mmol) to give a white solid (5.68 gm, 17.4 mmol, 94% yield).

(R)-2-Benzyl-1,6-bis((S)-4-benzyl-2-oxooxazolidin-3-yl)hexane-1,6-dione was synthesized as described in General Procedure B using (S,E)-2-benzyl-1,6-bis((S)-4-benzyl-2-oxooxazolidin-3-yl)hex-3-ene-1,6-dione (43 mg, 0.078 mmol) to give a white solid (40 mg, 0.072 mmol, 93% yield).

Intermediate 4: (R)-2-Benzylhexanedioic acid

C: (R)-2-Benzylhexanedioic acid

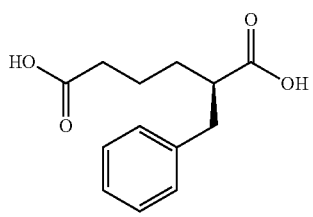 [SMILES: O=C(O)CCC[C@H](Cc1ccccc1)C(=O)O]

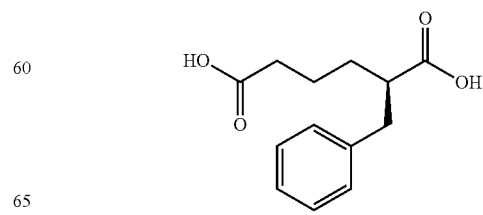

(R)-2-Benzylhexanedioic acid was synthesized as described in General Procedure A using (R)-2-benzyl-1,6-bis((S)-4-benzyl-2-oxooxazolidin-3-yl)hexane-1,6-dione (40 mg, 0.072 mmol) to give a white solid (15 mg, 0.065 mmol, 90% yield).

Intermediate 5:
(2S,5S,E)-2,5-Dibenzylhex-3-enedioic acid

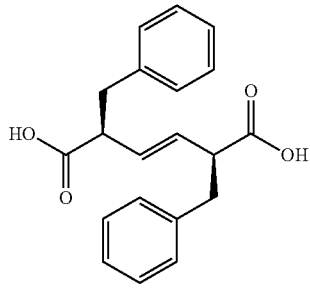 [SMILES: O=C(O)[C@H](/C=C/[C@H](Cc1ccccc1)C(=O)O)Cc1ccccc1]

(2S,5S,E)-2,5-Dibenzylhex-3-enedioic acid was synthesized as described in General Procedure A using (2S,5S,E)-2,5-dibenzyl-1,6-bis((S)-4-benzyl-2-oxooxazolidin-3-yl)hex-3-ene-1,6-dione (32 mg, 0.050 mmol) to give a white solid (13 mg, 0.040 mmol, 80% yield).

Intermediate 6:
(2R,5R)-2-Benzyl-5-isobutylhexanedioic acid

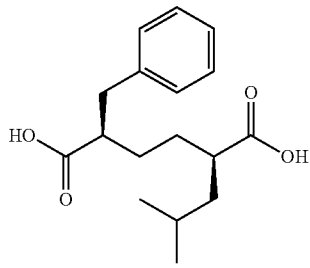 [SMILES: CC(C)C[C@@H](CC[C@H](Cc1ccccc1)C(=O)O)C(=O)O]

A: (3E)-1,6-Bis((7aS)-8,8-dimethyl-2,2-dioxidotetrahydro-3a,6-methano-2,1-benzothiazol-1(3H,4H)-yl)hex-3-ene-1,6-dione

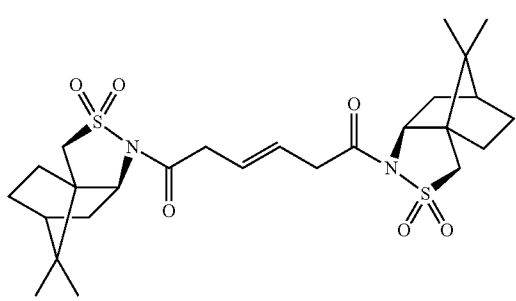

To a round bottom flask was added (2S)-(+)-bornane-10,2-sultam (6.24 gm, 29.0 mmol) and THF (40 mL). The resulting solution was cooled to −78° C. and then n-BuLi (1.6 M in hexanes, 18.6 mL, 29.7 mmol) was added dropwise. The reaction was stirred at −78° C. for 1 hr. Then a solution of (E)-hex-3-enedioyl dichloride in THF (2 mL) was slowly added. After 30 min the dry ice/acetone bath was replaced by an ice bath and the reaction was stirred at 0° C. for 1 hr. After this time, the reaction was quenched by addition of saturated aqueous NH$_4$Cl. The mixture was partitioned between EtOAc and water. The organic phase was isolated, dried over MgSO$_4$, filtered and concentrated. The crude product was purified using silica gel chromatography (ISCO system) eluting with a gradient of 0-100% EtOAc/Hex to give (3E)-1,6-bis((7aS)-8,8-dimethyl-2,2-dioxidotetrahydro-3a,6-methano-2,1-benzothiazol-1(3H,4H)-yl)hex-3-ene-1,6-dione (1.28 gm, 2.38 mmol, 17.2% yield) as a white solid. Anal. Calcd. for C$_{26}$H$_{38}$N$_2$O$_6$S$_2$ m/z 538.2. found: 539.1 (M+H)$^+$.

B: (2S,3E)-2-Benzyl-1,6-bis((7aS)-8,8-dimethyl-2,2-dioxidotetrahydro-3a,6-methano-2,1-benzothiazol-1(3H,4H)-yl)hex-3-ene-1,6-dione

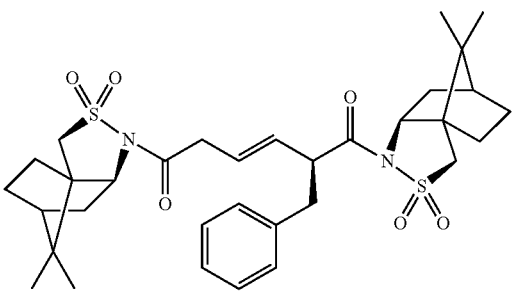

A solution of NaHMDS (1.0 M in THF, 2.38 mL, 2.38 mmol) was added dropwise over 10 min to a −78° C. solution of (3E)-1,6-bis((7aS)-8,8-dimethyl-2,2-dioxidotetrahydro-3a,6-methano-2,1-benzothiazol-1(3H,4H)-yl)hex-3-ene-1,6-dione (1.28 gm, 2.38 mmol) in THF (10 mL). After 45 min at −78° C., benzyl bromide was added dropwise. After 5 min the dry ice/acetone bath was replaced by an ice bath and the reaction was stirred at 0° C. for 3 hr. The reaction was quenched by addition of saturated aqueous NH$_4$Cl. The solution was then partitioned between EtOAc and water. The organic phase was isolated, dried over MgSO$_4$, filtered and concentrated. The crude product was purified by RP prep-HPLC (Method A). The desired fractions were concentrated to give (2S,3E)-2-Benzyl-1,6-bisz((7aS)-8,8-dimethyl-2,2-dioxidotetrahydro-3a,6-methano-2,1-benzothiazol-1(3H,4H)-yl)hex-3-ene-1,6-dione (232 mg, 0.369 mmol, 15.5% yield) as a white solid.

C: (2S,3E,5S)-2-Benzyl-1,6-bis((7aS)-8,8-dimethyl-2,2-dioxidotetrahydro-3a,6-methano-2,1-benzothiazol-1(3H,4H)-yl)-5-(2-methylprop-2-en-1-yl)hex-3-ene-1,6-dione

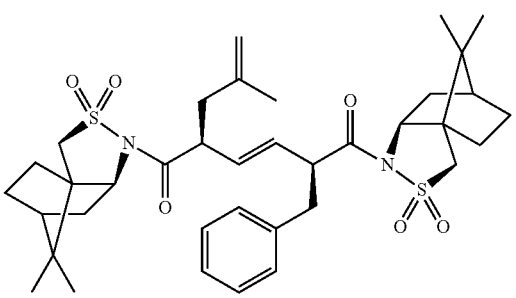

(2S,3E,5S)-2-Benzyl-1,6-bis((7aS)-8,8-dimethyl-2,2-dioxidotetrahydro-3a,6-methano-2,1-benzothiazol-1(3H,4H)-yl)-5-(2-methylprop-2-en-1-yl)hex-3-ene-1,6-dione was synthesized as described in General Procedure C using 3-bromo-2-methylpropene (216 mg, 0.343 mmol) to give a colorless solid (67 mg, 0.098 mmol, 29% yield). Anal. Calcd. for $C_{37}H_{50}N_2O_6S_2$ m/z 682.2. found: 683.2 (M+H)$^+$.

D: (2S,3E,5S)-2-Benzyl-1,6-bis((7aS)-8,8-dimethyl-2,2-dioxidotetrahydro-3a,6-methano-2,1-benzothiazol-1(3H,4H)-yl)-5-(2-methylpropyl)hex-3-ene-1,6-dione

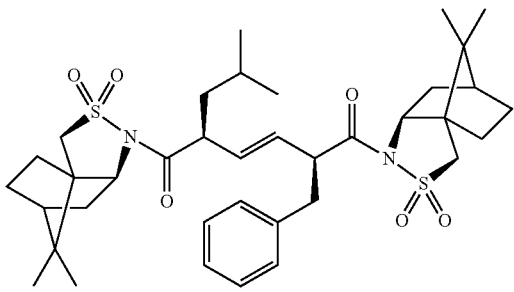

To a round bottom flask was added a solution of (2S,3E,5S)-2-benzyl-1,6-bis((7aS)-8,8-dimethyl-2,2-dioxidotetrahydro-3a,6-methano-2,1-benzothiazol-1(3H,4H)-yl)-5-(2-methylprop-2-en-1-yl)hex-3-ene-1,6-dione (67 mg, 0.098 mmol) in AcOH (10.5 mL) and 10% Pd/C (12 mg, 0.011 mmol). The reaction was stirred under an atmosphere of hydrogen (balloon) for 2 hr. The reaction mixture was diluted with EtOAc and filtered. The catalyst was rinsed with EtOAc and the filtrate was concentrated to give (2S,3E,5S)-2-benzyl-1,6-bis((7aS)-8,8-dimethyl-2,2-dioxidotetrahydro-3a,6-methano-2,1-benzothiazol-1(3H,4H)-yl)-5-(2-methylpropyl)hex-3-ene-1,6-dione (54 mg, 0.079 mmol, 80% yield) as a syrup. Anal. Calcd. for $C_{32}H_{52}N_2O_6S_2$ m/z 684.2. found: 685.2 (M+H)$^+$.

E: (2S,5S,E)-2-Benzyl-5-isobutylhex-3-enedioic acid

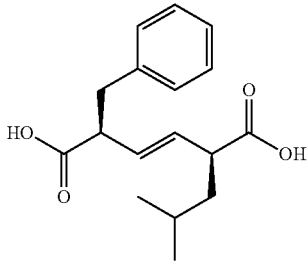 [SMILES: CC(C)C[C@@H](/C=C/[C@H](Cc1ccccc1)C(=O)O)C(=O)O]

To a round bottom flask was added (2S,3E,5S)-2-benzyl-1,6-bis((7aS)-8,8-dimethyl-2,2-dioxidotetrahydro-3a,6-methano-2,1-benzothiazol-1(3H,4H)-yl)-5-(2-methylpropyl)hex-3-ene-1,6-dione (54 mg, 0.079 mmol), THF (1 mL) and water (0.35 mL). The reaction was cooled to 0° C. and a solution of $H_2O_2$ (50% in water, 0.038 mL, 0.63 mmol) was added to the reaction mixture followed by LiOH monohydrate (13.2 mg, 0.315 mmol). The reaction was stirred at 0° C. for 35 min. The reaction was quenched by addition of saturated $Na_2SO_3$ (0.4 mL) and saturated $NaHCO_3$ (0.4 mL). The mixture was concentrated to remove most of the THF. The mixture was diluted with a small amount of water and extracted with EtOAc (2×) to remove the chiral auxiliary. The aqueous phase was then acidified and extracted with EtOAc (2×). The organic extracts were combined, dried over $MgSO_4$, filtered and concentrated to give (2S,5S,E)-2-benzyl-5-isobutylhex-3-enedioic acid (15 mg, 0.052 mmol, 66% yield) as a colorless solid.

F: (2R,5R)-2-Benzyl-5-isobutylhexanedioic acid

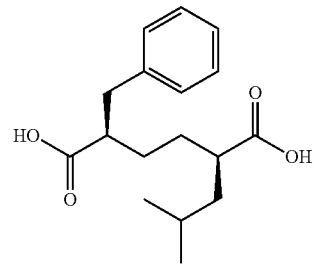 [SMILES: CC(C)C[C@@H](CC[C@H](Cc1ccccc1)C(=O)O)C(=O)O]

(2R,5R)-2-Benzyl-5-isobutylhexanedioic acid was synthesized as described in General Procedure B using (2S,5S,E)-2-benzyl-5-isobutylhex-3-enedioic acid (15 mg, 0.052 mmol) to give a white solid (15 mg, 0.051 mmol, 99% yield).

Intermediate 7: (2R,5R)-2-Benzyl-5-(3-tert-butoxy-3-oxopropyl)hexanedioic acid

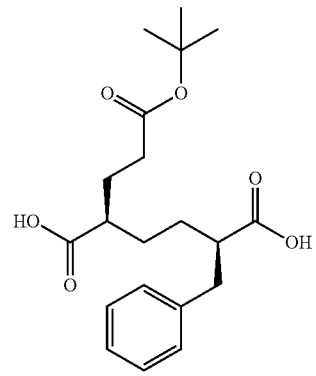 [SMILES: CC(C)(C)OC(=O)CC[C@@H](CC[C@H](Cc1ccccc1)C(=O)O)C(=O)O]

A: tert-Butyl (4S,5E,7S)-7-benzyl-8-((7aS)-8,8-dimethyl-2,2-dioxidotetrahydro-3a,6-methano-2,1-benzothiazol-1(3H,4H)-yl)-4-(((7aS)-8,8-dimethyl-2,2-dioxidotetrahydro-3a,6-methano-2,1-benzothiazol-1(3H,4H)-yl)carbonyl)-8-oxooct-5-enoate

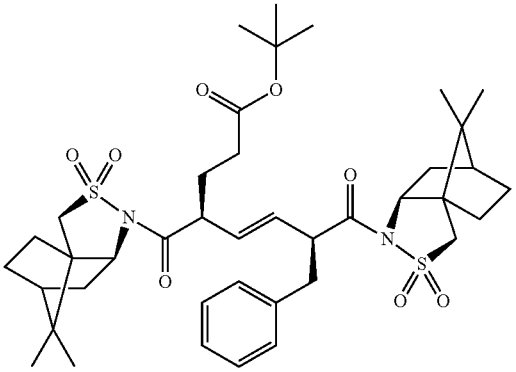

A solution of NaHMDS (1.0 M in THF, 0.347 mL, 0.347 mmol) was added dropwise to a −78° C. solution of (2S,3E)-2-benzyl-1,6-bis((7aS)-8,8-dimethyl-2,2-dioxidotetrahydro-3a,6-methano-2,1-benzothiazol-1(3H,4H)-yl)hex-3-ene-1,6-dione (183 mg, 0.289 mmol) in THF (1.1 mL). After 40 min at −78° C., tert-butyl acrylate (148 mg, 1.16 mmol) was added. After 5 min, the dry ice/acetone bath was replaced by an ice bath. The reaction mixture quickly turned red-orange in color. The reaction was stirred at 0° C. for 2.5 hr before it was quenched by addition of saturated NH₄Cl. The mixture was partitioned between EtOAc and water. The organic phase was isolated, washed with saturated aqueous NaCl, dried over MgSO₄, filtered and concentrated to give tert-butyl (4S,5E,7S)-7-benzyl-8-((7aS)-8,8-dimethyl-2,2-dioxidotetrahydro-3a,6-methano-2,1-benzothiazol-1(3H,4H)-yl)-4-(7aS)-8,8-dimethyl-2,2-dioxidotetrahydro-3a,6-methano-2,1-benzothiazol-1(3H,4H)-yl)carbonyl)-8-oxooct-5-enoate (78 mg, 0.10 mmol, 36% yield) as a yellow solid.

B: (2S,5S,E)-2-Benzyl-5-(3-tert-butoxy-3-oxopropyl)hex-3-enedioic acid

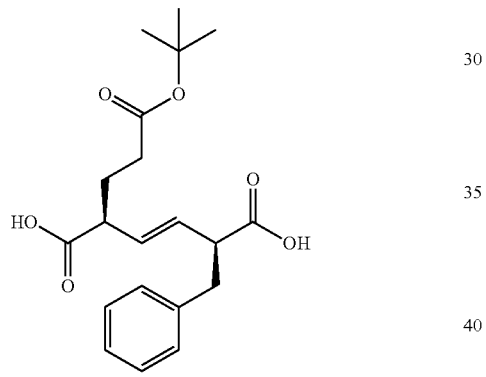

To a round bottom flask was added tert-butyl (4S,5E,7S)-7-benzyl-8-((7aS)-8,8-dimethyl-2,2-dioxidotetrahydro-3a,6-methano-2,1-benzothiazol-1(3H,4H)-yl)-4-(((7aS)-8,8-dimethyl-2,2-dioxidotetrahydro-3a,6-methano-2,1-benzothiazol-1(3H,4H)-yl)carbonyl)-8-oxooct-5-enoate (78 mg, 0.10 mmol), THF (0.8 mL) and water (0.25 mL). The reaction was cooled to 0° C. and a solution of H₂O₂ (50% in water, 0.038 mL, 0.62 mmol) was added to the reaction mixture followed by LiOH monohydrate (13.0 mg, 0.309 mmol). The reaction was stirred at 0° C. for 35 min. The reaction was quenched by the addition of saturated Na₂SO₃ (0.38 mL) and saturated NaHCO₃ (0.38 mL). The mixture was concentrated to remove most of the THF. The mixture was diluted with a small amount of water and extracted with EtOAc (2×) to remove chiral auxiliary. The aqueous phase was then acidified and extracted with EtOAc (2×). The organic extracts were combined, dried over MgSO₄, filtered and concentrated to give (2S,5S,E)-2-benzyl-5-(3-tert-butoxy-3-oxopropyl)hex-3-enedioic acid (24 mg, 0.065 mmol, 63% yield) as a colorless solid.

C: (2R,5R)-2-Benzyl-5-(3-tert-butoxy-3-oxopropyl)hexanedioic acid

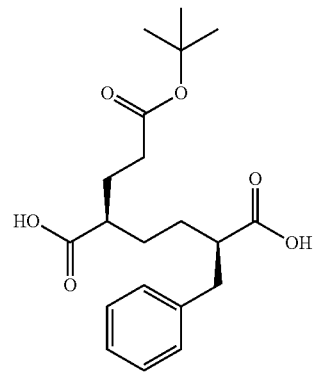 [SMILES: CC(C)(C)OC(=O)CC[C@@H](CC[C@H](Cc1ccccc1)C(=O)O)C(=O)O]

(2R,5R)-2-Benzyl-5-(3-tert-butoxy-3-oxopropyl)hexanedioic acid was synthesized as described in General Procedure B using (2S,5S,E)-2-benzyl-5-(3-tert-butoxy-3-oxopropyl)hex-3-enedioic acid (23.5 mg, 0.065 mmol) to give a colorless solid (21 mg, 0.056 mmol, 87% yield).

Intermediate 8:
(2R,5S)-2-Benzyl-5-propylhexanedioic acid

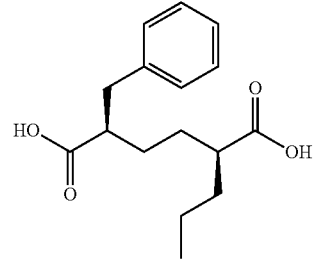 [SMILES: CCC[C@@H](CC[C@H](Cc1ccccc1)C(=O)O)C(=O)O]

A: (2S,5S,E)-2-Allyl-5-benzyl-1,6-bis((S)-4-benzyl-2-oxooxazolidin-3-yl)hex-3-ene-1,6-dione

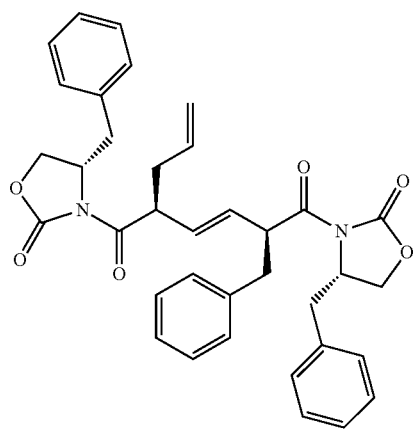 [SMILES: C=CC[C@@H](/C=C/[C@H](Cc1ccccc1)C(=O)N1C(=O)OC[C@@H]1Cc1ccccc1)C(=O)N1C(=O)OC[C@@H]1Cc1ccccc1]

(2S,5S,E)-2-Allyl-5-benzyl-1,6-bis((S)-4-benzyl-2-oxooxazolidin-3-yl)hex-3-ene-1,6-dione was synthesized as described in General Procedure E using allyl bromide (50.9 mg, 0.421 mmol) to give a colorless solid (29 mg, 0.049 mmol, 58% yield). Anal. Calcd. for $C_{36}H_{36}N_2O_6$ m/z 592.2. found: 593.2 (M+H)$^+$.

B: (2S,5S,E)-2-Allyl-5-benzylhex-3-enedioic acid

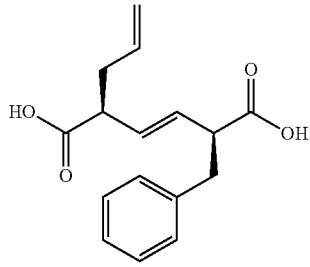 [SMILES: C=CC[C@@H](/C=C/[C@H](Cc1ccccc1)C(=O)O)C(=O)O]

(2S,5S,E)-2-Allyl-5-benzylhex-3-enedioic acid was synthesized as described in General Procedure A using (2S,5S,E)-2-allyl-5-benzyl-1,6-bis((S)-4-benzyl-2-oxooxazolidin-3-yl)hex-3-ene-1,6-dione (32.3 mg, 0.054 mmol) to give a colorless solid (11 mg, 0.040 mmol, 74% yield).

C: (2R,5S)-2-Benzyl-5-propylhexanedioic acid

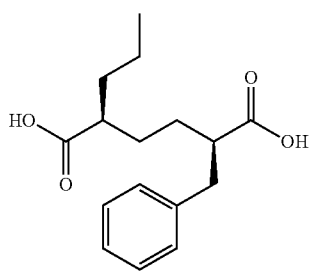 [SMILES: CCC[C@@H](CC[C@H](Cc1ccccc1)C(=O)O)C(=O)O]

(2R,5S)-2-Benzyl-5-propylhexanedioic acid was synthesized as described in General Procedure B using (2S,5S,E)-2-allyl-5-benzylhex-3-enedioic acid (11 mg, 0.040 mmol) to give a colorless solid (11 mg, 0.040 mmol, 99% yield).

Intermediate 9: (2R,5R)-2-(3-Chlorobenzyl)-5-(4-methoxybenzyl)hexanedioic acid

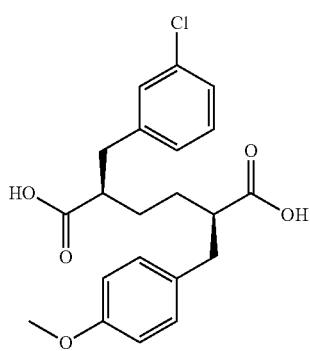

A: (S,E)-1,6-Bis((S)-4-benzyl-2-oxooxazolidin-3-yl)-2-(4-methoxybenzyl)hex-3-ene-1,6-dione

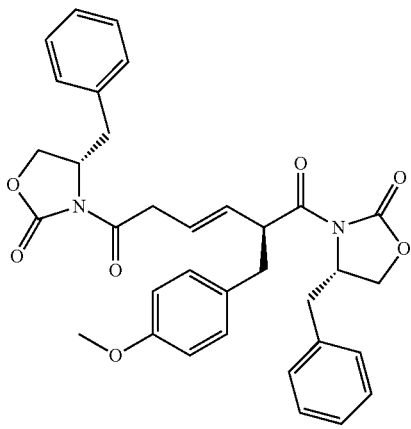 [SMILES: COc1ccc(C[C@@H](/C=C/CC(=O)N2C(=O)OC[C@@H]2Cc2ccccc2)C(=O)N2C(=O)OC[C@@H]2Cc2ccccc2)cc1]

(S,E)-1,6-Bis((S)-4-benzyl-2-oxooxazolidin-3-yl)-2-(4-methoxybenzyl)hex-3-ene-1,6-dione was synthesized as described in General Procedure C using 1-(bromomethyl)-4-methoxybenzene (1.74 mg, 8.65 mmol) to give a white solid (850 mg, 1.46 mmol, 16.9% yield). Anal. Calcd. for $C_{34}H_{34}N_2O_7$ m/z 582.5. found: 581.5 (M–H)$^+$.

B: (2S,5S,E)-1,6-Bis((S)-4-benzyl-2-oxooxazolidin-3-yl)-2-(3-chlorobenzyl)-5-(4-methoxybenzyl)hex-3-ene-1,6-dione

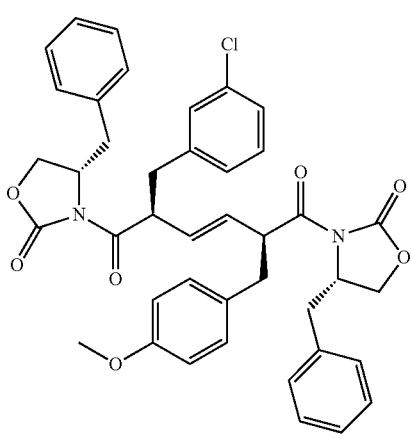 [SMILES: COc1ccc(C[C@@H](/C=C/[C@H](Cc2cccc(Cl)c2)C(=O)N2C(=O)OC[C@@H]2Cc2ccccc2)C(=O)N2C(=O)OC[C@@H]2Cc2ccccc2)cc1]

(2S,5S,E)-1,6-Bis((S)-4-benzyl-2-oxooxazolidin-3-yl)-2-(3-chlorobenzyl)-5-(4-methoxybenzyl)hex-3-ene-1,6-dione was synthesized as described in General Procedure E using 1-(bromomethyl)-3-chlorobenzene (0.178 gm, 0.865 mmol)

to give a white solid (385 mg, 0.544 mmol, 76% yield). Anal. Calcd. for $C_{41}H_{39}ClN_2O_7$ m/z 706.5. found: 707.5 $(M-H)^+$.

C: (2R,5R)-1,6-Bis((S)-4-benzyl-2-oxooxazolidin-3-yl)-2-(3-chlorobenzyl)-5-(4-methoxybenzyl)hexane-1,6-dione

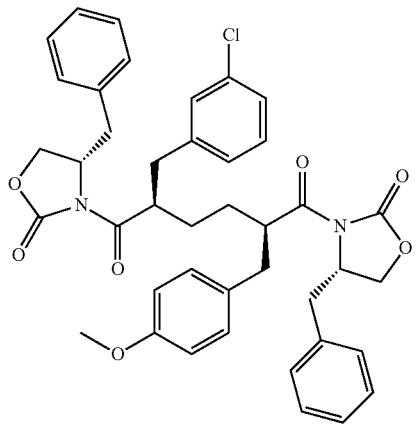 [SMILES: COc1ccc(C[C@@H](CC[C@H](Cc2cccc(Cl)c2)C(=O)N2C(=O)OC[C@@H]2Cc2ccccc2)C(=O)N2C(=O)OC[C@@H]2Cc2ccccc2)cc1]

(2R,5R)-1,6-Bis((S)-4-benzyl-2-oxooxazolidin-3-yl)-2-(3-chlorobenzyl)-5-(4-methoxybenzyl)hexane-1,6-dione was synthesized as described in General Procedure B using (2S,5S,E)-1,6-bis((S)-4-benzyl-2-oxooxazolidin-3-yl)-2-(3-chlorobenzyl)-5-(4-methoxybenzyl)hex-3-ene-1,6-dione (160 mg, 0.226 mmol) to give a white solid (145 mg, 0.204 mmol, 90% yield).

D: (2R,5R)-2-(3-Chlorobenzyl)-5-(4-methoxybenzyl)hexanedioic acid

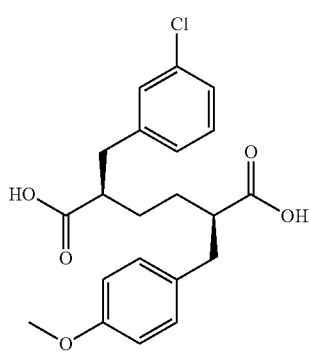

(2R,5R)-2-(3-Chlorobenzyl)-5-(4-methoxybenzyl)hexanedioic acid was synthesized as described in General Procedure A using (2R,5R)-1,6-Bis((S)-4-benzyl-2-oxooxazolidin-3-yl)-2-(3-chlorobenzyl)-5-(4-methoxybenzyl)hexane-1,6-dione (145 mg, 0.204 mmol) to give a white solid (38 mg, 0.097 mmol, 48% yield).

Intermediate 10: (2R,5R)-2-Benzyl-5-(4-methoxybenzyl)hexanedioic acid

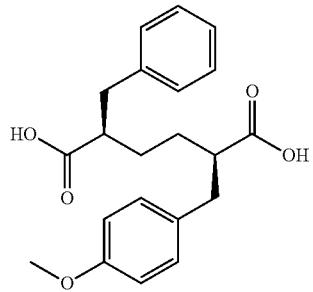 [SMILES: COc1ccc(C[C@@H](CC[C@H](Cc2ccccc2)C(=O)O)C(=O)O)cc1]

A: (2S,5S,E)-2-Benzyl-1,6-bis((S)-4-benzyl-2-oxooxazolidin-3-yl)-5-(4-methoxybenzyl)hex-3-ene-1,6-dione

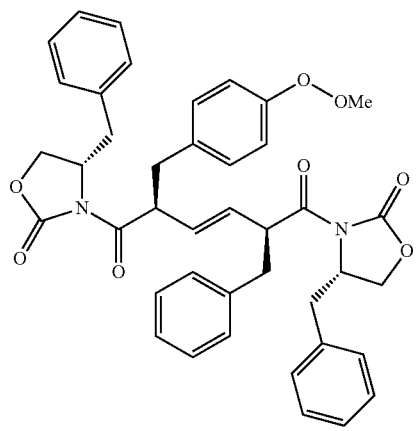 [SMILES: COOc1ccc(C[C@@H](/C=C/[C@H](Cc2ccccc2)C(=O)N2C(=O)OC[C@@H]2Cc2ccccc2)C(=O)N2C(=O)OC[C@@H]2Cc2ccccc2)cc1]

(2S,5S,E)-2-Benzyl-1,6-bis((S)-4-benzyl-2-oxooxazolidin-3-yl)-5-(4-methoxybenzyl)hex-3-ene-1,6-dione was synthesized as described in General Procedure E using 1-(bromomethyl)-4-methoxybenzene (200 mg, 0.995 mmol) to give a colorless solid (350 mg, 0.520 mmol, 52.3% yield). Anal. Calcd. for $C_{41}H_{40}N_2O_7$ m/z 672.5. found: 673.5 $(M+H)^+$.

B: (2S,5S,E)-2-Benzyl-5-(4-methoxybenzyl)hex-3-enedioic acid

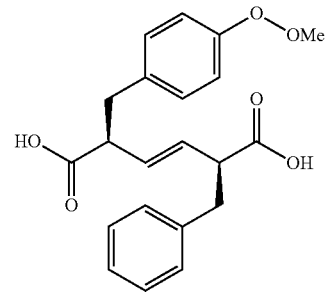 [SMILES: COOc1ccc(C[C@@H](/C=C/[C@H](Cc2ccccc2)C(=O)O)C(=O)O)cc1]

(2S,5S,E)-2-Benzyl-5-(4-methoxybenzyl)hex-3-enedioic acid was synthesized as described in General Procedure A using (2S,5S,E)-2-benzyl-1,6-bis((S)-4-benzyl-2-oxooxazolidin-3-yl)-5-(4-methoxybenzyl)hex-3-ene-1,6-dione (350 mg, 0.250 mmol) to give a colorless solid (100 mg, 0.282 mmol, 54.2% yield). Anal. Calcd. for $C_{21}H_{22}O_5$ m/z 354.4. found: 355.3 (M+H)$^+$.

C:
(2R,5R)-2-Benzyl-5-(4-methoxybenzyl)hexanedioic acid

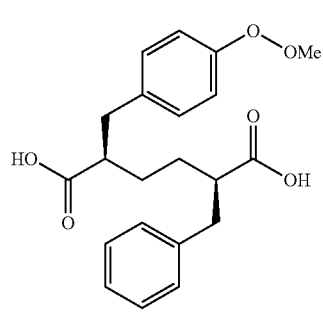 [SMILES: COOc1ccc(C[C@@H](CC[C@H](Cc2ccccc2)C(=O)O)C(=O)O)cc1]

(2R,5R)-2-Benzyl-5-(4-methoxybenzyl)hexanedioic acid was synthesized as described in General Procedure B using (2S,5S,E)-2-Benzyl-5-(4-methoxybenzyl)hex-3-enedioic acid (100 mg, 0.282 mmol) to give a colorless solid (93 mg, 0.26 mmol, 92% yield). Anal. Calcd. for $C_{21}H_{24}O_5$ m/z 356.4. found: 357.3 (M+H)$^+$.

Intermediate 11:
(2R,5R)-2-Benzyl-5-(4-hydroxybenzyl)hexanedioic acid

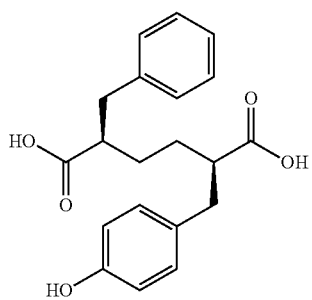

To a round bottom flask was added (2R,5R)-2-benzyl-5-(4-methoxybenzyl)hexanedioic acid (30 mg, 0.084 mmol) and 30% HBr in acetic acid (0.5 mL). The reaction was stirred at 120° C. for 16 h. Then the solvent was removed. The residue was purified by RP prep-HPLC (Method A). The fraction was concentrated to give (2R,5R)-2-benzyl-5-(4-hydroxybenzyl)hexanedioic acid (10 mg, 0.029 mmol, 35% yield) as an off-white solid.

Intermediate 12:
(2R,5R)-2,5-Bis(4-methoxybenzyl)hexanedioic acid

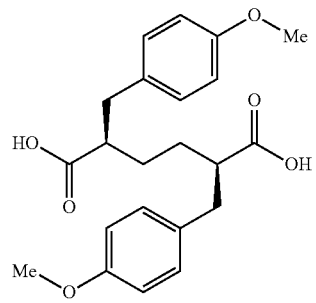

A: (2S,5S,E)-1,6-Bis((S)-4-benzyl-2-oxooxazolidin-3-yl)-2,5-bis(4-methoxybenzyl)hex-3-ene-1,6-dione

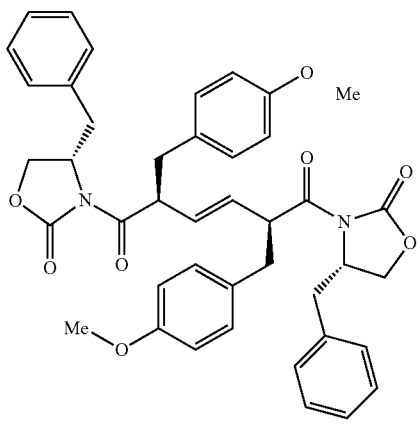 [SMILES: COc1ccc(C[C@@H](/C=C/[C@H](Cc2ccc(O)cc2)C(=O)N2C(=O)OC[C@@H]2Cc2ccccc2)C(=O)N2C(=O)OC[C@@H]2Cc2ccccc2)cc1 ; "Me"]

(2S,5S,E)-1,6-Bis((S)-4-benzyl-2-oxooxazolidin-3-yl)-2,5-bis(4-methoxybenzyl)hex-3-ene-1,6-dione was synthesized as described in General Procedure D using 1-(bromomethyl)-4-methoxybenzene (1.04 g, 5.19 mmol) to give a colorless solid (60 mg, 0.085 mmol, 6.6% yield). Anal. Calcd. for $C_{42}H_{42}N_2O_8$ m/z 702.4. found: 703.3 (M+H)$^+$.

B: (2S,5S,E)-2,5-Bis(4-methoxybenzyl)hex-3-enedioic acid-2,5-Bis(4-methoxybenzyl)hex-3-enedioic acid

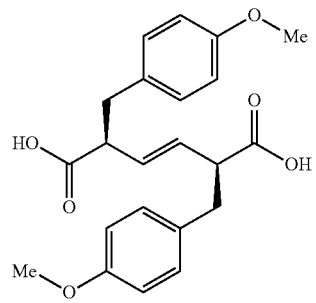 [SMILES: COc1ccc(C[C@@H](/C=C/[C@H](Cc2ccc(OC)cc2)C(=O)O)C(=O)O)cc1]

(2S,5S,E)-2,5-Bis(4-methoxybenzyl)hex-3-enedioic acid was synthesized as described in General Procedure A using (2R,5R,E)-1,6-bis((S)-4-benzyl-2-oxooxazolidin-3-yl)-2,5-bis(4-methoxybenzyl)hex-3-ene-1,6-dione (60 mg, 0.085 mmol) to give a colorless solid (15 mg, 0.039 mmol, 46% yield). $^1$H NMR (500 MHz, CDCl$_3$) δ ppm 6.98 (d, J=8.8 Hz, 4H), 6.80 (d, J=8.2 Hz, 4H), 5.48 (dd, J=5.5, 2.7 Hz, 2H), 3.82-3.75 (m, 6H), 3.23 (dd, J=6.0, 2.7 Hz, 2H), 2.93 (dd, J=13.7, 7.1 Hz, 2H), 2.68 (dd, J=14.0, 7.4 Hz, 2H).

C: (2R,5R)-2,5-Bis(4-methoxybenzyl)hexanedioic acid

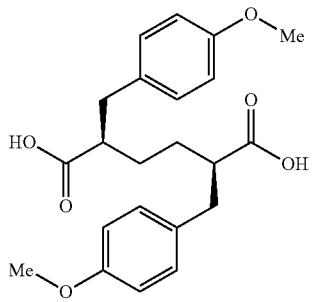

(2R,5R)-2,5-Bis(4-methoxybenzyl)hexanedioic acid was synthesized as described in General Procedure B using (2R,5R,E)-2,5-bis(4-methoxybenzyl)hex-3-enedioic acid (60 mg, 0.16 mmol) to give a colorless solid (56 mg, 0.15 mmol, 93% yield). Anal. Calcd. for C$_{22}$H$_{26}$O$_6$ m/z 386.4. found: 385.3 (M−H)$^+$; $^1$H NMR (400 MHz, CDCl$_3$) δ ppm 7.06 (d, J=8.3 Hz, 4H), 6.82 (d, J=8.3 Hz, 4H), 3.79 (s, 6H), 2.91 (dd, J=13.6, 7.5 Hz, 2H), 2.69-2.61 (m, 2H), 2.61-2.52 (m, 2H), 1.76-1.63 (m, 2H), 1.58-1.47 (m, 2H).

Intermediate 13: (2R,5R)-2-(3-Chlorobenzyl)-5-(cyclohexylmethyl)hexanedioic acid

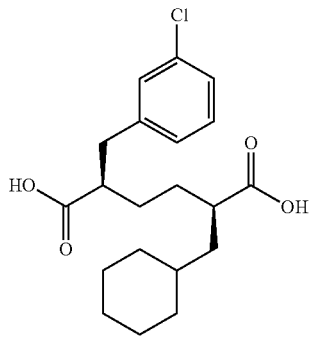 [SMILES: O=C(O)[C@H](CC[C@H](CC1CCCCC1)C(=O)O)Cc1cccc(Cl)c1]

To a solution of (2S,5S,E)-2-(3-chlorobenzyl)-5-(4-methoxybenzyl)hex-3-enedioic acid (113 mg, 0.291 mmol) in THF (5 mL) was added platinum(IV) oxide (60 mg, 0.26 mmol). The reaction was stirred at 1 atm of hydrogen (balloon) for 16 h. The reaction was filtered through CELITE® and washed with MeOH. The combined filtrate and MeOH washing was concentrated to give (2R,5R)-2-(cyclohexylmethyl)-5-((4-methoxycyclohexyl)methyl)hexanedioic acid (105 mg, 0.287 mmol, 98.5 yield) as an oil. Anal. Calcd. for C$_{20}$H$_{27}$ClO$_4$ m/z 366.4. found: 365.3 (M−H)$^+$.

Intermediate 14: (2R,5R)-2-Benzyl-5-(cyclohexylmethyl)hexanedioic acid

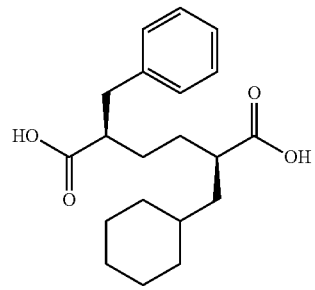 [SMILES: O=C(O)[C@H](CC[C@H](CC1CCCCC1)C(=O)O)Cc1ccccc1]

To a solution of (2R,5R)-2-(3-chlorobenzyl)-5-(cyclohexylmethyl)hexanedioic acid (37 mg, 0.10 mmol) in MeOH (2 mL) and EtOAc (2 mL) was bubbled through Argon for 5 min. Then 5% Pd/C (40 mg) was added to the solution. The reaction was stirred at 1 atm of hydrogen (balloon) for 2 hr. The reaction was filtered through CELITE® and washed with MeOH. The combined filtrate and MeOH wash was concentrated. The resulting residue was purified using RP prep-HPLC (Method B). The desired fraction was concentrated in vacuum and lyophilized with CH$_3$CN to give (2R,5R)-2-benzyl-5-(cyclohexylmethyl)hexanedioic acid (10 mg, 0.030 mmol, 30% yield) as a white solid.

Intermediate 15: (2R,5R)-2-(3-Chlorobenzyl)-5-(4-hydroxybenzyl)hexanedioic acid

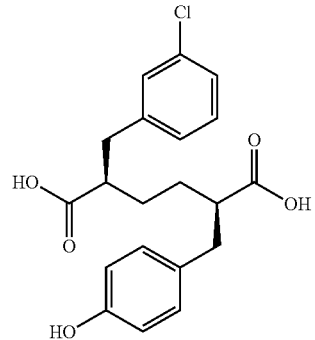 [SMILES: O=C(O)[C@H](CC[C@H](Cc1cccc(Cl)c1)C(=O)O)Cc1ccc(O)cc1]

To a round bottom flask was added (2R,5R)-2-(3-Chlorobenzyl)-5-(4-methoxybenzyl)hexanedioic acid (24 mg, 0.061 mmol) and pyridine hydrochloride (71 mg, 0.61 mmol). The reaction was stirred at 160° C. for 10 min. After cooling to rt, the reaction was diluted with water and extracted with EtOAc (2×5 mL). The combined EtOAc extracts were concentrated in vacuum. The resulting residue was purified using RP prep-HPLC (Method B) to give (2R,5R)-2-(3-chlorobenzyl)-5-(4-hydroxybenzyl)hexanedioic acid (14 mg, 0.037 mmol, 61% yield) as white solid. Anal. Calcd. for C$_{20}$H$_{21}$ClO$_5$ m/z 376.3. found: 375.2 (M−H)$^+$.

Intermediate 16: (2R,5R)-2,5-Bis(4-hydroxybenzyl)hexanedioic acid

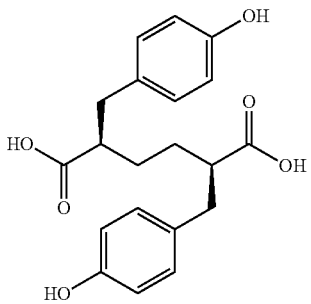 [SMILES: O=C(O)[C@H](CC[C@H](Cc1ccc(O)cc1)C(=O)O)Cc1ccc(O)cc1]

To a round bottom flask was added (2R,5R)-2,5-bis(4-methoxybenzyl)hexanedioic acid (10 mg, 0.026 mmol) and 30% HBr in acetic acid (0.5 mL). The reaction was stirred at 120° C. for 2 days. The solvent was removed and the residue was purified by RP prep-HPLC. The fraction was concentrated to give (2R,5R)-2,5-bis(4-hydroxybenzyl)hexanedioic acid (3.0 mg, 8.4 μmol, 32% yield) as an off-white solid. Anal. Calcd. for $C_{20}H_{22}O_6$ m/z 358.3. found: 357.3 (M–H)$^+$.

Intermediate 17: (2R,5R)-2-(4-Hydroxybenzyl)-5-(4-methoxybenzyl)hexanedioic acid

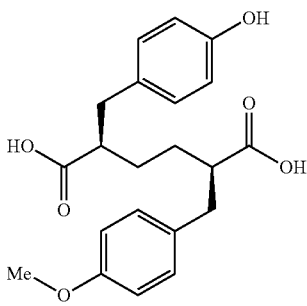 [SMILES: COc1ccc(C[C@@H](CC[C@H](Cc2ccc(O)cc2)C(=O)O)C(=O)O)cc1]

To a round bottom flask was added (2R,5R)-2,5-bis(4-methoxybenzyl)hexanedioic acid (124 mg, 0.321 mmol) and pyridine hydrochloride (371 mg, 3.21 mmol). The reaction was stirred at 160° C. for 20 min. After cooling to rt, the reaction was diluted with water and extracted with EtOAc (2×15 mL). The combined EtOAc extracts were concentrated in vacuum. The resulting residue was purified using RP prep-HPLC (Method B) to give (2R,5R)-2-(4-hydroxybenzyl)-5-(4-methoxybenzyl)hexanedioic acid (37 mg, 0.099 mmol, 31% yield) as white solid.

Intermediate 18: (2R,5R)-2,5-Bis(4-fluorobenzyl)hexanedioic acid

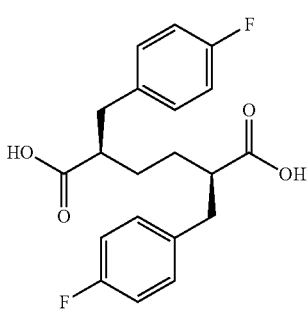 [SMILES: O=C(O)[C@H](CC[C@H](Cc1ccc(F)cc1)C(=O)O)Cc1ccc(F)cc1]

A: (2S,5S,E)-1,6-Bis((S)-4-benzyl-2-oxooxazolidin-3-yl)-2,5-bis(4-fluorobenzyl)hex-3-ene-1,6-dione

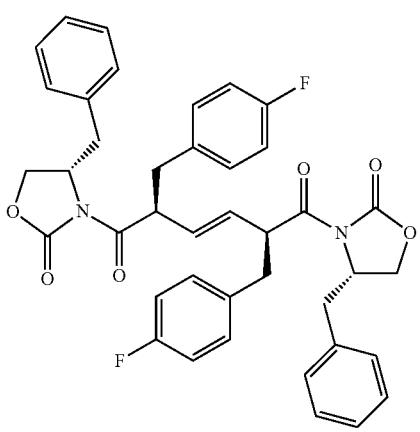 [SMILES: O=C1OC[C@H](Cc2ccccc2)N1C(=O)[C@H](/C=C/[C@H](Cc1ccc(F)cc1)C(=O)N1C(=O)OC[C@@H]1Cc1ccccc1)Cc1ccc(F)cc1]

(2S,5S,E)-1,6-Bis((S)-4-benzyl-2-oxooxazolidin-3-yl)-2,5-bis(4-fluorobenzyl)hex-3-ene-1,6-dione was synthesized as described in General Procedure D using 4-fluorobenzyl bromide (1.84 gm, 9.73 mmol) to give a colorless solid (465 mg, 0.545 mmol, 10.6% yield). Anal. Calcd. for $C_{40}H_{36}F_2N_2O_6$ m/z 678.2. found: 679.2 (M+H)$^+$.

B: (2S,5S,E)-2,5-Bis(4-fluorobenzyl)hex-3-enedioic acid

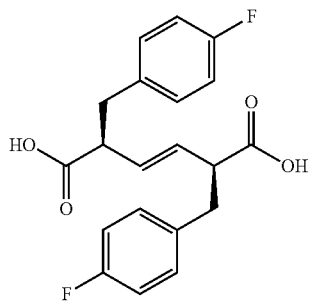 [SMILES: O=C(O)[C@H](/C=C/[C@H](Cc1ccc(F)cc1)C(=O)O)Cc1ccc(F)cc1]

(2S,5S,E)-2,5-Bis(4-fluorobenzyl)hex-3-enedioic acid was synthesized as described in General Procedure A using (2S,5S,E)-1,6-bis((S)-4-benzyl-2-oxooxazolidin-3-yl)-2,5-bis(4-fluorobenzyl)hex-3-ene-1,6-dione (465 mg, 0.685 mmol) to give a colorless solid (243 mg, 0.674 mmol, 98% yield).

C: (2R,5R)-2,5-Bis(4-fluorobenzyl)hexanedioic acid

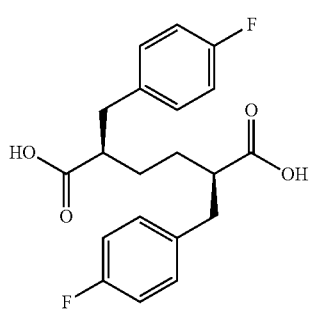 [SMILES: O=C(O)[C@H](CC[C@H](Cc1ccc(F)cc1)C(=O)O)Cc1ccc(F)cc1]

(2R,5R)-2,5-Bis(4-fluorobenzyl)hexanedioic acid was synthesized as described in General Procedure B using (2S,5S,E)-2,5-Bis(4-fluorobenzyl)hex-3-enedioic acid (243 mg, 0.674 mmol) to give a colorless solid (219 mg, 0.604 mmol, 90% yield). Anal. Calcd. for $C_{20}H_{20}FN_2O_4$ m/z 362.0. found: 363.0 (M+H)$^+$.

Intermediate 19:
(2R,5R)-2-Benzyl-5-(4-fluorobenzyl)hexanedioic acid

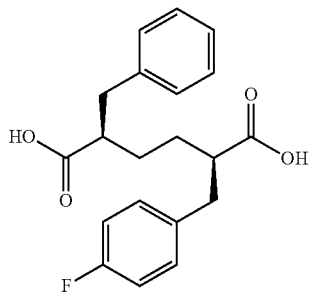 [SMILES: O=C(O)[C@H](CC[C@H](Cc1ccc(F)cc1)C(=O)O)Cc1ccccc1]

A: (2S,5S,E)-2-Benzyl-1,6-bis((S)-4-benzyl-2-oxooxazolidin-3-yl)-5-(4-fluorobenzyl)hex-3-ene-1,6-dione

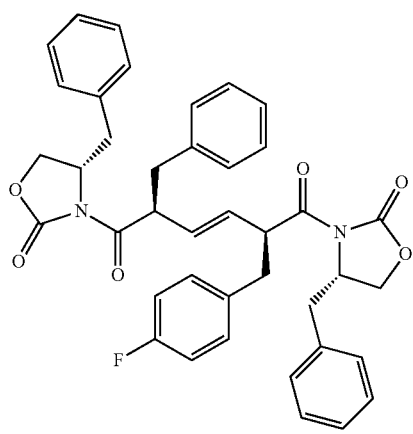 [SMILES: O=C1OC[C@H](Cc2ccccc2)N1C(=O)[C@H](/C=C/[C@H](Cc1ccc(F)cc1)C(=O)N1C(=O)OC[C@@H]1Cc1ccccc1)Cc1ccccc1]

(2S,5S,E)-2-Benzyl-1,6-bis((S)-4-benzyl-2-oxooxazolidin-3-yl)-5-(4-fluorobenzyl)hex-3-ene-1,6-dione was synthesized as described in General Procedure E using 1-(bromomethyl)-4-fluorobenzene (365 mg, 1.93 mmol) to give a colorless solid (310 mg, 0.469 mmol, 42.5% yield). Anal. Calcd. for $C_{40}H_{37}FN_2O_6$ m/z 660.5. found: 661.5 (M+H)$^+$.

B: (2S,5S,E)-2-Benzyl-5-(4-fluorobenzyl)hex-3-enedioic acid

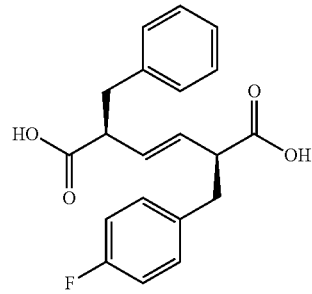 [SMILES: O=C(O)[C@H](/C=C/[C@H](Cc1ccc(F)cc1)C(=O)O)Cc1ccccc1]

(2S,5S,E)-2-Benzyl-5-(4-fluorobenzyl)hex-3-enedioic acid was synthesized as described in General Procedure A using (S,E)-2-benzyl-1,6-bis((S)-4-benzyl-2-oxooxazolidin-3-yl)-5-(4-fluorobenzyl)hex-3-ene-1,6-dione (303 mg, 0.459 mmol) to give a colorless solid (74 mg, 0.22 mmol, 47% yield). Anal. Calcd. for $C_{20}H_{19}FO_4$ m/z 342.3. found: 341.3 (M−H)$^+$.

C: (2R,5R)-2-Benzyl-5-(4-fluorobenzyl)hexanedioic acid

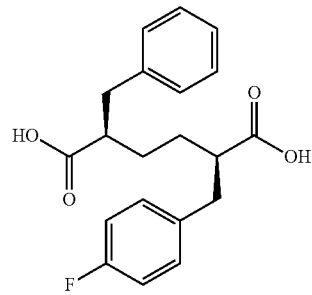 [SMILES: O=C(O)[C@H](CC[C@H](Cc1ccc(F)cc1)C(=O)O)Cc1ccccc1]

(2R,5R)-2-Benzyl-5-(4-fluorobenzyl)hexanedioic acid was synthesized as described in General Procedure B using (2S,5S,E)-2-benzyl-5-(4-fluorobenzyl)hex-3-enedioic acid (77 mg, 0.23 mmol) to give a white solid (70 mg, 0.20 mmol, 90% yield). Anal. Calcd. for $C_{20}H_{19}FO_4$ m/z 342.3. found: 341.3 (M−H)$^+$.

Intermediate 20:
(2R,5S)-2-(4-Fluorobenzyl)-5-propylhexanedioic acid

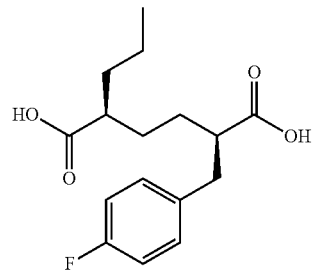 [SMILES: CCC[C@@H](CC[C@H](Cc1ccc(F)cc1)C(=O)O)C(=O)O]

A: (S,E)-1,6-Bis((S)-4-benzyl-2-oxooxazolidin-3-yl)-2-(4-fluorobenzyl)hex-3-ene-1,6-dione

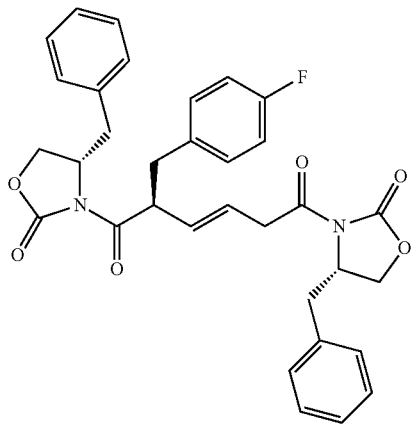 [SMILES: O=C(C/C=C/[C@H](Cc1ccc(F)cc1)C(=O)N1C(=O)OC[C@@H]1Cc1ccccc1)N1C(=O)OC[C@@H]1Cc1ccccc1]

(S,E)-1,6-Bis((S)-4-benzyl-2-oxooxazolidin-3-yl)-2-(4-fluorobenzyl)hex-3-ene-1,6-dione was synthesized as described in General Procedure C using 4-fluorobenzyl bromide (1.84 gm, 9.73 mmol) to give a colorless solid (311 mg, 0.545 mmol, 8.4% yield). Anal. Calcd. for $C_{33}H_{31}FN_2O_6$ m/z 570.2. found: 571.1 (M+H)$^+$.

B: (2S,5S,E)-2-Allyl-1,6-bis((S)-4-benzyl-2-oxooxazolidin-3-yl)-5-(4-fluorobenzyl)hex-3-ene-1,6-dione

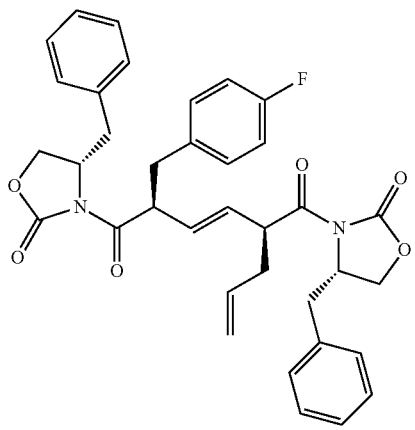 [SMILES: C=CC[C@@H](/C=C/[C@H](Cc1ccc(F)cc1)C(=O)N1C(=O)OC[C@@H]1Cc1ccccc1)C(=O)N1C(=O)OC[C@@H]1Cc1ccccc1]

A solution of NaHMDS (1.0 M in THF, 1.34 mL, 1.34 mmol) was slowly added dropwise over 10 min to a −78° C. solution of (S,E)-1,6-bis((S)-4-benzyl-2-oxooxazolidin-3-yl)-2-(4-fluorobenzyl)hex-3-ene-1,6-dione (763 mg, 1.34 mmol) in THF (4.8 mL). After the addition, the reaction mixture was allowed to stir for another 30 min at −78° C. and then a solution of allyl iodide (225 mg, 1.34 mmol) in THF (0.5 mL) was added dropwise. The reaction temperature was then warmed to −40° C. and stirred at −40° C. for 45 min. Then the reaction was warmed to 0° C. and stirred at 0° C. for an additional 1 hr. The reaction was quenched by the addition of saturated NH$_4$Cl. The mixture was then partitioned between EtOAc and water. The organic phase was isolated, washed with saturated aqueous NaCl, dried over MgSO$_4$ and concentrated. The crude product was purified using silica gel chromatography (ISCO system) eluting with a gradient of 0-100% EtOAc/Hex to give (2S,5S,E)-2-allyl-1,6-bis((S)-4-benzyl-2-oxooxazolidin-3-yl)-5-(4-fluorobenzyl)hex-3-ene-1,6-dione (470 mg, 0.770 mmol, 57.6% yield) as a foam. Anal. Calcd. for $C_{36}H_{35}FN_2O_6$ m/z 610.2. found: 611.2 (M+H)$^+$.

C: (2S,5S,E)-2-Allyl-5-(4-fluorobenzyl)hex-3-enedioic acid

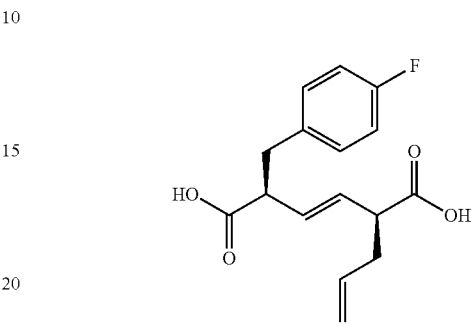

(2S,5S,E)-2-Allyl-5-(3-fluorobenzyl)hex-3-enedioic acid was synthesized as described in General Procedure A using (2S,5S,E)-2-allyl-1,6-bis((S)-4-benzyl-2-oxooxazolidin-3-yl)-5-(4-fluorobenzyl)hex-3-ene-1,6-dione (470 mg, 0.770 mmol) to give a colorless solid (230 mg, 0.787 mmol, 100% yield).

D: (2R,5S)-2-(4-Fluorobenzyl)-5-propylhexanedioic acid

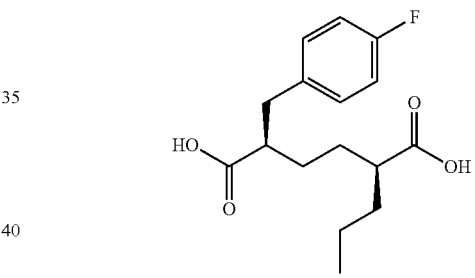

(2R,5S)-2-(4-Fluorobenzyl)-5-propylhexanedioic acid was synthesized as described in General Procedure B using (2S,5S,E)-2-Allyl-5-(4-fluorobenzyl)hex-3-enedioic acid (225 mg, 0.770 mmol) to give a colorless solid (210 mg, 92% yield).

Intermediate 21:
(2R,5S)-2-(3-Fluorobenzyl)-5-propylhexanedioic acid

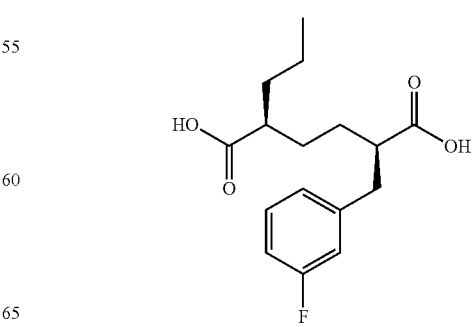

A: (S,E)-1,6-Bis((S)-4-benzyl-2-oxooxazolidin-3-yl)-2-(3-fluorobenzyl)hex-3-ene-1,6-dione

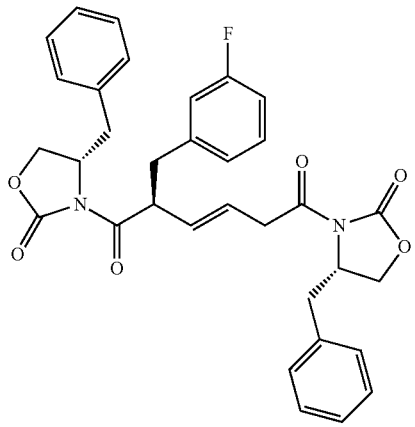 [SMILES: O=C(C/C=C/[C@H](Cc1cccc(F)c1)C(=O)N1C(=O)OC[C@@H]1Cc1ccccc1)N1C(=O)OC[C@@H]1Cc1ccccc1]

(S,E)-1,6-Bis((S)-4-benzyl-2-oxooxazolidin-3-yl)-2-(3-fluorobenzyl)hex-3-ene-1,6-dione was synthesized as described in General Procedure C using 3-fluorobenzyl bromide (0.603 gm, 3.19 mmol) to give a colorless solid (110 mg, 0.193 mmol, 5.5% yield). Anal. Calcd. for $C_{33}H_{31}FN_2O_6$ m/z 570.2. found: 571.1 $(M+H)^+$.

B: (2S,5S,E)-2-Allyl-1,6-bis((S)-4-benzyl-2-oxooxazolidin-3-yl)-5-(3-fluorobenzyl)hex-3-ene-1,6-dione

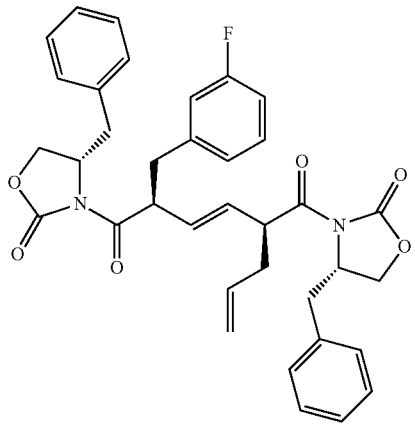 [SMILES: C=CC[C@@H](/C=C/[C@H](Cc1cccc(F)c1)C(=O)N1C(=O)OC[C@@H]1Cc1ccccc1)C(=O)N1C(=O)OC[C@@H]1Cc1ccccc1]

A solution of NaHMDS (1.0 M in THF, 0.313 mL, 0.313 mmol) was slowly added dropwise over 5 min to a −78° C. solution of (S,E)-1,6-bis((S)-4-benzyl-2-oxooxazolidin-3-yl)-2-(3-fluorobenzyl)hex-3-ene-1,6-dione (170 mg, 0.298 mmol) in THF (1.6 mL). After addition the reaction mixture was allowed to stir for another 25 min at −78° C. and then allyl bromide (108 mg, 0.894 mmol) was added dropwise. The reaction temperature was then slowly raised to 0° C. over 20 min and then stirred at 0° C. for an additional 1 hr. The reaction was quenched by addition of saturated $NH_4Cl$. The mixture was then partitioned between EtOAc and water. The organic phase was isolated, washed with saturated aqueous NaCl, dried over $MgSO_4$ and concentrated. The crude product was purified using silica gel chromatography (ISCO system) eluting with a gradient of 0-100% EtOAc/Hex to give (2S,5S,E)-2-allyl-1,6-bis((S)-4-benzyl-2-oxooxazolidin-3-yl)-5-(3-fluorobenzyl)hex-3-ene-1,6-dione (46 mg, 0.075 mmol, 25% yield) as a foam. Anal. Calcd. for $C_{36}H_{35}FN_2O_6$ m/z 610.2. found: 611.0 $(M+H)^+$.

C: (2S,5S,E)-2-Allyl-5-(3-fluorobenzyl)hex-3-enedioic acid

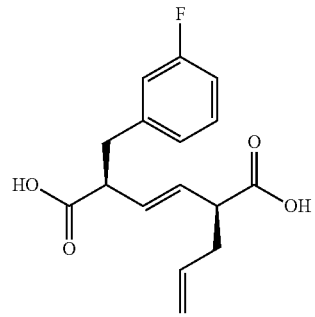 [SMILES: C=CC[C@@H](/C=C/[C@H](Cc1cccc(F)c1)C(=O)O)C(=O)O]

(2S,5S,E)-2-Allyl-5-(3-fluorobenzyl)hex-3-enedioic acid was synthesized as described in General Procedure A using (2S,5S,E)-2-allyl-1,6-bis((S)-4-benzyl-2-oxooxazolidin-3-yl)-5-(3-fluorobenzyl)hex-3-ene-1,6-dione (46 mg, 0.075 mmol) to give a colorless solid (22 mg, 95% yield).

D: (2R,5S)-2-(3-Fluorobenzyl)-5-propylhexanedioic acid

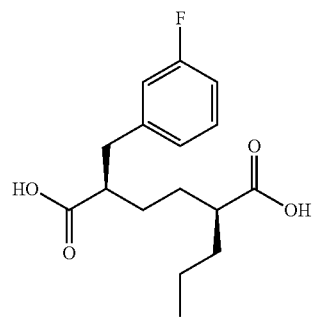 [SMILES: CCC[C@@H](CC[C@H](Cc1cccc(F)c1)C(=O)O)C(=O)O]

(2R,5S)-2-(3-Fluorobenzyl)-5-propylhexanedioic acid was synthesized as described in General Procedure B using (2S,5S,E)-2-allyl-5-(3-fluorobenzyl)hex-3-enedioic acid (21 mg, 0.071 mmol) to give a colorless solid (20 mg, 96% yield).

Intermediate 22: (2R,5S)-2-(4-Hydroxybenzyl)-5-propylhexanedioic acid

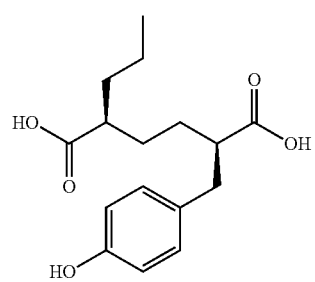

A: (S,E)-2-Allyl-1,6-bis((S)-4-benzyl-2-oxooxazolidin-3-yl)hex-3-ene-1,6-dione

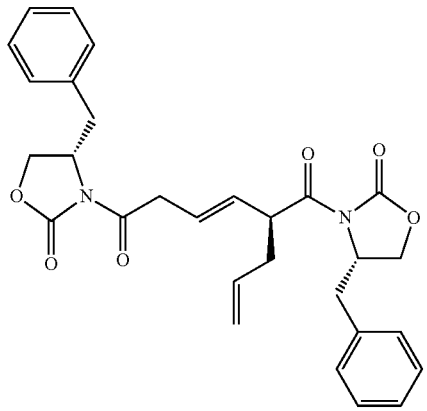 [SMILES: C=CC[C@@H](/C=C/CC(=O)N1C(=O)OC[C@@H]1Cc1ccccc1)C(=O)N1C(=O)OC[C@@H]1Cc1ccccc1]

(S,E)-2-Allyl-1,6-bis((S)-4-benzyl-2-oxooxazolidin-3-yl)hex-3-ene-1,6-dione was synthesized as described in General Procedure C using allyl iodide (0.205 gm, 1.22 mmol) to give a colorless solid (118 mg, 0.235 mmol, 11.6% yield). Anal. Calcd. for $C_{29}H_{30}N_2O_6$ m/z 502.3. found: 503.3 (M+H)$^+$.

B: (2S,5S,E)-2-Allyl-1,6-bis((S)-4-benzyl-2-oxooxazolidin-3-yl)-5-(4-(benzyloxy)benzyl)hex-3-ene-1,6-dione

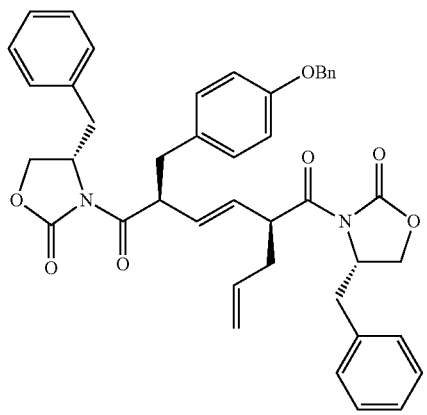 [SMILES: C=CC[C@@H](/C=C/[C@H](Cc1ccc(OCc2ccccc2)cc1)C(=O)N1C(=O)OC[C@@H]1Cc1ccccc1)C(=O)N1C(=O)OC[C@@H]1Cc1ccccc1]

A solution of NaHMDS (1.0 M in THF, 0.258 mL, 0.258 mmol) was added dropwise to a −78° C. solution of (S,E)-2-allyl-1,6-bis((S)-4-benzyl-2-oxooxazolidin-3-yl)hex-3-ene-1,6-dione (118 mg, 0.235 mmol) in THF (1.0 mL). After stirring at −78° C. for 40 min, a solution of 1-(benzyloxy)-4-(bromomethyl)benzene (78 mg, 0.282 mmol) in THF (0.2 mL) was added dropwise. The reaction temperature was then slowly raised to 0° C. over 45 min. After 30 min at 0° C., the reaction temperature was allowed to reach rt. After 2 h at rt, the reaction mixture was quenched by addition of saturated NH$_4$Cl. The mixture was partitioned between EtOAc and water. The organic phase was isolated, washed with saturated aqueous NaCl, dried over MgSO$_4$ and concentrated. The crude product was purified using silica gel chromatography (ISCO system) eluting with a gradient of 0-100% EtOAc/Hex to give (2S,5S,E)-2-allyl-1,6-bis((S)-4-benzyl-2-oxooxazolidin-3-yl)-5-(4-(benzyloxy)benzyl)hex-3-ene-1,6-dione (47 mg, 0.067 mmol, 29%) as a white solid. Anal. Calcd. for $C_{43}H_{42}N_2O_7$ m/z 698.2. found: 699.2 (M+H)$^+$.

C: (2S,5S,E)-2-Allyl-5-(4-(benzyloxy)benzyl)hex-3-enedioic acid

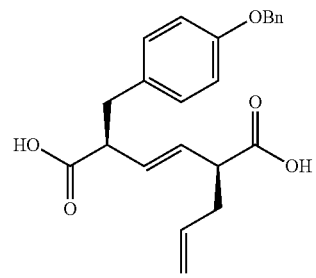 [SMILES: C=CC[C@@H](/C=C/[C@H](Cc1ccc(OCc2ccccc2)cc1)C(=O)O)C(=O)O]

(2S,5S,E)-2-Allyl-5-(4-(benzyloxy)benzyl)hex-3-enedioic acid was synthesized as described in General Procedure A using (2S,5S,E)-2-allyl-1,6-bis((S)-4-benzyl-2-oxooxazolidin-3-yl)-5-(4-(benzyloxy)benzyl)hex-3-ene-1,6-dione (46 mg, 0.066 mmol) to give a colorless solid (20 mg, 80% yield).

D: (2R,5S)-2-(4-Hydroxybenzyl)-5-propylhexanedioic acid

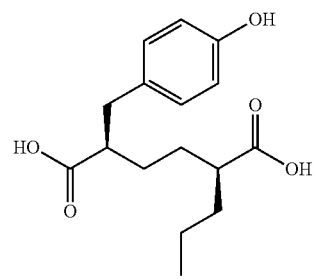 [SMILES: CCC[C@@H](CC[C@H](Cc1ccc(O)cc1)C(=O)O)C(=O)O]

(2R,5S)-2-(4-Hydroxybenzyl)-5-propylhexanedioic acid was synthesized as described in General Procedure B using (2S,5S,E)-2-Allyl-5-(4-(benzyloxy)benzyl)hex-3-enedioic acid (18 mg, 0.048 mmol) to give a colorless solid (13 mg, 88% yield).

Intermediate 23: (2R,5R)-2,5-Dibenzyl-6-((4S,7S,10aS)-7-(methoxycarbonyl)-5-oxooctahydro-2H-pyrido[2,1-b][1,3]thiazepin-4-ylamino)-6-oxohexanoic acid

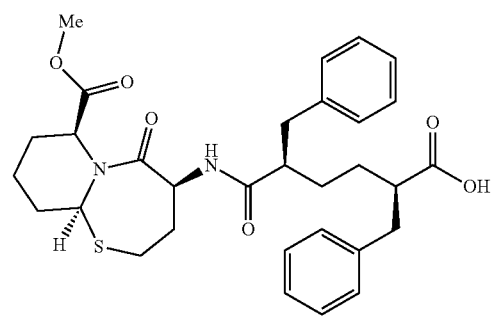 [SMILES: COC(=O)[C@@H]1CCC[C@@H]2SCC[C@H](NC(=O)[C@H](CC[C@H](Cc3ccccc3)C(=O)O)Cc3ccccc3)C(=O)N21]

(2R,5R)-2,5-Dibenzyl-6-((4S,7S,10aS)-7-(methoxycarbonyl)-5-oxooctahydro-2H-pyrido[2,1-b][1,3]thiazepin-4-ylamino)-6-oxohexanoic acid was synthesized as described in General Procedure G using (2R,5R)-2,5-dibenzylhexanedioic acid (200 mg, 0.613 mmol) and (4S,7S,10aS)-methyl 4-amino-5-oxooctahydro-2H-pyrido[2,1-b][1,3]thiazepine-7-carboxylate (249 mg, 0.643 mmol) to give a white solid (278 mg, 80% yield). $^1$H NMR (400 MHz, CDCl$_3$) δ ppm 7.31-7.09 (10H, m), 6.88 (1H, d, J=6.6 Hz), 5.30 (1H, t, J=4.7 Hz), 5.17-5.11 (1H, m), 5.07-4.98 (1H, m), 3.68 (3H, s), 3.22-3.11 (1H, m), 3.02-2.92 (1H, m), 2.90-2.81 (1H, m), 2.80-2.63 (4H, m), 2.46-2.37 (2H, m), 2.06-1.96 (2H, m), 1.86-1.75 (2H, m), 1.72-1.47 (7H, m).

Intermediate 24: (2R,5R)-2,5-Dibenzyl-6-oxo-6-((R)-2-oxo-1-phenylazepan-3-ylamino)hexanoic acid

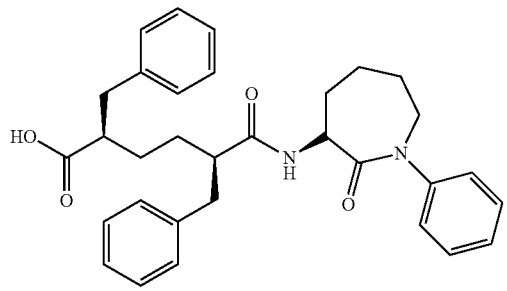

A: (2S,5S,E)-Methyl 2,5-dibenzyl-6-((S)-4-benzyl-2-oxooxazolidin-3-yl)-6-oxohex-3-enoate

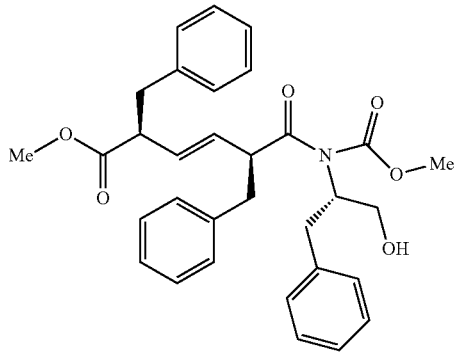 [SMILES: COC(=O)[C@H](/C=C/[C@H](Cc1ccccc1)C(=O)N(C(=O)OC)[C@H](CO)Cc1ccccc1)Cc1ccccc1]

(2S,5S,E)-Methyl 2,5-dibenzyl-6-((S)-4-benzyl-2-oxooxazolidin-3-yl)-6-oxohex-3-enoate formed as a byproduct during the concentration from MeOH after the chiral separation of Intermediate 3A to give the methyl ester (1.05 gm). Anal. Calcd. for C$_{32}$H$_{35}$NO$_6$ m/z 529.6. found: 530.4 (M+H)$^+$; $^1$H NMR (400 MHz, CDCl$_3$) δ ppm 7.13-7.29 (9H, m), 7.00-7.11 (6H, m), 5.62 (1H, d, J=8.25 Hz), 5.47-5.52 (2H, m), 4.26-4.39 (1H, m), 4.00 (2H, d, J=4.95 Hz), 3.78 (3H, s), 3.61 (3H, s), 3.23-3.34 (1H, m), 2.88-3.06 (3H, m), 2.58-2.81 (4H, m).

B: (2S,5S,E)-2,5-Dibenzyl-6-methoxy-6-oxohex-3-enoic acid

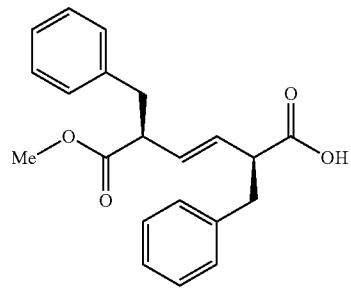 [SMILES: COC(=O)[C@H](/C=C/[C@H](Cc1ccccc1)C(=O)O)Cc1ccccc1]

(2S,5S,E)-2,5-Dibenzyl-6-methoxy-6-oxohex-3-enoic acid was synthesized as described in General Procedure A using (2S,5S,E)-methyl 2,5-dibenzyl-6-((S)-4-benzyl-2-oxooxazolidin-3-yl)-6-oxohex-3-enoate (600 mg, 1.21 mmol) to give a clear oil (360 mg, 88% yield). Anal. Calcd. for C$_{21}$H$_{22}$O$_4$ m/z 338.4. found: 339.1 (M+H)$^+$.

C: (2R,5R)-2,5-Dibenzyl-6-methoxy-6-oxohexanoic acid

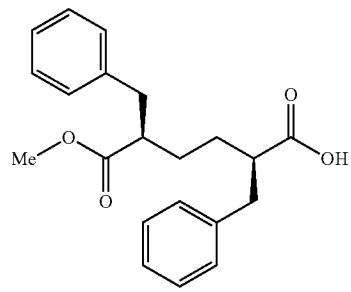 [SMILES: COC(=O)[C@H](CC[C@H](Cc1ccccc1)C(=O)O)Cc1ccccc1]

(2R,5R)-2,5-Dibenzyl-6-methoxy-6-oxohexanoic acid was synthesized as described in General Procedure B using (2S,5S,E)-2,5-dibenzyl-6-methoxy-6-oxohex-3-enoic acid (300 mg, 0.887 mmol) to give a white solid (290 mg, 96% yield).

D: (2R,5R)-Methyl 2,5-dibenzyl-6-oxo-6-((R)-2-oxo-1-phenylazepan-3-ylamino)hexanoate

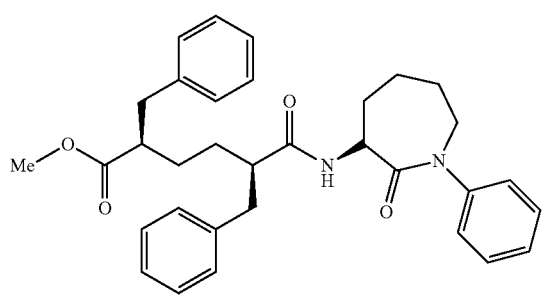

To a round bottom flask was added (2R,5R)-2,5-dibenzyl-6-methoxy-6-oxohexanoic acid (278 mg, 0.817 mmol), (S)-3-amino-1-phenylazepan-2-one trifluoroacetic acid salt (260 mg, 0.817 mmol), HOBT (163 mg, 1.062 mmol), EDC (204 mg, 1.062 mmol), Hunig's base (317 mg, 2.45 mmol) and DMF (5 mL). The reaction was stirred at rt for 2 days. The reaction mixture was partitioned between EtOAc and water. The organic phase was isolated, washed with aqueous 0.5 N HCl, saturated aqueous NaHCO₃ and saturated aqueous NaCl. The organic phase was then dried over MgSO₄, filtered and concentrated. The resulting residue was purified using silica gel chromatography (ISCO system) eluting with a gradient of 30-60% EtOAc/Hex to give (2R,5R)-methyl 2,5-dibenzyl-6-oxo-6-((R)-2-oxo-1-phenylazepan-3-ylamino) hexanoate (305 mg, 0.579 mmol, 70.9% yield) as a white solid. $^1$H NMR (400 MHz, CDCl₃) δ ppm 7.38 (t, J=7.7 Hz, 2H), 7.32-7.20 (m, 5H), 7.20-7.06 (m, 8H), 6.75 (d, J=6.2 Hz, 1H), 4.70 (dd, J=10.0, 6.3 Hz, 1H), 3.90 (dd, J=15.3, 11.4 Hz, 1H), 3.67-3.47 (m, 4H), 2.95-2.82 (m, 2H), 2.77-2.57 (m, 3H), 2.43-2.30 (m, 1H), 2.02-1.78 (m, 3H), 1.77-1.39 (m, 5H), 1.35-1.20 (m, 2H).

E: (2R,5R)-2,5-Dibenzyl-6-oxo-6-((R)-2-oxo-1-phenylazepan-3-ylamino)hexanoic acid

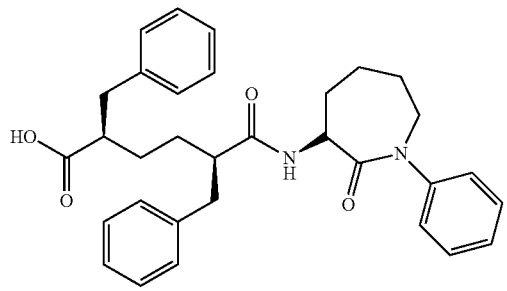

To a round bottom flask was added (2R,5R)-methyl 2,5-dibenzyl-6-oxo-6-((R)-2-oxo-1-phenylazepan-3-ylamino) hexanoate (300 mg, 0.570 mmol), 2 M LiOH in water (5.0 mL, 10 mmol) and MeOH (5 mL). The reaction was stirred at rt for 2 days. The reaction mixture was then cooled in an ice-bath and aqueous 1 M HCl was added slowly to adjust the pH to 4. A white precipitate was formed. The product was collected by filtration and washed with water (2×5 mL) to give (2R,5R)-2,5-dibenzyl-6-oxo-6-((R)-2-oxo-1-phenylazepan-3-ylamino)hexanoic acid (280 mg, 0.546 mmol, 96% yield) as a white solid. Anal. Calcd. for C₃₂H₃₆N₂O₄ m/z 512.4. found: 513.3 (M+H)⁺.

Intermediate 25: (S)-3-Amino-1-phenylazepan-2-one monotrifluoromethyl acetate

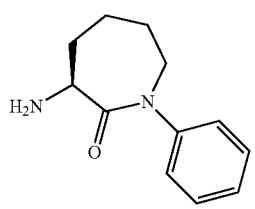

A: Di-tert-Butyl ((3S)-2-oxoazepan-3-yl)imidodicarbonate

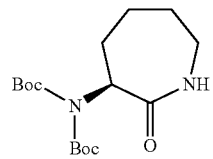 [SMILES: CC(C)(C)OC(=O)N(C(=O)OC(C)(C)C)[C@H]1CCCCNC1=O]

A solution of Boc anhydride (478 mg, 2.19 mmol) in DCM (1 mL) was slowly added to a 0° C. solution of (S)-tert-butyl 2-oxoazepan-3-ylcarbamate (500 mg, 2.19 mmol) and DMAP (268 mg, 2.19 mmol) in DCM (7.5 mL). The reaction mixture was then stirred at rt. After 1 h, TLC showed only a small amount of product. Then TEA (0.222 gm, 2.19 mmol) was added. The reaction mixture was stirred for 2 days. The reaction mixture was concentrated and the residue was partitioned between EtOAc and saturated NH₄Cl. The organic phase was isolated, washed with saturated aqueous NaCl, dried over MgSO₄, filtered and concentrated. The crude product was purified using silica gel chromatography (ISCO system) eluting with a gradient of 0-100% EtOAc/Hex to give di-tert-butyl ((3S)-2-oxoazepan-3-yl)imidodicarbonate. (434 mg, 1.32 mmol, 60.3% yield) as a solid. $^1$H NMR (400 MHz, CDCl₃) δ ppm 5.83 (1H, d, J=6.6 Hz), 4.54 (1H, dd, J=9.1, 6.9 Hz), 4.29 (1H, dd, J=15.4, 4.9 Hz), 3.30 (1H, dd, J=15.4, 11.5 Hz), 2.13-2.04 (1H, m), 1.97-1.88 (2H, m), 1.87-1.75 (1H, m), 1.69-1.56 (1H, m), 1.53 (9H, s), 1.46 (10H, s).

B: Di-tert-Butyl ((3S)-2-oxo-1-phenylazepan-3-yl) imidodicarbonate

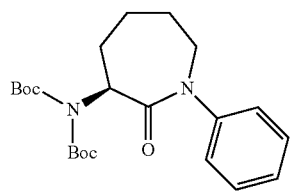 [SMILES: CC(C)(C)OC(=O)N(C(=O)OC(C)(C)C)[C@H]1CCCCN(c2ccccc2)C1=O]

To a mixture of di-tert-butyl ((3S)-2-oxoazepan-3-yl)imidodicarbonate was added TEA (267 mg, 2.64 mmol), triphenylbismuth (786 mg, 1.78 mmol), copper(II) acetate (324 mg, 1.78 mmol) and 3 Å molecular sieves (1 gm) in DCM (6 mL). The reaction mixture was stirred at rt overnight. The reaction mixture was diluted with EtOAc and filtered through CELITE®. The CELITE® was rinsed with EtOAc and CHCl₃. The filtrate was then concentrated. The crude product was purified using silica gel chromatography (ISCO system) eluting with a gradient of 0-100% EtOAc/Hex to give di-tert-butyl ((3S)-2-oxo-1-phenylazepan-3-yl)imidodicarbonate (357 mg, 0.883 mmol, 66.8% yield) as an oil. $^1$H NMR (400

MHz, CDCl₃) δ ppm 7.46-7.16 (5H, m), 5.21-5.05 (1H, m), 4.82-4.66 (1H, m), 4.41-4.26 (2H, m), 3.53-3.14 (2H, m), 1.97-1.24 (21H, m).

C: (S)-3-Amino-1-phenylazepan-2-one monotrifluoromethyl acetate

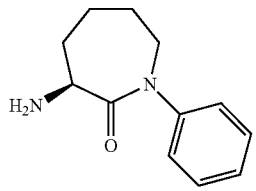 [SMILES: N[C@H]1CCCCN(c2ccccc2)C1=O]

To a solution of di-tert-butyl ((3S)-2-oxo-1-phenylazepan-3-yl)imidodicarbonate (356 mg, 0.880 mmol) in DCM (2.5 mL) at 0° C. was slowly added TFA (1 mL). The reaction mixture was then stirred at rt for 1 hr. The reaction mixture was concentrated and dried under vacuum to give (S)-3-amino-1-phenylazepan-2-one monotrifluoromethyl acetate (290 mg, 0.911 mmol, 100% yield) as an oil. Anal. Calcd. for C₁₂H₁₆N₂O m/z 204.1. found: 205.0 (M+H)⁺.

Intermediate 26: (4S,7S,10aS)-Methyl 4-(methylamino)-5-oxooctahydro-2H-pyrido[2,1-b][1,3]thiazepine-7-carboxylate

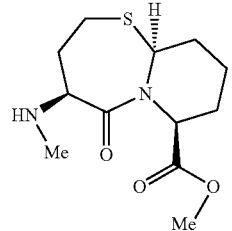 [SMILES: CN[C@H]1CCS[C@H]2CCC[C@@H](C(=O)OC)N2C1=O]

A: (4S,7S,10aS)-Methyl 5-oxo-4-(2,2,2-trifluoroacetamido)octahydro-2H-pyrido[2,1-b][1,3]thiazepine-7-carboxylate

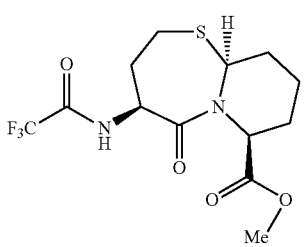 [SMILES: COC(=O)[C@@H]1CCC[C@@H]2SCC[C@H](NC(=O)C(F)(F)F)C(=O)N21]

Trifluoroacetic anhydride (48.8 mg, 0.232 mmol) was added to a 0° C. solution of (4S,7S,10aS)-methyl 4-amino-5-oxooctahydro-2H-pyrido[2,1-b][1,3]thiazepine-7-carboxylate (50 mg, 0.19 mmol) and DIPEA (30 mg, 0.23 mmol) in DCM (1 mL). The ice bath was removed and the reaction mixture was stirred at rt overnight. The reaction was diluted with DCM. The solution was washed with water. The organic solution was then dried over MgSO₄, filtered and concentrated to give (4S,7S,10aS)-methyl 5-oxo-4-(2,2,2-trifluoroacetamido)octahydro-2H-pyrido[2,1-b][1,3]thiazepine-7-carboxylate (65 mg, 0.18 mmol, 95% yield) of a white foam.

B: (4S,7S,10aS)-Methyl 5-oxo-4-(2,2,2-trifluoro-N-methylacetamido)octahydro-2H-pyrido[2,1-b][1,3]thiazepine-7-carboxylate

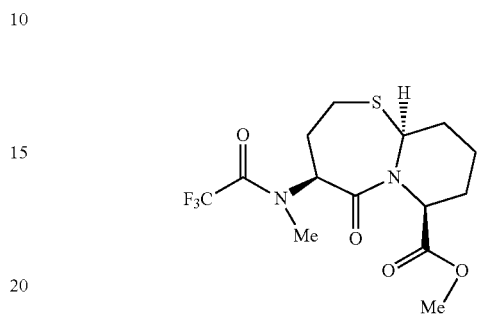

Iodomethane (77 mg, 0.54 mmol) and K₂CO₃ (150 mg, 1.08 mmol) were added to a solution of (4S,7S,10aS)-methyl 5-oxo-4-(2,2,2-trifluoroacetamido)octahydro-2H-pyrido[2,1-b][1,3]thiazepine-7-carboxylate (64 mg, 0.18 mmol) in DMF (1 mL). The reaction mixture was stirred at rt overnight. The reaction mixture was partitioned between EtOAc and water. The organic phase was isolated, washed with saturated NaHCO₃ and saturated aqueous NaCl, dried over MgSO₄, filtered and concentrated to give (4S,7S,10aS)-methyl 5-oxo-4-(2,2,2-trifluoro-N-methylacetamido)octahydro-2H-pyrido[2,1-b][1,3]thiazepine-7-carboxylate (47.6 mg, 0.129 mmol, 72% yield) of a yellow oil. Anal. Calcd. for C₁₄H₁₉F₃N₂O₄S m/z 368.3. found: 391.1 (M+Na)⁺.

C: (4S,7S,10aS)-Methyl 4-(methylamino)-5-oxooctahydro-2H-pyrido[2,1-b][1,3]thiazepine-7-carboxylate

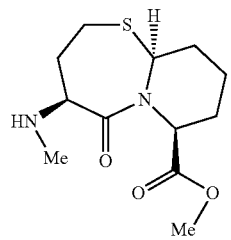 [SMILES: CN[C@H]1CCS[C@H]2CCC[C@@H](C(=O)OC)N2C1=O]

A solution of K₂CO₃ (18.8 mg, 0.136 mmol) in water (0.16 mL) was added to a solution of (4S,7S,10aS)-methyl 5-oxo-4-(2,2,2-trifluoro-N-methylacetamido)octahydro-2H-pyrido[2,1-b][1,3]thiazepine-7-carboxylate (45.6 mg, 0.124 mmol) in MeOH (0.4 mL). The reaction mixture was stirred at rt for 2 hr. After a total of 3 hr, a stream of nitrogen gas was used to partially evaporate the MeOH. The residue was then partitioned between CHCl₃ and saturated aqueous NaCl. The aqueous layer was isolated and extracted once again with CHCl₃. All organic phases were combined, dried over MgSO₄ and concentrated to give (4S,7S,10aS)-methyl 4-(methylamino)-5-oxooctahydro-2H-pyrido[2,1-b][1,3]thiazepine-7-carboxylate (34 mg, 0.12 mmol, 100% yield) of a yellow oil. Anal. Calcd. for C₁₂H₂₀N₂O₃S m/z 272.3. found: 273.2 (M+H)⁺.

Intermediate 27: (S)-Methyl 3-(3-amino-2-oxoazepan-1-yl)propanoate

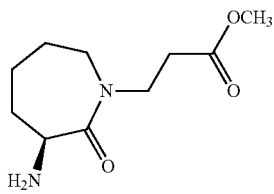 [SMILES: COC(=O)CCN1CCCC[C@H](N)C1=O]

A: (S)-tert-Butyl 2-oxoazepan-3-ylcarbamate

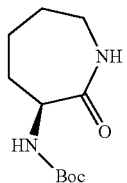

To a round bottom flask was added (S)-3-aminoazepan-2-one (2.00 g, 15.6 mmol), NaHCO₃ (1.311 g, 15.60 mmol), THF (20 mL) and Boc anhydride (3.80 mL, 16.4 mmol). The reaction was stirred at rt for 18 hr. The reaction was diluted with EtOAc (150 mL) and washed with water (3×50 mL) and saturated aqueous NaCl (50 mL). The organic layer was separated, dried over MgSO₄, filtered and concentrated to give (S)-tert-butyl 2-oxoazepan-3-ylcarbamate as a white solid. $^1$H NMR (500 MHz, CDCl₃) δ ppm 6.10 (br. s., 1H), 5.90 (br. s., 1H), 4.30 (dd, J=11.0, 6.0 Hz, 1H), 3.29-3.20 (m, 2H), 2.14-1.97 (m, 2H), 1.90-1.73 (m, 2H), 1.49-1.35 (m, 11H).

B: (S)-Methyl 3-(3-(tert-butoxycarbonylamino)-2-oxoazepan-1-yl)propanoate

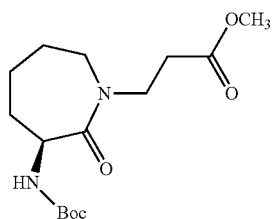 [SMILES: COC(=O)CCN1CCCC[C@H](NC(=O)OC(C)(C)C)C1=O]

To a round bottom flask was added (S)-tert-butyl 2-oxoazepan-3-ylcarbamate (500 mg, 2.19 mmol), THF (10 mL) and a 6 M solution of LiHMDS in THF (0.475 mL, 2.85 mmol). The reaction was stirred at rt for 1 hr before it was cooled to 0° C. Then, methyl acrylate (0.237 mL, 2.63 mmol) was added to the reaction and the reaction was slowly warmed up to rt and stirred at rt overnight. The reaction was concentrated and purified using RP prep-HPLC (Method A) to give (S)-methyl 3-(3-(tert-butoxycarbonylamino)-2-oxoazepan-1-yl)propanoate (140 mg, 0.445 mmol, 20.3% yield) as a white solid. Anal. Calcd. for C₁₅H₂₆N₂O₅ m/z 314.3. found: 315.2 (M+H)⁺; $^1$H NMR (500 MHz, CDCl₃) δ ppm 5.96 (d, J=5.5 Hz, 1H), 4.34 (dd, J=11.0, 6.0 Hz, 1H), 3.77 (ddd, J=13.6, 6.7, 6.6 Hz, 1H), 3.69 (s, 3H), 3.61 (ddd, J=13.9, 7.1, 7.0 Hz, 1H), 3.57-3.47 (m, 1H), 3.33 (dd, J=14.8, 4.4 Hz, 1H), 2.65-2.50 (m, 2H), 2.04 (d, J=13.2 Hz, 1H), 1.94 (d, J=13.7 Hz, 1H), 1.88-1.74 (m, 2H), 1.50-1.40 (m, 9H), 1.41-1.25 (m, 2H); $^{13}$C NMR (126 MHz, CDCl₃) δ ppm 173.15, 172.24, 155.16, 79.35, 53.34, 51.80, 49.88, 45.50, 32.51, 28.39, 27.86, 27.74.

C: (S)-Methyl 3-(3-amino-2-oxoazepan-1-yl)propanoate

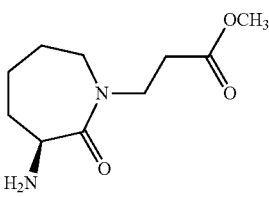 [SMILES: COC(=O)CCN1CCCC[C@H](N)C1=O]

To a round bottom flask was added (S)-methyl 3-(3-(tert-butoxycarbonylamino)-2-oxoazepan-1-yl)propanoate (15 mg, 0.048 mmol) and a solution of 4 N HCl (119 µL, 0.477 mmol) in dioxane. The reaction was stirred at rt for 3 hr. The reaction was concentrated and the residue was dried over vacuum pump for 5 hr to give (S)-methyl 3-(3-amino-2-oxoazepan-1-yl)propanoate (10 mg, 0.047 mmol, 98% yield) as a white semi-solid.

Intermediate 28: (S)-Methyl 2-(3-amino-2-oxoazepan-1-yl)acetate

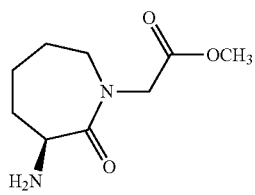 [SMILES: COC(=O)CN1CCCC[C@H](N)C1=O]

A: (S)-Methyl 2-(3-(tert-butoxycarbonylamino)-2-oxoazepan-1-yl)acetate

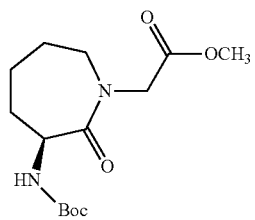 [SMILES: COC(=O)CN1CCCC[C@H](NC(=O)OC(C)(C)C)C1=O]

To a round bottom flask was added (S)-tert-butyl 2-oxoazepan-3-ylcarbamate (130 mg, 0.569 mmol), THF (10 mL) and LiHMDS (0.190 mL, 1.14 mmol). The reaction was stirred at rt for 30 min. Then methyl 2-bromoacetate (0.079 mL, 0.85 mmol) was added to the reaction and the reaction mixture was stirred at rt overnight. The reaction mixture was concentrated and purified by RP prep-HPLC to give (S)-methyl 2-(3-(tert-butoxycarbonylamino)-2-oxoazepan-1-yl) acetate (60 mg, 0.20 mmol, 35% yield) as a clear oil. Anal. Calcd. for $C_{14}H_{24}N_2O_5$ m/z 300.3. found: 301.2 (M+H)$^+$; $^1$H NMR (500 MHz, CDCl$_3$) δ ppm 5.89 (br. s., 1H), 4.40 (d, J=4.4 Hz, 1H), 4.13 (br. s., 2H), 3.79-3.56 (m, 4H), 3.15 (d, J=12.1 Hz, 1H), 2.07-1.87 (m, 2H), 1.75 (d, J=10.4 Hz, 2H), 1.62-1.49 (m, 2H), 1.39 (br. s., 9H); $^{13}$C NMR (126 MHz, CDCl$_3$) δ ppm 173.82, 169.55, 155.20, 79.55, 53.36, 52.17, 50.71, 50.63, 32.21, 28.31, 27.80, 26.87.

B: (S)-Methyl 2-(3-amino-2-oxoazepan-1-yl)acetate

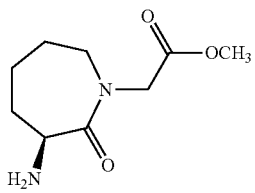 [SMILES: COC(=O)CN1CCCC[C@H](N)C1=O]

To a round bottom flask was added (S)-methyl 2-(3-(tert-butoxycarbonylamino)-2-oxoazepan-1-yl)acetate (30 mg, 0.10 mmol) and a solution of 4 N HCl in dioxane (1 mL). The reaction was stirred at rt for 2 hr. The reaction was concentrated to give (S)-methyl 2-(3-amino-2-oxoazepan-1-yl)acetate (18 mg, 0.090 mmol, 90% yield) as a white solid.

Intermediate 29: (3R,8aS)-3-Amino-2,2-dimethyltetrahydro-2H-pyrrolo[2,1-b][1,3]thiazin-4(3H)-one mono hydrochloride salt

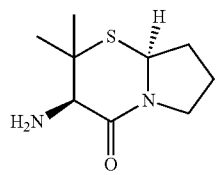

A: (R)-2-(Benzyloxycarbonylamino)-3-mercapto-3-methylbutanoic acid

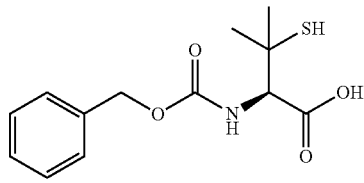 [SMILES: CC(C)(S)[C@H](NC(=O)OCc1ccccc1)C(=O)O]

To a round bottom flask was added (R)-2-amino-3-mercapto-3-methylbutanoic acid (5.06 g, 33.9 mmol), N-(benzyloxycarbonyloxy)succinimide (8.87 g, 35.6 mmol), MeOH (50 mL) followed by DIPEA (11.9 mL, 67.8 mmol). The reaction was stirred at rt for 1 hr. The reaction was concentrated and the residue was diluted with EtOAc (120 mL). The organics was washed with water (2×50 mL) and saturated aqueous NaCl (50 mL). The organic layer was separated, dried over MgSO$_4$, filtered and concentrated to give (R)-2-(benzyloxycarbonylamino)-3-mercapto-3-methylbutanoic acid (4.78 g, 16.9 mmol, 49.7% yield) as a clear oil. Anal. Calcd. for $C_{13}H_{17}NO_4S$ m/z 283.3. found: 282.3 (M–H)$^+$; $^1$H NMR (500 MHz, CDCl$_3$) δ ppm 7.45-7.30 (m, 5H), 6.09-5.84 (m, 1H), 5.20-5.01 (m, 2H), 4.37-4.18 (m, 1H), 1.53 (br. s., 3H), 1.39 (br. s., 3H); $^{13}$C NMR (126 MHz, CDCl$_3$) δ ppm 156.43, 136.49, 128.44, 128.28, 128.02, 53.12, 41.51, 30.83, 29.72, 11.64.

B: (R)-Benzyl 1-(4,4-diethoxybutylamino)-3-mercapto-3-methyl-1-oxobutan-2-ylcarbamate

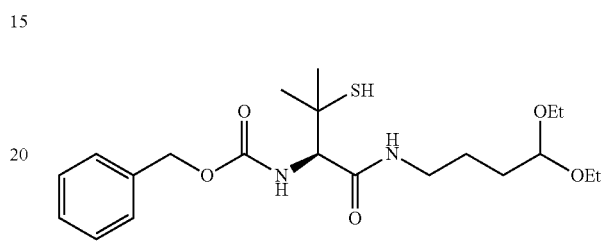

To a round bottom flask was added (R)-2-(benzyloxycarbonylamino)-3-mercapto-3-methylbutanoic acid (4.68 g, 16.52 mmol), HOBT (2.53 g, 16.52 mmol), EDC (3.17 g, 16.52 mmol), DCM (50 mL), TEA (2.302 mL, 16.52 mmol) and 4,4-diethoxybutan-1-amine (2.66 g, 16.52 mmol). The reaction was stirred at rt overnight. The reaction was diluted with DCM (150 mL). The organics was washed with water (2×150 mL), saturated aqueous NaCl (100 mL). The organic layer was separated, dried over MgSO$_4$, filtered and concentrated to give (R)-benzyl 1-(4,4-diethoxybutylamino)-3-mercapto-3-methyl-1-oxobutan-2-ylcarbamate (6.90 gm, 16.2 mmol, 98% yield) as an oil.

C: Benzyl (3R,8aS)-2,2-dimethyl-4-oxohexahydro-2H-pyrrolo[2,1-b][1,3]thiazin-3-ylcarbamate

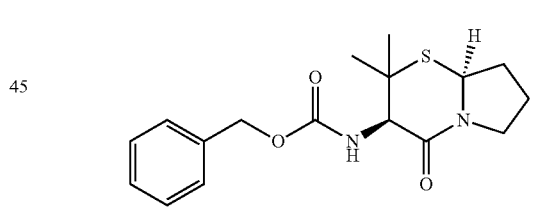

To a round bottom flask was added (R)-benzyl 1-(4,4-diethoxybutylamino)-3-mercapto-3-methyl-1-oxobutan-2-ylcarbamate (6.90 g, 16.2 mmol), DCM (50 mL) and TFA (1.87 mL, 24.3 mmol). The reaction was stirred at rt for 5 hr. The reaction was diluted with DCM (200 mL) and the organics was washed with saturated aqueous NaHCO$_3$ (200 mL), water (200 mL) and saturated aqueous NaCl (200 mL). The organic layer was separated, dried over MgSO$_4$, filtered and concentrated. The residue was purified using silica gel chromatography (ISCO system) eluting with a gradient of 0-100% EtOAc/Hex to give benzyl (3R,8aS)-2,2-dimethyl-4-oxohexahydro-2H-pyrrolo[2,1-b][1,3]thiazin-3-ylcarbamate (1.89 g, 5.65 mmol, 34.9% yield) as a clear oil. Anal. Calcd. for $C_{12}H_{22}N_2O_3S$ m/z 334.3. found: 335.2 (M+H)$^+$; $^1$H NMR (500 MHz, CDCl$_3$) δ ppm 7.29-7.44 (m, 5H), 5.92 (d, J=7.15

Hz, 1H), 5.14 (s, 3H), 4.57 (d, J=7.70 Hz, 1H), 3.89-3.68 (m, 1H), 3.60-3.40 (m, 1H), 2.55-2.34 (m, 1H), 2.18-2.00 (m, 1H), 1.99-1.83 (m, 2H), 1.51 (s, 3H), 1.13 (s, 3H); $^{13}$C NMR (126 MHz, CDCl$_3$) δ ppm 167.31, 157.00, 136.19, 128.54, 128.20, 128.08, 67.23, 60.46, 55.12, 48.93, 46.26, 33.10, 29.56, 27.70, 23.39.

D: (3R,8aS)-3-Amino-2,2-dimethyltetrahydro-2H-pyrrolo[2,1-b][1,3]thiazin-4(3H)-one mono hydrochloride salt

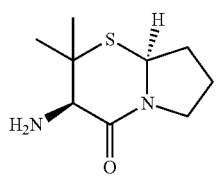

To a round bottom flask was added benzyl (3R,8aS)-2,2-dimethyl-4-oxohexahydro-2H-pyrrolo[2,1-b][1,3]thiazin-3-ylcarbamate (1.65 gm, 4.93 mmol), DCM (20 mL) and TMSI (1.343 mL, 9.87 mmol). The reaction was stirred at rt overnight. The reaction was concentrated and the residue was diluted with ether (150 mL). Then 4N HCl was added to the reaction and solid precipitated. Collect the solid by filtration. The solid was then dissolved in water (50 mL) and the aqueous was washed with EtOAc (3×10 mL) and DCM (2×10 mL). The aqueous layer was dried over lyophilizer overnight. The solid was then dissolved in saturated aqueous Na$_2$CO$_3$ solution (15 mL). The aqueous solution was extracted with DCM (4×15 mL). The combined organic layer was washed with water (15 mL) and saturated aqueous NaCl (15 mL). The organic layer was separated, dried over MgSO$_4$, filtered and concentrated. The residue was treated with 4N HCl in dioxane. The solution was dried to give (3R,8aS)-3-amino-2,2-dimethyltetrahydro-2H-pyrrolo[2,1-b][1,3]thiazin-4(3H)-one, HCl (700 mg, 2.81 mmol, 56.9% yield) as an off-white solid. Anal. Calcd. for C$_9$H$_{16}$N$_2$OS m/z 200.3. found: 201.2 (M+H)$^+$; $^1$H NMR (500 MHz, CD$_3$OD) δ ppm 5.15-5.30 (m, 1H), 4.32 (s, 1H), 3.81-3.70 (m, 1H), 3.60-3.49 (m, 1H), 2.55-2.38 (m, 1H), 2.15-2.04 (m, 1H), 2.03-1.85 (m, 2H), 1.64 (s, 3H), 1.28 (s, 3H).

Intermediate 30: (3R,9aS)-3-Amino-2,2-dimethylhexahydropyrido[2,1-b][1,3]thiazin-4(6H)-one

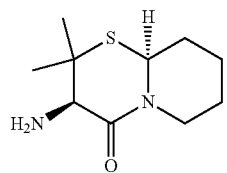

A: (R)-(9H-Fluoren-9-yl)methyl 1-(5-hydroxypentylamino)-3-methyl-1-oxo-3-(tritylthio)butan-2-ylcarbamate

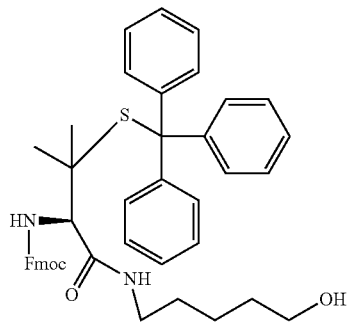

To a round bottom flask was added (R)-2-(((9H-fluoren-9-yl)methoxy)carbonylamino)-3-methyl-3-(tritylthio)butanoic acid (400 mg, 0.652 mmol), HOBT (120 mg, 0.782 mmol), Hunig's Base (0.137 mL, 0.782 mmol), DMF (1 mL) and DCM (5 mL). The reaction was stirred at rt for 1 hr. Then 5-aminopentan-1-ol (67.2 mg, 0.652 mmol) was added to the reaction and the reaction was stirred at rt overnight. The reaction was diluted with EtOAc (50 mL) and washed with water (4×15 mL) and saturated aqueous NaCl (15 mL). The organic layer was separated, dried over MgSO$_4$, filtered and concentrated. The residue was purified using silica gel chromatography (ISCO system) eluting with a gradient of 0-100% EtOAc/Hex to give (R)-(9H-fluoren-9-yl)methyl 1-(5-hydroxypentylamino)-3-methyl-1-oxo-3-(tritylthio)butan-2-ylcarbamate (300 mg, 0.429 mmol, 65.9% yield) as a white solid. $^1$H NMR (500 MHz, CDCl$_3$) δ ppm 7.76 (d, J=7.70 Hz, 2H), 7.69-7.50 (m, 8H), 7.39 (t, J=7.42 Hz, 2H), 7.33-7.15 (m, 11H), 5.74-5.41 (m, 2H), 4.45-4.11 (m, 3H), 3.67-3.39 (m, 2H), 3.35-3.07 (m, 2H), 1.56-1.41 (m, 4H), 1.42-1.31 (m, 2H), 1.33-1.24 (m, 2H), 1.18 (br. s., 3H), 1.11 (s, 3H); $^{13}$C NMR (126 MHz, CDCl$_3$) δ ppm 144.86, 141.28, 129.96, 127.86, 127.69, 127.07, 126.76, 125.11, 119.95, 68.35, 62.48, 53.38, 47.11, 39.35, 32.11, 29.01, 26.43, 22.93, 22.69, 14.09.

B: (R)-(9H-Fluoren-9-yl)methyl 3-methyl-1-oxo-1-(5-oxopentylamino)-3-(tritylthio)butan-2-ylcarbamate

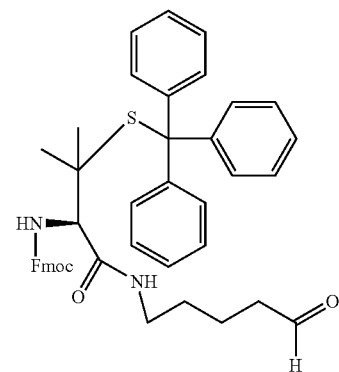

To a round bottom dry flask was added DCM (2 mL), and a 2 M solution of oxalyl chloride in DCM (0.100 mL, 0.200 mmol). The reaction was cooled to −78° C. Then slowly was DMSO (0.028 mL, 0.401 mmol) added over 5 min. The reaction was stirred at −78° C. for 30 min. Then (R)-(9H-fluoren-9-yl)methyl 1-(5-hydroxypentylamino)-3-methyl-1-oxo-3-(tritylthio)butan-2-ylcarbamate (100 mg, 0.143 mmol) in DCM (3 mL) was added to the reaction over 5 min and the reaction was stirred at −78° C. for 45 min. Then TEA (0.088 mL, 0.630 mmol) was added to the reaction and the reaction was stirred for additional 30 min at −35° C. The reaction was quenched with EtOAc (2 mL). The reaction was diluted with EtOAc (20 mL) and washed with saturated aqueous NaHCO$_3$ (10 mL), water (10 mL) and saturated aqueous NaCl (10 mL). The organic layer was separated, dried over MgSO$_4$, filtered and concentrated to give (R)-(9H-fluoren-9-yl)methyl 3-methyl-1-oxo-1-(5-oxopentylamino)-3-(tritylthio)butan-2-ylcarbamate (95 mg, 0.14 mmol, 95% yield).

C: (9H-Fluoren-9-yl)methyl (3R,9aS)-2,2-dimethyl-4-oxooctahydropyrido[2,1-b][1,3]thiazin-3-ylcarbamate

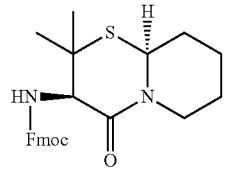

To a round bottom flask was added (R)-(9H-fluoren-9-yl)methyl 3-methyl-1-oxo-1-(5-oxopentylamino)-3-(tritylthio)butan-2-ylcarbamate (35 mg, 0.050 mmol), DCM (1 mL) and TFA (0.077 mL, 1.0 mmol). The reaction mixture was stirred at rt for 15 min. The reaction mixture was diluted with EtOAc (20 mL) and washed with saturated aqueous NaHCO$_3$ (10 mL), water (10 mL) and saturated aqueous NaCl (10 mL). The organic layer was separated, dried over MgSO$_4$, filtered and concentrated. The residue was purified using silica gel chromatography (ISCO system) eluting with a gradient of 0-100% EtOAc/Hex to give (9H-fluoren-9-yl)methyl (3R,9aS)-2,2-dimethyl-4-oxooctahydropyrido[2,1-b][1,3]thiazin-3-ylcarbamate (12 mg, 0.027 mmol, 55% yield) as a white solid. Anal. Calcd. for C$_{25}$H$_{28}$N$_2$O$_3$S m/z 436.3. found: 437.2 (M+H)$^+$; $^1$H NMR (500 MHz, CDCl$_3$) δ ppm 7.78 (d, J=7.15 Hz, 2H), 7.63 (t, J=6.60 Hz, 2H), 7.41 (td, J=7.42, 3.30 Hz, 2H), 7.33 (t, J=7.42 Hz, 2H), 5.84 (d, J=8.80 Hz, 1H), 4.90 (dd, J=8.80, 3.85 Hz, 1H), 4.63 (d, J=8.80 Hz, 1H), 4.54-4.35 (m, 2H), 4.26 (t, J=7.15 Hz, 1H), 4.16-3.99 (m, 1H), 3.22 (ddd, J=13.06, 8.39, 4.40 Hz, 1H), 2.00 (dt, J=8.80, 4.40 Hz, 1H), 1.93-1.81 (m, 1H), 1.80-1.67 (m, 3H), 1.62-1.52 (m, 1H), 1.39-1.24 (m, 3H), 1.19 (s, 3H).

D: (3R,9aS)-3-Amino-2,2-dimethylhexahydropyrido[2,1-b][1,3]thiazin-4(6H)-one

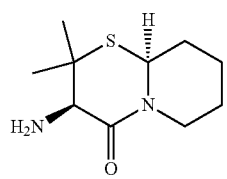

To a round bottom flask was added (9H-fluoren-9-yl)methyl (3R)-2,2-dimethyl-4-oxooctahydropyrido[2,1-b][1,3]thiazin-3-ylcarbamate (37 mg, 0.085 mmol), DCM (1 mL) and piperidine (0.017 mL, 0.17 mmol). The reaction was stirred at rt for 3 hr. The solvent was removed and the residue was dried over vacuum pump overnight to give (3R)-3-amino-2,2-dimethylhexahydropyrido[2,1-b][1,3]thiazin-4(6H)-one (17 mg, 0.080 mmol, 94% yield).

Intermediate 31: (3R,9aS)-3-Aminohexahydropyrido[2,1-b][1,3]thiazin-4(6H)-one

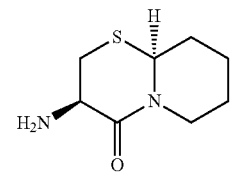 [SMILES: N[C@H]1CS[C@H]2CCCCN2C1=O]

(3R,9aS)-3-Aminohexahydropyrido[2,1-b][1,3]thiazin-4(6H)-one (350 mg, 1.879 mmol) was synthesized as described for the preparation of Intermediate 30 using (R)-2-(((9H-fluoren-9-yl)methoxy)carbonylamino)-3-(tritylthio)propanoic acid in step A. $^1$H NMR (500 MHz, CD$_3$OD) δ ppm 4.66-4.58 (m, 1H), 4.51 (dd, J=11.55, 2.75 Hz, 1H), 4.20 (dd, J=11.27, 5.22 Hz, 1H), 3.28-3.22 (m, 1H), 3.01 (dd, J=13.20, 4.95 Hz, 1H), 2.81 (td, J=12.65, 2.75 Hz, 1H), 2.10-1.99 (m, 1H), 1.95 (d, J=7.15 Hz, 2H), 1.82-1.71 (m, 1H), 1.67 (d, J=13.75 Hz, 1H), 1.53-1.41 (m, 1H); $^{13}$C NMR (126 MHz, CD$_3$OD) δ ppm 165.13, 60.06, 52.13, 47.02, 35.88, 25.73, 25.18, 24.71.

Intermediate 32: (S)-3-Amino-1-phenylpiperidin-2-one mono hydrochloride

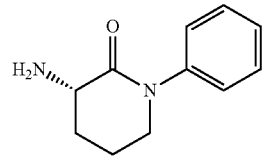

A: (S)-tert-Butyl 2-oxo-1-phenylpiperidin-3-ylcarbamate

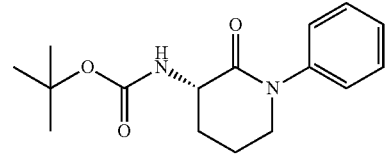 [SMILES: CC(C)(C)OC(=O)N[C@H]1CCCN(c2ccccc2)C1=O]

To a sealed-vial was added (S)-tert-butyl 2-oxopiperidin-3-ylcarbamate (162 mg, 0.756 mmol), potassium phosphate (321 mg, 1.51 mmol), iodobenzene (0.101 mL, 0.907 mmol), ethylenediamine (0.020 mL, 0.30 mmol), dioxane (3 mL) and molecular sieves followed by copper(I) iodide (57.6 mg, 0.302 mmol). The vial was purged with nitrogen gas and sealed. Then the reaction was stirred at 110° C. for 40 hr. The reaction was diluted with EtOAc (30 mL) and washed with water (20 mL) and saturated aqueous NaCl (20 mL). The organic layer was separated, dried over MgSO$_4$, filtered and concentrated. The residue was purified by RP prep-HPLC (Method A) to give (S)-tert-butyl 2-oxo-1-phenylpiperidin-3-ylcarbamate (100 mg, 0.344 mmol, 45.6% yield) as a white solid. Anal. Calcd. for C$_{16}$H$_{22}$N$_2$O$_3$ m/z 290.3. found: 291.2 (M+H)$^+$; $^1$H NMR (500 MHz, CDCl$_3$) δ ppm 7.40 (t, J=7.70 Hz, 2H), 7.33-7.20 (m, 3H), 5.56 (br. s., 1H), 4.37-4.20 (m, 1H), 3.78-3.66 (m, 2H), 2.63 (dd, J=12.37, 5.77 Hz, 1H), 2.16-1.97 (m, 2H), 1.81-1.661 (m, 1H), 1.47 (s, 9H).

B: (S)-3-Amino-1-phenylpiperidin-2-one mono hydrochloride

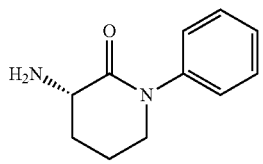 [SMILES: N[C@H]1CCCN(c2ccccc2)C1=O]

To a round bottom flask was added (S)-tert-butyl 2-oxo-1-phenylpiperidin-3-ylcarbamate (100 mg, 0.344 mmol) and 4 N HCl in dioxane (2.2 mL). The reaction was stirred at rt for 3 hr. The solvent was removed to give (S)-3-amino-1-phenylpiperidin-2-one (70 mg, 0.31 mmol, 90% yield) as an HCl salt. Anal. Calcd. for C$_{11}$H$_{14}$N$_2$O m/z 190.2. found: 191.2 (M+H)$^+$.

Intermediate 33: (Z)-3-Amino-4,4-dimethyl-1-phenyl-3,4-dihydro-1H-azepin-2(7H)-one

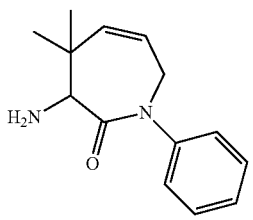 [SMILES: CC1(C)C=CCN(c2ccccc2)C(=O)C1N]

A: (Z)-Ethyl 2-(4-methoxyphenylimino)acetate

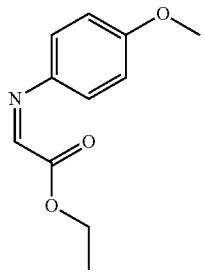

To a round bottom flask was added 4-methoxyaniline (10 g, 81 mmol), toluene (100 mL) and Na$_2$SO$_4$ (40 gm). Then a solution of ethyl 2-oxoacetate (8.29 gm, 81 mmol) in toluene (20 mL) was slowly added to the reaction over 45 min. The reaction was stirred at rt for an additional 30 min. Then, the Na$_2$SO$_4$ was filtered off and the filtrate was concentrated to give (Z)-ethyl 2-(4-methoxyphenylimino)acetate (5.0 g, 24 mmol, 30% yield) as a clear oil.

B: Ethyl 2-(4-methoxyphenylamino)-3,3-dimethylpent-4-enoate

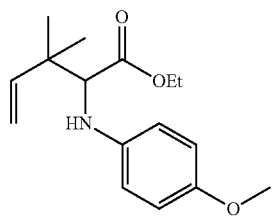 [SMILES: C=CC(C)(C)C(Nc1ccc(OC)cc1)C(=O)OCC]

To a round bottom flask was added (Z)-ethyl 2-(4-methoxyphenylimino)acetate (4000 mg, 19.30 mmol) and DMF (30 mL). The reaction was cooled to 0° C. Then, 1-bromo-3-methylbut-2-ene (3740 mg, 25.09 mmol) was added to the reaction followed by zinc (1641 mg, 25.09 mmol) and a drop of TMS-Cl (0.247 mL, 1.93 mmol). The reaction mixture was slowly warmed up to rt over 45 min and then stirred at rt for 20 min. The reaction mixture was cooled to 0° C. and aqueous 5% NH$_4$Cl (10 mL) was added to the reaction. The reaction was extracted with ether (3×50 mL). The combined ether layer was washed with water (100 mL) and saturated aqueous NaCl (100 mL). The organic layer was separated, dried over MgSO$_4$, filtered and concentrated. The residue was purified using silica gel chromatography (ISCO system) eluting with a gradient of 0-60% EtOAc/Hex to give ethyl 2-(4-methoxyphenylamino)-3,3-dimethylpent-4-enoate (1.1 g, 4.0 mmol, 21% yield) as a yellow oil. $^1$H NMR (500 MHz, CDCl$_3$) δ ppm 6.76 (d, J=9.35 Hz, 2H), 6.60 (d, J=8.80 Hz, 2H), 5.96 (dd, J=17.32, 10.72 Hz, 1H), 5.19-5.08 (m, 2H), 4.15 (q, 2H), 3.85 (s, 1H), 3.77-3.71 (m, 4H), 1.23 (t, J=7.15 Hz, 3H), 1.21 (s, 3H), 1.17 (s, 3H); $^{13}$C NMR (126 MHz, CDCl$_3$) δ ppm 173.09, 152.71, 143.47, 141.42, 115.30, 114.79, 113.92, 66.02, 60.54, 55.69, 40.06, 24.89, 23.70, 14.27.

C: Ethyl 2-(tert-butoxycarbonylamino)-3,3-dimethyl-pent-4-enoate

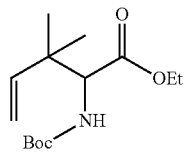 [SMILES: C=CC(C)(C)C(NC(=O)OC(C)(C)C)C(=O)OCC]

To a round bottom flask was added iodobenzene diacetate (5.34 g, 16.6 mmol) and dry MeOH (50 mL). Then, a solution of ethyl 2-(4-methoxyphenylamino)-3,3-dimethylpent-4-enoate (1.00 g, 3.61 mmol) in MeOH (10 mL) was added to the reaction flask over 30 min. The reaction was stirred at rt for an additional 1 hr. Then aqueous 1 N HCl (72.1 mL, 72.1 mmol) was added to the reaction and the reaction was stirred at rt for 90 min. The reaction was extracted with DCM (2×50 mL). The combined DCM layers were extracted with aqueous 1 N HCl (2×20 mL). The pH of combined aqueous solution was adjusted to 8-9 using solid Na$_2$CO$_3$. Then DCM (50 mL)

was added to the aqueous solution followed by di-tert-butyl dicarbonate (5.02 mL, 21.6 mmol). The reaction was stirred at rt overnight. The reaction was transferred to separatory funnel and the layers were separated. The aqueous layer was extracted with DCM (2×30 mL). The combined DCM layers were washed with brine (50 mL), dried over MgSO$_4$, filtered and concentrated. The residue was purified using silica gel chromatography (ISCO system) eluting with a gradient of 0-50% EtOAc/Hex to give ethyl 2-(tert-butoxycarbonylamino)-3,3-dimethylpent-4-enoate (500 mg, 1.84 mmol, 51.1% yield) as a clear oil. $^1$H NMR (500 MHz, CDCl$_3$) δ ppm 5.89-5.75 (m, 1H), 5.11-4.95 (m, 3H), 4.23-4.06 (m, 3H), 1.41 (s, 9H), 1.29-1.23 (m, 3H), 1.05-1.10 (m, 6H).

D: 2-(tert-Butoxycarbonylamino)-3,3-dimethylpent-4-enoic acid

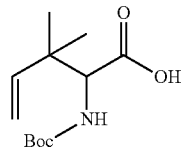 [SMILES: C=CC(C)(C)C(NC(=O)OC(C)(C)C)C(=O)O]

To a round bottom flask was added ethyl 2-(tert-butoxycarbonylamino)-3,3-dimethylpent-4-enoate (280 mg, 1.03 mmol), EtOH (20 mL) and aqueous 1 N NaOH (5.16 mL, 5.16 mmol). The reaction was stirred at 70° C. overnight. The reaction was cooled to rt and KOH (232 mg, 4.13 mmol) was added and the reaction was stirred at rt for 3 days. The solvent was removed and the residue was dissolved in water (15 mL). The aqueous solution was washed with DCM (5 mL). The pH of the aqueous layer was then adjusted to <4 using aqueous 1 N HCl. Then, the aqueous solution was extracted with DCM (5×10 mL). The combined organic layers were washed with saturated aqueous NaCl (20 mL). The organic layer was separated, dried over MgSO$_4$, filtered and concentrated to give 2-(tert-butoxycarbonylamino)-3,3-dimethylpent-4-enoic acid (240 mg, 0.986 mmol, 96% yield) as beige solid. $^1$H NMR (500 MHz, CDCl$_3$) δ ppm 5.87 (dd, J=17.32, 10.72 Hz, 1H), 5.23-5.03 (m, 2H), 4.98 (d, J=8.25 Hz, 1H), 4.17 (d, J=8.80 Hz, 1H), 1.45 (s, 9H), 1.16 (d, J=4.40 Hz, 6H).

E: tert-Butyl 1-(allyl(phenyl)amino)-3,3-dimethyl-1-oxopent-4-en-2-ylcarbamate

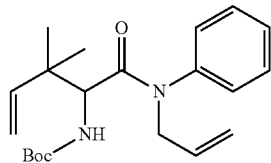 [SMILES: C=CCN(C(=O)C(NC(=O)OC(C)(C)C)C(C)(C)C=C)c1ccccc1]

To a round bottom flask was added 2-(tert-butoxycarbonylamino)-3,3-dimethylpent-4-enoic acid (120 mg, 0.493 mmol), N-allylaniline (0.134 mL, 0.986 mmol), EtOAc (5 mL) and Hunig's Base (0.258 mL, 1.48 mmol). The reaction mixture was cooled to 0° C. 1-propanephosphonic acid cyclic anhydride (314 mg, 0.986 mmol) was added and the reaction was stirred at 0° C. for 5 min and then at rt for 3 days. The reaction mixture was diluted with EtOAc (20 mL) and washed with water (10 mL) and saturated aqueous NaCl (10 mL). The organic layer was separated, dried over MgSO$_4$, filtered and concentrated. The residue was purified by RP prep-HPLC (Method A) to give tert-butyl 1-(allyl(phenyl)amino)-3,3-dimethyl-1-oxopent-4-en-2-ylcarbamate (70 mg, 0.20 mmol, 40% yield) as clear oil. Anal. Calcd. for C$_{21}$H$_{30}$N$_2$O$_3$ m/z 358.2. found: 359.2 (M+H)$^+$.

F: (Z)-tert-Butyl 4,4-dimethyl-2-oxo-1-phenyl-2,3,4,7-tetrahydro-1H-azepin-3-ylcarbamate

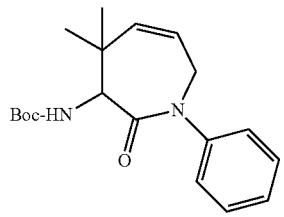

To a round bottom flask was added tert-butyl 1-(allyl(phenyl)amino)-3,3-dimethyl-1-oxopent-4-en-2-ylcarbamate (60 mg, 0.17 mmol) and 1,2-dichloroethane (2 mL). The reaction was charged with argon and brought to 60° C. Then, the Grubbs II catalyst (21 mg, 0.025 mmol) was added and the reaction was stirred at 60° C. for 4 hr and then at rt overnight. The reaction was concentrated and the residue was purified by RP prep-HPLC (Method A) to give (Z)-tert-butyl 4,4-dimethyl-2-oxo-1-phenyl-2,3,4,7-tetrahydro-1H-azepin-3-ylcarbamate (15 mg, 0.045 mmol, 27% yield) as a clear oil. Anal. Calcd. for C$_{19}$H$_{26}$N$_2$O$_3$ m/z 330.2. found: 331.2 (M+H)$^+$; $^1$H NMR (500 MHz, CDCl$_3$) δ ppm 7.38 (t, J=7.69 Hz, 2H), 7.30-7.25 (m, 1H), 7.21 (d, J=7.03 Hz, 2H), 5.82-5.71 (m, 2H), 5.71-5.64 (m, 1H), 5.10 (d, J=8.35 Hz, 1H), 4.82 (d, J=17.58 Hz, 1H), 3.76 (dd, J=17.58, 7.91 Hz, 1H), 1.50-1.44 (m, 9H), 1.20-1.16 (m, 3H), 0.99 (s, 3H).

G: (Z)-3-Amino-4,4-dimethyl-1-phenyl-3,4-dihydro-1H-azepin-2(7H)-one

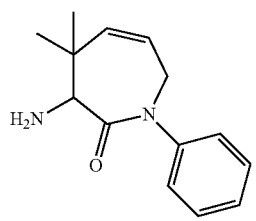 [SMILES: CC1(C)C=CCN(c2ccccc2)C(=O)C1N]

To a round bottom flask was added (Z)-tert-butyl 4,4-dimethyl-2-oxo-1-phenyl-2,3,4,7-tetrahydro-1H-azepin-3-ylcarbamate (7 mg, 0.02 mmol) and 4 N HCl in dioxane (1 mL). The reaction was stirred at rt for 1 hr. The solvent was removed to give (Z)-3-amino-4,4-dimethyl-1-phenyl-3,4-dihydro-1H-azepin-2(7H)-one (4 mg, 0.02 mmol, 82% yield) as mono hydrochloride salt. Anal. Calcd. for $C_{14}H_{18}N_2O$ m/z 230.2. found: 231.2 (M+H)+.

Intermediate 34:
3-Amino-4,4-dimethyl-1-phenylazepan-2-one

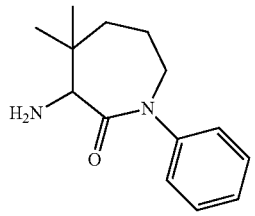 [SMILES: CC1(C)CCCN(c2ccccc2)C(=O)C1N]

A: tert-Butyl
4,4-dimethyl-2-oxo-1-phenylazepan-3-ylcarbamate

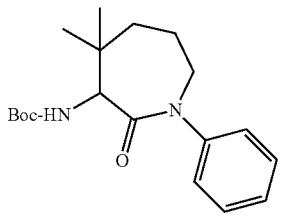

To a 2-neck round bottom flask was added (Z)-tert-butyl 4,4-dimethyl-2-oxo-1-phenyl-2,3,4,7-tetrahydro-1H-azepin-3-ylcarbamate (7 mg, 0.02 mmol), 10% Pd/C (2.3 mg, 0.021 mmol) and EtOAc (1 mL). The reaction was then charged with hydrogen with a balloon and then stirred at rt for 2 hr. The reaction was filtered through CELITE® and the filtrate was concentrated to give tert-butyl 4,4-dimethyl-2-oxo-1-phenylazepan-3-ylcarbamate (6.5 mg, 0.020 mmol, 92% yield) as a clear film. Anal. Calcd. for $C_{19}H_{28}N_2O_3$ m/z 332.2. found: 333.2 (M+H)+.

B: 3-Amino-4,4-dimethyl-1-phenylazepan-2-one

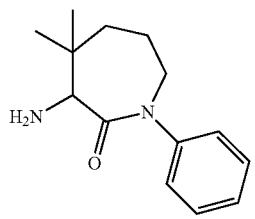 [SMILES: CC1(C)CCCN(c2ccccc2)C(=O)C1N]

To a round bottom flask was added tert-butyl 4,4-dimethyl-2-oxo-1-phenylazepan-3-ylcarbamate (6.5 mg, 0.020 mmol) and 4 N HCl in dioxane (1 mL). The reaction was stirred at rt for 1 hr. The solvent was removed to give 3-amino-4,4-dimethyl-1-phenylazepan-2-one (3.8 mg, 0.016 mmol, 84% yield) as the mono hydrochloride salt. Anal. Calcd. for $C_{14}H_{20}N_2O$ m/z 232.2. found: 233.2 (M+H)+.

Intermediate 35: (4S,7S,10aS)-4-Amino-7-(1,3,4-oxadiazol-2-yl)hexahydro-2H-pyrido[2,1-b][1,3]thiazepin-5(7H)-one 2,2,2-trifluoroacetate

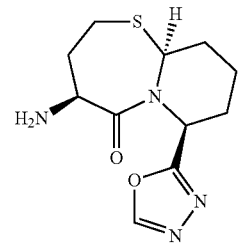 [SMILES: N[C@H]1CCS[C@H]2CCC[C@@H](c3nnco3)N2C1=O]

A: (4S,7S,10aS)-Methyl 4-(tert-butoxycarbonylamino)-5-oxooctahydro-2H-pyrido[2,1-b][1,3]thiazepine-7-carboxylate

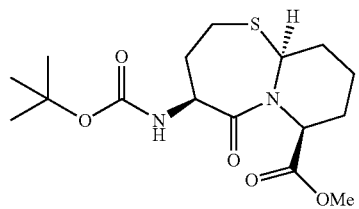 [SMILES: COC(=O)[C@@H]1CCC[C@@H]2SCC[C@H](NC(=O)OC(C)(C)C)C(=O)N21]

To a solution of (4S,7S,10aS)-methyl 4-amino-5-oxooctahydro-2H-pyrido[2,1-b][1,3]thiazepine-7-carboxylate (100 mg, 0.387 mmol) in DCM (2 mL) was added di-tert-butyl dicarbonate (93 mg, 0.43 mmol) and followed by TEA (0.059 mL, 0.43 mmol). The reaction was stirred at rt for 4 hr. The mixture was diluted with EtOAc. The organics were washed with water and saturated aqueous NaCl. The organic layer was separated, dried over $MgSO_4$, filtered and concentrated. The residue was purified using silica gel chromatography (ISCO system) eluting with a gradient of 0-50% EtOAc/Hex to give (4S,7S,10aS)-methyl 4-(tert-butoxycarbonylamino)-5-oxooctahydro-2H-pyrido[2,1-b][1,3]thiazepine-7-carboxylate (139 mg, 0.387 mmol, 100% yield) as a white solid.

B: (4S,7S,10aS)-4-(tert-Butoxycarbonylamino)-5-oxooctahydro-2H-pyrido[2,1-b][1,3]thiazepine-7-carboxylic acid

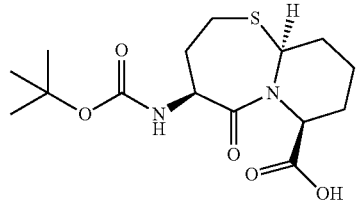 [SMILES: CC(C)(C)OC(=O)N[C@H]1CCS[C@H]2CCC[C@@H](C(=O)O)N2C1=O]

To a solution of (4S,7S,10aS)-methyl 4-(tert-butoxycarbonylamino)-5-oxooctahydro-2H-pyrido[2,1-b][1,3]thiazepine-7-carboxylate (0.139 g, 0.387 mmol) in MeOH (6 mL) was added NaOH (1 N in water, 387 µL, 0.387 mmol). The mixture was stirred at rt overnight. HPLC showed only 20% conversion. Additional NaOH (1 N in water, 387 µL, 0.387 mmol) was added and the reaction was stirred for an additional 3 days. The mixture was cooled with ice-water and the reaction was carefully neutralized with aqueous 1 N HCl to pH<7. The reaction was extracted with DCM. The organic layer was washed with water, dried over MgSO$_4$, filtered and concentrated to give (4S,7S,10aS)-4-(tert-butoxycarbonylamino)-5-oxooctahydro-2H-pyrido[2,1-b][1,3]thiazepine-7-carboxylic acid (133 mg, 0.386 mmol, 99% yield) as a white solid.

C: tert-Butyl (4S,7S,10aS)-7-(hydrazinecarbonyl)-5-oxooctahydro-2H-pyrido[2,1-b][1,3]thiazepin-4-ylcarbamate

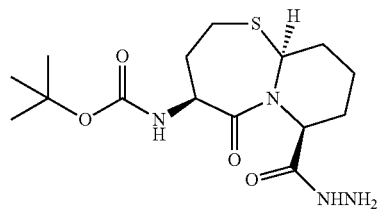 [SMILES: CC(C)(C)OC(=O)N[C@H]1CCS[C@H]2CCC[C@@H](C(=O)NN)N2C1=O]

To a solution of (4S,7S,10aS)-4-(tert-butoxycarbonylamino)-5-oxooctahydro-2H-pyrido[2,1-b][1,3]thiazepine-7-carboxylic acid (121 mg, 0.351 mmol) and N-methylmorpholine (0.048 mL, 0.44 mmol) in DCM (2 mL) at 0° C. was added isobutyl carbonochloridate (0.053 mL, 0.40 mmol). The mixture was stirred at 0° C. for 40 min. Then, hydrazine (0.044 mL, 1.4 mmol) was added and the reaction was stirred at rt for 1 hr. The mixture was diluted with EtOAc and washed with water and saturated aqueous NaCl. The organic layer was separated, dried over MgSO$_4$, filtered and concentrated to give tert-butyl (4S,7S,10aS)-7-(hydrazinecarbonyl)-5-oxooctahydro-2H-pyrido[2,1-b][1,3]thiazepin-4-ylcarbamate (125 mg, 0.349 mmol, 99% yield) as a white solid. Anal. Calcd. for C$_{15}$H$_{26}$N$_4$O$_4$S m/z 358.4. found: 359.1 (M+H)$^+$.

D: tert-Butyl (4S,7S,10aS)-7-(1,3,4-oxadiazol-2-yl)-5-oxooctahydro-2H-pyrido[2,1-b][1,3]thiazepin-4-ylcarbamate

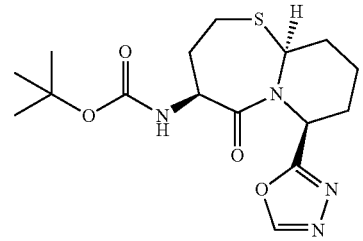 [SMILES: CC(C)(C)OC(=O)N[C@H]1CCS[C@H]2CCC[C@@H](c3nnco3)N2C1=O]

To a round bottom flask was added tert-butyl (4S,7S,10aS)-7-(hydrazinecarbonyl)-5-oxooctahydro-2H-pyrido[2,1-b][1,3]thiazepin-4-ylcarbamate (0.13 g, 0.35 mmol) and trimethoxymethane (2.50 mL, 22.9 mmol). The reaction was heated at 70° C. for 5 hr. and then at 95° C. for 18 hr. The reaction was concentrated. The residue was purified using silica gel chromatography (ISCO system) eluting with a gradient of 0-60% EtOAc/Hex to give tert-butyl (4S,7S,10aS)-7-(1,3,4-oxadiazol-2-yl)-5-oxooctahydro-2H-pyrido[2,1-b][1,3]thiazepin-4-ylcarbamate (94 mg, 0.26 mmol, 73% yield) as a white solid. Anal. Calcd. for C$_{16}$H$_{24}$N$_4$O$_4$S m/z 368.4. found: 369.1 (M+H)$^+$.

E: (4S,7S,10aS)-4-Amino-7-(1,3,4-oxadiazol-2-yl)hexahydro-2H-pyrido[2,1-b][1,3]thiazepin-5(7H)-one 2,2,2-trifluoroacetate

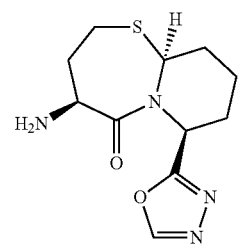 [SMILES: N[C@H]1CCS[C@H]2CCC[C@@H](c3nnco3)N2C1=O]

To a solution of tert-butyl (4S,7S,10aS)-7-(1,3,4-oxadiazol-2-yl)-5-oxooctahydro-2H-pyrido[2,1-b][1,3]thiazepin-4-ylcarbamate (22 mg, 0.060 mmol) in DCM (0.6 mL) at 0° C., was added TFA (0.323 mL, 4.20 mmol). The mixture was stirred at rt for 1.5 hr. The reaction was concentrated to give (4S,7S,10aS)-4-amino-7-(1,3,4-oxadiazol-2-yl)hexahydro-2H-pyrido[2,1-b][1,3]thiazepin-5 (7H)-one 2,2,2-trifluoroacetate (23 mg, 0.060 mmol, 100% yield). Anal. Calcd. for C$_{11}$H$_{16}$N$_4$O$_2$S m/z 268.4. found: 269.2 (M+H)$^+$.

Intermediate 36: (4S,7S,10aS)-4-Amino-5-oxooctahydro-2H-pyrido[2,1-b][1,3]thiazepine-7-carbonitrile

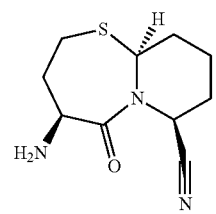 [SMILES: N#C[C@@H]1CCC[C@@H]2SCC[C@H](N)C(=O)N12]

A: tert-Butyl (4S,7S,10aS)-7-carbamoyl-5-oxooctahydro-2H-pyrido[2,1-b][1,3]thiazepin-4-ylcarbamate

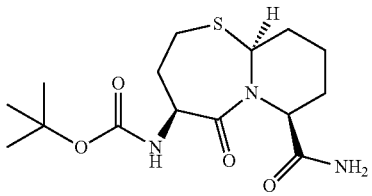 [SMILES: CC(C)(C)OC(=O)N[C@H]1CCS[C@H]2CCC[C@@H](C(N)=O)N2C1=O]

Isobutyl chloroformate (31.2 mg, 0.229 mmol) was added to a solution of (4S,7S,10aS)-4-(tert-Butoxycarbonylamino)-5-oxooctahydro-2H-pyrido[2,1-b][1,3]thiazepine-7-carboxylic acid (75 mg, 0.22 mmol) and 4-methylmorpholine (26.4 mg, 0.261 mmol) in DCM at 0° C. After stirring for 30 min at 0° C., NH₄OH was added. The ice bath was removed and the reaction mixture was stirred at rt for 30 min. The reaction mixture was concentrated and the residue was partitioned between EtOAc and aqueous 0.5 N HCl. The organic phase was isolated, washed with saturated aqueous NaHCO₃ and saturated aqueous NaCl, dried over MgSO₄, filtered and concentrated to give tert-butyl (4S,7S,10aS)-7-carbamoyl-5-oxooctahydro-2H-pyrido[2,1-b][1,3]thiazepin-4-ylcarbamate (67 mg, 0.20 mmol, 90% yield) as an oil. Anal. Calcd. for $C_{15}H_{25}N_3O_4S$ m/z 343.4. found: 344.3 (M+H)⁺.

B: tert-Butyl (4S,7S,10aS)-7-cyano-5-oxooctahydro-2H-pyrido[2,1-b][1,3]thiazepin-4-ylcarbamate

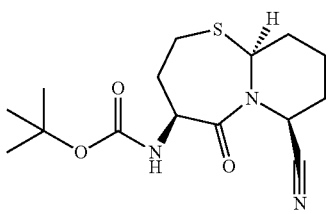 [SMILES: CC(C)(C)OC(=O)N[C@H]1CCS[C@H]2CCC[C@@H](C#N)N2C1=O]

Triethylamine (58.8 mg, 0.581 mmol) was added to a 0° C. solution of tert-butyl (4S,7S,10aS)-7-carbamoyl-5-oxooctahydro-2H-pyrido[2,1-b][1,3]thiazepin-4-ylcarbamate (57 mg, 0.17 mmol) in DCM (1.2 mL). TFAA (52.3 mg, 0.249 mmol) was then slowly added to the reaction. The ice bath was removed and the reaction mixture was left to stir at rt for 1 hr. The reaction was diluted with DCM (2 mL) and quenched by the addition of aqueous 10% Na₂CO₃ (2 mL). The aqueous phase was isolated and extracted with DCM (2 mL). All organic phases were combined, dried over MgSO₄, filtered and concentrated. The crude product was purified using silica gel chromatography (ISCO system) eluting with a gradient of 0-100% EtOAc/Hex to give tert-butyl (4S,7S,10aS)-7-cyano-5-oxooctahydro-2H-pyrido[2,1-b][1,3]thiazepin-4-ylcarbamate (36 mg, 0.11 mmol, 67% yield) as a light yellow solid. Anal. Calcd. for $C_{15}H_{23}N_3O_3S$ m/z 325.4. found: 326.3 (M+H)⁺.

C: (4S,7S,10aS)-4-Amino-5-oxooctahydro-2H-pyrido[2,1-b][1,3]thiazepine-7-carbonitrile

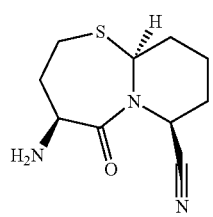 [SMILES: N#C[C@@H]1CCC[C@@H]2SCC[C@H](N)C(=O)N12]

Trifluoroacetic acid (0.15 mL) was added to a 0° C. solution of tert-butyl (4S,7S,10aS)-7-cyano-5-oxooctahydro-2H-pyrido[2,1-b][1,3]thiazepin-4-ylcarbamate (36 mg, 0.11 mmol) in DCM (0.35 mL). The reaction mixture was then stirred at rt for 45 min. The reaction mixture was concentrated. The residue was partitioned between EtOAc and saturated aqueous NaHCO₃. The EtOAc was isolated, dried over MgSO₄, filtered and concentrated give (4S,7S,10aS)-4-amino-5-oxooctahydro-2H-pyrido[2,1-b][1,3]thiazepine-7-carbonitrile (15 mg, 0.067 mmol, 60% yield).

Intermediate 37: (4S,7S,10aS)-4-Amino-5-oxo-N-(thiazol-2-yl)octahydro-2H-pyrido[2,1-b][1,3]thiazepine-7-carboxamide hydrochloride salt

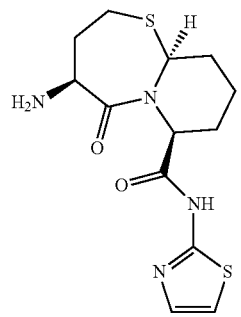 [SMILES: N[C@H]1CCS[C@H]2CCC[C@@H](C(=O)Nc3nccs3)N2C1=O]

A: tert-Butyl (4S,7S,10aS)-5-oxo-7-(thiazol-2-ylcarbamoyl)octahydro-2H-pyrido[2,1-b][1,3]thiazepin-4-ylcarbamate

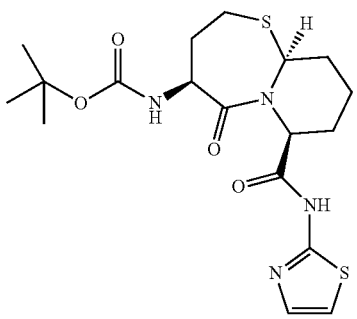 [SMILES: CC(C)(C)OC(=O)N[C@H]1CCS[C@H]2CCC[C@@H](C(=O)Nc3nccs3)N2C1=O]

DIPEA (0.036 mL, 0.21 mmol) was added to a cold (0° C.) mixture of (4S,7S,10aS)-4-(tert-butoxycarbonylamino)-5-oxooctahydro-2H-pyrido[2,1-b][1,3]thiazepine-7-carboxylic acid (55 mg, 0.16 mmol), thiazol-2-amine (19.2 mg, 0.192 mmol) and 1-hydroxy-7-azabenzotriazole (26.1 mg, 0.192 mmol) in DMF (0.6 mL). Then EDC (36.7 mg, 0.192 mmol) was added. The reaction was stirred at rt for 8 hr. The crude mixture was purified by RP prep-HPLC (Method B) to give tert-butyl (4S,7S,10aS)-5-oxo-7-(thiazol-2-ylcarbamoyl)octahydro-2H-pyrido[2,1-b][1,3]thiazepin-4-ylcarbamate (35 mg, 0.082 mmol, 51% yield) as a white solid. Anal. Calcd. for $C_{18}H_{26}N_4O_4S_2$ m/z 426.5. found: 427.1 (M+H)⁺; ¹H NMR (400 MHz, CDCl₃) δ ppm 7.45 (s, 1H), 6.98 (s, 1H), 5.96 (m, 1H), 5.37 (br s, 1H), 5.28 (br s, 1H), 3.35 (m, 2H), 2.94 (m, 2H), 2.36 (m, 1H), 2.45 (m, 1H), 2.05 (m, 2H), 1.53-1.50 (m, 4H), 1.50 (s, 9H).

B: (4S,7S,10aS)-4-Amino-5-oxo-N-(thiazol-2-yl)octahydro-2H-pyrido[2,1-b][1,3]thiazepine-7-carboxamide hydrochloride salt

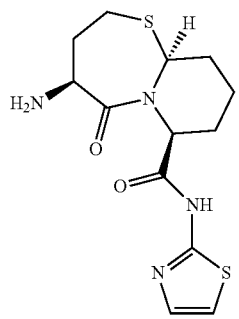 [SMILES: N[C@H]1CCS[C@H]2CCC[C@@H](C(=O)Nc3nccs3)N2C1=O]

To a round bottom flask was added tert-butyl (4S,7S,10aS)-5-oxo-7-(thiazol-2-ylcarbamoyl)octahydro-2H-pyrido[2,1-b][1,3]thiazepin-4-ylcarbamate (35 mg, 0.082 mmol) and 4 M HCl in dioxane (1 mL). The mixture was stirred at rt for 1 h. The reaction mixture was concentrated to give (4S,7S,10aS)-4-amino-5-oxo-N-(thiazol-2-yl)octahydro-2H-pyrido[2,1-b][1,3]thiazepine-7-carboxamide hydrochloride salt (30 mg, 0.082 mmol, 100% yield).

Intermediate 38: (4S,7S,10aS)-4-Amino-5-oxo-N-propyloctahydro-2H-pyrido[2,1-b][1,3]thiazepine-7-carboxamide hydrochloride salt

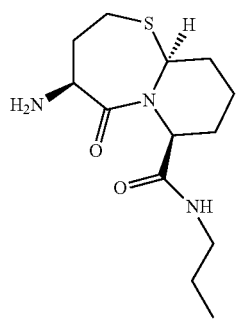

A: tert-Butyl (4S,7S,10aS)-5-oxo-7-(propylcarbamoyl)octahydro-2H-pyrido[2,1-b][1,3]thiazepin-4-ylcarbamate

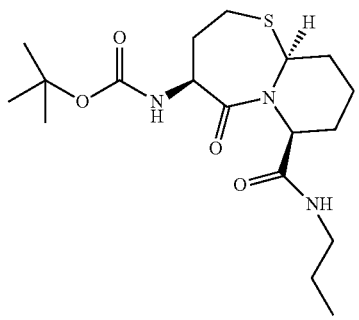 [SMILES: CCCNC(=O)[C@@H]1CCC[C@@H]2SCC[C@H](NC(=O)OC(C)(C)C)C(=O)N21]

DIPEA (0.033 mL, 0.19 mmol) was added to a cold (0° C.) mixture of (4S,7S,10aS)-4-(tert-butoxycarbonylamino)-5-oxooctahydro-2H-pyrido[2,1-b][1,3]thiazepine-7-carboxylic acid (50 mg, 0.15 mmol), propan-1-amine (10.3 mg, 0.174 mmol) and 1-hydroxy-7-azabenzotriazole (23.7 mg, 0.174 mmol) in DMF (0.3 mL). Then, EDC (33.4 mg, 0.174 mmol) was added. The reaction was stirred at rt for 8 hr. The crude mixture was purified by RP prep-HPLC (Method B) to give tert-butyl (4S,7S,10aS)-5-oxo-7-(propylcarbamoyl)octahydro-2H-pyrido[2,1-b][1,3]thiazepin-4-ylcarbamate (56 mg, 0.15 mmol, 100% yield) as a white solid. Anal. Calcd. for $C_{18}H_{31}N_3O_4S$ m/z 385.5. found: 386.2 (M+H)$^+$. $^1$H NMR (400 MHz, CDCl$_3$) δ ppm 6.02 (br s, 1H), 5.27 (br s, 1H), 5.02 (br s, 1H), 4.77 (m, 1H), 3.23 (m, 2H), 2.89 (m, 1H), 2.36 (m, 1H), 2.41 (m, 2H), 2.05 (m, 2H), 1.53-1.50 (m, 6H), 1.50 (s, 9H), 0.90 (t, J=7.5 Hz, 3H).

B: (4S,7S,10aS)-4-Amino-5-oxo-N-propyloctahydro-2H-pyrido[2,1-b][1,3]thiazepine-7-carboxamide hydrochloride salt

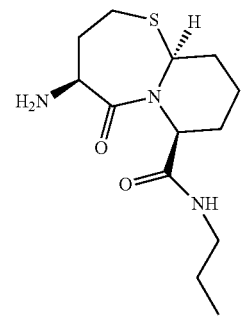 [SMILES: CCCNC(=O)[C@@H]1CCC[C@@H]2SCC[C@H](N)C(=O)N21]

To a round bottom flask was added tert-butyl (4S,7S,10aS)-5-oxo-7-(propylcarbamoyl)octahydro-2H-pyrido[2,1-b][1,3]thiazepin-4-ylcarbamate (43 mg, 0.11 mmol) and 4 M HCl in dioxane (1 mL). The mixture was stirred at rt for 1 hr. The reaction mixture was concentrated to give (4S,7S,10aS)-4-Amino-5-oxo-N-propyloctahydro-2H-pyrido[2,1-b][1,3]thiazepine-7-carboxamide hydrochloride salt (36 mg, 0.11 mmol, 100% yield).

Intermediate 39: (4S,10aR)-4-Aminohexahydropyrido[1,2-a][1,4]diazepine-1,5(2H,7H)-dione

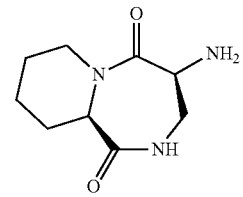 [SMILES: N[C@H]1CNC(=O)[C@H]2CCCCN2C1=O]

A: (R)-Methyl 1-((S)-2-(benzyloxycarbonylamino)-3-(tert-butoxycarbonylamino)propanoyl)piperidine-2-carboxylate

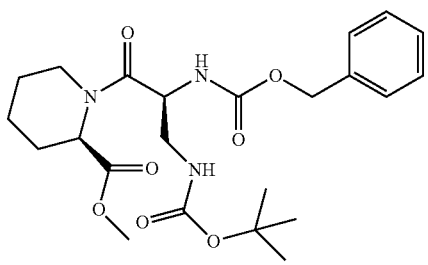 [SMILES: COC(=O)[C@H]1CCCCN1C(=O)[C@H](CNC(=O)OC(C)(C)C)NC(=O)OCc1ccccc1]

To a suspension of (S)-2-(benzyloxycarbonylamino)-3-(tert-butoxycarbonylamino)propanoic acid (2.26 g, 6.68 mmol) in DCM (50 mL) was added (R)-methyl piperidine-2-carboxylate HCl salt (1.00 g, 5.57 mmol), followed by EDC (1.60 g, 8.35 mmol), HOBT (1.71 g, 11.1 mmol), and TEA (2.33 mL, 16.7 mmol). The reaction mixture was stirred at rt for 6 hr. The reaction mixture was diluted with water and extracted with EtOAc (2×30 mL). The combined EtOAc layers were washed with water and saturated aqueous NaCl, dried over $Na_2SO_4$, filtered and concentrated. The crude product was purified using silica gel chromatography (ISCO system) eluting with a gradient of 30-70% EtOAc/Hex to give (R)-methyl 1-((S)-2-(benzyloxycarbonylamino)-3-(tert-butoxycarbonylamino)propanoyl)piperidine-2-carboxylate (1.80 g, 3.88 mmol, 69.8% yield) as a white foam. Anal. Calcd. for $C_{23}H_{33}N_3O_7$ m/z 463.5. found: 464.3 $(M+H)^+$.

B: (R)-Methyl 1-((S)-3-amino-2-(benzyloxycarbonylamino)propanoyl)piperidine-2-carboxylate trifluoroacetate

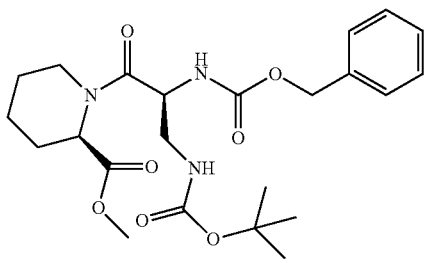 [SMILES: COC(=O)[C@H]1CCCCN1C(=O)[C@H](CNC(=O)OC(C)(C)C)NC(=O)OCc1ccccc1]

To a round bottom flask was added (R)-methyl 1-((S)-2-(benzyloxycarbonylamino)-3-(tert-butoxycarbonylamino)propanoyl)piperidine-2-carboxylate (1.80 gm, 3.88 mmol), DCM (5 mL) and TFA (5 mL). The reaction mixture was stirred at rt for 1 hr. The reaction mixture was then concentrated and dried under vacuum for 3 hr to afford (R)-methyl 1-((S)-3-amino-2-(benzyloxycarbonylamino)propanoyl)piperidine-2-carboxylate trifluoroacetate (1.87 g, 3.92 mmol, 100% yield) as a colorless oil. Anal. Calcd. for $C_{18}H_{25}N_3O_5$ m/z 363.4. found: 364.3 $(M+H)^+$.

C: Benzyl (4S,10aR)-1,5-dioxodecahydropyrido[1,2-a][1,4]diazepin-4-ylcarbamate

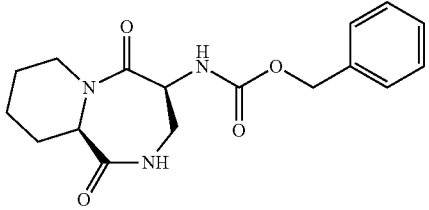 [SMILES: O=C(N[C@H]1CNC(=O)[C@H]2CCCCN2C1=O)OCc1ccccc1]

To a solution of (R)-methyl 1-((S)-3-amino-2-(benzyloxycarbonylamino)propanoyl)piperidine-2-carboxylate trifluoroacetate (601 mg, 1.26 mmol) in $ClCH_2CH_2Cl$ (10 mL) at rt was added trimethylaluminum in toluene (1.89 mL, 3.78 mmol). The reaction was stirred in a sealed bottle at 75° C. for 3 days. After cooling to rt, the reaction was quenched with water and then aqueous 1 N HCl solution until the solution became clear. The aqueous solution was extracted with DCM (2×30 mL). The combined organic layers were washed with saturated aqueous NaCl, dried over $Na_2SO_4$, filtered and concentrated. The resulting residue was purified using silica gel chromatography (ISCO system) eluting with a gradient of 50-100% EtOAc/Hex to give benzyl (4S,10aR)-1,5-dioxodecahydropyrido[1,2-a][1,4]diazepin-4-ylcarbamate (71 mg, 0.21 mmol, 17% yield) as a white solid. Anal. Calcd. for $C_{17}H_{21}N_3O_4$ m/z 331.4. found: 332.3 $(M+H)^+$; $^1$H NMR (400 MHz, $CDCl_3$) δ ppm 7.65-7.02 (m, 5H), 6.20 (d, J=5.5 Hz, 1H), 5.59 (s, 1H), 5.35-4.96 (m, 2H), 4.58 (s, 1H), 4.15 (d, J=13.3 Hz, 1H), 3.99-3.70 (m, 1H), 3.26-2.82 (m, 2H), 2.46-2.14 (m, 1H), 1.93-1.37 (m, 6H).

D: (4S,10aR)-4-Aminohexahydropyrido[1,2-a][1,4]diazepine-1,5(2H,7H)-dione

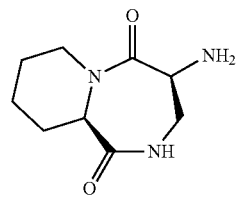 [SMILES: N[C@H]1CNC(=O)[C@H]2CCCCN2C1=O]

Argon was bubbled through a solution of benzyl (4S,10aR)-1,5-dioxodecahydropyrido[1,2-a][1,4]diazepin-4-ylcarbamate (37 mg, 0.11 mmol) in EtOAc (3 mL) for 5 min at rt. Then, 5% Pd/C (30 mg, 0.014 mmol) was added to the solution. The reaction mixture was stirred at rt under hydrogen (50 psi) for 3 hr. The reaction mixture was filtered through CELITE® and the filtrate was concentrated under reduced pressure to give (4S,10aR)-4-aminohexahydropyrido[1,2-a][1,4]diazepine-1,5(2H,7H)-dione (19 mg, 0.096 mmol, 86% yield) as a white solid. Anal. Calcd. for $C_9H_{15}N_3O_2$ m/z 197.2. found: 198.2 $(M+H)^+$.

Intermediate 40: (4S,10aS)-4-Aminohexahydro-2H-pyrido[2,1-b][1,3]thiazepin-5(7H)-one

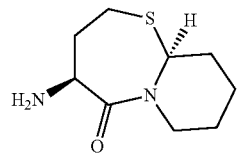 [SMILES: N[C@H]1CCS[C@H]2CCCCN2C1=O]

A: (S)—S-3-(Benzyloxycarbonylamino)-4-(5-hydroxypentylamino)-4-oxobutyl ethanethioate

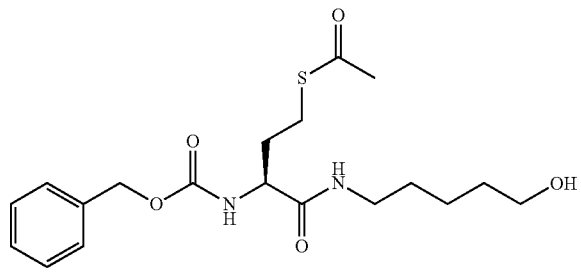 [SMILES: CC(=O)SCC[C@H](NC(=O)OCc1ccccc1)C(=O)NCCCCCO]

To a round bottom flask was added (S)-4-(acetylthio)-2-(benzyloxycarbonylamino)butanoic acid (312 mg, 1.00 mmol), 5-aminopentan-1-ol (119 mg, 1.15 mmol), DCM (5 mL), EDC (211 mg, 1.10 mmol) and HOBt (184 mg, 1.20 mmol). The light yellow mixture was stirred at rt for 16 hr. The reaction mixture was diluted with EtOAc (60 mL), washed with 5% aqueous KHSO$_4$ (2×), saturated aqueous NaHCO$_3$ (2×), water, and saturated aqueous NaCl. The organic layer was separated, dried over Na$_2$SO$_4$, filtered and concentrated. The residue was purified using silica gel chromatography (ISCO system) eluting with a gradient of 0-100% EtOAc/Hex to give (S)—S-3-(benzyloxycarbonylamino)-4-(5-hydroxypentylamino)-4-oxobutyl ethanethioate (311 mg, 0.784 mmol, 78% yield) as a white solid. Anal. Calcd. for C$_{19}$H$_{28}$N$_2$O$_5$S m/z 396.5. found: 397.3 (M+H)$^+$; $^1$H NMR (400 MHz, CDCl$_3$) δ ppm 7.47-7.28 (m, 5H), 6.41 (s, 1H), 5.59 (d, J=6.7 Hz, 1H), 5.11 (s, 2H), 4.13 (d, J=6.7 Hz, 1H), 3.63 (dd, J=11.6, 6.1 Hz, 2H), 3.28 (dd, J=12.7, 6.3 Hz, 2H), 2.97 (dt, J=14.5, 7.4 Hz, 1H), 2.91-2.75 (m, 1H), 2.34 (s, 3H), 2.21-2.00 (m, 1H), 1.91 (dt, J=14.4, 7.2 Hz, 1H), 1.72-1.48 (m, 5H), 1.48-1.34 (m, 2H).

B: (S)—S-3-(Benzyloxycarbonylamino)-4-oxo-4-(5-oxopentylamino)butyl ethanethioate

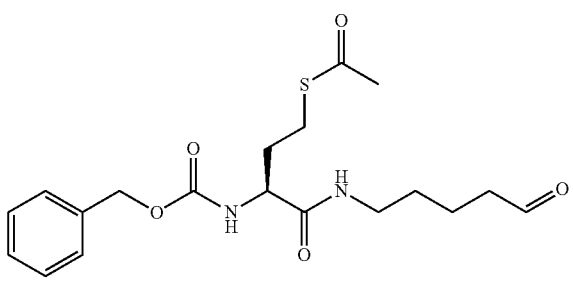 [SMILES: CC(=O)SCC[C@H](NC(=O)OCc1ccccc1)C(=O)NCCCCC=O]

To a solution of oxalyl chloride (2 M solution in DCM, 0.093 mL, 1.1 mmol) in DCM (1.5 mL) cooled to −78° C. was added DMSO (0.150 mL, 2.12 mmol) dropwise followed by a solution of (S)—S-3-(benzyloxycarbonylamino)-4-(5-hydroxypentylamino)-4-oxobutyl ethanethioate (300 mg, 0.757 mmol) in DCM (3 mL). After the addition, the resulting solution was stirred at −78° C. for 45 min. Then, TEA (0.464 mL, 3.33 mmol) was added. The mixture was stirred at −30° C. to −35° C. for 1 hr. The reaction was quenched with addition of EtOAc and 5% of aqueous KHSO$_4$. The separated organic layer was washed with 5% aqueous KHSO$_4$, water, saturated aqueous NaHCO$_3$, saturated aqueous NaCl, dried over Na$_2$SO$_4$, filtered and concentrated. The residue was purified using silica gel chromatography (ISCO system) eluting with a gradient of 0-100% EtOAc/Hex to give (S)—S-3-(benzyloxycarbonylamino)-4-oxo-4-(5-oxopentylamino)butyl ethanethioate (200 mg, 0.507 mmol, 67.0% yield) as a white solid. $^1$H NMR (400 MHz, CDCl$_3$) δ ppm 9.76 (s, 1H), 7.45-7.28 (m, 5H), 6.42 (s, 1H), 5.53 (d, J=6.6 Hz, 1H), 5.12 (s, 2H), 4.13 (d, J=6.7 Hz, 1H), 3.28 (dd, J=12.9, 6.4 Hz, 2H), 2.97 (dd, J=14.2, 7.1 Hz, 1H), 2.91-2.76 (m, 1H), 2.48 (dd, J=10.0, 3.8 Hz, 2H), 2.34 (s, 3H), 2.12 (td, J=14.0, 6.3 Hz, 1H), 1.91 (dt, J=14.3, 7.3 Hz, 1H), 1.74-1.47 (m, 4H).

C: (S)-Benzyl 4-mercapto-1-oxo-1-(5-oxopentylamino)butan-2-ylcarbamate

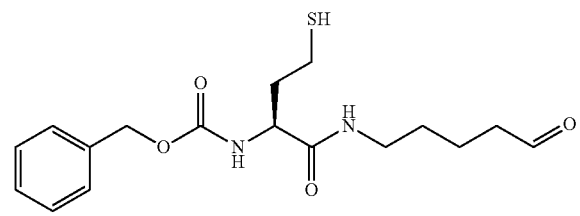 [SMILES: O=CCCCCNC(=O)[C@H](CCS)NC(=O)OCc1ccccc1]

A solution of (S)—S-3-(benzyloxycarbonylamino)-4-oxo-4-(5-oxopentylamino)butyl ethanethioate (195 mg, 0.494 mmol) in methanol (4 mL) was purged with argon for 10 min and then cooled to 0° C. Sodium methoxide in MeOH (25%, 0.12 mL) was added to the reaction. The mixture was stirred at 0° C. for 10 min. The reaction was quenched with saturated aqueous NH$_4$Cl solution. The reaction was extracted with EtOAc (2×). The combined EtOAc extracts were washed with saturated aqueous NH$_4$Cl solution, water, saturated aqueous NaCl, dried over Na$_2$SO$_4$, filtered and concentrated. The white solid residue was dried under vacuum to give (S)-benzyl 4-mercapto-1-oxo-1-(5-oxopentylamino)butan-2-ylcarbamate (150 mg, 0.426 mmol, 86% yield) as a white solid. Anal. Calcd. for C$_{12}$H$_{24}$N$_2$O$_4$S m/z 352.4. found: 353.23 (M+H)$^+$.

D: Benzyl (4S,10aS)-5-oxooctahydro-2H-pyrido[2,1-b][1,3]thiazepin-4-ylcarbamate

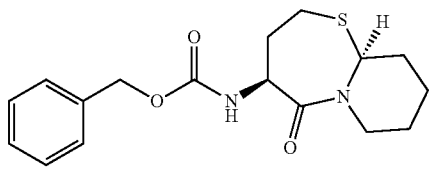 [SMILES: O=C(N[C@H]1CCS[C@H]2CCCCN2C1=O)OCc1ccccc1]

To a solution of (S)-benzyl 4-mercapto-1-oxo-1-(5-oxopentylamino)butan-2-ylcarbamate (150 mg, 0.426 mmol) in DCM (5 mL) at rt was added a couple drops of TFA (by pipette). The mixture was stirred at 50° C. (gentle refluxing) for 1.5 hr. The reaction mixture was cooled to rt and concentrated. The residue was diluted with EtOAc. The EtOAc solution was washed with saturated aqueous NaHCO$_3$, saturated aqueous NaCl (2×), dried over Na$_2$SO$_4$, filtered and concentrated. The residue was purified using silica gel chromatography (ISCO system) eluting with a gradient of 0-70% EtOAc/Hex to give benzyl (4S,10aS)-5-oxooctahydro-2H-pyrido[2,1-b][1,3]thiazepin-4-ylcarbamate (115 mg, 0.344 mmol, 81% yield). Anal. Calcd. for C$_{12}$H$_{22}$N$_2$O$_3$S m/z 334.3. found: 335.3 (M+H)$^+$; $^1$H NMR (400 MHz, CDCl$_3$) δ ppm 7.43-7.26 (m, 5H), 6.25 (d, J=6.5 Hz, 1H), 5.28 (dd, J=7.7, 3.0 Hz, 1H), 5.10 (d, J=2.5 Hz, 2H), 4.86 (ddd, J=10.3, 6.8, 3.3 Hz, 1H), 4.28 (d, J=13.8 Hz, 1H), 3.19 (ddd, J=14.1, 11.0, 2.7

Hz, 1H), 3.07-2.87 (m, 1H), 2.70 (ddd, J=14.4, 6.1, 3.0 Hz, 1H), 2.44-2.25 (m, 1H), 2.06-1.89 (m, 2H), 1.86-1.60 (m, 3H), 1.60-1.39 (m, 2H).

E: (4S,10aS)-4-Aminohexahydro-2H-pyrido[2,1-b][1,3]thiazepin-5(7H)-one

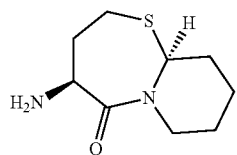 [SMILES: N[C@H]1CCS[C@H]2CCCCN2C1=O]

To a solution of benzyl (4S,10aS)-5-oxooctahydro-2H-pyrido[2,1-b][1,3]thiazepin-4-ylcarbamate (103 mg, 0.308 mmol) in DCM (2 mL) stirred at rt was added iodotrimethylsilane (0.054 mL, 0.40 mmol) dropwise. After addition, the resulting yellowish solution was stirred at rt under argon for 1 hr. Additional TMSI (0.054 mL, 0.40 mmol) was added. The yellowish reaction mixture stirred for an additional 1 hr. The reaction was quenched by addition of a drop of 1 N aqueous HCl and then diluted with EtOAc. The organic layer extracted with aqueous 1 N HCl (2×2.5 mL). The combined HCl extracts were washed with EtOAc and basified with 1 N aqueous NaOH solution to pH 9-10. The aqueous solution was extracted with DCM (3×10 mL). The combined DCM extracts were washed with saturated aqueous NaCl, dried over $Na_2SO_4$, filtered and concentrated to give (4S,10aS)-4-aminohexahydro-2H-pyrido[2,1-b][1,3]thiazepin-5(7H)-one (50.8 mg, 0.254 mmol, 82% yield) as a colorless oil. Anal. Calcd. for $C_9H_{16}N_2OS$ m/z 200.3. found: 201.3 (M+H)$^+$; $^1$H NMR (400 MHz, CDCl$_3$) δ ppm 5.33 (t, J=3.8 Hz, 1H), 4.37-4.24 (m, 1H), 4.07 (dd, J=10.0, 4.5 Hz, 1H), 3.06-2.87 (m, 2H), 2.63 (ddd, J=14.5, 7.5, 3.2 Hz, 1H), 2.27-2.15 (m, 1H), 2.03-1.92 (m, 2H), 1.92-1.77 (m, 3H), 1.76-1.41 (m, 4H).

Intermediate 41: (S)-3-Amino-1-(pyridin-3-ylmethyl)azepan-2-one

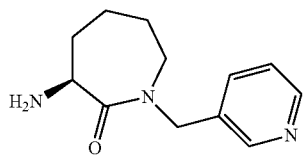 [SMILES: N[C@H]1CCCCN(Cc2cccnc2)C1=O]

A: (S)-tert-Butyl 2-oxo-1-(pyridin-3-ylmethyl)azepan-3-ylcarbamate

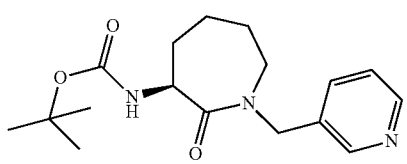 [SMILES: CC(C)(C)OC(=O)N[C@H]1CCCCN(Cc2cccnc2)C1=O]

To a stirred solution of (S)-tert-butyl 2-oxoazepan-3-ylcarbamate (230 mg, 1.01 mmol) in DMF (1 mL) was added sodium hydride (129 mg, 3.22 mmol) at rt under argon. The reaction mixture was stirred at rt for 10 min followed by the addition of 3-(chloromethyl)pyridine hydrochloride (197 mg, 1.54 mmol) at rt. The reaction was allowed to stir at rt for an additional 30 min. The reaction was quenched with water and extracted with EtOAc. The organic layer was washed with water, saturated aqueous NaCl, dried over MgSO$_4$, filtered and concentrated. The crude product was purified using silica gel chromatography (ISCO system) eluting with a gradient of 0-80% EtOAc/Hex to give (S)-tert-butyl 2-oxo-1-(pyridin-3-ylmethyl)azepan-3-ylcarbamate (155 mg, 0.485 mmol, 48.2% yield) as colorless oil. Anal. Calcd. for $C_{17}H_{25}N_3O_3$ m/z 319.4. found: 320.2 (M+H)$^+$.

B: (S)-3-Amino-1-(pyridin-3-ylmethyl)azepan-2-one

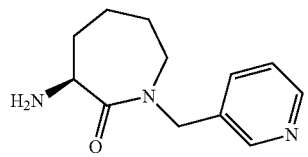 [SMILES: N[C@H]1CCCCN(Cc2cccnc2)C1=O]

In a round bottomed flask, to a stirred solution of (S)-tert-butyl 2-oxo-1-(pyridin-3-ylmethyl)azepan-3-ylcarbamate (150 mg, 0.470 mmol) in DCM (3 mL) was added 2,2,2-trifluoroacetic acid (0.186 mL, 2.35 mmol) at rt under argon. The reaction mixture was stirred at rt for 4 hr. The reaction mixture was concentrated and the residue was dried under vacuum to give (S)-3-amino-1-(pyridin-3-ylmethyl)azepan-2-one (110 mg, 0.502 mmol, 100% yield). Anal. Calcd. for $C_{12}H_{17}N_3O$ m/z 219.3. found: 220.3 (M+H)$^+$.

Intermediate 42: (S)-3-Amino-1-benzylazepan-2-one hydrochloride

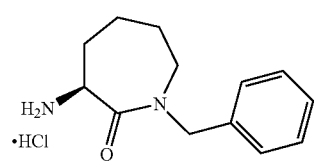 [SMILES: Cl ; N[C@H]1CCCCN(Cc2ccccc2)C1=O]

A: (S)-tert-Butyl 1-benzyl-2-oxoazepan-3-ylcarbamate

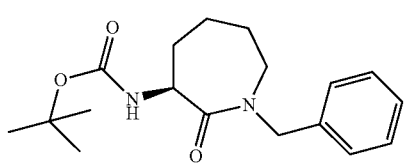 [SMILES: CC(C)(C)OC(=O)N[C@H]1CCCCN(Cc2ccccc2)C1=O]

To a stirring solution of (S)-tert-butyl 2-oxoazepan-3-ylcarbamate (250 mg, 1.10 mmol) in DMF (1 mL) was added a solution of 20 weight % LiHMDS in THF (870 mg, 1.04 mmol) at −70° C. under argon. The reaction mixture was stirred at −70° C. for 10 min followed by the addition of (bromomethyl)benzene (0.137 mL, 1.15 mmol) at the same temperature. Then the reaction was allowed to stir at rt for 30 min. The reaction was quenched with water and extracted with EtOAc. The organic layer was washed with water, saturated aqueous NaCl, dried over MgSO$_4$, filtered and concentrated. The crude product was purified using silica gel chromatography (ISCO system) eluting with a gradient of 0-80% EtOAc/Hex to give (S)-tert-butyl 1-benzyl-2-oxoazepan-3-ylcarbamate (300 mg, 0.942 mmol, 86% yield) as a colorless oil. Anal. Calcd. for $C_{18}H_{26}N_2O_3$ m/z 318.4. found: 319.3 (M+H)$^+$.

B: (S)-3-Amino-1-benzylazepan-2-one hydrochloride

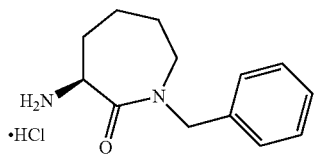 [SMILES: Cl ; N[C@H]1CCCCN(Cc2ccccc2)C1=O]

To a solution of (S)-tert-butyl 1-benzyl-2-oxoazepan-3-ylcarbamate (340 mg, 1.07 mmol) in DCM (5 mL) was added solution of 4 M HCl in dioxane (0.243 mL, 0.971 mmol) at rt under argon. The reaction was allowed to stir at rt for 5 hr. The reaction mixture was concentrated and dried under vacuum to give (S)-3-amino-1-benzylazepan-2-one hydrochloride (210 mg, 0.962 mmol, 99% yield) as a white solid. Anal. Calcd. for $C_{13}H_{18}N_2O$ m/z 218.3. found: 219.3 (M+H)$^+$.

Intermediate 43: (S)-3-Amino-1-(3-methoxybenzyl)azepan-2-one

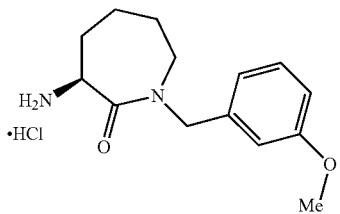 [SMILES: Cl ; COc1cccc(CN2CCCC[C@H](N)C2=O)c1]

(S)-3-Amino-1-(3-methoxybenzyl)azepan-2-one (175 mg, 0.705 mmol) was synthesized as described for the preparation of Intermediate 42 using 1-(bromomethyl)-3-methoxybenzene in step A. Anal. Calcd. for $C_{14}H_{20}N_2O_2$ m/z 248.3. found: 249.3 (M+H)$^+$.

Intermediate 44: (S,Z)-3-Amino-1-benzyl-3,4,7,8-tetrahydroazocin-2(1H)-one

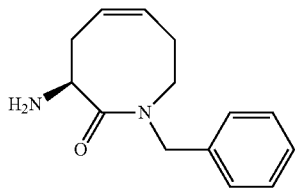 [SMILES: N[C@H]1C/C=C\CCN(Cc2ccccc2)C1=O]

A: (E)-N-Benzylidenebut-3-en-1-amine

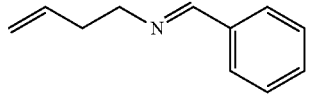

To a solution of but-3-en-1-amine (580 mg, 8.16 mmol) in anhydrous MeOH (20 mL) was added a dozen molecular sieve beads. Benzaldehyde (865 mg, 8.16 mmol) was added dropwise. The mixture was stirred at rt for 18 hr, The reaction mixture was filtered, and the filtrate was concentrated to dryness to give (E)-N-benzylidenebut-3-en-1-amine (1.30 gm, 8.16 mmol, 99% yield) as a pale yellow oil. $^1$H NMR (400 MHz, CDCl$_3$) δ ppm 8.28 (s, 1H), 7.76-7.70 (m, 2H), 7.41 (dd, J=5.0, 1.8 Hz, 3H), 5.86 (ddt, J=17.1, 10.2, 6.8 Hz, 1H), 5.20-4.97 (m, 2H), 3.69 (td, J=7.2, 1.2 Hz, 2H), 2.47 (td, J=7.1, 1.1 Hz, 2H).

B: N-Benzylbut-3-en-1-amine

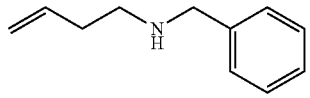

To a solution of (E)-N-benzylidenebut-3-en-1-amine (1.298 gm, 8.15 mmol) in EtOH (25 mL) cooled to 0° C. was added NaBH$_4$ (0.324 g, 8.56 mmol) portionwise over 40 min. After addition, the reaction mixture was stirred at rt for 3 hr. The reaction mixture was filtered and the filtrate was concentrated to give a white semi-solid residue. To the residue 50 mL of DCM was added. The resulting milky solution was stirred for 15 min and then was filtered. The obtained clear filtrate was concentrated to give N-benzylbut-3-en-1-amine (1.30 g, 6.85 mmol, 84% yield) as a pale yellow oil. Anal. Calcd. for $C_{11}H_{15}N$ m/z 161.2. found: 162.0 (M+H)$^+$; $^1$H NMR (400 MHz, CDCl$_3$) δ ppm 7.42-7.21 (m, 5H), 5.79 (ddt, J=17.1, 10.2, 6.9 Hz, 1H), 5.13-4.99 (m, 2H), 3.80 (d, J=6.8 Hz, 2H), 3.29 (q, J=6.8 Hz, 1H), 2.71 (q, J=6.9 Hz, 1H), 2.29 (q, J=6.8 Hz, 1H), 1.25 (dt, J=9.1, 7.1 Hz, 1H), 1.12-1.03 (m, 1H).

C: (S)-tert-Butyl 1-(benzyl(but-3-enyl)amino)-1-oxopent-4-en-2-ylcarbamate

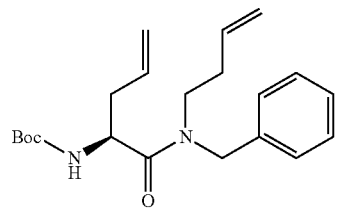 [SMILES: C=CCCN(Cc1ccccc1)C(=O)[C@H](CC=C)NC(=O)OC(C)(C)C]

To a solution of (S)-2-(tert-butoxycarbonylamino)pent-4-enoic acid (400 mg, 1.86 mmol), N-benzylbut-3-en-1-amine (449 mg, 2.79 mmol) in DMF (5 mL) was added EDC (410 mg, 2.14 mmol), HOBt (370 mg, 2.42 mmol) and followed by TEA (0.259 mL, 1.858 mmol). The reaction was stirred at rt for 3 days. The reaction was diluted with EtOAc and washed with water (2×), 1 M aqueous KHSO$_4$ (2×), saturated aqueous NaHCO$_3$ (2×) and saturated aqueous NaCl. The organic layer was separated, dried over Na$_2$SO$_4$, filtered and concentrated. The crude product was purified using silica gel chromatography (ISCO system) eluting with a gradient of 0-60% EtOAc/Hex to give (S)-tert-butyl 1-(benzyl(but-3-enyl)amino)-1-oxopent-4-en-2-ylcarbamate (270 mg, 0.753 mmol, 40.5% yield). Anal. Calcd. for C$_{21}$H$_{30}$N$_2$O$_3$ m/z 358.4. found: 359.1 (M+H)$^+$; $^1$H NMR (400 MHz, CDCl$_3$) δ ppm 7.43-7.13 (m, 5H), 5.85-5.62 (m, 2H), 5.40-5.27 (m, 1H), 5.19-4.97 (m, 3H), 4.87 and 4.37 (d, J=14.9 Hz, 1H), 4.76-4.51 (m, 2H), 3.59-3.22 (m, 3H), 2.39 (ddq, J=25.6, 21.3, 7.1 Hz, 4H), 1.44 and 1.42 (s, 9H).

D: (S,Z)-tert-Butyl 1-benzyl-2-oxo-1,2,3,4,7,8-hexahydroazocin-3-ylcarbamate

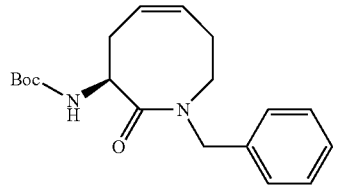 [SMILES: CC(C)(C)OC(=O)N[C@H]1C/C=C\CCN(Cc2ccccc2)C1=O]

A solution of (S)-tert-butyl 1-(benzyl(but-3-enyl)amino)-1-oxopent-4-en-2-ylcarbamate (255 mg, 0.711 mmol) in ClCH$_2$CH$_2$Cl (120 mL) was degassed with argon for 5 min. Then, the Grubbs II catalyst (30 mg, 0.036 mmol) was added. The reaction mixture was stirred at 55-60° C. under argon for 13 hr. The reaction mixture was then cooled to rt and concentrated. The brownish residue was purified using silica gel chromatography (ISCO system) eluting with a gradient of 0-30% EtOAc/Hex to give (S,Z)-tert-butyl 1-benzyl-2-oxo-1,2,3,4,7,8-hexahydroazocin-3-ylcarbamate (110 mg, 0.333 mmol, 46.8% yield) as a colorless oil. $^1$H NMR (400 MHz, CDCl$_3$) δ ppm 7.36-7.19 (m, 5H), 5.95 (d, J=6.5 Hz, 1H), 5.75-5.65 (m, 1H), 5.49-5.39 (m, 1H), 4.96 (d, J=14.8 Hz, 1H), 4.88 (q, J=6.8 Hz, 1H), 4.17 (d, J=14.9 Hz, 1H), 3.89-3.75 (m, 1H), 3.17 (dt, J=15.3, 5.8 Hz, 1H), 2.94-2.83 (m, 1H), 2.51-2.39 (m, 1H), 2.38-2.25 (m, 2H), 1.46 (s, 9H).

E: (S,Z)-3-Amino-1-benzyl-3,4,7,8-tetrahydroazocin-2(1H)-one

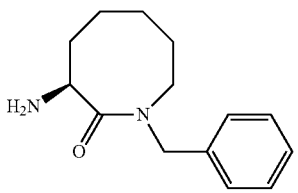

To a solution of (S,Z)-tert-butyl 1-benzyl-2-oxo-1,2,3,4,7,8-hexahydroazocin-3-ylcarbamate (10 mg, 0.030 mmol) in DCM (0.2 mL) at rt was added TFA (0.2 mL). The clear solution was stirred at rt for 40 min. The reaction mixture was concentrated and dried in vacuum to give (S,Z)-3-amino-1-benzyl-3,4,7,8-tetrahydroazocin-2(1H)-one (7.0 mg, 0.030 mmol, 100% yield) as an oil. Anal. Calcd. for C$_{14}$H$_{18}$N$_2$O m/z 230.3. found: 231.1 (M+H)$^+$.

Intermediate 45: (S)-3-Amino-1-benzylazocan-2-one trifluoroacetate

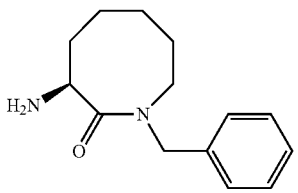 [SMILES: N[C@H]1CCCCCN(Cc2ccccc2)C1=O]

A: (S)-tert-Butyl 1-benzyl-2-oxoazocan-3-ylcarbamate

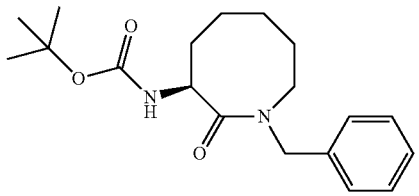 [SMILES: CC(C)(C)OC(=O)N[C@H]1CCCCCN(Cc2ccccc2)C1=O]

A suspension of (S,Z)-tert-butyl 1-benzyl-2-oxo-1,2,3,4,7,8-hexahydroazocin-3-ylcarbamate (86 mg, 0.26 mmol) and 5% Pd/C (15 mg) in EtOAc (1 mL) was stirred under a hydrogen balloon for 1 hr. The reaction mixture was filtered and the filtrate was concentrated and dried under high vacuum to afford (S)-tert-butyl 1-benzyl-2-oxoazocan-3-ylcarbamate (86 mg, 0.26 mmol, 99% yield) as a colorless oil. $^1$H NMR (400 MHz, CDCl$_3$) δ ppm 7.42-7.14 (m, 5H), 5.71 (d, J=7.5 Hz, 1H), 5.17 (d, J=14.7 Hz, 1H), 4.72 (t, J=9.4 Hz, 1H), 4.02 (d, J=14.7 Hz, 1H), 3.75 (t, J=14.2 Hz, 1H), 3.17 (d, J=15.7 Hz, 1H), 2.18-1.98 (m, 1H), 1.82-1.34 (m, 7H), 1.47 (s, 9H).

B: (S)-3-Amino-1-benzylazocan-2-one trifluoroacetate

To a solution of (S)-tert-butyl 1-benzyl-2-oxoazocan-3-ylcarbamate (9.0 mg, 0.027 mmol) in DCM (0.2 mL) at rt was added TFA (0.2 mL). The clear solution was stirred at rt for 1 hr. The reaction mixture was concentrated and dried under vacuum to give (S)-3-Amino-1-benzylazocan-2-one trifluoroacetate (6.3 mg, 0.027 mmol, 100% yield) as a colorless oil. Anal. Calcd. for $C_{14}H_{20}N_2O$ m/z 232.3. found: 233.1 $(M+H)^+$.

Intermediate 46: (2R,5R)-2-Benzyl-5-(2-tert-butoxy-2-oxoethyl)hexanedioic acid

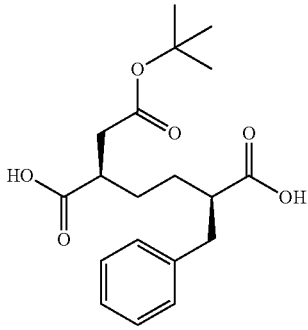 [SMILES: CC(C)(C)OC(=O)C[C@@H](CC[C@H](Cc1ccccc1)C(=O)O)C(=O)O]

(2R,5R)-2-Benzyl-5-(2-tert-butoxy-2-oxoethyl)hexanedioic acid (33 mg, 0.094 mmol) was synthesized as described for the preparation of Intermediate 7 using tert-butyl bromoacetate in step A.

Intermediate 47: (S)-3-Amino-1-(3-chlorobenzyl)azepan-2-one hydrochloride

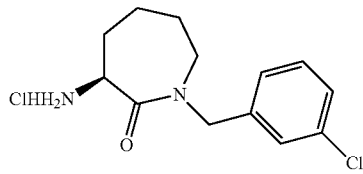

(S)-3-Amino-1-(3-chlorobenzyl)azepan-2-one hydrochloride (190 mg, 0.657 mmol) was synthesized as described for the preparation of Intermediate 42 using 1-(bromomethyl)-3-chlorobenzene in step A.

Intermediate 48: (S)-3-Amino-1-(2-chlorobenzyl)azepan-2-one hydrochloride

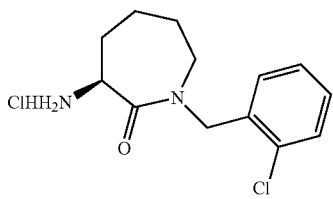

(S)-3-Amino-1-(2-chlorobenzyl)azepan-2-one hydrochloride (270 mg, 0.934 mmol) was synthesized as described for the preparation of Intermediate 42 using 1-(bromomethyl)-2-chlorobenzene in step A. Anal. Calcd. for $C_{18}H_{25}ClN_2O_3$ m/z 352.8. found: 353.2 $(M+H)^+$.

Intermediate 49: (S)-3-Amino-1-(3-chlorophenyl)azepan-2-one hydrochloride

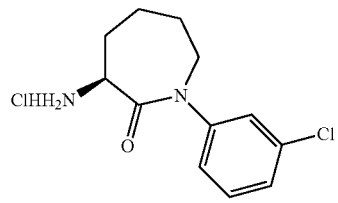

A: (S)-tert-Butyl 1-(3-chlorophenyl)-2-oxoazepan-3-ylcarbamate

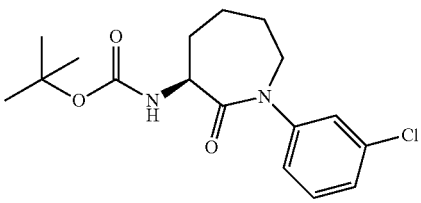 [SMILES: CC(C)(C)OC(=O)N[C@H]1CCCCN(c2cccc(Cl)c2)C1=O]

To a stirred solution of (S)-tert-butyl 2-oxoazepan-3-ylcarbamate (400 mg, 1.75 mmol) in DCM (7.5 mL) was added TEA (0.488 mL, 3.50 mmol) followed by copper (II) acetate (477 mg, 2.63 mmol) and 3-chlorophenylboronic acid (548 mg, 3.50 mmol) at rt under argon. Then, activated molecular sieves (~1 gm) were added. The reaction mixture was stirred at rt for 36 hr. The reaction mixture was filtered through CELITE®. The filtrate was concentrated. The residue was purified using silica gel chromatography (ISCO system) eluting with a gradient of 0-100% EtOAc/Hex to give (S)-tert-butyl 1-(3-chlorophenyl)-2-oxoazepan-3-ylcarbamate (60.0 mg, 0.177 mmol, 10.1% yield) as white solid. Anal. Calcd. for $C_{17}H_{23}ClN_2O_3$ m/z 338.8. found: 339.1 $(M+H)^+$.

B: (S)-3-Amino-1-(3-chlorophenyl)azepan-2-one hydrochloride

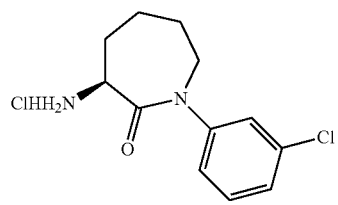

To a stirred solution of (S)-tert-butyl 1-(3-chlorophenyl)-2-oxoazepan-3-ylcarbamate (35 mg, 0.10 mmol) in DCM (2 mL) was added 4.0 M HCl in dioxane (0.258 mL, 1.03 mmol) at rt under argon. The reaction was stirred at rt for 6 hr. The reaction mixture was concentrated and dried under vacuum to give (S)-3-amino-1-(3-chlorophenyl)azepan-2-one hydrochloride (27 mg, 0.098 mmol, 95% yield) as white solid. Anal. Calcd. for $C_{12}H_{15}ClN_2O$ m/z 238.2. found: 239.1 $(M+H)^+$.

Intermediate 50: (S)-3-Amino-1-(4-chlorophenyl) azepan-2-one hydrochloride

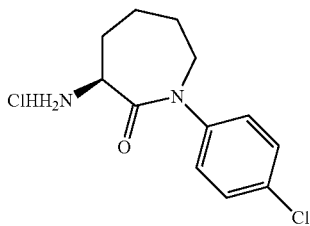

(S)-3-Amino-1-(4-chlorophenyl)azepan-2-one hydrochloride (35 mg, 0.127 mmol) was synthesized as described for the preparation of Intermediate 49 using 4-chlorophenylboronic acid in step A. Anal. Calcd. for $C_{12}H_{15}ClN_2O$ m/z 238.8. found: 239.2 (M+H)$^+$.

Intermediate 51: (S,Z)-3-Amino-1-benzyl-3,4-dihydro-1H-azepin-2(7H)-one

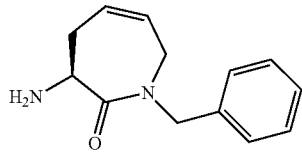 [SMILES: N[C@H]1CC=CCN(Cc2ccccc2)C1=O]

(S,Z)-3-Amino-1-benzyl-3,4-dihydro-1H-azepin-2(7H)-one (6.15 mg, 0.028 mmol) was synthesized as described for the preparation of Intermediate 44 using prop-2-en-1-amine in step A. Anal. Calcd. for $C_{13}H_{16}N_2O$ m/z 216.2. found: 217.0 (M+H)$^+$.

Intermediate 52: (S,Z)-3-Amino-1-phenyl-3,4-dihydro-1H-azepin-2(7H)-one trifluoroacetate

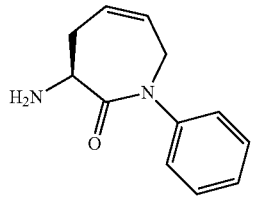 [SMILES: N[C@H]1CC=CCN(c2ccccc2)C1=O]

A: (S)-tert-Butyl 1-(allyl(phenyl)amino)-1-oxopent-4-en-2-ylcarbamate

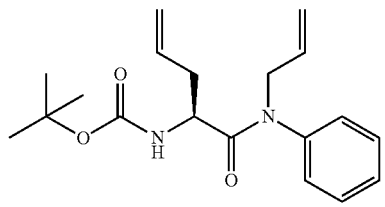 [SMILES: C=CC[C@H](NC(=O)OC(C)(C)C)C(=O)N(CC=C)c1ccccc1]

A solution of N-propylphosphonic acid anhydride cyclic trimer (50% reagent in EtOAc solution, 1.26 mL, 2.14 mmol) was added to a degassed solution of (S)-2-(tert-butoxycarbonylamino)pent-4-enoic acid (230 mg, 1.07 mmol), N-allylaniline (142 mg, 1.07 mmol), and Hunig's Base (0.560 mL, 3.21 mmol) at 0° C. The reaction mixture was stirred under argon for 2 min at 0° C. and then warmed to rt and stirred for 1 hr. The reaction mixture was diluted with EtOAc, washed with saturated aqueous NaHCO$_3$ and saturated aqueous NaCl, dried over Na$_2$SO$_4$, filtered and concentrated. The crude product was purified using silica gel chromatography (ISCO system) eluting with a gradient of 0-30% EtOAc/Hex to give (S)-tert-butyl 1-(allyl(phenyl)amino)-1-oxopent-4-en-2-ylcarbamate (195 mg, 0.590 mmol, 55.2% yield) as a colorless oil. $^1$H NMR (400 MHz, CDCl$_3$) δ ppm 7.43 (t, J=7.4 Hz, 2H), 7.36 (t, J=7.3 Hz, 1H), 7.24 (d, J=7.5 Hz, 2H), 5.91-5.78 (m, 1H), 5.63-5.49 (m, 1H), 5.23 (d, J=8.4 Hz, 1H), 5.18-5.05 (m, 2H), 5.05-4.94 (m, 2H), 4.43-4.19 (m, 3H), 2.33-2.23 (m, 1H), 2.20-2.08 (m, 1H), 1.45 (s, 9H).

B: (S,Z)-tert-Butyl 2-oxo-1-phenyl-2,3,4,7-tetrahydro-1H-azepin-3-ylcarbamate

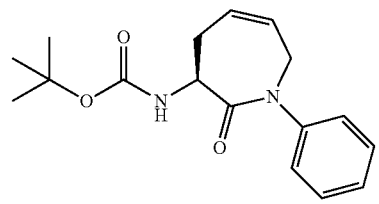 [SMILES: CC(C)(C)OC(=O)N[C@H]1CC=CCN(c2ccccc2)C1=O]

A solution of (S)-tert-butyl 1-(allyl(phenyl)amino)-1-oxopent-4-en-2-ylcarbamate (0.98 g, 2.97 mmol) in ClCH$_2$CH$_2$Cl (400 mL) was degassed with argon for 5 min. Then, Grubbs II catalyst (0.126 g, 0.148 mmol) was added. The reaction was stirred at 60° C. under argon for 16 hr. The reaction mixture was cooled to rt and concentrated to dryness. The brownish residue was purified using silica gel chromatography (ISCO system) eluting with a gradient of 0-30% EtOAc/Hex to give (S,Z)-tert-butyl 2-oxo-1-phenyl-2,3,4,7-tetrahydro-1H-azepin-3-ylcarbamate (0.787 g, 2.60 mmol, 88% yield) as a white solid. $^1$H NMR (400 MHz, CDCl$_3$) δ ppm 7.42-7.34 (m, 2H), 7.30-7.24 (m, 1H), 7.24-7.19 (m, 2H), 6.06-5.66 (m, 2H), 5.23-5.10 (m, 1H), 4.79 (dd, J=21.1, 17.3 Hz, 1H), 3.85-3.71 (m, 1H), 2.85-2.70 (m, 1H), 2.43-2.29 (m, 1H), 1.55-1.43 (m, 10H).

C: (S,Z)-3-Amino-1-phenyl-3,4-dihydro-1H-azepin-2(7H)-one trifluoroacetate

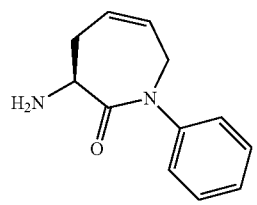 [SMILES: N[C@H]1CC=CCN(c2ccccc2)C1=O]

To a round bottom flask was added (S,Z)-tert-butyl 2-oxo-1-phenyl-2,3,4,7-tetrahydro-1H-azepin-3-ylcarbamate (85 mg, 0.28 mmol), DCM (1 mL) and TFA (1 mL). The reaction mixture was stirred at rt for 2 hr. The reaction mixture was concentrated and dried under high vacuum for 1 h to afford (S,Z)-3-amino-1-phenyl-3,4-dihydro-1H-azepin-2(7H)-one, trifluoroacetate (87 mg, 0.28 mmol, 98% yield) as an oil. Anal. Calcd. for $C_{12}H_{14}N_2O$ m/z 202.2. found: 203.1 $(M+H)^+$.

Intermediate 53: (7S,10aR,Z)-7-Amino-1,2,3,4,7,8-hexahydropyrido[1,2-a]azepin-6(10aH)-one hydrochloride

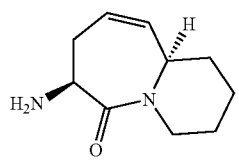 [SMILES: N[C@H]1CC=C[C@H]2CCCCN2C1=O]

A: (R)-tert-Butyl 2-(methoxy(methyl)carbamoyl)piperidine-1-carboxylate

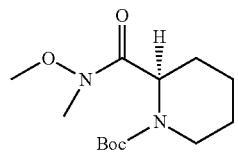 [SMILES: CON(C)C(=O)[C@H]1CCCCN1C(=O)OC(C)(C)C]

N,O-dimethylhydroxylamine hydrochloride (2.45 gm, 25.1 mmol) was added to a solution of (R)-1-(tert-butoxycarbonyl)piperidine-2-carboxylic acid (4.80 gm, 25.1 mmol) in DCM (65 mL). TEA (7.41 gm, 73.3 mmol) was then added followed by PyBOP (11.91 mg, 23.03 mmol). The light yellow reaction mixture was stirred at rt for 3 days. The reaction mixture was diluted with DCM (250 mL) and poured into a separatory funnel containing aqueous 1 N HCl (40 mL). The organic phase was isolated, washed with saturated NaHCO₃ (2×40 mL) and saturated aqueous NaCl (40 mL), dried over MgSO₄, filtered and concentrated. The crude product was purified using silica gel chromatography (ISCO system) eluting with a gradient of 0-100% EtOAc/Hex to give (R)-tert-butyl 2-(methoxy(methyl)carbamoyl)piperidine-1-carboxylate (5.57 gm, 20.5 mmol, 98% yield) as a colorless oil. $^1$H NMR (400 MHz, CDCl₃) δ ppm 5.15-4.84 (1H, m), 4.05-3.85 (1H, m), 3.77 (3H, s), 3.55-3.35 (1H, m), 3.19 (3H, s), 1.99 (1H, d, J=13.7 Hz), 1.77-1.56 (3H, m), 1.44 (11H, s).

B: (R)-tert-Butyl 2-formylpiperidine-1-carboxylate

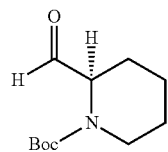

LiAlH₄ (110 mg, 2.89 mmol) was added in portions to a 0° C. solution of (R)-tert-butyl 2-(methoxy(methyl)carbamoyl)piperidine-1-carboxylate (525 mg, 1.93 mmol) in ether (9 mL). The reaction mixture was then stirred at rt for 30 min. The reaction mixture was cooled to 0° C. and carefully quenched by dropwise addition of aqueous 5% KHSO₄ (10 mL). The mixture was then extracted with ether (2×15 mL). The organic extracts were combined, washed with 10% aqueous citric acid, 5% aqueous NaHCO₃ and saturated aqueous NaCl. The ether was then dried over MgSO₄, filtered and concentrated to give (R)-tert-butyl 2-formylpiperidine-1-carboxylate (392 mg, 1.84 mmol, 95% yield) of a colorless oil. $^1$H NMR (400 MHz, CDCl₃) δ ppm 9.59 (1H, s), 4.71-4.44 (1H, m), 4.12-3.79 (1H, m), 3.05-2.78 (1H, m), 2.17 (1H, d, J=11.5 Hz), 1.73-1.55 (4H, m), 1.46 (9H, s), 1.34-1.18 (1H, m).

C: (R)-tert-Butyl 2-vinylpiperidine-1-carboxylate)

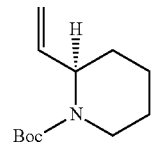

NaHMDS (1.0 M in THF, 18.6 mL, 18.6 mmol) was slowly added over 15 min to a 0° C. solution of methyltriphenylphosphonium bromide (7.19 gm, 20.1 mmol) in THF (65 mL). The yellow mixture was stirred at 0° C. for 45 min and then cooled to −78° C. A solution of (R)-tert-butyl 2-formylpiperidine-1-carboxylate (3.30 gm, 15.5 mmol) in THF (10 mL) was added dropwise. The reaction mixture was then stirred at 0° C. for 1 hr. The reaction was quenched by the addition of saturated aqueous NH₄Cl. The solution was partitioned between EtOAc and water. The aqueous phase was isolated and extracted with EtOAc. All organic phases were combined, dried over MgSO₄, filtered and concentrated. The crude product was purified using silica gel chromatography (ISCO system) eluting with a gradient of 0-100% EtOAc/Hex to give (R)-tert-butyl 2-vinylpiperidine-1-carboxylate (2.53 gm, 12.0 mmol, 77% yield) as an orange oil. Anal. Calcd. for $C_{12}H_{21}N_0$ m/z 211.3. found: 212.0 $(M+H)^+$.

D: (R)-2-Vinylpiperidine hydrochloride

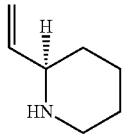

A solution of HCl (4 N in 1,4-dioxane, 11.1 mL, 47.9 mmol) was added to an ice bath cooled reaction vessel containing (R)-tert-butyl 2-vinylpiperidine-1-carboxylate (2.53 gm, 12.0 mmol). The reaction mixture was then stirred at rt for 2 hr. The reaction mixture was concentrated and dried under vacuum to give (R)-2-vinylpiperidine hydrochloride (1.62 gm, 11.0 mmol, 92% yield) as a white solid. $^1$H NMR (400 MHz, CD₃OD) δ ppm 5.89 (1H, ddd, J=17.5, 10.6, 6.6 Hz), 5.50-5.37 (2H, m), 3.74-3.64 (1H, m), 3.38 (1H, d, J=12.6 Hz), 3.09-2.98 (1H, m), 2.04-1.83 (3H, m), 1.74-1.55 (3H, m).

E: tert-Butyl (S)-1-oxo-1-((R)-2-vinylpiperidin-1-yl)pent-4-en-2-ylcarbamate

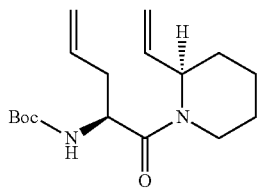 [SMILES: C=CC[C@H](NC(=O)OC(C)(C)C)C(=O)N1CCCC[C@@H]1C=C]

DIPEA (1.801 gm, 13.94 mmol) was slowly added to a 0° C. mixture of (S)-2-(tert-butoxycarbonylamino)pent-4-enoic acid (1.00 gm, 4.65 mmol), (R)-2-vinylpiperidine hydrochloride (0.720 gm, 4.88 mol), EDC (1.02 gm, 5.34 mmol) and HOBt (0.818 gm, 5.34 mmol) in DCM (19 mL). The yellow reaction mixture was then stirred at rt for 3 days. The reaction mixture was concentrated to remove the DCM and the residue was partitioned between EtOAc and 0.5 N aqueous HCl. The organic phase was isolated, washed with saturated aqueous NaHCO$_3$ and saturated aqueous NaCl, dried over MgSO$_4$, filtered and concentrated. The crude product was purified using silica gel chromatography (ISCO system) eluting with a gradient of 0-100% EtOAc/Hex to give tert-butyl (S)-1-oxo-1-((R)-2-vinylpiperidin-1-yl)pent-4-en-2-ylcarbamate (1.00 gm, 3.24 mmol, 69.8% yield) as a colorless oil. Anal. Calcd. for C$_{17}$H$_{28}$N$_2$O$_3$ m/z 308.3. found: 309.0 (M+H)$^+$.

F: tert-Butyl (7S,10aR,Z)-6-oxo-1,2,3,4,6,7,8,10a-octahydropyrido[1,2-a]azepin-7-ylcarbamate

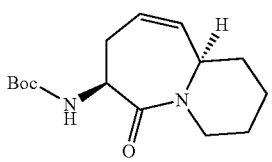 [SMILES: CC(C)(C)OC(=O)N[C@H]1CC=C[C@H]2CCCCN2C1=O]

A solution of tert-butyl (S)-1-oxo-1-((R)-2-vinylpiperidin-1-yl)pent-4-en-2-ylcarbamate (1.00 gm, 3.24 mmol) in DCE (350 mL) was purged with argon for 10 min. Grubbs II catalyst (0.124 gm, 0.146 mmol) was added and the reaction mixture was heated at 60° C. under argon for 18 hr. The reaction mixture was concentrated. The crude product was purified using silica gel chromatography (ISCO system) eluting with a gradient of 0-100% EtOAc/Hex to give tert-butyl (7S,10aR,Z)-6-oxo-1,2,3,4,6,7,8,10a-octahydropyrido[1,2-a]azepin-7-ylcarbamate (653 mg, 2.33 mmol, 71.8% yield) as a solid. Anal. Calcd. for C$_{15}$H$_{24}$N$_2$O$_3$ m/z 280.3. found: 281.0 (M+H)$^+$.

G: (7S,10aR,Z)-7-Amino-1,2,3,4,7,8-hexahydropyrido[1,2-a]azepin-6(10aH)-one hydrochloride

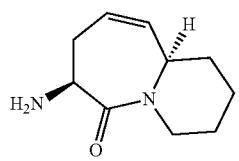

A solution of HCl (4.0 N in 1,4-dioxane, 2.33 mL, 9.32 mmol) was added to a 0° C. solution of tert-butyl (7S,10aR,Z)-6-oxo-1,2,3,4,6,7,8,10a-octahydropyrido[1,2-a]azepin-7-ylcarbamate (653 mg, 2.33 mmol) in 1,4-dioxane (0.93 mL). The reaction mixture was then stirred at rt for 1 hr. The reaction mixture was concentrated and dried under vacuum to give (7S,10aR,Z)-7-amino-1,2,3,4,7,8-hexahydropyrido[1,2-a]azepin-6(10aH)-one hydrochloride (504 mg, 2.33 mmol, 100% yield) as a tan solid. Anal. Calcd. for C$_{10}$H$_{16}$N$_2$O m/z 180.2. found: 181.0 (M+H)$^+$.

Intermediate 54: (7S,10aR)-7-Aminooctahydropyrido[1,2-a]azepin-6(7H)-one hydrochloride

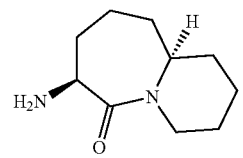

To round bottom flask, 10% Pd/C (35 mg, 0.022 mmol) was added to a solution of (7S,10aR,Z)-7-amino-1,2,3,4,7,8-hexahydropyrido[1,2-a]azepin-6(10aH)-one hydrochloride (3.23 gm, 1.49 mmol) in MeOH (5 mL). A hydrogen atmosphere was introduced via balloon and the reaction mixture was stirred for 3 hr. The reaction mixture was diluted with MeOH and filtered. The filtrate was concentrated and the residue was dried under vacuum to give (7S,10aR)-7-aminooctahydropyrido[1,2-a]azepin-6(7H)-one hydrochloride (299 mg, 1.37 mmol, 92% yield) as a light yellow solid. Anal. Calcd. for C$_{10}$H$_{18}$N$_2$O m/z 182.2. found: 183.0 (M+H)$^+$.

Intermediate 55: (7S,11aR,Z)-7-Amino-3,4,7,8,9,11a-hexahydro-1H-pyrido[1,2-a]azocin-6(2H)-one hydrochloride

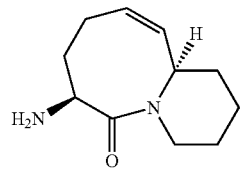 [SMILES: N[C@H]1CC/C=C\[C@H]2CCCCN2C1=O]

(7S,11aR,Z)-7-Amino-3,4,7,8,9,11a-hexahydro-1H-pyrido[1,2-a]azocin-6(2H)-one hydrochloride (538 mg, 2.332 mmol) was synthesized as described for the preparation of Intermediate 53 using (S)-2-(tert-butoxycarbonylamino)hex-5-enoic acid in step E. Anal. Calcd. for C$_{11}$H$_{18}$N$_2$O m/z 194.2. found: 195.0 (M+H)$^+$.

Intermediate 56: (7S,11aS)-7-Aminooctahydro-1H-pyrido[1,2-a]azocin-6(2H)-one hydrogen chloride

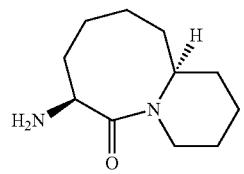

(7S,11aS)-7-Aminooctahydro-1H-pyrido[1,2-a]azocin-6 (2H)-one hydrogen chloride (273 mg, 1.17 mmol) was synthesized as described for the preparation of Intermediate 54 using (7S,11aR,Z)-7-amino-3,4,7,8,9,11a-hexahydro-1H-pyrido[1,2-a]azocin-6(2H)-one hydrochloride. Anal. Calcd. for $C_{11}H_{20}N_2O$ m/z 196.2. found: 197.0 (M+H)$^+$.

Intermediate 57: Benzyl (4S,10aS)-5-oxo-8-(trifluoromethyl)octahydro-2H-pyrido[2,1-b][1,3]thiazepin-4-ylcarbamate

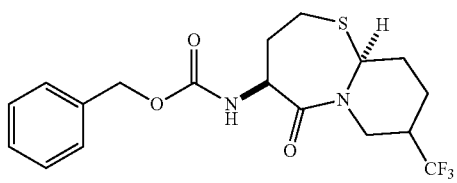

Benzyl (4S,10aS)-5-oxo-8-(trifluoromethyl)octahydro-2H-pyrido[2,1-b][1,3]thiazepin-4-ylcarbamate (465 mg, 1.155 mmol) was synthesized as described for the preparation of Intermediate 40 using 4-(aminomethyl)-5,5,5-trifluoropentan-1-ol in step A. Anal. Calcd. for $C_{18}H_{21}F_3N_2O_3S$ m/z 402.2. found: 403.1 (M+H)$^+$.

Intermediate 58: Benzyl (4S,8S,10aS)-5-oxo-8-(trifluoromethyl)octahydro-2H-pyrido[2,1-b][1,3]thiazepin-4-ylcarbamate

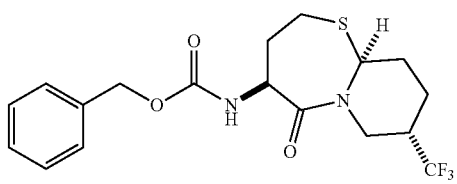 [SMILES: O=C(N[C@H]1CCS[C@H]2CCC(C(F)(F)F)CN2C1=O)OCc1ccccc1]

A diastereomeric mixture of Intermediate 57 (465 mg, 1.16 mmol) was separated using RP prep-HPLC (Method A) to give benzyl (4S,8S,10aS)-5-oxo-8-(trifluoromethyl)octahydro-2H-pyrido[2,1-b][1,3]thiazepin-4-ylcarbamate (135 mg, 0.335 mmol, 29.0% yield) (first eluting diastereomer) as a colorless oil. Anal. Calcd. for $C_{18}H_{21}F_3N_2O_3S$ m/z 402.2. found: 403.0 (M+H)$^+$; $^1$H NMR (400 MHz, CDCl$_3$) δ ppm 7.42-7.28 (m, 5H), 6.29 (d, J=6.2 Hz, 1H), 5.10 (d, J=2.4 Hz, 2H), 5.13-5.07 (m, 1H), 4.67 (ddd, J=10.8, 6.4, 1.9 Hz, 1H), 4.44 (dd, J=14.8, 2.2 Hz, 1H), 3.35-3.23 (m, 2H), 2.77 (ddd, J=14.5, 5.1, 2.9 Hz, 1H), 2.69-2.56 (m, 1H), 2.32 (dddd, J=17.4, 10.4, 5.7, 3.0 Hz, 2H), 2.05-1.94 (m, 1H), 1.87-1.74 (m, 1H), 1.73-1.51 (m, 2H).

Intermediate 59: Benzyl (4S,8R,10aS)-5-oxo-8-(trifluoromethyl)octahydro-2H-pyrido[2,1-b][1,3]thiazepin-4-ylcarbamate

A diastereomer mixture of Intermediate 57 (465 mg, 1.16 mmol) was separated using RP prep-HPLC (Method A) to give benzyl (4S,8R,10aS)-5-oxo-8-(trifluoromethyl)octahydro-2H-pyrido[2,1-b][1,3]thiazepin-4-ylcarbamate (156 mg, 0.388 mmol, 33.5% yield) (later eluting diastereomer) as a colorless oil. Anal. Calcd. for $C_{18}H_{21}F_3N_2O_3S$ m/z 402.2. found: 403.0 (M+H)$^+$; $^1$H NMR (400 MHz, CDCl$_3$) δ ppm 7.41-7.28 (m, 5H), 6.18 (d, J=6.8 Hz, 1H), 5.30-5.21 (m, 1H), 5.10 (d, J=1.4 Hz, 2H), 4.87 (ddd, J=10.3, 6.9, 3.2 Hz, 1H), 4.57 (dd, J=13.4, 4.6 Hz, 1H), 3.22 (ddd, J=14.1, 11.1, 2.7 Hz, 1H), 2.95 (t, J=12.8 Hz, 1H), 2.73 (ddd, J=14.5, 5.9, 3.0 Hz, 1H), 2.42-2.23 (m, 2H), 2.18-1.97 (m, 2H), 1.94-1.84 (m, 1H), 1.83-1.60 (m, 2H).

Intermediate 60: (4S,8S,10aS)-4-Amino-8-(trifluoromethyl)hexahydro-2H-pyrido[2,1-b][1,3]thiazepin-5(7H)-one

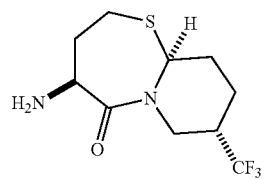 [SMILES: N[C@H]1CCS[C@H]2CC[C@H](C(F)(F)F)CN2C1=O]

To a solution of benzyl (4S,8S,10aS)-5-oxo-8-(trifluoromethyl)octahydro-2H-pyrido[2,1-b][1,3]thiazepin-4-ylcarbamate (101 mg, 0.251 mmol) in DCM (1.2 mL) stirred at rt was added iodotrimethylsilane (150 mg, 0.752 mmol) dropwise. After the addition, the resulting yellowish solution was stirred at rt under argon for 2 hr. The reaction mixture was quenched by the dropwise addition of 1 N aqueous HCl, diluted with EtOAc, and extracted with 1 N aqueous HCl (2×3 mL). The combined HCl extracts were washed with EtOAc (2×). The aqueous layer was then basified with 1 N aqueous NaOH solution to pH 9-10 and extracted with DCM (3×10 mL). The combined DCM extracts were washed with water, saturated aqueous NaCl, dried over Na$_2$SO$_4$, filtered and concentrated to give (4S,8S,10aS)-4-amino-8-(trifluoromethyl)hexahydro-2H-pyrido[2,1-b][1,3]thiazepin-5(7H)-one (45 mg, 0.17 mmol, 66% yield) as a white solid. Anal. Calcd. for $C_{10}H_{15}F_3N_2OS$ m/z 268.2. found: 269.0 (M+H)$^+$; $^1$H NMR (400 MHz, CDCl$_3$) δ ppm 5.14 (t, J=7.2 Hz, 1H), 4.46 (dd, J=14.7, 2.6 Hz, 1H), 3.88 (dd, J=10.5, 2.8 Hz, 1H), 3.30 (dd, J=14.8, 6.6 Hz, 1H), 3.13 (ddd, J=14.2, 11.0, 2.9 Hz, 1H), 2.74 (ddd, J=14.5, 5.9, 3.1 Hz, 1H), 2.66-2.54 (m, 1H), 2.35-2.23 (m, 1H), 2.18 (ddt, J=14.0, 5.8, 2.9 Hz, 1H), 2.08-1.94 (m, 1H), 1.89-1.55 (m, 5H).

Intermediate 61: (4S,8R,10aS)-4-Amino-8-(trifluoromethyl)hexahydro-2H-pyrido[2,1-b][1,3]thiazepin-5(7H)-one

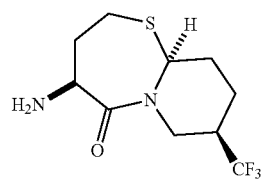 [SMILES: N[C@H]1CCS[C@H]2CC[C@@H](C(F)(F)F)CN2C1=O]

(4S,8R,10aS)-4-Amino-8-(trifluoromethyl)hexahydro-2H-pyrido[2,1-b][1,3]thiazepin-5(7H)-one (50 mg, 0.19 mmol) was synthesized as described for the preparation of Intermediate 60 using benzyl (4S,8R,10aS)-5-oxo-8-(trifluoromethyl)octahydro-2H-pyrido[2,1-b][1,3]thiazepin-4-ylcarbamate. Anal. Calcd. for $C_{10}H_{15}F_3N_2OS$ m/z 268.2. found: 269.0 (M+H)$^+$; $^1$H NMR (400 MHz, CDCl$_3$) δ ppm 5.30 (dd, J=5.3, 3.8 Hz, 1H), 4.60 (dd, J=13.4, 4.3 Hz, 1H), 4.06 (dd, J=10.0, 4.2 Hz, 1H), 3.04 (ddd, J=14.3, 9.9, 3.0 Hz, 1H), 2.91 (t, J=12.8 Hz, 1H), 2.66 (ddd, J=14.6, 7.2, 3.1 Hz, 1H), 2.39-2.16 (m, 2H), 2.05 (dddd, J=14.5, 9.7, 7.8, 4.1 Hz, 2H), 1.94-1.85 (m, 1H), 1.80-1.64 (m, 4H).

Intermediate 62: (S)-3-Amino-1-(2-methoxyphenyl)azepan-2-one trifluoroacetate

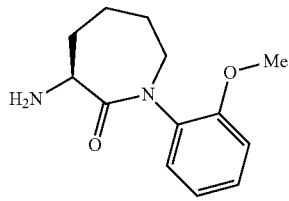 [SMILES: COc1ccccc1N1CCCC[C@H](N)C1=O]

A: (S,Z)-tert-Butyl 1-(2-methoxyphenyl)-2-oxo-2,3,4,7-tetrahydro-1H-azepin-3-ylcarbamate

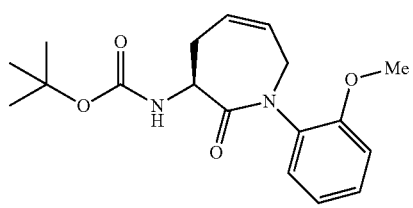 [SMILES: COc1ccccc1N1CC=CC[C@H](NC(=O)OC(C)(C)C)C1=O]

(4S,8R,10aS)-4-Amino-8-(trifluoromethyl)hexahydro-2H-pyrido[2,1-b][1,3]thiazepin-5(7H)-one (30 mg, 0.090 mmol) was synthesized as described for the preparation of Intermediate 52 using N-allyl-2-methoxyaniline in step A. $^1$H NMR (400 MHz, CDCl$_3$) δ ppm 7.32-7.23 (m, 1H), 7.14 (dd, J=8.1, 1.6 Hz, 1H), 7.02-6.89 (m, 2H), 5.94-5.72 (m, 3H), 5.18-5.04 (m, 1H), 4.75 (d, J=17.5 Hz, 1H), 3.79 (s, 3H), 3.53 (dd, J=17.6, 7.1 Hz, 1H), 2.75 (d, J=16.7 Hz, 1H), 2.47-2.32 (m, 1H), 1.46 (s, 9H).

B: (S)-tert-Butyl 1-(2-methoxyphenyl)-2-oxoazepan-3-ylcarbamate

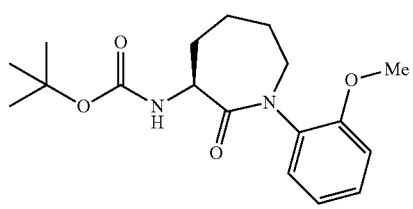 [SMILES: COc1ccccc1N1CCCC[C@H](NC(=O)OC(C)(C)C)C1=O]

A solution of (S,Z)-tert-butyl 1-(2-methoxyphenyl)-2-oxo-2,3,4,7-tetrahydro-1H-azepin-3-ylcarbamate (30 mg, 0.090 mmol) in EtOAc (2 mL) was purged with argon for 5 min. Then, 5% Pd/C (25 mg, 0.24 mmol) was added. The reaction mixture was stirred under a hydrogen balloon for 2 hr. The reaction mixture was filtered and the filtrate was concentrated to afford (S)-tert-butyl 1-(2-methoxyphenyl)-2-oxoazepan-3-ylcarbamate (28 mg, 0.084 mmol, 93% yield) as a foam. Anal. Calcd. for $C_{18}H_{26}N_2O_4$ m/z 334.4. found: 335.1 (M+H)$^+$.

C: (S)-3-Amino-1-(2-methoxyphenyl)azepan-2-one trifluoroacetate

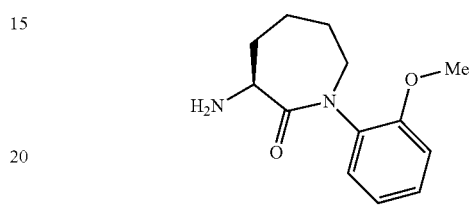

To a round bottom flask was added (S)-tert-butyl 1-(2-methoxyphenyl)-2-oxoazepan-3-ylcarbamate (27 mg, 0.081 mmol), DCM (1 mL) and TFA (1 mL). The reaction mixture was stirred at rt for 2 hr. The reaction mixture was concentrated under reduced pressure and then dried under high vacuum to give (S)-3-amino-1-(2-methoxyphenyl)azepan-2-one trifluoroacetate (28 mg, 0.080 mmol, 100% yield) as an oil.

Intermediate 63: (S,Z)-3-Amino-1-phenyl-1,4,5,8-tetrahydroazocin-2(3H)-one

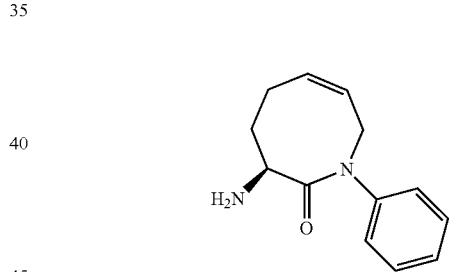

(S,Z)-3-Amino-1-phenyl-1,4,5,8-tetrahydroazocin-2(3H)-one (175 mg, 0.692 mmol) was synthesized as described for the preparation of Intermediate 52 using (S)-2-(tert-butoxycarbonylamino)hex-5-enoic acid in step A. Anal. Calcd. for $C_{13}H_{16}N_2O$ m/z 216.2. found: 217.0 (M+H)$^+$.

Intermediate 64: (S)-3-Amino-1-phenylazocan-2-one

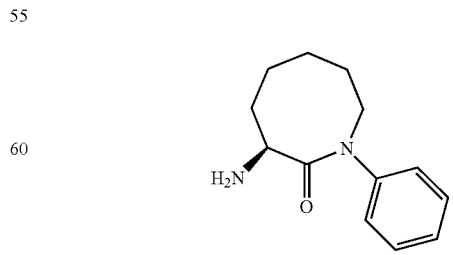

(S)-3-Amino-1-phenylazocan-2-one (87 mg, 0.34 mmol) was synthesized as described for the preparation of Intermediate 54 using (S,Z)-3-amino-1-phenyl-1,4,5,8-tetrahydroazocin-2(3H)-one. Anal. Calcd. for $C_{13}H_{18}N_2O$ m/z 218.2. found: 219.0 $(M+H)^+$.

Intermediate 65: (S)-3-Amino-1-(3-methoxyphenyl)azepan-2-one trifluoroacetate

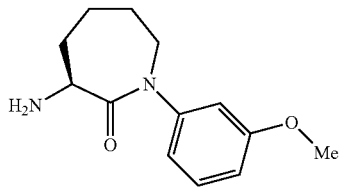 [SMILES: COc1cccc(N2CCCC[C@H](N)C2=O)c1]

(S)-3-Amino-1-(3-methoxyphenyl)azepan-2-one trifluoroacetate (143 mg, 0.411 mmol) was synthesized as described for the preparation of Intermediate 62 using N-allyl-3-methoxyaniline in step A.

Intermediate 66: (4S,7S,10aS)-4-Amino-7-(methoxymethyl)hexahydro-2H-pyrido[2,1-b][1,3]thiazepin-5(7H)-one hydrochloride

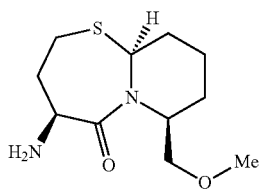 [SMILES: COC[C@@H]1CCC[C@@H]2SCC[C@H](N)C(=O)N12]

A: tert-Butyl (4S,7S,10aS)-7-(hydroxymethyl)-5-oxooctahydro-2H-pyrido[2,1-b][1,3]thiazepin-4-ylcarbamate

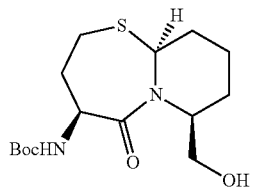 [SMILES: CC(C)(C)OC(=O)N[C@H]1CCS[C@H]2CCC[C@@H](CO)N2C1=O]

$LiBH_4$ (2 M in THF, 1.57 mL, 3.14 mmol) was added dropwise to a 0° C. solution of (4S,7S,10aS)-methyl 4-(tert-butoxycarbonylamino)-5-oxooctahydro-2H-pyrido[2,1-b][1,3]thiazepine-7-carboxylate (750 mg, 2.09 mL) in THF (8 mL). The reaction mixture was then stirred at rt overnight. The reaction mixture was cooled to 0° C. and carefully quenched by slow addition of saturated aqueous $NH_4Cl$. After 10 min of stirring, the mixture was partitioned between EtOAc and water. The organic phase was isolated, washed with saturated aqueous NaCl, dried over $MgSO_4$, filtered and concentrated to give tert-butyl (4S,7S,10aS)-7-(hydroxymethyl)-5-oxooctahydro-2H-pyrido[2,1-b][1,3]thiazepin-4-ylcarbamate (513 mg, 1.55 mmol, 74.2% yield) as a white solid. Anal. Calcd. for $C_{15}H_{26}N_2O_4S$ m/z 330.4. found: 330.9 $(M+H)^+$.

B: tert-Butyl (4S,7S,10aS)-7-(methoxymethyl)-5-oxooctahydro-2H-pyrido[2,1-b][1,3]thiazepin-4-ylcarbamate

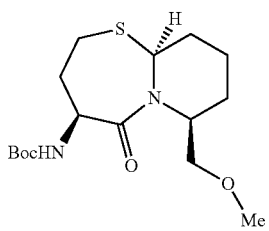 [SMILES: COC[C@@H]1CCC[C@@H]2SCC[C@H](NC(=O)OC(C)(C)C)C(=O)N12]

A solution of potassium tert-butoxide (1 M in THF, 1.55 mL, 1.55 mmol) was added dropwise to a 0° C. solution of tert-butyl (4S,7S,10aS)-7-(hydroxymethyl)-5-oxooctahydro-2H-pyrido[2,1-b][1,3]thiazepin-4-ylcarbamate (513 mg, 1.55 mmol) in THF (5 mL). The reaction mixture turned yellow in color. After 15 min of stirring, iodomethane (441 mg, 3.10 mmol) was added. The ice bath was removed and the reaction mixture was stirred at rt overnight. Water was added to the reaction and the mixture was concentrated to remove most of the THF. The aqueous solution was then extracted with EtOAc. The organic phase was isolated, washed with saturated aqueous NaCl, dried over $MgSO_4$, filtered and concentrated. The crude product was purified using silica gel chromatography (ISCO system) eluting with a gradient of 0-60% EtOAc/Hex to give tert-butyl (4S,7S,10aS)-7-(methoxymethyl)-5-oxooctahydro-2H-pyrido[2,1-b][1,3]thiazepin-4-ylcarbamate (83 mg, 0.24 mmol, 16% yield) as a colorless oil. Anal. Calcd. for $C_{16}H_{28}N_2O_4S$ m/z 344.4. found: 345.1 $(M+H)^+$.

C: (4S,7S,10aS)-4-Amino-7-(methoxymethyl)hexahydro-2H-pyrido[2,1-b][1,3]thiazepin-5(7H)-one hydrochloride

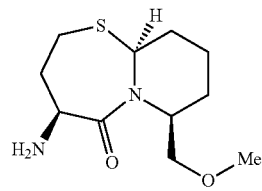 [SMILES: COC[C@@H]1CCC[C@@H]2SCC[C@H](N)C(=O)N12]

A solution of HCl (4.0 N in dioxane, 1 mL) was added to a reaction flask containing tert-butyl (4S,7S,10aS)-7-(methoxymethyl)-5-oxooctahydro-2H-pyrido[2,1-b][1,3]thiazepin-4-ylcarbamate (83 mg, 0.24 mmol). The reaction mixture was then stirred at rt overnight. The reaction mixture was concentrated. Ether was added to the residue. A white solid formed. The mixture was stirred for 5 min and then filtered. The solid was dried under vacuum to give (4S,7S,10aS)-4-Amino-7-(methoxymethyl)hexahydro-2H-pyrido[2,1-b][1,3]thiazepin-5(7H)-one hydrochloride (63 mg, 0.22 mmol, 93% yield) as a white solid. Anal. Calcd. for $C_{11}H_{20}N_2O_2S$ m/z 244.4. found: 245.1 (M+H)$^+$.

Intermediate 67: (S)-3-Amino-1-(pyridin-3-yl)azepan-2-one trifluoroacetate

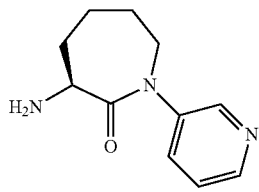 [SMILES: N[C@H]1CCCCN(c2cccnc2)C1=O]

(S)-3-Amino-1-(pyridin-3-yl)azepan-2-one trifluoroacetate (36 mg, 0.11 mmol) was synthesized as described for the preparation of Intermediate 62 using N-allylpyridin-3-amine in step A. Anal. Calcd. for $C_{11}H_{15}N_3O$ m/z 205.2. found: 206.1 (M+H)$^+$.

Intermediate 68: (S,Z)-3-Amino-1-o-tolyl-3,4-dihydro-1H-azepin-2(7H)-one trifluoroacetate

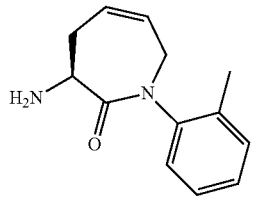

(S,Z)-3-Amino-1-o-tolyl-3,4-dihydro-1H-azepin-2(7H)-one trifluoroacetate (17 mg, 0.051 mmol) was synthesized as described for the preparation of Intermediate 52 using N-allyl-2-methylaniline in step A. Anal. Calcd. for $C_{13}H_{16}N_2O$ m/z 216.2. found: 217.1 (M+H)$^+$.

Intermediate 69: (S)-3-Amino-1-o-tolylazepan-2-one trifluoroacetate

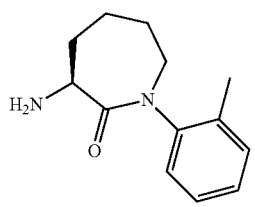 [SMILES: Cc1ccccc1N1CCCC[C@H](N)C1=O]

(S)-3-Amino-1-o-tolylazepan-2-one trifluoroacetate (17 mg, 0.051 mmol) was synthesized as described for the preparation of Intermediate 62 using N-allyl-2-methylaniline in step A. Anal. Calcd. for $C_{13}H_{18}N_2O$ m/z 218.2. found: 219.1 (M+H)$^+$.

Intermediate 70: (2R,5R)-2,5-Dibenzyl-6-((S)-1-(2-methoxyphenyl)-2-oxoazepan-3-ylamino)-6-oxohexanoic acid

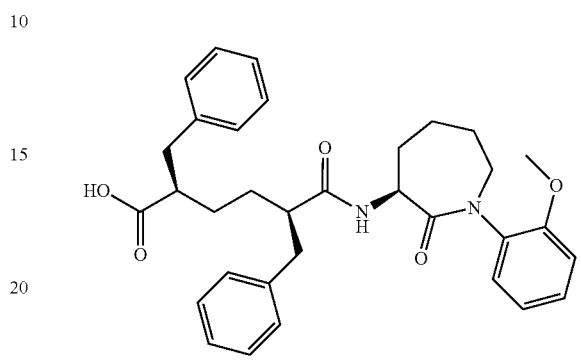

DIC (302 mg, 2.39 mmol) was added dropwise over several minutes to a 0° C. solution of (2R,5R)-2,5-dibenzylhexanedioic acid (744 mg, 2.28 mmol) in DCM (24 mL)/DMF (4 mL). The colorless reaction mixture was then stirred at rt overnight. The reaction mixture was concentrated to remove DCM. Then (S)-3-amino-1-(2-methoxyphenyl)azepan-2-one, HCl (647 mg, 2.39 mmol) was added to the DMF solution followed by TEA (577 mg, 5.70 mmol). The mixture was stirred at rt for 2.5 hr. The reaction mixture was partitioned between a 1:2 mixture of EtOAc and saturated aqueous NH$_4$Cl. The organic phase was isolated, washed with saturated aqueous NaCl, dried over MgSO$_4$, filtered and concentrated. The crude product was purified by RP prep-HPLC (Method A) give (2R,5R)-2,5-dibenzyl-6-((S)-1-(2-methoxyphenyl)-2-oxoazepan-3-ylamino)-6-oxohexanoic acid (500 mg, 0.921 mmol, 40.4% yield) as a white solid Anal. Calcd. for $C_{33}H_{38}N_2O_5$ m/z 542.6. found: 543.3 (M+H)$^+$.

Intermediate 71: (2R,5R)-2,5-Dibenzyl-6-oxo-6-((S)-2-oxo-1-o-tolylazepan-3-ylamino)hexanoic acid

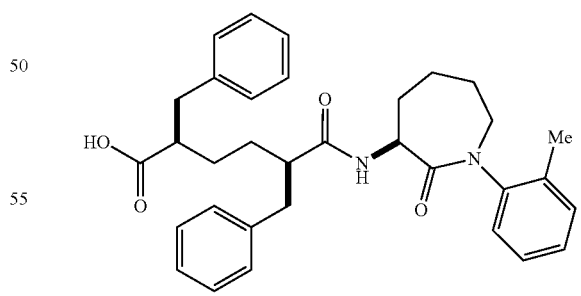

(2R,5R)-2,5-Dibenzyl-6-oxo-6-((S)-2-oxo-1-o-tolylazepan-3-ylamino)hexanoic acid (65 mg, 0.12 mmol) was synthesized as described for the preparation of Intermediate 70 using (S)-3-amino-1-o-tolylazepan-2-one. Anal. Calcd. for $C_{33}H_{38}N_2O_4$ m/z 526.4. found: 527.4 (M+H)$^+$; $^1$H NMR (400 MHz, CDCl$_3$) δ ppm 7.37-6.84 (m, 16H), 4.84-4.72 (m, 1H), 4.01-3.78 (m, 1H), 3.51 and 3.28 (dd, J=15.0, 4.8 Hz, 1H), 3.04-2.81 (m, 2H), 2.79-2.61 (m, 3H), 2.50-2.37 (m, 1H), 2.18 (s, 1H), 2.13 (s, 2H), 2.03-1.44 (m, 10H).

Intermediate 72: (4S,7R,10aS)-4-Amino-7-methyl-hexahydro-2H-pyrido[2,1-b][1,3]thiazepin-5(7H)-one

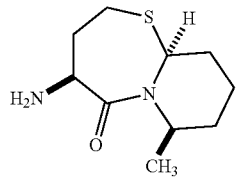

A: (R)-3-(tert-Butoxycarbonylamino)butanoic acid

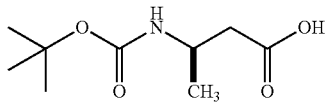

To a stirred suspension of (R)-3-aminobutanoic acid (2.415 g, 23.42 mmol) in dioxane (15 mL) and water (15.00 mL) was added TEA (4.90 mL, 35.1 mmol) dropwise. To the resulting light brown solution cooled at 0° C. was added portionwise di-tert-butyl carbonate (4.69 g, 26.9 mmol). The mixture was then stirred at rt for 16 hr. The reaction mixture was partitioned between water (80 mL) and EtOAc (80 mL). The separated aqueous layer was washed with EtOAc and acidified with 1 M aqueous KHSO$_4$ to pH=3 and extracted with EtOAc (2x). The combined EtOAc extracts were washed with saturated aqueous NaCl (2x), dried over Na$_2$SO$_4$, filtered and concentrated to give (R)-3-(tert-butoxycarbonylamino)butanoic acid (4.301 g, 21.16 mmol, 90% yield) as a pale yellow solid. $^1$H NMR (400 MHz, CDCl$_3$) δ ppm 4.92 (s, 1H), 4.14-3.96 (m, 2H), 2.56 (d, J=5.2 Hz, 2H), 1.45 (s, 9H), 1.25 (d, J=6.9 Hz, 3H).

B: (R)-tert-Butyl 4-(methoxy(methyl)amino)-4-oxobutan-2-ylcarbamate

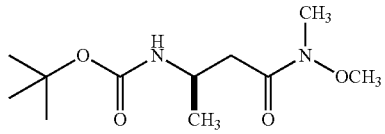 [SMILES: CON(C)C(=O)C[C@@H](C)NC(=O)OC(C)(C)C]

To a solution of (R)-3-(tert-butoxycarbonylamino)butanoic acid (4.30 g, 21.16 mmol) in DMF (20 mL) and DCM (20.00 mL) was added EDC (4.46 g, 23.27 mmol) and HOBt (4.21 g, 27.5 mmol). The mixture was stirred at rt for 15 min, then N,O-dimethylhydroxylamine hydrochloride (3.10 g, 31.7 mmol) was added, followed by TEA (5.90 mL, 42.3 mmol) dropwise. The resulting light yellow suspension was stirred at rt for 7 hr. The reaction was quenched with addition of water (100 mL). The mixture was extracted with EtOAc (2x). The combined EtOAc extracts were washed with water (2x), 0.3 M aqueous KHSO$_4$, saturated aqueous NaHCO$_3$ (2x), saturated aqueous NaCl (2x), dried over Na$_2$SO$_4$, filtered and concentrated to give (R)-tert-butyl 4-(methoxy(methyl)amino)-4-oxobutan-2-ylcarbamate (2.48 g, 10.1 mmol, 47.6% yield) as a pale yellow solid. $^1$H NMR (400 MHz, CDCl$_3$) δ ppm 5.32 (s, 1H), 4.14-3.96 (m, 1H), 3.68 (s, 3H), 3.18 (s, 3H), 2.71 (dd, J=15.6, 4.6 Hz, 1H), 2.61-2.49 (m, 1H), 1.41 (d, J=17.2 Hz, 9H), 1.24 (d, J=6.7 Hz, 3H).

C: (R)-tert-Butyl 4-oxobutan-2-ylcarbamate

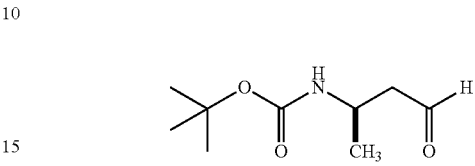

To a solution of (R)-tert-butyl 4-(methoxy(methyl)amino)-4-oxobutan-2-ylcarbamate (2.48 g, 10.1 mmol) in Et$_2$O (25 mL) cooled to −5° C. was added dropwise a 2.0 M solution of LAH in THF (6.28 mL, 12.6 mmol). After the addition, the resulting slightly milky solution was stirred at 0° C. for 1.5 hr. The reaction mixture was quenched with 1 M aqueous KHSO$_4$ (20 mL) and diluted with water (30 mL). The resulting solution with white milky precipitate was extracted with Et$_2$O (3x). The combined Et$_2$O extracts were washed with 0.5 M aqueous KHSO$_4$ (2x20 mL), saturated aqueous NaHCO$_3$, water, and saturated aqueous NaCl, dried over Na$_2$SO$_4$, filtered and concentrated. The residue was dried under vacuum to give (R)-tert-butyl 4-oxobutan-2-ylcarbamate (1.57 g, 8.40 mmol, 84% yield) as a colorless oil. $^1$H NMR (400 MHz, CDCl$_3$) δ ppm 9.76 (s, 1H), 4.64 (s, 1H), 4.20-4.08 (m, 1H), 2.69-2.52 (m, 2H), 1.43 (s, 9H), 1.24 (d, J=6.8 Hz, 3H).

D: (R,E)-Ethyl 5-(tert-butoxycarbonylamino)hex-2-enoate

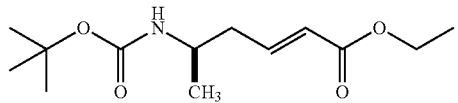 [SMILES: CCOC(=O)/C=C/C[C@@H](C)NC(=O)OC(C)(C)C]

To a solution of (R)-tert-butyl 4-oxobutan-2-ylcarbamate (1.54 g, 8.22 mmol) in THF (25 mL) at rt was added (carbethoxymethylene)triphenylphosphorane (6.30 g, 18.1 mmol) in portions. The resulting clear solution was stirred at rt under argon for 3 days. The reaction mixture was concentrated and the oily residue was purified using silica gel chromatography (ISCO system) eluting with a gradient of 0-60% EtOAc/Hex to give (R,E)-ethyl 5-(tert-butoxycarbonylamino)hex-2-enoate (1.70 g, 6.61 mmol, 80% yield) as a colorless oil. $^1$H NMR (400 MHz, CDCl$_3$) δ ppm 6.91 (dt, J=15.3, 7.5 Hz, 1H), 5.92-5.82 (m, 1H), 4.37 (s, 1H), 4.19 (q, J=7.1 Hz, 2H), 3.83 (s, 1H), 2.37 (t, J=6.6 Hz, 2H), 1.44 (s, 9H), 1.29 (t, J=7.1 Hz, 3H), 1.15 (d, J=6.7 Hz, 3H).

E: (R)-Ethyl 5-(tert-butoxycarbonylamino)hexanoate

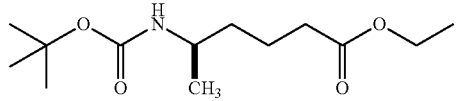 [SMILES: CCOC(=O)CCC[C@@H](C)NC(=O)OC(C)(C)C]

A suspension of (R,E)-ethyl 5-(tert-butoxycarbonylamino)hex-2-enoate (1.70 g, 6.61 mmol) and 5% Pd/C (350 mg) in ethanol (35 mL) was vigorously stirred under the atmosphere of hydrogen balloon for 1.5 hr. The reaction mixture was filtered and the filtrate were concentrated to give (R)-ethyl 5-(tert-butoxycarbonylamino)hexanoate (1.71 g, 6.58 mmol, 100% yield) as a colorless oil. $^1$H NMR (400 MHz, CDCl$_3$) δ ppm 4.34 (s, 1H), 4.12 (q, J=7.1 Hz, 2H), 3.66 (s, 1H), 2.31 (td, J=7.5, 1.6 Hz, 2H), 1.75-1.57 (m, 2H), 1.51-1.38 (m, 2H), 1.44 (s, 9H), 1.25 (t, J=7.1 Hz, 3H), 1.12 (d, J=6.6 Hz, 3H).

F: (R)-tert-Butyl 6-hydroxyhexan-2-ylcarbamate

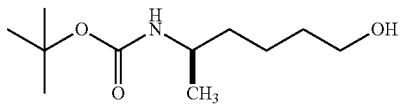

To a solution of (R)-ethyl 5-(tert-butoxycarbonylamino)hexanoate (1.70 g, 6.56 mmol) in THF (20 mL) was added dropwise a 2.0 M lithium borohydride solution in THF (6.56 mL, 13.1 mmol). After the addition, the reaction mixture was stirred at rt for 20 hr and then 45° C. for 7 hr and again at rt overnight. The reaction mixture was cooled to 0° C. and was quenched carefully with pH 3 buffer solution. Then the resulting white suspension was stirred at rt for 1 hr. The mixture was then partitioned between 1 N aqueous HCl and DCM. The aqueous phase was extracted with DCM (2×). The combined DCM extracts were washed with water (2×), saturated aqueous NaCl, dried over Na$_2$SO$_4$, filtered and concentrated. The obtained oily residue was dried under high vacuum to afford (R)-tert-butyl 6-hydroxyhexan-2-ylcarbamate (1.42 g, 6.53 mmol, 100% yield) as a colorless oil. Anal. Calcd. for C$_{11}$H$_{23}$NO$_3$ m/z 217.3. found: 218.1 (M+H)$^+$; $^1$H NMR (400 MHz, CDCl$_3$) δ ppm 4.34 (s, 2H), 3.64 (d, J=6.3 Hz, 2H), 1.68-1.50 (m, 2H), 1.44 (s, 9H), 1.51-1.32 (m, 5H), 1.12 (d, J=6.6 Hz, 3H).

G: (R)-5-Aminohexan-1-ol trifluoroacetate

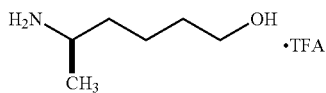

To a stirred solution of (R)-tert-butyl 6-hydroxyhexan-2-ylcarbamate (0.530 g, 2.44 mmol) in DCM (1.5 mL) was added TFA (1.88 mL, 24.4 mmol). The resulting clear solution was stirred at rt for 1 hr. The reaction was concentrated. The obtained oily residue was dried under vacuum to give (R)-5-aminohexan-1-ol trifluoroacetate as a light brown oil.

H: (4S,7R,10aS)-4-Amino-7-methylhexahydro-2H-pyrido[2,1-b][1,3]thiazepin-5(7H)-one

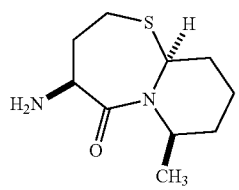

(4S,7R,10aS)-4-Amino-7-methylhexahydro-2H-pyrido[2,1-b][1,3]thiazepin-5(7H)-one (135 mg, 0.599 mmol) was synthesized as described for the preparation of Intermediate 40 using (R)-5-aminohexan-1-ol trifluoroacetate in step A. Anal. Calcd. for C$_{10}$H$_{18}$N$_2$O$_5$ m/z 214.3. found: 215.1 (M+H)$^+$; $^1$H NMR (400 MHz, CDCl$_3$) δ ppm 5.40-5.28 (m, 1H), 4.70-4.55 (m, 1H), 4.00 (ddd, J=14.7, 9.6, 5.2 Hz, 1H), 2.98-2.83 (m, 1H), 2.71-2.56 (m, 1H), 2.29-2.13 (m, 1H), 2.03-1.45 (m, 7H), 1.57-1.45 (m, 1H), 1.39-1.31 (m, 1H), 1.31 (d, J=7.0 Hz, 3H).

Intermediate 73: (4S,7S,10aS)-4-Amino-7-vinyl-hexahydro-2H-pyrido[2,1-b][1,3]thiazepin-5(7H)-one

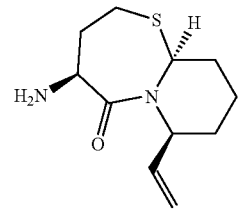

A: tert-Butyl (4S,7S,10aS)-7-formyl-5-oxooctahydro-2H-pyrido[2,1-b][1,3]thiazepin-4-ylcarbamate

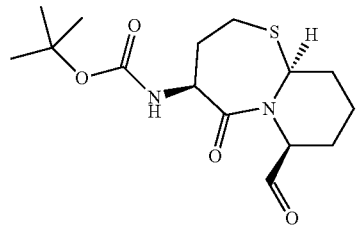 [SMILES: CC(C)(C)OC(=O)N[C@H]1CCS[C@H]2CCC[C@@H](C=O)N2C1=O]

To a round bottom flask was added DCM (10 mL) and a 2 M solution of (COCl)$_2$ in DCM (1.57 mL, 3.14 mmol). The reaction mixture was cooled to −78° C. Then, DMSO (0.445 mL, 6.27 mmol) was slowly added to the reaction mixture over 10 min. The reaction mixture was stirred at −78° C. for 15 min. Then, tert-butyl (4S,7S,10aS)-7-(hydroxymethyl)-5-oxooctahydro-2H-pyrido[2,1-b][1,3]thiazepin-4-ylcarbamate (740 mg, 2.24 mmol) in DCM (5 mL) was added to the reaction mixture over 10 min. The reaction mixture was stirred at −78° C. for 1 hr. Then, TEA (1.37 mL, 9.85 mmol) was added to the reaction, which was slowly warmed to 0° C. over 20 min. The reaction mixture was diluted with DCM (50 mL). The organics were washed with saturated aqueous NaHCO$_3$(50 mL), water (100 mL) and saturated aqueous NaCl (50 mL). The organic layer was separated, dried over MgSO$_4$, filtered and concentrated. The residue was purified using silica gel chromatography (ISCO system) eluting with a gradient of 0-50% EtOAc/Hex to give tert-butyl (4S,7S,10aS)-7-formyl-5-oxooctahydro-2H-pyrido[2,1-b][1,3]thiazepin-4-ylcarbamate (450 mg, 1.37 mmol, 61.2% yield) as a white solid. Anal. Calcd. for C$_{15}$H$_{24}$N$_2$O$_4$S m/z 328.4. found: 329.0 (M+H)$^+$; $^1$H NMR (400 MHz, CDCl$_3$) δ ppm 9.73 (s, 1H), 5.95 (d, J=6.2 Hz, 1H), 5.44-5.21 (m, 1H), 5.02 (d, J=6.0

Hz, 1H), 4.97-4.74 (m, 1H), 3.54-3.24 (m, 1H), 3.06-2.78 (m, 1H), 2.63-2.26 (m, 2H), 2.16-1.75 (m, 3H), 1.52 (d, J=53.2 Hz, 12H).

B: tert-Butyl (4S,7S,10aS)-5-oxo-7-vinyloctahydro-2H-pyrido[2,1-b][1,3]thiazepin-4-ylcarbamate

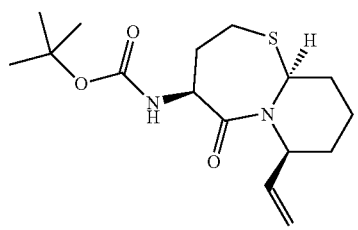 [SMILES: C=C[C@@H]1CCC[C@@H]2SCC[C@H](NC(=O)OC(C)(C)C)C(=O)N12]

To a stirred suspension of methyltriphenoxyphosphonium iodide (716 mg, 1.58 mmol) in dry THF (5 mL) under argon at 0° C. was added dropwise a solution of 0.5 M potassium hexamethyldisilazide in toluene (3.17 mL, 1.58 mmol). The reaction mixture was stirred for 10 min at 0° C. and then for 20 min at rt. Then, the reaction temperature was lowered to −78° C. and a solution of tert-butyl (4S,7S,10aS)-7-formyl-5-oxooctahydro-2H-pyrido[2,1-b][1,3]thiazepin-4-ylcarbamate (400 mg, 1.22 mmol) in dry THF (5.00 mL) was added. The reaction mixture was stirred for 3 hr at rt. The reaction mixture was diluted with saturated aqueous NH$_4$Cl (100 mL) and extracted with EtOAc (2×40 mL). The combined EtOAc layers were washed with water, saturated aqueous NaCl, dried over Na$_2$SO$_4$, filtered & concentrated. The residue was purified using silica gel chromatography (ISCO system) eluting with a gradient of 0-30% EtOAc/Hex to give tert-butyl (4S,7S,10aS)-5-oxo-7-vinyloctahydro-2H-pyrido[2,1-b][1,3]thiazepin-4-ylcarbamate (360 mg, 1.10 mmol, 91% yield) as a white foam. $^1$H NMR (400 MHz, CDCl$_3$) δ ppm 6.48-6.18 (m, 1H), 6.07-5.81 (m, 1H), 5.50-5.22 (m, 2H), 5.22-4.99 (m, 2H), 4.92-4.69 (m, 1H), 3.20-2.98 (m, 1H), 2.85-2.61 (m, 1H), 2.49-2.26 (m, 1H), 2.17-1.96 (m, 2H), 1.96-1.65 (m, 4H), 1.66-1.52 (m, 1H), 1.43 (s, 9H).

C: (4S,7S,10aS)-4-Amino-7-vinylhexahydro-2H-pyrido[2,1-b][1,3]thiazepin-5(7H)-one

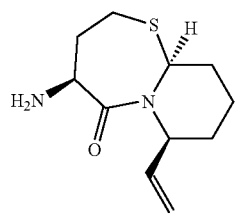

To a solution of tert-butyl (4S,7S,10aS)-5-oxo-7-vinyloctahydro-2H-pyrido[2,1-b][1,3]thiazepin-4-ylcarbamate (44 mg, 0.13 mmol) in DCM (1 mL) was added TFA (1.0 mL, 13 mmol). The reaction was stirred at rt for 1 hr. The reaction mixture was concentrated and dried under high vacuum to afford (4S,7S,10aS)-4-amino-7-vinylhexahydro-2H-pyrido[2,1-b][1,3]thiazepin-5(7H)-one trifluoroacetate (46 mg, 0.134 mmol, 100% yield) as an oil. Anal. Calcd. for C$_{11}$H$_{18}$N$_2$OS m/z 226.3. found: 227.1 (M+H)$^+$.

Intermediate 74: 4S,7R,10aS)-4-Amino-7-ethyl-hexahydro-2H-pyrido[2,1-b][1,3]thiazepin-5(7H)-one trifluoroacetate

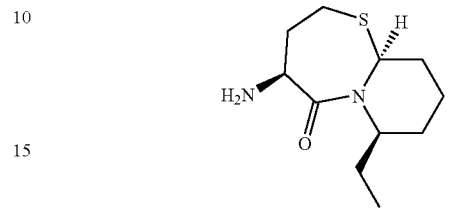

A: tert-Butyl (4S,7R,10aS)-7-ethyl-5-oxooctahydro-2H-pyrido[2,1-b][1,3]thiazepin-4-ylcarbamate

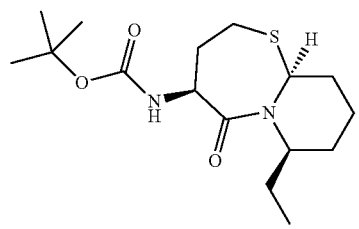

A solution of tert-butyl (4S,7S,10aS)-5-oxo-7-vinyloctahydro-2H-pyrido[2,1-b][1,3]thiazepin-4-ylcarbamate (66 mg, 0.20 mmol) in MeOH (2 mL) was purged with argon for 2 min. Then, 10% Pd/C (80 mg, 0.75 mmol) was added. The reaction mixture was stirred for under a hydrogen balloon for 3 days. The reaction mixture was filtered. The filtrate was concentrated and dried under the high vacuum to give tert-butyl (4S,7R,10aS)-7-ethyl-5-oxooctahydro-2H-pyrido[2,1-b][1,3]thiazepin-4-ylcarbamate (52 mg, 0.16 mmol, 78% yield) as a white solid. $^1$H NMR (400 MHz, CDCl$_3$) δ ppm 6.02 (d, J=5.5 Hz, 1H), 5.39-5.15 (m, 1H), 4.92-4.66 (m, 1H), 4.53-4.30 (m, 1H), 3.38-3.14 (m, 1H), 2.97-2.66 (m, 1H), 2.46-2.20 (m, 1H), 2.15-1.62 (m, 8H), 1.62-1.35 (m, 10H), 0.93 (t, J=7.4 Hz, 3H).

B: (4S,7R,10aS)-4-Amino-7-ethylhexahydro-2H-pyrido[2,1-b][1,3]thiazepin-5(7H)-one trifluoroacetate

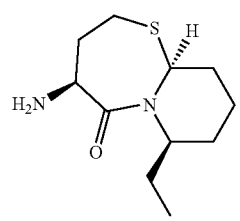

To a solution of tert-butyl (4S,7R,10aS)-7-ethyl-5-oxooctahydro-2H-pyrido[2,1-b][1,3]thiazepin-4-ylcarbamate (52 mg, 0.16 mmol) in DCM (1 mL) was added TFA (1.0 mL, 13 mmol). The reaction mixture was stirred at rt for 1 hr. The reaction mixture was concentrated and dried under high vacuum to afford (4S,7R,10aS)-4-amino-7-ethylhexahydro-2H-pyrido[2,1-b][1,3]thiazepin-5(7H)-one trifluoroacetate (54 mg, 0.16 mmol, 100% yield) as an oil. Anal. Calcd. for $C_{11}H_{20}N_2OS$ m/z 228.3. found: 229.2 (M+H)$^+$.

Intermediate 75: (S)-1-(2-Methoxyphenyl)-3-(methylamino)azepan-2-one hydrochloride

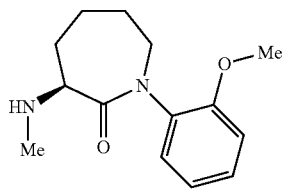 [SMILES: CN[C@H]1CCCCN(c2ccccc2OC)C1=O]

A: (S)-tert-Butyl 1-(2-methoxyphenyl)-2-oxoazepan-3-yl(methyl)carbamate

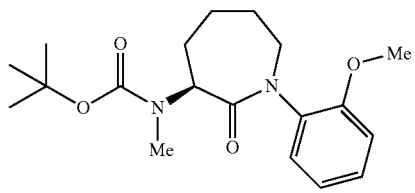 [SMILES: COc1ccccc1N1CCCC[C@H](N(C)C(=O)OC(C)(C)C)C1=O]

THF (0.8 mL) was added to a reaction vessel containing (S)-tert-butyl 1-(2-methoxyphenyl)-2-oxoazepan-3-ylcarbamate (53 mg, 0.16 mmol). NaH (60% dispersion in oil, 25.4 mg, 0.634 mmol) was then added to the reaction mixture followed by iodomethane (180 mg, 1.27 mmol). The turbid mixture was left to stir at rt for 2 hr. The reaction was quenched by addition of water. The mixture was concentrated to remove some of the THF. The mixture was then partitioned between EtOAc and water. The organic phase was isolated, washed with saturated aqueous NaCl, dried over MgSO$_4$, filtered and concentrated to give (S)-tert-butyl 1-(2-methoxyphenyl)-2-oxoazepan-3-yl(methyl)carbamate (52 mg, 0.15 mmol, 94% yield) as a colorless oil.

B: (S)-1-(2-methoxyphenyl)-3-(methylamino)azepan-2-one hydrochloride

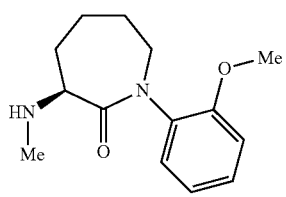 [SMILES: CN[C@H]1CCCCN(c2ccccc2OC)C1=O]

A solution of 4 N HCl in dioxane (0.15 mL, 0.60 mmol) was added dropwise to a 0° C. solution of (S)-tert-butyl 1-(2-methoxyphenyl)-2-oxoazepan-3-yl(methyl)carbamate (52 mg, 0.15 mmol) in dioxane (0.6 mL). The reaction mixture was then stirred at rt for 2 hr. The reaction mixture was concentrated and dried under vacuum to give (S)-1-(2-methoxyphenyl)-3-(methylamino)azepan-2-one hydrochloride (41.5 mg, 0.146 mmol, 98% yield) as a white solid. Anal. Calcd. for $C_{14}H_{20}N_2O_2$ m/z 248.3. found: 249.2 (M+H)$^+$.

Intermediate 76: (2R,5S)-2-(4-Fluorobenzyl)-5-((S)-1-(2-methoxyphenyl)-2-oxoazepan-3-ylcarbamoyl)octanoic acid

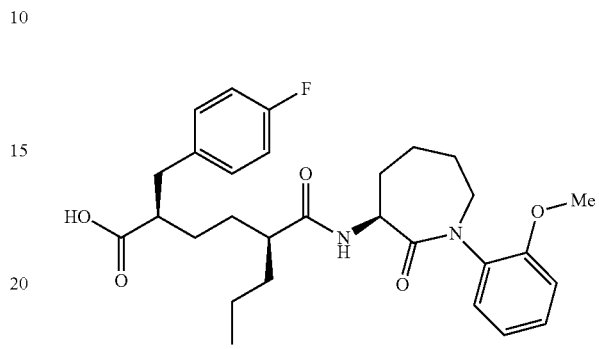

EDC (84 mg, 0.44 mmol) was added in portions to a 0° C. solution of (2R,5S)-2-(4-fluorobenzyl)-5-propylhexanedioic acid (130 mg, 0.439 mmol) in DCM (6 mL) and DMF (1 mL). The reaction mixture was then stirred at rt overnight. The reaction mixture was concentrated to remove the DCM. (S)-3-Amino-1-(2-methoxyphenyl)azepan-2-one (143 mg, 0.526 mmol) was then added to the DMF solution followed by TEA (111 mg, 1.10 mmol). After 3 hr, the reaction mixture was concentrated to remove the DCM. The solution was then partitioned between EtOAc and 10% aqueous KHSO$_4$. The organic phase was isolated, washed with saturated aqueous NaCl, dried over MgSO$_4$, filtered and concentrated to give 2 regioisomers, which were separated using chiral separation (Method B) to give (2R,5S)-2-(4-4luorobenzyl)-5-((S)-1-(2-methoxyphenyl)-2-oxoazepan-3-ylcarbamoyl)octanoic acid (60 mg, 0.12 mmol, 27% yield).

Intermediate 77: (4S,7S,10aS)-4-Amino-7-(trifluoromethyl)hexahydro-2H-pyrido[2,1-b][1,3]thiazepin-5(7H)-one

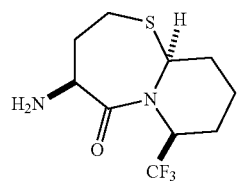

(4S,7S,10aS)-4-Amino-7-(trifluoromethyl)hexahydro-2H-pyrido[2,1-b][1,3]thiazepin-5(7H)-one (53 mg, 0.20 mmol) was synthesized as described for the preparation of Intermediate 59 using 5-amino-6,6,6-trifluorohexan-1-ol in step A followed by the preparation of Intermediate 61. Anal. Calcd. for $C_{10}H_{15}F_3N_2OS$ m/z 268.3. found: 269.0 (M+H)$^+$; $^1$H NMR (400 MHz, CDCl$_3$) δ ppm 5.42-5.27 (m, 1H), 5.21 (t, J=7.0 Hz, 1H), 3.99 (dd, J=10.3, 2.7 Hz, 1H), 3.15 (ddd, J=13.9, 10.9, 2.6 Hz, 1H), 2.81 (ddd, J=14.4, 6.3, 2.9 Hz, 1H), 2.23 (ddt, J=14.2, 6.0, 2.9 Hz, 1H), 2.19-2.07 (m, 1H), 2.06-1.79 (m, 7H), 1.54-1.39 (m, 1H).

Intermediate 78: (4S,7R,10aS)-4-Amino-7-(trifluoromethyl)hexahydro-2H-pyrido[2,1-b][1,3]thiazepin-5(7H)-one

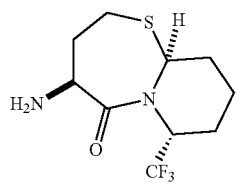

(4S,7R,10aS)-4-Amino-7-(trifluoromethyl)hexahydro-2H-pyrido[2,1-b][1,3]thiazepin-5(7H)-one (39 mg, 0.15 mmol) was synthesized as described for the preparation of Intermediate 58 using 5-amino-6,6,6-trifluorohexan-1-ol in step A followed by the preparation of Intermediate 60. Anal. Calcd. for $C_{10}H_{15}F_3N_2OS$ m/z 268.3. found: 269.0 (M+H)$^+$; $^1$H NMR (400 MHz, CDCl$_3$) δ ppm 5.29 (dd, J=4.4, 2.8 Hz, 1H), 5.13-4.99 (m, 1H), 3.95 (dd, J=10.6, 3.6 Hz, 1H), 3.07 (ddd, J=14.5, 10.0, 3.3 Hz, 1H), 2.74 (ddd, J=14.6, 6.7, 3.3 Hz, 1H), 2.48-2.29 (m, 2H), 2.24 (ddt, J=13.8, 6.9, 3.4 Hz, 1H), 2.16-2.02 (m, 2H), 1.94-1.69 (m, 5H).

Intermediate 79: (2R,5R)-2,5-Bis(4-fluorobenzyl)-6-oxo-6-((S)-2-oxo-1-phenylazepan-3-ylamino)hexanoic acid

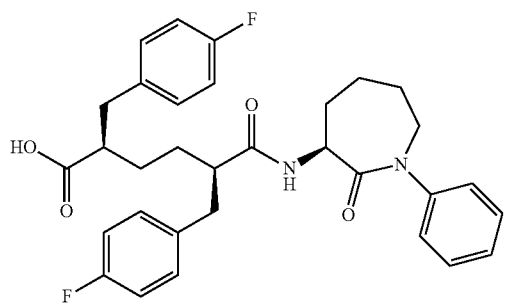 [SMILES: O=C(O)[C@H](CC[C@H](Cc1ccc(F)cc1)C(=O)N[C@H]1CCCCN(c2ccccc2)C1=O)Cc1ccc(F)cc1]

EDC (16 mg, 0.083 mmol) was added to a 0° C. solution of (2R,5R)-2,5-Bis(4-fluorobenzyl)hexanedioic acid (30 mg, 0.083 mmol) in DMF (1 mL) and DCM (5 mL). The ice bath was removed and the reaction mixture was stirred at rt overnight. The reaction mixture was concentrated to remove most of the DCM. (S)-3-Amino-1-phenylazepan-2-one (21 mg, 0.085 mmol) was added followed by TEA (18.4 mg, 0.182 mmol). The reaction mixture was left to stir at rt for 3 hr. The reaction mixture was partitioned between EtOAc and 5% aqueous KHSO$_4$. The organic phase was isolated, washed with saturated aqueous NaCl, dried over MgSO$_4$, filtered and concentrated. The crude product was purified using silica gel chromatography (ISCO system) eluting with a gradient of 0-100% EtOAc/Hex to give (2R,5R)-2,5-bis(4-fluorobenzyl)-6-oxo-6-((S)-2-oxo-1-phenylazepan-3-ylamino)hexanoic acid (32 mg, 0.058 mmol, 71% yield) as a colorless syrup. Anal. Calcd. for $C_{32}H_{34}F_2N_2O_4$ m/z 548.3. found: 549.1 (M+H)$^+$.

Intermediate 80: (S)-tert-Butyl 1-isobutyl-2-oxoazepan-3-ylcarbamate

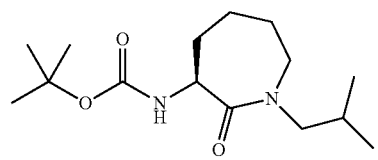 [SMILES: CC(C)CN1CCCC[C@H](NC(=O)OC(C)(C)C)C1=O]

To a solution of (S)-tert-butyl 2-oxoazepan-3-ylcarbamate (116 mg, 0.510 mmol) in DMF (2 mL) at 0° C. was added sodium hydride (60% in oil, 23 mg, 0.57 mmol) in 2 portions. After stirring for 5 min, isobutyl bromide (175 mg, 1.28 mmol) was added to the reaction mixture and the mixture was stirred at rt for 20 h. Saturated aqueous NH$_4$Cl (2 mL) was added to the mixture and crude product was extracted with methylene chloride (3 mL) and the combined organic layers were dried (Na$_2$SO$_4$) and concentrated. The crude product was purified using silica gel chromatography to afford (S)-tert-Butyl 1-isobutyl-2-oxoazepan-3-ylcarbamate (46.4 mg, 0.247 mmol, 49% yield). Anal. Calcd. for $C_{15}H_{28}N_2O_3$ m/z 284.2. found: 285.2 (M+H)$^+$; $^1$H NMR (400 MHz, DMSO-d$_6$) δ ppm 6.44 (d, J=6.64 Hz, 1H), 4.26 (t, J=9 Hz, 1H), 3.57-3.50 (m, 1H), 3.26-3.17 (m, 2H), 3.10-3.05 (m, 1H), 1.84-1.62 (m, 5H), 1.37 (s, 9H), 1.34-1.24 (m, 2H), 0.84-0.80 (m, 6H).

Intermediate 81: (2R,5S)-2-Benzyl-5-methylhexanedioic acid

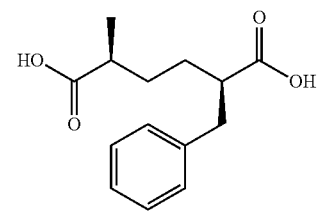 [SMILES: C[C@@H](CC[C@H](Cc1ccccc1)C(=O)O)C(=O)O]

A: (2S,5S,E)-2-Benzyl-1,6-bis((S)-4-benzyl-2-oxooxazolidin-3-yl)-5-methylhex-3-ene-1,6-dione

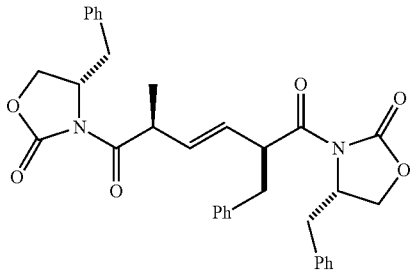 [SMILES: C[C@@H](/C=C/[C@H](Cc1ccccc1)C(=O)N1C(=O)OC[C@@H]1Cc1ccccc1)C(=O)N1C(=O)OC[C@@H]1Cc1ccccc1]

To a solution of (S,E)-2-benzyl-1,6-bis((S)-4-benzyl-2-oxooxazolidin-3-yl)hex-3-ene-1,6-dione (250 mg, 0.450 mmol) in THF (50 mL) at −78° C., a solution of NaHMDS (1 M in THF, 0.54 mL, 0.54 mmol) in diluted in THF (2.5 mL) was added dropwise. The reaction mixture was stirred for 1 hr at −78° C. and then methyl iodide (0.078 g, 0.55 mmol) was added in two portions. The reaction mixture was warmed to rt and allowed to stir overnight. Saturated aqueous NH$_4$Cl (3 mL) was added to the reaction mixture and crude product was extracted with ethyl acetate (5 mL). The organic layer was separated, dried (Na$_2$SO$_4$) and concentrated to afford crude product, which was purified using silica gel chromatography to afford (2S,5S,E)-2-benzyl-1,6-bis((S)-4-benzyl-2-oxooxazolidin-3-yl)-5-methylhex-3-ene-1,6-dione (137 mg, 0.243 mmol, 54% yield). Anal. Calcd. for C$_{34}$H$_{34}$N$_2$O$_6$ m/z 566.2. found 565.2 (M$^-$): $^1$H NMR (400 MHz, CDCl$_3$) δ ppm 7.36-7.30 (m, 5H), 7.29-7.26 (m, 5H), 7.25-7.18 (m, 3H), 7.08-7.05 (m, 2H), 5.75-5.62 (m, 2H), 4.72-4.57 (m, 3H), 4.36-4.29 (m, 1H), 4.23-4.12 (m, 4H), 3.28-3.21 (m, 2H), 3.10 (m, 1H), 2.84 (m, 1H), 2.76 (m, 1H), 2.61 (m, 1H), 1.24 (d, J=6.8 Hz, 3H).

B: (2R,5S)-2-Benzyl-1,6-bis((S)-4-benzyl-2-oxooxazolidin-3-yl)-5-methylhexane-1,6-dione

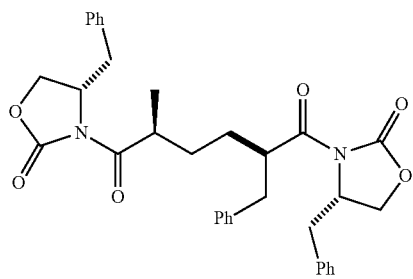

To a solution of (2S,5S,E)-2-benzyl-1,6-bis((S)-4-benzyl-2-oxooxazolidin-3-yl)-5-methylhex-3-ene-1,6-dione (250 mg, 0.440 mmol) in EtOAc (5 mL) was added 10% Pd/C (73 mg, 0.069 mmol). The reaction mixture was purged with nitrogen and stirred under an atmosphere of hydrogen (balloon) overnight. The reaction mixture was filtered through CELITE® and concentrated to afford (2R,5S)-2-benzyl-1,6-bis((S)-4-benzyl-2-oxooxazolidin-3-yl)-5-methylhexane-1,6-dione (223 mg, 0.392 mmol, 89% yield) which was used without further purification. Anal. Calcd. for C$_{34}$H$_{36}$N$_2$O$_6$ m/z 568.3. found: 569.0 (M+H)$^+$; $^1$H NMR (400 MHz, CDCl$_3$) δ ppm 7.33-7.29 (m, 4H), 7.24-7.21 (m, 8H), 7.04-7.02 (m, 3H), 4.64-4.62 (m, 2H), 4.19-4.11 (m, 4H), 4.04 (m, 1H), 3.66 (bs, 1H), 3.32 (m, 1H), 3.01-2.9 (m, 2H), 2.78 (m, 1H), 2.61 (m, 1H), 2.40 (m, 1H), 1.71-1.62 (m, 4H), 0.91 (t, J=7.4 Hz, 3H).

C: (2R,5S)-2-Benzyl-5-methylhexanedioic acid

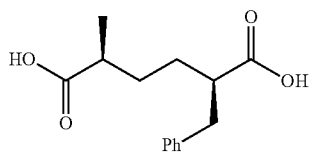 [SMILES: C[C@@H](CC[C@H](Cc1ccccc1)C(=O)O)C(=O)O]

An aqueous solution of 50% H$_2$O$_2$ (0.12 mL, 2.1 mmol) was added to a solution of (2R,5S)-2-benzyl-1,6-bis((S)-4-benzyl-2-oxooxazolidin-3-yl)-5-methylhexane-1,6-dione (200 mg, 0.352 mmol) in THF (3 mL) and water (1 mL) at 0° C. After 5 min of stirring, LiOH.H$_2$O (44 mg, 1.1 mmol) was added and the reaction mixture was stirred for 1 hr at rt. Saturated aqueous Na$_2$SO$_3$ (0.2 mL) and saturated aqueous NaHCO$_3$ (0.2 mL) were added and the reaction mixture was concentrated to remove the organic solvent. The aqueous solution was extracted with DCM (3 mL) to remove organic impurities. The aqueous phase was then acidified using aqueous 5 N HCl to pH<2. The cloudy mixture was extracted with DCM (2×2 mL). The organic extracts were combined, dried over Na$_2$SO$_4$ and concentrated to give (2R,5S)-2-benzyl-5-methylhexanedioic acid (52 mg, 0.21 mmol, 59% yield) as a white powder. Anal. Calcd. for C$_{14}$H$_{18}$O$_4$ m/z 250.1. found: 249.2 (M$^-$): $^1$H NMR (400 MHz, CDCl$_3$) δ ppm 7.28 (m, 2H), 7.17 (m, 3H), 2.99 (m, 1H), 2.75 (m, 1H), 2.65 (m, 1H), 2.4 (m, 1H), 1.79 (m, 1H), 1.63 (m, 2H), 1.44 (m, 1H), 1.15 (d, J=7 Hz, 3H).

Intermediate 82:
(2R,5S)-2-Benzyl-5-ethylhexanedioic acid

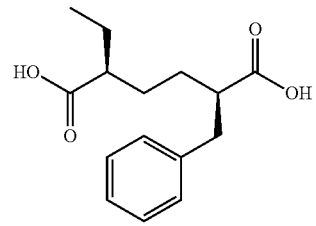 [SMILES: CC[C@@H](CC[C@H](Cc1ccccc1)C(=O)O)C(=O)O]

A: (2S,5S,E)-2-Benzyl-1,6-bis((S)-4-benzyl-2-oxooxazolidin-3-yl)-5-ethylhex-3-ene-1,6-dione

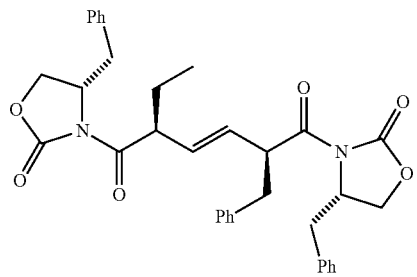 [SMILES: CC[C@@H](/C=C/[C@H](Cc1ccccc1)C(=O)N1C(=O)OC[C@@H]1Cc1ccccc1)C(=O)N1C(=O)OC[C@@H]1Cc1ccccc1]

To a solution of (S,E)-2-benzyl-1,6-bis((S)-4-benzyl-2-oxooxazolidin-3-yl)hex-3-ene-1,6-dione (600 mg, 1.08 mmol) in THF (50 mL) at −78° C., a solution of NaHMDS (1 M in THF, 1.4 mL, 1.4 mmol) in diluted with THF (2.5 mL) was added dropwise. The reaction mixture was stirred for 1 hr at −78° C. and ethyl iodide (1.70 g, 10.9 mmol) was added dropwise. The reaction mixture was warmed to rt and allowed to stir overnight. Saturated aqueous NH$_4$Cl (3 mL) was added to the reaction mixture and the crude product was extracted with EtOAc (4×5 mL). The organic layer was separated, dried (Na$_2$SO$_4$) and concentrated to afford the crude product, which was purified using silica gel chromatography to afford (2S,5S,E)-2-benzyl-1,6-bis((S)-4-benzyl-2-oxooxazolidin-3-yl)-5-ethylhex-3-ene-1,6-dione (100 mg, 0.172 mmol, 16% yield). Anal. Calcd. for $C_{35}H_{36}N_2O_6$ m/z 580.3. found 579.2 (M⁻); ¹H NMR (400 MHz, CDCl₃) δ ppm 7.33-7.29 (m, 5H), 7.27-7.24 (m, 5H), 7.19-7.16 (m, 3H), 7.05 (m, 2H), 5.7 (dd, 1H), 5.58 (dd, 1H), 4.71 (q, 1H), 4.66-4.57 (m, 2H), 4.20-4.07 (m, 6H), 3.27-3.19 (m, 2H), 3.08 (m, 1H), 2.82 (m, 1H), 2.71 (m, 1H), 2.58 (m, 1H), 1.8-1.75 (m, 1H), 1.52-1.45 (m, 1H), 0.81 (t, J=7.6 Hz, 3H).

B: (2R,5S)-2-Benzyl-1,6-bis((S)-4-benzyl-2-oxooxazolidin-3-yl)-5-ethylhexane-1,6-dione

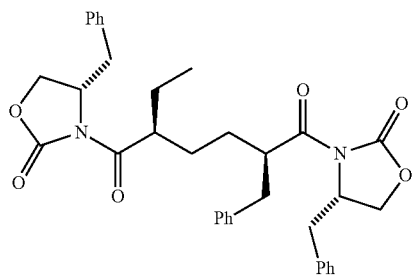 [SMILES: CC[C@@H](CC[C@H](Cc1ccccc1)C(=O)N1C(=O)OC[C@@H]1Cc1ccccc1)C(=O)N1C(=O)OC[C@@H]1Cc1ccccc1]

To a solution of (2S,5S,E)-2-benzyl-1,6-bis((S)-4-benzyl-2-oxooxazolidin-3-yl)-5-methylhex-3-ene-1,6-dione (250 mg, 0.431 mmol) in EtOAc (5 mL) was added 10% Pd/C (80 mg, 0.075 mmol). The reaction mixture was purged with nitrogen and stirred under an atmosphere of hydrogen (balloon) overnight. The reaction mixture was filtered through CELITE® and concentrated to afford (2R,5S)-2-benzyl-1,6-bis((S)-4-benzyl-2-oxooxazolidin-3-yl)-5-ethylhexane-1,6-dione (221 mg, 0.379 mmol, 88% yield), which was used without further purification. Anal. Calcd. for $C_{35}H_{38}N_2O_6$ m/z 582.3. found 579.2 (M⁻); ¹H NMR (400 MHz, CDCl₃) δ ppm 7.35-7.31 (m, 5H), 7.27-7.21 (m, 7H), 7.04-7.02 (m, 3H), 4.68-4.66 (m, 2H), 4.19-4.11 (m, 4H), 4.04 (m, 1H), 3.66 (bs, 1H), 3.32 (m, 1H), 3.05-3.0 (m, 2H), 2.80 (m, 1H), 2.68 (m, 1H), 2.36 (m, 1H), 1.75-1.68 (m, 4H) 1.25 (t, J=7.2 Hz, 2H), 0.92 (t, J=7.2 Hz, 3H).

C: (2R,5S)-2-Benzyl-5-ethylhexanedioic acid

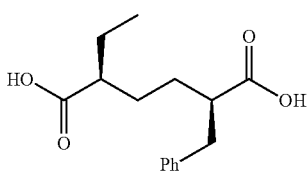 [SMILES: CC[C@@H](CC[C@H](Cc1ccccc1)C(=O)O)C(=O)O]

A solution of 50% aqueous $H_2O_2$ (0.15 mL, 2.6 mmol) was added to a solution of (2R,5S)-2-benzyl-1,6-bis((S)-4-benzyl-2-oxooxazolidin-3-yl)-5-methylhexane-1,6-dione (250 mg, 0.43 mmol) in THF (3 mL) and water (1 mL) at 0° C. After 5 min of stirring, LiOH.H₂O (54.1 mg, 1.29 mmol) was added and the reaction mixture was stirred for 1 hr at rt. Saturated aqueous $Na_2SO_3$ (0.2 mL) and saturated aqueous $NaHCO_3$ (0.2 mL) were added and the reaction mixture was concentrated to remove the organic solvent. The aqueous solution was extracted with DCM (3 mL) to remove organic impurities. The aqueous phase was then acidified using aqueous 5 N HCl to pH<2. The cloudy mixture was extracted with DCM (2×2 mL). The organic extracts were combined, dried over $Na_2SO_4$ and concentrated to give (2R,5S)-2-benzyl-5-ethylhexanedioic acid (80 mg, 0.31 mmol, 71% yield) as a white solid. Anal. Calcd. for $C_{15}H_{20}O_4$ m/z 264.1. found: 263.2 (M⁻); ¹H NMR (400 MHz, CDCl₃) δ ppm 7.30-7.28 (m, 2H), 7.22-7.16 (m, 3H), 2.99 (m, 1H), 2.74 (m, 1H), 2.66-2.63 (m, 1H), 2.26-2.23 (m, 1H), 1.72-1.25 (m, 6H), 0.91 (t, J=7.2 Hz, 3H).

Example 1

Dimethyl (4S,7S,10aS,4'S,7'S,10a'S)-4,4'-(((2R,5R)-2,5-dibenzyl-1,6-dioxo-1,6-hexanediyl)diimino)bis(5-oxooctahydro-7H-pyrido[2,1-b][1,3]thiazepine-7-carboxylate)

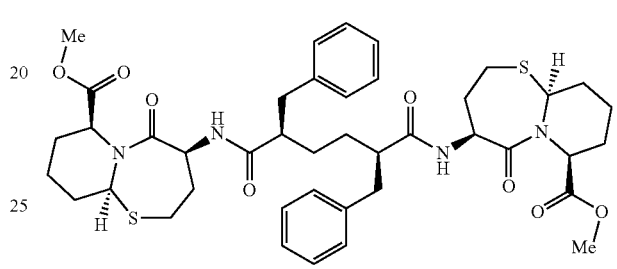

Dimethyl (4S,7S,10aS,4'S,7'S,10a'S)-4,4'-(((2R,5R)-2,5-dibenzyl-1,6-dioxo-1,6-hexanediyl)diimino)bis(5-oxooctahydro-7H-pyrido[2,1-b][1,3]thiazepine-7-carboxylate) was synthesized as described in General Procedure F using Intermediate 3 (40.8 mg, 0.125 mmol) and (4S,7S,10aS)-methyl 4-amino-5-oxooctahydro-2H-pyrido[2,1-b][1,3]thiazepine-7-carboxylate (71 mg, 0.28 mmol) to give a white solid (74 mg, 73% yield). Anal. Calcd. for $C_{42}H_{54}N_4O_8S_2$ m/z 806.0. found: 807.0 (M+H)⁺; ¹H NMR (400 MHz, CDCl₃) δ ppm 7.28-7.19 (4H, m), 7.18-7.09 (6H, m), 7.05 (2H, d, J=6.6 Hz), 5.34 (2H, t, J=4.4 Hz), 5.16-5.09 (2H, m), 5.02-4.92 (2H, m), 3.69 (6H, s), 3.14 (2H, t, J=11.5 Hz), 2.87-2.76 (4H, m), 2.75-2.67 (2H, m), 2.46-2.32 (4H, m), 2.07-1.99 (4H, m), 1.85-1.44 (14H, m).

Example 2

Dimethyl (4S,7S,10aS,4'S,7'S,10a'S)-4,4'-(((2S,3E,5S)-2,5-dibenzyl-1,6-dioxo-3-hexene-1,6-diyl)diimino)bis(5-oxooctahydro-7H-pyrido[2,1-b][1,3]thiazepine-7-carboxylate)

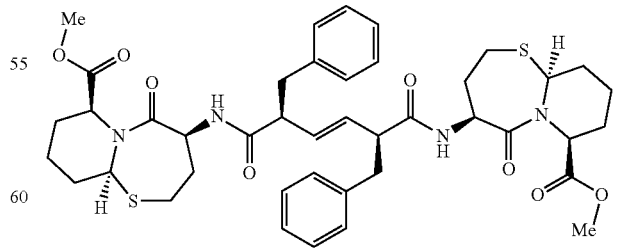

Dimethyl (4S,7S,10aS,4'S,7'S,10a'S)-4,4'-(((2S,3E,5S)-2,5-dibenzyl-1,6-dioxo-3-hexene-1,6-diyl)diimino)bis(5-oxooctahydro-7H-pyrido[2,1-b][1,3]thiazepine-7-carboxylate) was synthesized as described in General Procedure F using Intermediate 5 (12 mg, 0.038 mmol) and (4S,7S,10aS)-methyl 4-amino-5-oxooctahydro-2H-pyrido[2,1-b][1,3]thiazepine-7-carboxylate (22 mg, 0.084 mmol) to give a white solid (6.5 mg, 21% yield). Anal. Calcd. for $C_{42}H_{54}N_4O_8S_2$ m/z 804.0. found: 805.3 (M+H)+; 1H NMR (400 MHz, CDCl3) δ ppm 7.29-7.07 (10H, m), 6.91 (2H, d, J=6.4 Hz), 5.59-5.54 (2H, m), 5.37-5.30 (2H, m), 5.17-5.11 (2H, m), 5.00-4.92 (2H, m), 3.71 (6H, s), 3.27-3.16 (2H, m), 3.09-2.96 (4H, m), 2.90-2.80 (2H, m), 2.75-2.63 (2H, m), 2.47-2.35 (2H, m), 2.08-1.93 (4H, m), 1.75-1.56 (10H, m).

Example 3

Methyl (4S,7S,10aS)-4-(((2R)-2-benzyl-6-(((4S,7S,10aS)-7-(methoxycarbonyl)-5-oxooctahydro-7H-pyrido[2,1-b][1,3]thiazepin-4-yl)amino)-6-oxohexanoyl)amino)-5-oxooctahydro-7H-pyrido[2,1-b][1,3]thiazepine-7-carboxylate

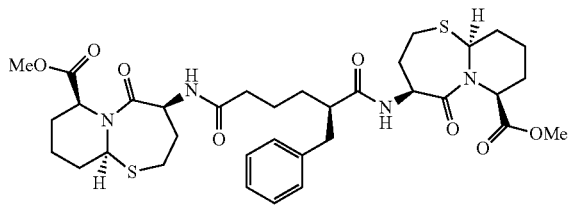 [SMILES: COC(=O)[C@@H]1CCC[C@@H]2SCC[C@H](NC(=O)CCC[C@H](Cc3ccccc3)C(=O)N[C@H]3CCS[C@H]4CCC[C@@H](C(=O)OC)N4C3=O)C(=O)N21]

Methyl (4S,7S,10aS)-4-(2R)-2-benzyl-6-(((4S,7S,10aS)-7-(methoxycarbonyl)-5-oxooctahydro-7H-pyrido[2,1-b][1,3]thiazepin-4-yl)amino)-6-oxohexanoyl)amino)-5-oxooctahydro-7H-pyrido[2,1-b][1,3]thiazepine-7-carboxylate was synthesized as described in General Procedure F using Intermediate 4 (15 mg, 0.061 mmol) and (4S,7S,10aS)-methyl 4-amino-5-oxooctahydro-2H-pyrido[2,1-b][1,3]thiazepine-7-carboxylate (34.9 mg, 0.135 mmol) to give a white solid (25 mg, 56% yield). Anal. Calcd. for $C_{35}H_{48}N_4O_8S_2$ m/z 716.6. found: 717.6 (M+H)+; 1H NMR (400 MHz, CDCl3) δ ppm 7.62 (1H, d, J=6.8 Hz), 7.40 (1H, d, J=7.3 Hz), 7.29-7.22 (2H, m), 7.21-7.11 (3H, m), 5.37 (1H, t, J=4.6 Hz), 5.33 (1H, t, J=4.4 Hz), 5.18-5.07 (3H, m), 5.07-5.00 (1H, m), 3.73 (3H, s), 3.69 (3H, s), 3.29-3.19 (1H, m), 3.18-3.09 (1H, m), 2.93 (1H, ddd, J=14.4, 6.4, 2.7 Hz), 2.87-2.73 (3H, m), 2.56-2.48 (1H, m), 2.48-2.36 (2H, m), 2.36-2.26 (2H, m), 2.25-2.17 (1H, m), 2.09-1.93 (5H, m), 1.82-1.48 (12H, m).

Example 4

Methyl (7S,10aS)-4-(2R,5R)-5-benzyl-2-isobutyl-6-(((4S,7S,10aS)-7-(methoxycarbonyl)-5-oxooctahydro-7H-pyrido[2,1-b][1,3]thiazepin-4-yl)amino)-6-oxohexanoyl)amino)-5-oxooctahydro-7H-pyrido[2,1-b][1,3]thiazepine-7-carboxylate

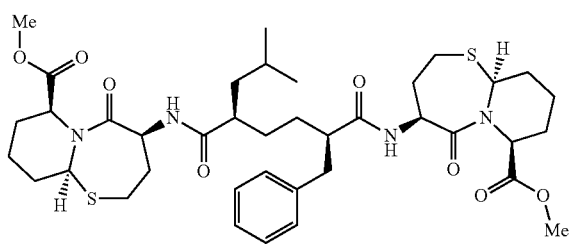 [SMILES: COC(=O)[C@@H]1CCC[C@@H]2SCC[C@H](NC(=O)[C@H](CC[C@H](CC(C)C)C(=O)N[C@H]3CCS[C@H]4CCC[C@@H](C(=O)OC)N4C3=O)Cc3ccccc3)C(=O)N21]

Methyl (7S,10aS)-4-(2R,5R)-5-benzyl-2-isobutyl-6-(((4S,7S,10aS)-7-(methoxycarbonyl)-5-oxooctahydro-7H-pyrido[2,1-b][1,3]thiazepin-4-yl)amino)-6-oxohexanoyl)amino)-5-oxooctahydro-7H-pyrido[2,1-b][1,3]thiazepine-7-carboxylate was synthesized as described in General Procedure F using Intermediate 6 (15 mg, 0.051 mmol) and (4S,7S,10aS)-methyl 4-amino-5-oxooctahydro-2H-pyrido[2,1-b][1,3]thiazepine-7-carboxylate (33.1 mg, 0.128 mmol) to give a white solid (17 mg, 43% yield). Anal. Calcd. for $C_{39}H_{56}N_4O_8S_2$ m/z 772.3. found: 773.2 (M+H)+; 1H NMR (400 MHz, CDCl3) δ ppm 7.42 (1H, d, J=6.6 Hz), 7.27-7.21 (2H, m), 7.20-7.09 (4H, m), 5.40 (1H, t, J=4.7 Hz), 5.33 (1H, t, J=4.7 Hz), 5.21-5.17 (1H, m), 5.16-5.08 (2H, m), 5.02-4.95 (1H, m), 3.74 (3H, s), 3.69 (3H, s), 3.33-3.23 (1H, m), 3.20-3.11 (1H, m), 2.97-2.87 (1H, m), 2.87-2.69 (3H, m), 2.49-2.34 (3H, m), 2.28-2.18 (2H, m), 2.11-1.92 (5H, m), 1.85-1.76 (1H, m), 1.76-1.36 (18H, m), 1.24-1.15 (1H, m), 0.86 (7H, dd, J=8.5, 6.3 Hz).

Example 5

Dimethyl (4S,7S,10aS,4'S,7'S,10a'S)-7,7'-(((2R,5R)-2,5-dibenzyl-1,6-dioxo-1,6-hexanediyl)diimino)bis(6-oxodecahydropyrido[1,2-a]azepine-4-carboxylate)

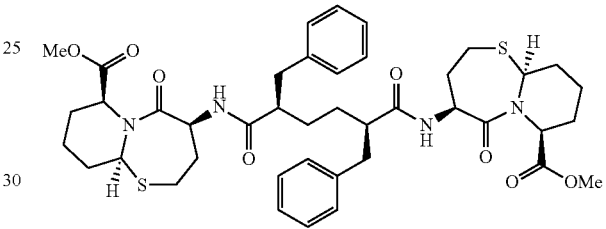

Dimethyl (4S,7S,10aS,4'S,7'S,10a'S)-7,7'-(((2R,5R)-2,5-dibenzyl-1,6-dioxo-1,6-hexanediyl)diimino)bis(6-oxodecahydropyrido[1,2-a]azepine-4-carboxylate) was synthesized as described in General Procedure F using Intermediate 3 (10 mg, 0.031 mmol) and (4S,7S,10aS)-methyl 7-amino-6-oxodecahydropyrido[1,2-a]azepine-4-carboxylate (16 mg, 0.067 mmol) to give a white solid (8.0 mg, 34% yield). Anal. Calcd. for $C_{44}H_{58}N_4O_8$ m/z 770.5. found: 771.5 (M+H)+.

Example 6

Dimethyl (4S,7S,10aS,4'S,7'S,10a'S)-4,4'-(((2R,5R)-2,5-dibenzyl-1,6-dioxo-1,6-hexanediyl)bis(methylimino))bis(5-oxooctahydro-7H-pyrido[2,1-b][1,3]thiazepine-7-carboxylate)

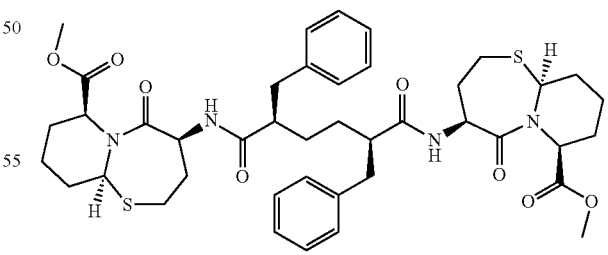

Dimethyl (4S,7S,10aS,4'S,7'S,10a'S)-4,4'-(((2R,5R)-2,5-dibenzyl-1,6-dioxo-1,6-hexanediyl)bis(methylimino))bis(5-oxooctahydro-7H-pyrido[2,1-b][1,3]thiazepine-7-carboxylate) was synthesized as described in General Procedure F using Intermediate 3 (16 mg, 0.049 mmol) and Intermediate 26 (29.4 mg, 0.108 mmol) to give a white solid (11 mg, 27% yield). Anal. Calcd. for $C_{44}H_{58}H_4O_8S_2$ m/z 770.5. found: 771.5 (M+H)+.

Example 7

(2R,5R)-2,5-Dibenzyl-N1,N6-bis((4S,7S,10aS)-7-(methoxymethyl)-5-oxooctahydro-2H-pyrido[2,1-b][1,3]thiazepin-4-yl)hexanediamide

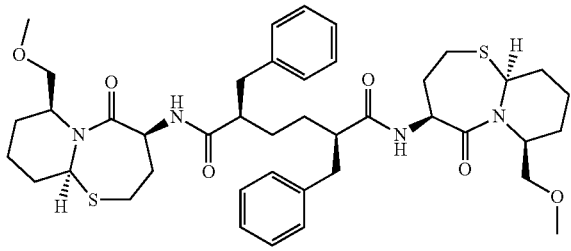 [SMILES: COC[C@@H]1CCC[C@@H]2SCC[C@H](NC(=O)[C@H](CC[C@H](Cc3ccccc3)C(=O)N[C@H]3CCS[C@H]4CCC[C@@H](COC)N4C3=O)Cc3ccccc3)C(=O)N12]

A: (2R,5R)-2,5-Dibenzyl-N1,N6-bis((4S,7S,10aS)-7-(hydroxymethyl)-5-oxooctahydro-2H-pyrido[2,1-b][1,3]thiazepin-4-yl)hexanediamide

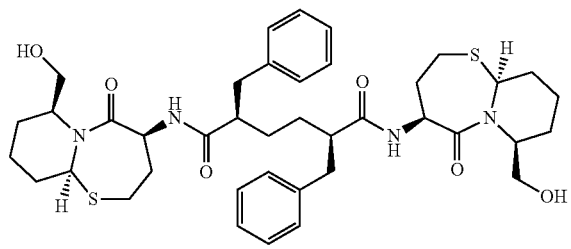 [SMILES: O=C(N[C@H]1CCS[C@H]2CCC[C@@H](CO)N2C1=O)[C@H](CC[C@H](Cc1ccccc1)C(=O)N[C@H]1CCS[C@H]2CCC[C@@H](CO)N2C1=O)Cc1ccccc1]

To a round bottom flask at 0° C. was added Example 1 (52 mg, 0.064 mmol) and THF (0.25 mL) followed by LiBH$_4$ (2.0 M in THF, 0.1 mL, 0.2 mmol). The ice bath was removed and the reaction mixture was stirred at rt overnight. The reaction mixture was carefully quenched by addition of saturated NH$_4$Cl. After 15 min of stirring, the solution was partitioned between EtOAc and water. The aqueous phase was acidified using 1 N aqueous HCl. The EtOAc layer was then isolated, washed with saturated aqueous NaCl, dried over MgSO$_4$, filtered and concentrated to give (2R,5R)-2,5-dibenzyl-N1, N6-bis((4S,7S,10aS)-7-(hydroxymethyl)-5-oxooctahydro-2H-pyrido[2,1-b][1,3]thiazepin-4-yl)hexanediamide (44 mg, 0.059 mmol, 91% yield) of a white solid. Anal. Calcd. for C$_{40}$H$_{54}$N$_4$O$_6$S$_2$ m/z 750.5. found: 751.3 (M+H)$^+$.

B: (2R,5R)-2,5-Dibenzyl-N1,N6-bis((4S,7S,10aS)-7-(methoxymethyl)-5-oxooctahydro-2H-pyrido[2,1-b][1,3]thiazepin-4-yl)hexanediamide

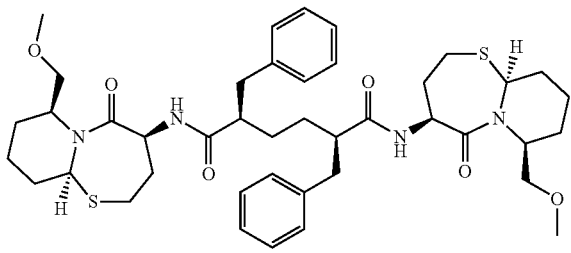 [SMILES: COC[C@@H]1CCC[C@@H]2SCC[C@H](NC(=O)[C@H](CC[C@H](Cc3ccccc3)C(=O)N[C@H]3CCS[C@H]4CCC[C@@H](COC)N4C3=O)Cc3ccccc3)C(=O)N12]

To a round bottom flask at 0° C. was added (2R,5R)-2,5-dibenzyl-N1,N6-bis((4S,7S,10aS)-7-(hydroxymethyl)-5-oxooctahydro-2H-pyrido[2,1-b][1,3]thiazepin-4-yl)hexanediamide (24.4 mg, 0.032 mmol), THF (0.15 mL) and followed by KOtBu (1.0M in THF, 0.0715 mL, 0.071 mmol). The reaction was then warmed to rt and stirred for 15 min. Then, iodomethane (18.5 mg, 0.130 mmol) was added. The reaction was stirred at rt for 4 hr. LC/MS showed a mixture of starting material, mono-ether product and desired di-ether product. Another 71 µL of KOtBu solution was added along with another 8 µL of iodomethane. The reaction mixture was stirred at rt overnight. The reaction mixture was quenched by addition of saturated aqueous NH$_4$Cl. The solution was partitioned between EtOAc and water. The organic phase was isolated, washed with saturated aqueous NaCl, dried over MgSO$_4$, filtered and concentrated. The crude product was purified by RP prep-HPLC (Method A). The fraction containing the product was concentrated to give (2R,5R)-2,5-dibenzyl-N1,N6-bis((4S,7S,10aS)-7-(methoxymethyl)-5-oxooctahydro-2H-pyrido[2,1-b][1,3]thiazepin-4-yl)hexanediamide (3.0 mg, 0.0037 mmol, 12% yield) of a white solid. Anal. Calcd. for C$_{42}$H$_{58}$N$_4$O$_6$S$_2$ m/z 778.5. found: 779.2 (M+H)$^+$; $^1$H NMR (400 MHz, CDCl$_3$) δ ppm 7.25-7.20 (4H, m), 7.18-7.11 (6H, m), 6.97-6.91 (2H, m), 5.28-5.23 (2H, m), 4.96-4.89 (2H, m), 4.71-4.65 (2H, m), 3.73-3.67 (2H, m), 3.41-3.36 (2H, m), 3.35 (6H, s), 3.23-3.15 (2H, m), 2.85-2.78 (2H, m), 2.73-2.64 (4H, m), 2.40-2.31 (2H, m), 2.09-1.95 (4H, m), 1.92-1.77 (4H, m), 1.72-1.62 (4H, m), 1.61-1.53 (4H, m), 1.51-1.44 (2H, m), 1.40-1.31 (2H, m).

Example 8

Dimethyl (4S,7S,10aS,4'S,7'S,10a'S)-4,4'-(((2R,5R)-2,5-bis(4-methoxybenzyl)-1,6-dioxo-1,6-hexanediyl)diimino)bis(5-oxooctahydro-7H-pyrido[2,1-b][1,3]thiazepine-7-carboxylate)

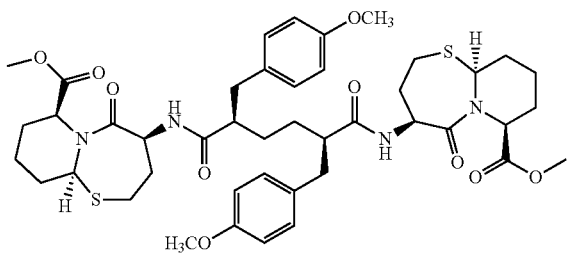

Dimethyl (4S,7S,10aS,4'S,7'S,10a'S)-4,4'-(((2R,5R)-2,5-bis(4-methoxybenzyl)-1,6-dioxo-1,6-hexanediyl)diimino)bis(5-oxooctahydro-7H-pyrido[2,1-b][1,3]thiazepine-7-carboxylate) was synthesized as described in General Procedure F using Intermediate 12 (10 mg, 0.026 mmol) and (4S,7S,10aS)-methyl 4-amino-5-oxooctahydro-2H-pyrido[2,1-b][1,3]thiazepine-7-carboxylate (26.7 mg, 0.104 mmol) to give a white solid (16 mg, 68% yield). Anal. Calcd. for C$_{44}$H$_{58}$N$_4$O$_{10}$S$_2$ m/z 866.3. found: 867.3 (M+H)$^+$; $^1$H NMR (400 MHz, CDCl$_3$) δ ppm 7.05 (d, J=7.9 Hz, 4H), 6.96 (d, J=6.2 Hz, 2H), 6.78 (d, J=8.3 Hz, 4H), 5.35 (br. s., 2H), 5.15 (br. s., 2H), 4.98 (br. s., 2H), 3.77 (s, 6H), 3.71 (s, 6H), 3.18 (t, J=12.1 Hz, 2H), 2.91-2.71 (m, 4H), 2.70-2.57 (m, 2H), 2.41 (br. s., 2H), 2.31 (br. s., 2H), 2.04 (br. s., 4H), 1.89 (br. s., 2H), 1.68 (d, J=7.9 Hz, 10H), 1.46 (br. s., 2H); $^{13}$C NMR (101 MHz, CDCl$_3$) δ ppm 173.50, 173.34, 171.38, 158.09, 131.56, 129.97, 113.71, 58.66, 55.23, 52.17, 51.16, 50.68, 49.49, 38.55, 32.32, 31.01, 30.02, 29.68, 24.90, 17.01.

Example 9

Dimethyl (4S,7S,10aS,4'S,7'S,10a'S)-4,4'-(((2R,5R)-2,5-bis(4-hydroxybenzyl)-1,6-dioxo-1,6-hexanediyl)diimino)bis(5-oxooctahydro-7H-pyrido[2,1-b][1,3]thiazepine-7-carboxylate)

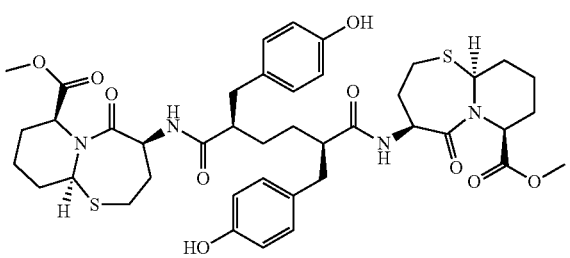

Dimethyl (4S,7S,10aS,4'S,7'S,10a'S)-4,4'-(((2R,5R)-2,5-bis(4-hydroxybenzyl)-1,6-dioxo-1,6-hexanediyl)diimino)bis(5-oxooctahydro-7H-pyrido[2,1-b][1,3]thiazepine-7-carboxylate) was synthesized as described in General Procedure F using Intermediate 16 (3 mg, 0.0084 mmol) and (4S,7S,10aS)-methyl 4-amino-5-oxooctahydro-2H-pyrido[2,1-b][1,3]thiazepine-7-carboxylate (8.7 mg, 0.033 mmol) to give a white solid (3.0 mg, 41% yield). Anal. Calcd. for $C_{42}H_{54}N_4O_{10}S_2$ m/z 838.3. found: 839.2 (M+H)$^+$; $^1$H NMR (500 MHz, CDCl$_3$) δ ppm 7.51 (d, J=6.6 Hz, 2H), 6.98 (d, J=8.2 Hz, 4H), 6.71 (d, J=8.8 Hz, 4H), 5.34 (t, J=4.4 Hz, 2H), 5.09 (d, J=4.4 Hz, 2H), 5.02-4.93 (m, 2H), 3.70 (s, 6H), 3.08 (t, J=11.5 Hz, 2H), 2.87-2.78 (m, 2H), 2.74 (dd, J=13.7, 8.8 Hz, 2H), 2.59-2.69 (m, 2H), 2.38 (d, J=6.6 Hz, 4H), 1.99 (br. s., 5H), 1.84-1.56 (m, 10H), 1.47 (br. s., 2H).

Example 10

(4S,7S,10aS)-Methyl 4-((2R,5R)-2,5-dibenzyl-6-((S)-1-(3-methoxy-3-oxopropyl)-2-oxoazepan-3-ylamino)-6-oxohexanamido)-5-oxooctahydro-2H-pyrido[2,1-b][1,3]thiazepine-7-carboxylate

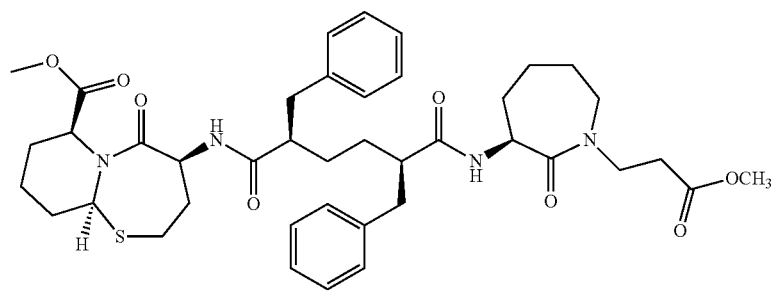

(4S,7S,10aS)-Methyl 4-((2R,5R)-2,5-dibenzyl-6-((S)-1-(3-methoxy-3-oxopropyl)-2-oxoazepan-3-ylamino)-6-oxohexanamido)-5-oxooctahydro-2H-pyrido[2,1-b][1,3]thiazepine-7-carboxylate was synthesized as described in General Procedure H using Intermediate 23 (5.0 mg, 0.0088 mmol) and Intermediate 27 (4.4 mg, 0.018 mmol) to give a white solid (2.1 mg, 29% yield). Anal. Calcd. for $C_{41}H_{54}N_4O_8S$ m/z 762.5. found: 763.5 (M+H)$^+$; $^1$H NMR (500 MHz, CDCl$_3$) δ ppm 7.26-7.06 (m, 10H), 5.50 (d, J=3.3 Hz, 1H), 5.15 (d, J=6.6 Hz, 1H), 4.98 (dd, J=8.8, 4.4 Hz, 1H), 4.44 (d, J=11.0 Hz, 1H), 3.67-3.62 (m, 6H), 3.62-3.48 (m, 2H), 3.36 (dd, J=15.4, 4.4 Hz, 1H), 3.12 (d, J=9.3 Hz, 1H), 2.89-2.72 (m, 3H), 2.72-2.59 (m, 4H), 2.59-2.50 (m, 2H), 2.36 (d, J=12.1 Hz, 1H), 2.06 (d, J=7.1 Hz, 1H), 1.97 (d, J=11.5 Hz, 1H), 1.87 (d, J=12.1 Hz, 1H), 1.84-1.54 (m, 10H), 1.54-1.40 (m, 2H), 1.39-1.27 (m, 2H).

Example 11

(4S,7S,10aS)-Methyl 4-((2R,5R)-2,5-dibenzyl-6-((S)-1-(2-methoxy-2-oxoethyl)-2-oxoazepan-3-ylamino)-6-oxohexanamido)-5-oxooctahydro-2H-pyrido[2,1-b][1,3]thiazepine-7-carboxylate

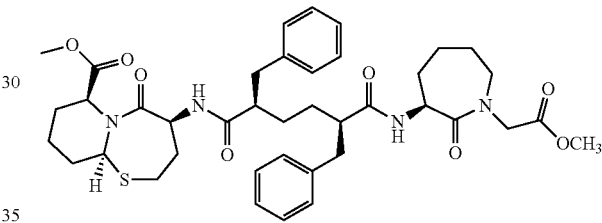

(4S,7S,10aS)-Methyl 4-((2R,5R)-2,5-dibenzyl-6-((S)-1-(2-methoxy-2-oxoethyl)-2-oxoazepan-3-ylamino)-6-oxohexanamido)-5-oxooctahydro-2H-pyrido[2,1-b][1,3]thiazepine-7-carboxylate was synthesized as described in General Procedure H using Intermediate 23 (7.0 mg, 0.012 mmol) and Intermediate 28 (5.0 mg, 0.025 mmol) to give a white solid (2.8 mg, 29% yield). Anal. Calcd. for $C_{40}H_{52}N_4O_8S$ m/z 748.5. found: 749.5 (M+H)$^+$; $^1$H NMR (500 MHz, CDCl$_3$) δ ppm 7.28-7.08 (m, 10H), 5.53 (dd, J=6.3, 3.0 Hz, 1H), 5.03-4.95 (m, 2H), 4.65-4.55 (m, 1H), 4.25-4.15 (m, 1H), 4.08-4.01 (m, 1H), 3.72 (dd, J=15.4, 10.4 Hz, 1H), 3.67 (s, 3H), 3.64 (s, 3H), 3.35 (d, J=2.7 Hz, 1H), 3.11-3.01 (m, 1H), 2.83 (ddd, J=14.3, 6.9, 3.0 Hz, 1H), 2.80-2.62 (m, 6H), 2.34 (d, J=13.7 Hz, 1H), 2.15-2.04 (m, 1H), 2.03-1.94 (m, 1H), 1.90-1.82 (m, 1H), 1.79-1.51 (m, 13H), 1.35-1.25 (m, 2H).

Example 12

(4S,7S,10aS)-Methyl 4-((2R,5R)-2,5-dibenzyl-6-((3R,8aS)-2,2-dimethyl-4-oxohexahydro-2H-pyrrolo[2,1-b][1,3]thiazin-3-ylamino)-6-oxohexanamido)-5-oxooctahydro-2H-pyrido[2,1-b][1,3]thiazepine-7-carboxylate

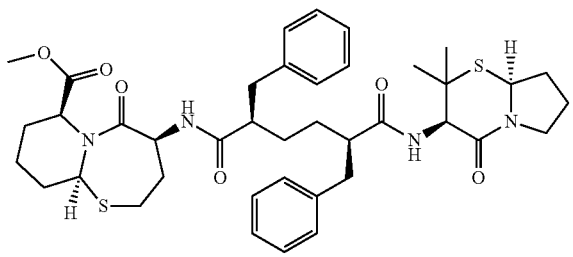 [SMILES: COC(=O)[C@@H]1CCC[C@@H]2SCC[C@H](NC(=O)[C@H](CC[C@H](Cc3ccccc3)C(=O)N[C@@H]3C(=O)N4CCC[C@@H]4SC3(C)C)Cc3ccccc3)C(=O)N21]

(4S,7S,10aS)-Methyl 4-((2R,5R)-2,5-dibenzyl-6-((3R,8aS)-2,2-dimethyl-4-oxohexahydro-2H-pyrrolo[2,1-b][1,3]thiazin-3-ylamino)-6-oxohexanamido)-5-oxooctahydro-2H-pyrido[2,1-b][1,3]thiazepine-7-carboxylate was synthesized as described in General Procedure H using Intermediate 23 (15 mg, 0.026 mmol) and Intermediate 29 (8.0 mg, 0.040 mmol) to give a white solid (15 mg, 72% yield). Anal. Calcd. for $C_{40}H_{52}N_4O_6S_2$ m/z 748.4. found: 749.3 (M+H)+; $^1$H NMR (500 MHz, CD$_3$OD) δ ppm 8.14 (d, J=7.70 Hz, 1H), 7.95 (d, J=9.35 Hz, 1H), 7.28-7.08 (m, 10H), 5.56 (dd, J=6.05, 2.75 Hz, 1H), 5.21-5.12 (m, 1H), 5.07-4.99 (m, 2H), 4.79 (d, J=9.35 Hz, 1H), 3.69-3.57 (m, 4H), 3.43-3.35 (m, 1H), 3.12-3.04 (m, 1H), 2.94 (br. s., 1H), 2.88-2.77 (m, 3H), 2.75-2.66 (m, 3H), 2.43 (dd, J=13.20, 6.60 Hz, 1H), 2.36 (d, J=13.75 Hz, 1H), 2.16-1.88 (m, 4H), 1.88-1.68 (m, 5H), 1.68-1.57 (m, 5H), 0.87 (s, 3H), 0.84 (s, 3H).

Example 13

(4S,7S,10aS)-Methyl 4-((2R,5R)-2,5-dibenzyl-6-((3R,9aS)-2,2-dimethyl-4-oxooctahydropyrido[2,1-b][1,3]thiazin-3-ylamino)-6-oxohexanamido)-5-oxooctahydro-2H-pyrido[2,1-b][1,3]thiazepine-7-carboxylate

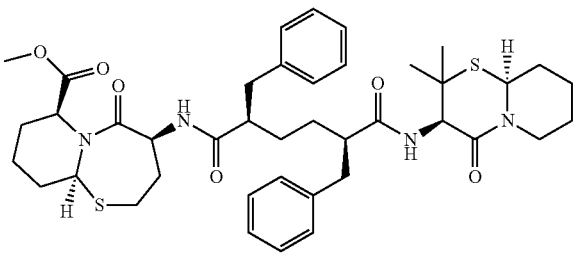 [SMILES: COC(=O)[C@@H]1CCC[C@@H]2SCC[C@H](NC(=O)[C@H](CC[C@H](Cc3ccccc3)C(=O)N[C@@H]3C(=O)N4CCCC[C@@H]4SC3(C)C)Cc3ccccc3)C(=O)N21]

(4S,7S,10aS)-Methyl 4-((2R,5R)-2,5-dibenzyl-6-((3R,9aS)-2,2-dimethyl-4-oxooctahydropyrido[2,1-b][1,3]thiazin-3-ylamino)-6-oxohexanamido)-5-oxooctahydro-2H-pyrido[2,1-b][1,3]thiazepine-7-carboxylate was synthesized as described in General Procedure H using Intermediate 23 (15 mg, 0.026 mmol) and Intermediate 30 (8.7 mg, 0.026 mmol) to give a white solid (12 mg, 56% yield). Anal. Calcd. for $C_{41}H_{54}N_4O_6S_2$ m/z 762.4. found: 763.4 (M+H)+; $^1$H NMR (500 MHz, CD$_3$OD) δ ppm 8.09 (d, J=7.70 Hz, 1H), 7.94 (d, J=9.35 Hz, 1H), 7.28-7.06 (m, 10H), 5.54 (dd, J=6.32, 3.02 Hz, 1H), 5.13-5.07 (m, 1H), 5.03 (dd, J=10.17, 3.57 Hz, 1H), 4.82-4.78 (m, 1H), 4.76 (d, J=9.35 Hz, 1H), 4.20 (d, J=13.20 Hz, 1H), 3.63 (s, 3H), 3.14-3.04 (m, 1H), 3.00-2.91 (m, 1H), 2.91-2.76 (m, 4H), 2.77-2.66 (m, 3H), 2.41-2.28 (m, 1H), 2.14-2.03 (m, 1H), 2.02-1.87 (m, 2H), 1.84-1.51 (m, 14H), 0.99 (s, 3H), 0.74 (s, 3H).

Example 14

(4S,7S,10aS)-Methyl 4-((2R,5R)-2,5-dibenzyl-6-oxo-6-((3R,9aS)-4-oxooctahydropyrido[2,1-b][1,3]thiazin-3-ylamino)hexanamido)-5-oxooctahydro-2H-pyrido[2,1-b][1,3]thiazepine-7-carboxylate

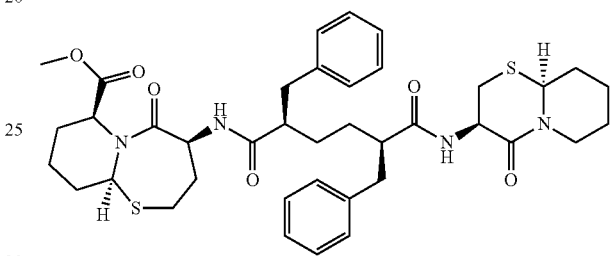

(4S,7S,10aS)-Methyl 4-((2R,5R)-2,5-dibenzyl-6-((3R)-2,2-dimethyl-4-oxooctahydropyrido[2,1-b][1,3]thiazin-3-ylamino)-6-oxohexanamido)-5-oxooctahydro-2H-pyrido[2,1-b][1,3]thiazepine-7-carboxylate was synthesized as described in General Procedure H using Intermediate 23 (10 mg, 0.018 mmol) and Intermediate 31 (3.3 mg, 0.018 mmol) to give a white solid (7.0 mg, 51% yield). Anal. Calcd. for $C_{39}H_{50}N_4O_6S_2$ m/z 734.4. found: 735.3 (M+H)+; $^1$H NMR (500 MHz, CD$_3$OD) δ ppm 7.23 (dd, J=7.42, 3.57 Hz, 4H), 7.20-7.10 (m, 6H), 7.08 (d, J=6.60 Hz, 1H), 6.77 (d, J=6.05 Hz, 1H), 5.36 (t, J=4.40 Hz, 1H), 5.12 (d, J=4.40 Hz, 1H), 5.06-4.98 (m, 1H), 4.69-4.60 (m, 1H), 4.52 (dd, J=9.90, 3.30 Hz, 1H), 4.22 (dd, J=9.07, 4.67 Hz, 1H), 3.73-3.65 (m, 3H), 3.19-3.09 (m, 2H), 2.98 (dd, J=12.10, 5.50 Hz, 2H), 2.88-2.71 (m, 5H), 2.52-2.35 (m, 3H), 2.24 (t, J=11.55 Hz, 1H), 2.04 (d, J=4.95 Hz, 2H), 1.98-1.51 (m, 14H).

Example 15

(4S,7S,10aS)-Methyl 4-((2R,5R)-2,5-dibenzyl-6-oxo-6-((S)-2-oxo-1-phenylpiperidin-3-ylamino)hexanamido)-5-oxooctahydro-2H-pyrido[2,1-b][1,3]thiazepine-7-carboxylate

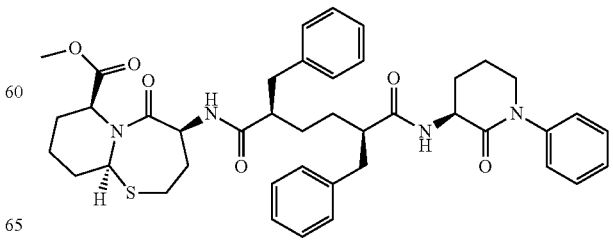

(4S,7S,10aS)-Methyl 4-((2R,5R)-2,5-dibenzyl-6-oxo-6-((S)-2-oxo-1-phenylpiperidin-3-ylamino)hexanamido)-5-oxooctahydro-2H-pyrido[2,1-b][1,3]thiazepine-7-carboxylate was synthesized as described in General Procedure H using Intermediate 23 (10 mg, 0.018 mmol) and Intermediate 32 (3.4 mg, 0.018 mmol) to give a white solid (5.0 mg, 36% yield). Anal. Calcd. for $C_{42}H_{50}N_4O_6S$ m/z 738.4. found: 739.4 $(M+H)^+$; $^1$H NMR (500 MHz, $CD_3OD$) δ ppm 7.46-7.35 (m, 2H), 7.32-7.25 (m, 3H), 7.23-7.08 (m, 10H), 5.49 (dd, J=6.32, 3.02 Hz, 1H), 5.08-5.02 (m, 1H), 4.98-4.91 (m, 1H), 4.17 (dd, J=11.00, 6.05 Hz, 1H), 3.97 (s, 1H), 3.73 (d, J=7.15 Hz, 1H), 3.64 (s, 3H), 3.09 (s, 1H), 2.89-2.76 (m, 2H), 2.76-2.65 (m, 3H), 2.65-2.51 (m, 2H), 2.31 (br. s., 1H), 2.11-1.91 (m, 5H), 1.90-1.80 (m, 1H), 1.77-1.55 (m, 7H), 1.57-1.46 (m, 2H).

Example 16

(4S,7S,10aS)-Methyl 4-((2R,5R)-2,5-dibenzyl-6-((S,Z)-4,4-dimethyl-2-oxo-1-phenyl-2,3,4,7-tetrahydro-1H-azepin-3-ylamino)-6-oxohexanamido)-5-oxooctahydro-2H-pyrido[2,1-b][1,3]thiazepine-7-carboxylate

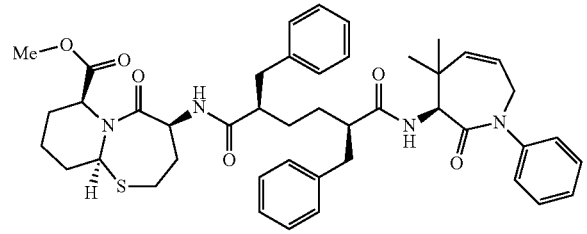 [SMILES: COC(=O)[C@@H]1CCC[C@@H]2SCC[C@H](NC(=O)[C@H](CC[C@H](Cc3ccccc3)C(=O)N[C@@H]3C(=O)N(c4ccccc4)CC=CC3(C)C)Cc3ccccc3)C(=O)N21]

(4S,7S,10aS)-Methyl 4-((2R,5R)-2,5-dibenzyl-6-((S,Z)-4,4-dimethyl-2-oxo-1-phenyl-2,3,4,7-tetrahydro-1H-azepin-3-ylamino)-6-oxohexanamido)-5-oxooctahydro-2H-pyrido[2,1-b][1,3]thiazepine-7-carboxylate was synthesized as described in General Procedure H using Intermediate 23 (10 mg, 0.018 mmol) and Intermediate 33 (4.1 mg, 0.018 mmol) to give a white solid (4.0 mg, 27% yield). Anal. Calcd. for $C_{45}H_{54}N_4O_6S$ m/z 778.4. found: 779.4 $(M+H)^+$; $^1$H NMR (500 MHz, $CD_3OD$) δ ppm 8.00-8.08 (m, 1H), 7.31 (t, J=7.70 Hz, 2H), 7.27-7.09 (m, 11H), 6.98 (d, J=7.70 Hz, 2H), 5.77 (ddd, J=11.41, 8.11, 3.57 Hz, 1H), 5.63-5.49 (m, 2H), 5.38 (d, J=9.35 Hz, 1H), 5.04-4.97 (m, 1H), 4.96-4.90 (m, 1H), 3.75 (dd, J=17.60, 8.25 Hz, 1H), 3.59 (s, 3H), 3.03-2.88 (m, 2H), 2.84-2.65 (m, 5H), 2.62-2.53 (m, 1H), 2.34 (d, J=13.75 Hz, 1H), 2.16-2.01 (m, 1H), 1.96 (d, J=10.45 Hz, 1H), 1.89-1.79 (m, 2H), 1.76-1.47 (m, 6H), 1.41-1.30 (m, 1H), 0.89-0.80 (s, 3H), 0.54-0.46 (s, 3H).

Example 17

(4S,7S,10aS)-Methyl 4-((2R,5R)-2,5-dibenzyl-6-((S)-4,4-dimethyl-2-oxo-1-phenylazepan-3-ylamino)-6-oxohexanamido)-5-oxooctahydro-2H-pyrido[2,1-b][1,3]thiazepine-7-carboxylate

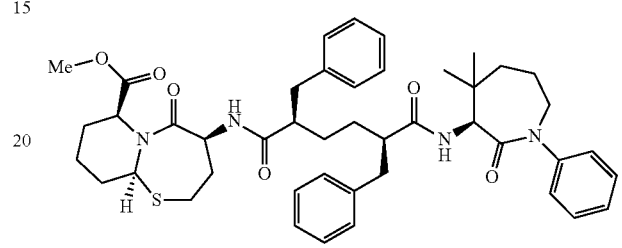

(4S,7S,10aS)-Methyl 4-((2R,5R)-2,5-dibenzyl-6-((S)-4,4-dimethyl-2-oxo-1-phenylazepan-3-ylamino)-6-oxohexanamido)-5-oxooctahydro-2H-pyrido[2,1-b][1,3]thiazepine-7-carboxylate was synthesized as described in General Procedure H using Intermediate 23 (10 mg, 0.018 mmol) and Intermediate 34 (4.1 mg, 0.018 mmol) to give a white solid (4.0 mg, 27% yield). Anal. Calcd. for $C_{45}H_{56}N_4O_6S$ m/z 780.4. found: 781.5 $(M+H)^+$; $^1$H NMR (500 MHz, $CD_3OD$) δ ppm 7.32 (t, J=7.70 Hz, 2H), 7.28-7.10 (m, 11H), 7.00 (d, J=7.70 Hz, 2H), 5.52 (dd, J=6.05, 2.75 Hz, 1H), 5.07-4.97 (m, 2H), 4.94-4.88 (m, 1H), 4.12-4.00 (m, 1H), 3.60 (s, 3H), 3.58-3.51 (m, 1H), 2.98-2.82 (m, 2H), 2.82-2.63 (m, 5H), 2.59-2.50 (m, 1H), 2.38-2.27 (m, 1H), 2.13-2.02 (m, 1H), 1.97 (br. s., 2H), 1.86-1.75 (m, 3H), 1.75-1.55 (m, 7H), 1.48 (s, 1H), 1.32-1.24 (m, 1H), 0.80 (s, 3H), 0.45 (s, 3H).

Example 18

Dimethyl (1S,9S,1'S,9'S)-9,9'-(((2R,5R)-2,5-dibenzyl-1,6-dioxo-1,6-hexanediyl)diimino)bis(10-oxooctahydro-6H-pyridazino[1,2-a][1,2]diazepine-1-carboxylate)

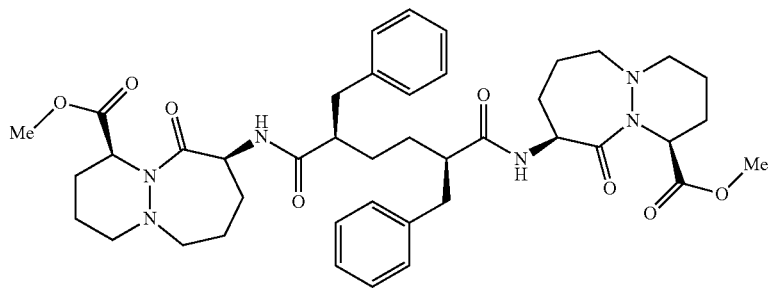 [SMILES: COC(=O)[C@@H]1CCCN2CCC[C@H](NC(=O)[C@H](CC[C@H](Cc3ccccc3)C(=O)N[C@H]3CCCN4CCC[C@@H](C(=O)OC)N4C3=O)Cc3ccccc3)C(=O)N12]

A: Di-tert-butyl (1S,9S,1'S,9'S)-9,9'-(((2R,5R)-2,5-dibenzyl-1,6-dioxo-1,6-hexanediyl)diimino)bis(10-oxooctahydro-6H-pyridazino[1,2-a][1,2]diazepine-1-carboxylate)

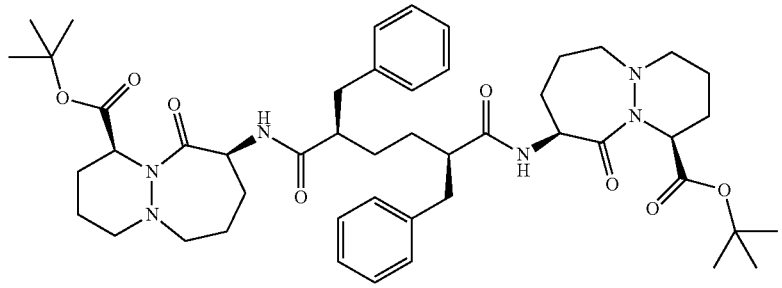 [SMILES: CC(C)(C)OC(=O)[C@@H]1CCCN2CCC[C@H](NC(=O)[C@H](CC[C@H](Cc3ccccc3)C(=O)N[C@H]3CCCN4CCC[C@@H](C(=O)OC(C)(C)C)N4C3=O)Cc3ccccc3)C(=O)N12]

Di-tert-butyl (1S,9S,1'S,9'S)-9,9'-(((2R,5R)-2,5-dibenzyl-1,6-dioxo-1,6-hexanediyl)diimino)bis(10-oxooctahydro-6H-pyridazino[1,2-a][1,2]diazepine-1-carboxylate) was synthesized as described in General Procedure F using Intermediate 3 (11 mg, 0.034 mmol) and (1S,9S)-tert-butyl 9-amino-10-oxooctahydro-1H-pyridazino[1,2-a][1,2]diazepine-1-carboxylate (28.7 mg, 0.101 mmol) to give a white solid (28 mg, 97% yield). Anal. Calcd. for $C_{48}H_{68}N_6O_8$ m/z 856.9. found: 857.8 (M+H)⁺.

B: (1S,9S,1'S,9'S)-9,9'-(((2R,5R)-2,5-Dibenzyl-1,6-dioxo-1,6-hexanediyl)diimino)bis(10-oxooctahydro-6H-pyridazino[1,2-a][1,2]diazepine-1-carboxylic acid)

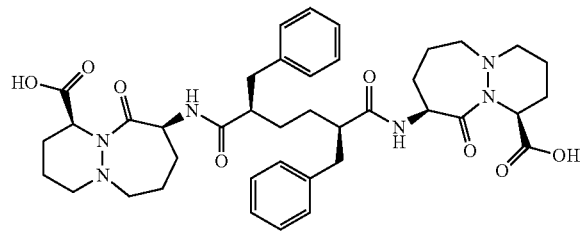 [SMILES: O=C(N[C@H]1CCCN2CCC[C@@H](C(=O)O)N2C1=O)[C@H](CC[C@H](Cc1ccccc1)C(=O)N[C@H]1CCCN2CCC[C@@H](C(=O)O)N2C1=O)Cc1ccccc1]

TFA (0.075 mL) was added to a solution of di-tert-butyl (1S,9S,1'S,9'S)-9,9'-(((2R,5R)-2,5-dibenzyl-1,6-dioxo-1,6-hexanediyl)diimino)bis(10-oxooctahydro-6H-pyridazino[1,2-a][1,2]diazepine-1-carboxylate) (28 mg, 0.033 in DCM, 0.25 mL). The reaction mixture was stirred overnight at rt. The reaction mixture was concentrated and placed under vacuum to give (1S,9S,1'S,9'S)-9,9'-(((2R,5R)-2,5-dibenzyl-1,6-dioxo-1,6-hexanediyl)diimino)bis(10-oxooctahydro-6H-pyridazino[1,2-a][1,2]diazepine-1-carboxylic acid) (25 mg, 0.033 mmol, 100% yield). Anal. Calcd. for $C_{40}H_{52}N_6O_8$ m/z 744.8. found: 745.6 (M+H)⁺.

C: Dimethyl (1S,9S,1'S,9'S)-9,9'-(((2R,5R)-2,5-dibenzyl-1,6-dioxo-1,6-hexanediyl)diimino)bis(10-oxooctahydro-6H-pyridazino[1,2-a][1,2]diazepine-1-carboxylate)

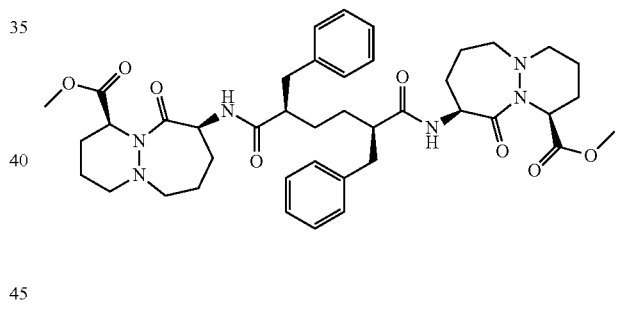

TMS-diazomethane (2.0 $\underline{M}$ in hexanes, 0.067 mL, 0.13 mmol) was added to a 0° C. solution of previous (1S,9S,1'S,9'S)-9,9'-(((2R,5R)-2,5-dibenzyl-1,6-dioxo-1,6-hexanediyl)diimino)bis(10-oxooctahydro-6H-pyridazino[1,2-a][1,2]diazepine-1-carboxylic acid) (25 mg, 0.033 mmol) in DCM (0.16 mL) and MeOH (0.016 mL). The reaction mixture was then stirred at rt for 1 hr. The reaction mixture was concentrated. The residue was purified by RP prep-HPLC (Method A) to give dimethyl (1S,9S,1'S,9'S)-9,9'-(((2R,5R)-2,5-dibenzyl-1,6-dioxo-1,6-hexanediyl)diimino)bis(10-oxooctahydro-6H-pyridazino[1,2-a][1,2]diazepine-1-carboxylate) (5.0 mg, 0.0065 mmol, 19% yield). Anal. Calcd. for $C_{42}H_{56}N_6O_8$ m/z 772.8. found: 773.6 (M+H)⁺; ¹H NMR (400 MHz, CDCl₃) δ ppm 7.29-7.09 (10H, m), 6.74 (2H, d, J=7.1 Hz), 5.28-5.17 (2H, m), 4.98 (2H, d, J=5.5 Hz), 3.72 (6H, s), 3.30-3.22 (2H, m), 3.16 (2H, t, J=12.1 Hz), 2.99-2.80 (4H, m), 2.71 (2H, dd, J=13.5, 5.8 Hz), 2.57-2.48 (2H, m), 2.44-

2.28 (4H, m), 1.92-1.64 (12H, m), 1.61-1.50 (2H, m), 1.44-1.35 (2H, m), 1.09-0.97 (2H, m).

Example 19

Dimethyl (4S,7S,10aS,4'S,7'S,10a'S)-4,4'-(((2R,5R)-2,5-bis(4-fluorobenzyl)-1,6-dioxo-1,6-hexanediyl)diimino)bis(5-oxooctahydro-7H-pyrido[2,1-b][1,3]thiazepine-7-carboxylate)

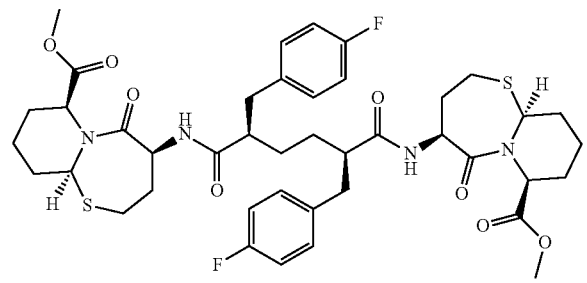 [SMILES: COC(=O)[C@@H]1CCC[C@@H]2SCC[C@H](NC(=O)[C@H](CC[C@H](Cc3ccc(F)cc3)C(=O)N[C@H]3CCS[C@H]4CCC[C@@H](C(=O)OC)N4C3=O)Cc3ccc(F)cc3)C(=O)N21]

Dimethyl (4S,7S,10aS,4'S,7'S,10a'S)-4,4'-(((2R,5R)-2,5-bis(4-fluorobenzyl)-1,6-dioxo-1,6-hexanediyl)diimino)bis(5-oxooctahydro-7H-pyrido[2,1-b][1,3]thiazepine-7-carboxylate) was synthesized as described in General Procedure F using Intermediate 18 (15 mg, 0.041 mmol) and (4S,7S,10aS)-methyl 4-amino-5-oxooctahydro-2H-pyrido[2,1-b][1,3]thiazepine-7-carboxylate (24 mg, 0.091 mmol) to give a white solid (22 mg, 63% yield). Anal. Calcd. for $C_{42}H_{52}F_2N_4O_8S_2$ m/z 842.5. found: 843.3 (M+H)$^+$.

Example 20

(2R,5R)—N1,N6-Bis((4S,7S,10aS)-7-(1,3,4-oxadiazol-2-yl)-5-oxooctahydro-2H-pyrido[2,1-b][1,3]thiazepin-4-yl)-2,5-dibenzylhexanediamide

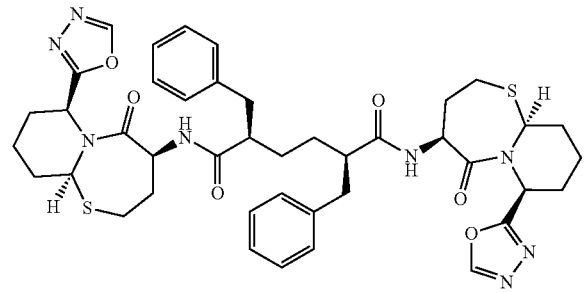 [SMILES: O=C(N[C@H]1CCS[C@H]2CCC[C@@H](c3nnco3)N2C1=O)[C@H](CC[C@H](Cc1ccccc1)C(=O)N[C@H]1CCS[C@H]2CCC[C@@H](c3nnco3)N2C1=O)Cc1ccccc1]

(2R,5R)—N1,N6-Bis((4S,7S,10aS)-7-(1,3,4-oxadiazol-2-yl)-5-oxooctahydro-2H-pyrido[2,1-b][1,3]thiazepin-4-yl)-2,5-dibenzylhexanediamide was synthesized as described in General Procedure F using Intermediate 3 (7.0 mg, 0.021 mmol) and Intermediate 35 (19 mg, 0.049 mmol) to give a white solid (12 mg, 65% yield). Anal. Calcd. for $C_{42}H_{50}N_8O_6S_2$ m/z 826.5. found: 827.2 (M+H)$^+$; $^1$H NMR (500 MHz, CDCl$_3$) δ ppm 8.42 (s, 2H), 7.35-7.10 (m, 10H), 6.90 (br, 2H), 5.90 (m, 2H), 5.31 (m, 2H), 5.06 (m, 2H), 3.13 (m, 2H), 2.90-2.60 (m, 6H), 2.58 (m, 2H), 2.45 (m, 2H), 2.12 (m, 4H), 1.98 (m, 4H), 1.80-1.38 (m, 10H).

Example 21

(4S,7S,10aS)-Methyl 4-((2R,5R)-2,5-dibenzyl-6-((4R,7S,10aR)-7-(methoxycarbonyl)-5-oxooctahydro-2H-pyrido[2,1-b][1,3]thiazepin-4-ylamino)-6-oxohexanamido)-5-oxooctahydro-2H-pyrido[2,1-b][1,3]thiazepine-7-carboxylate

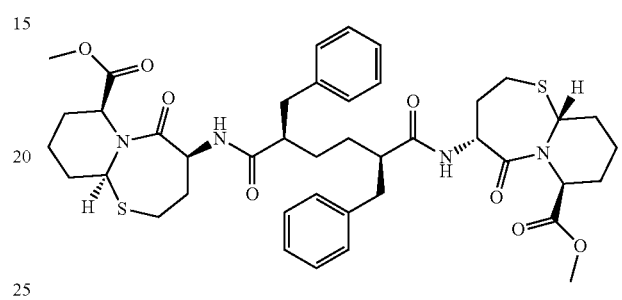

(4S,7S,10aS)-Methyl 4-((2R,5R)-2,5-dibenzyl-6-((4R,7S,10aR)-7-(methoxycarbonyl)-5-oxooctahydro-2H-pyrido[2,1-b][1,3]thiazepin-4-ylamino)-6-oxohexanamido)-5-oxooctahydro-2H-pyrido[2,1-b][1,3]thiazepine-7-carboxylate was synthesized as described in General Procedure H using Intermediate 23 (5.0 mg, 0.0088 mmol) and (4R,7S,10aR)-methyl 4-amino-5-oxooctahydro-2H-pyrido[2,1-b][1,3]thiazepine-7-carboxylate (2.2 mg, 0.0097 mmol) to give a white solid (3.2 mg, 40% yield). Anal. Calcd. for $C_{42}H_{54}N_4O_8S_2$ m/z 806.4. found: 807.4 (M+H)$^+$.

Example 22

(2R,5R)-2,5-Dibenzyl-N1,N6-bis((4S,7S,10aS)-7-cyano-5-oxooctahydro-2H-pyrido[2,1-b][1,3]thiazepin-4-yl)hexanediamide

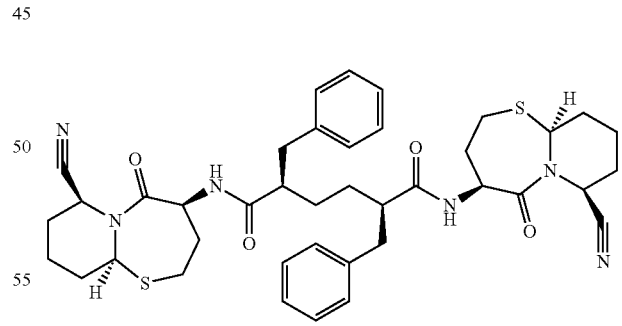

(2R,5R)-2,5-Dibenzyl-N1,N6-bis((4S,7S,10aS)-7-cyano-5-oxooctahydro-2H-pyrido[2,1-b][1,3]thiazepin-4-yl)hexanediamide was synthesized as described in General Procedure F using Intermediate 3 (9.0 mg, 0.028 mmol) and Intermediate 36 (14 mg, 0.061 mmol) to give a white solid (3.7 mg, 8.2% yield). Anal. Calcd. for $C_{40}H_{48}N_6O_4S_2$ m/z 740.6. found: 741.5 (M+H)$^+$; $^1$H NMR (400 MHz, CDCl$_3$) δ ppm 7.30-7.09 (12H, m), 5.45-5.41 (2H, m), 5.31-5.26 (2H, m), 5.05-4.96 (2H, m), 3.08-2.98 (2H, m), 2.89-2.80 (2H, m), 2.73-2.64 (4H, m), 2.52-2.44 (2H, m), 2.41-2.26 (4H, m), 2.24-2.13 (4H, m), 2.08-1.91 (4H, m), 1.85-1.70 (4H, m), 1.64-1.53 (4H, m).

Example 23

(4S,7S,10aS)-Methyl 4-((2R,5R)-2,5-dibenzyl-6-oxo-6-((S)-2-oxo-2,3,4,5-tetrahydro-1H-benzo[b]azepin-3-ylamino)hexanamido)-5-oxooctahydro-2H-pyrido[2,1-b][1,3]thiazepine-7-carboxylate

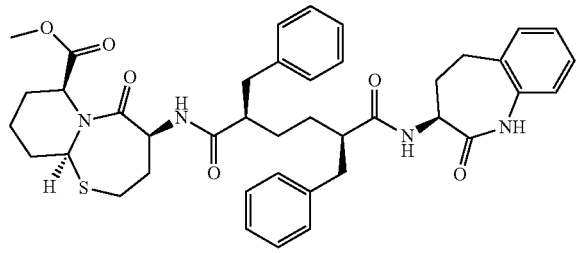 [SMILES: COC(=O)[C@@H]1CCC[C@@H]2SCC[C@H](NC(=O)[C@H](CC[C@H](Cc3ccccc3)C(=O)N[C@H]3CCc4ccccc4NC3=O)Cc3ccccc3)C(=O)N21]

(4S,7S,10aS)-Methyl 4-((2R,5R)-2,5-dibenzyl-6-oxo-6-((S)-2-oxo-2,3,4,5-tetrahydro-1H-benzo[b]azepin-3-ylamino)hexanamido)-5-oxooctahydro-2H-pyrido[2,1-b][1,3]thiazepine-7-carboxylate was synthesized as described in General Procedure H using Intermediate 23 (5.0 mg, 0.0088 mmol) and (S)-3-amino-4,5-dihydro-1H-benzo[b]azepin-2(3H)-one (1.6 mg, 0.0088 mmol) to give a white solid (5.1 mg, 80% yield). Anal. Calcd. for $C_{41}H_{48}N_4O_6S$ m/z 724.9. found: 725.3 (M+H)$^+$; $^1$H NMR (400 MHz, CDCl$_3$) δ ppm 7.24-6.90 (m, 14H), 6.28-6.20 (m, 1H), 5.29-5.20 (m, 1H), 5.04-4.97 (m, 2H), 4.93-4.84 (m, 2H), 4.30-4.20 (m, 1H), 3.60-3.53 (m, 3H), 3.20-3.04 (m, 1H), 2.82-2.50 (m, 8H), 2.37-2.19 (m, 4H), 1.96-1.88 (m, 2H), 1.85-1.68 (m, 2H), 1.67-1.31 (m, 6H), 1.27-1.14 (m, 1H).

Example 24

(2R,5R)-2,5-Dibenzyl-N1-((4R,7S,10aS)-5-oxo-7-(thiazol-2-ylcarbamoyl)octahydro-2H-pyrido[2,1-b][1,3]thiazepin-4-yl)-N6-((4S,7S,10aS)-5-oxo-7-(thiazol-2-ylcarbamoyl)octahydro-2H-pyrido[2,1-b][1,3]thiazepin-4-yl)hexanediamide

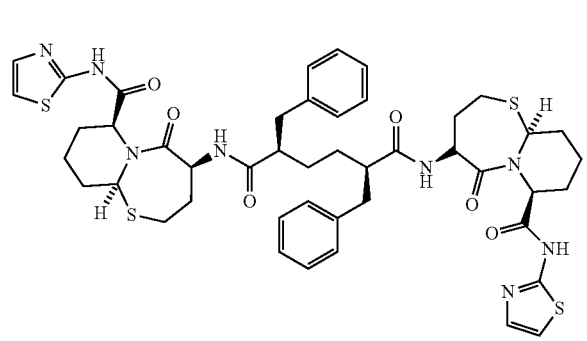

(2R,5R)-2,5-Dibenzyl-N1-((4R,7S,10aS)-5-oxo-7-(thiazol-2-ylcarbamoyl)octahydro-2H-pyrido[2,1-b][1,3]thiazepin-4-yl)-N6-((4S,7S,10aS)-5-oxo-7-(thiazol-2-ylcarbamoyl)octahydro-2H-pyrido[2,1-b][1,3]thiazepin-4-yl)hexanediamide was synthesized as described in General Procedure F using Intermediate 3 (10 mg, 0.031 mmol) and Intermediate 37 (25 mg, 0.069 mmol) to give a white solid (14 mg, 46% yield). Anal. Calcd. for $C_{46}H_{54}N_8O_6S_4$ m/z 942.7. found: 943.5 (M+H)$^+$; $^1$H NMR (400 MHz, CDCl$_3$) δ ppm 7.21-7.11 (m, 14H), 5.38 (br s, 2H), 5.11 (m, 4H), 3.15 (m, 2H), 2.76 (m, 6H), 2.36 (m, 4H), 2.12 (m, 4H), 1.85-1.40 (m, 14H).

Example 25

(2R,5R)-2,5-Dibenzyl-N1,N6-bis((4S,7S,10aS)-5-oxo-7-(propylcarbamoyl)octahydro-2H-pyrido[2,1-b][1,3]thiazepin-4-yl)hexanediamide

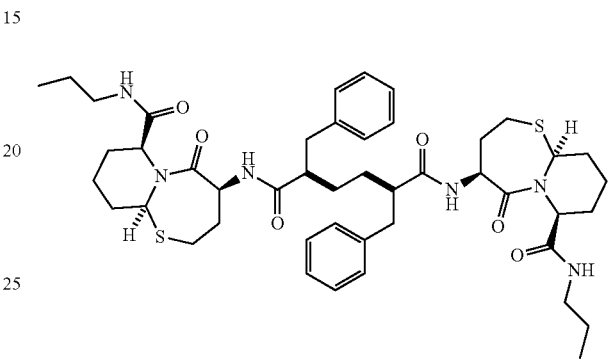

(2R,5R)-2,5-Dibenzyl-N1,N6-bis((4S,7S,10aS)-5-oxo-7-(propylcarbamoyl)octahydro-2H-pyrido[2,1-b][1,3]thiazepin-4-yl)hexanediamide was synthesized as described in General Procedure F using Intermediate 3 (7.9 mg, 0.024 mmol) and Intermediate 38 (18 mg, 0.056 mmol) to give a light yellow solid (15 mg, 70% yield). Anal. Calcd. for $C_{46}H_{64}N_6O_6S_2$ m/z 860.7. found: 861.6 (M+H)$^+$; $^1$H NMR (400 MHz, CDCl$_3$) δ ppm 7.24-7.13 (m, 10H), 5.31 (m, 2H), 4.94 (m, 4H), 3.33-3.13 (m, 6H), 2.76 (m, 6H), 2.35 (m, 4H), 2.08 (m, 4H), 1.70-1.47 (m, 18H), 0.90 (m, 6H).

Example 26

(4S,7S,10aS)-Methyl 4-((2R,5R)-2,5-dibenzyl-6-((4R,10aR)-1,5-dioxodecahydropyrido[1,2-a][1,4]diazepin-4-ylamino)-6-oxohexanamido)-5-oxooctahydro-2H-pyrido[2,1-b][1,3]thiazepine-7-carboxylate

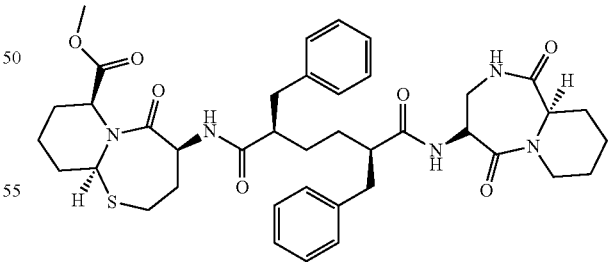

(4S,7S,10aS)-Methyl 4-((2R,5R)-2,5-dibenzyl-6-((4R,10aR)-1,5-dioxodecahydropyrido[1,2-a][1,4]diazepin-4-ylamino)-6-oxohexanamido)-5-oxooctahydro-2H-pyrido[2,1-b][1,3]thiazepine-7-carboxylate was synthesized as described in General Procedure H using Intermediate 23 (20 mg, 0.035 mmol) and Intermediate 39 (7.0 mg, 0.035 mmol) to give a white solid (15 mg, 56% yield). Anal. Calcd. for $C_{40}H_{51}N_5O_7S$ m/z 745.7. found: 746.5 (M+H)$^+$; $^1$H NMR (400 MHz, DMSO-d$_6$) δ ppm 7.92-7.70 (m, 3H), 7.29-7.02

(m, 7H), 5.67-5.52 (m, 1H), 5.09-4.91 (m, 2H), 4.36 (d, J=13.0 Hz, 1H), 3.83-3.75 (m, 1H), 3.73-3.64 (m, 1H), 3.64-3.52 (m, 4H), 3.22-2.98 (m, 2H), 2.82-2.61 (m, 4H), 2.60-2.34 (m, 8H), 2.18 (d, J=13.8 Hz, 1H), 2.09-1.88 (m, 2H), 1.86-1.73 (m, 2H), 1.71-1.15 (m, 12H).

Example 27

Methyl (4S,7S,10aS)-4-(((2R,5R)-2-benzyl-7-tert-butoxy-5-(((4S,7S,10aS)-7-(methoxycarbonyl)-5-oxooctahydro-7H-pyrido[2,1-b][1,3]thiazepin-4-yl)carbamoyl)-7-oxoheptanoyl)amino)-5-oxooctahydro-7H-pyrido[2,1-b][1,3]thiazepine-7-carboxylate

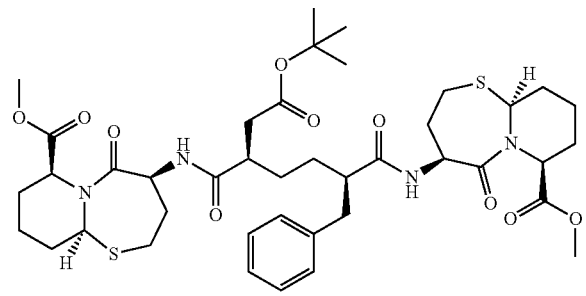 [SMILES: COC(=O)[C@@H]1CCC[C@@H]2SCC[C@H](NC(=O)[C@H](CC[C@H](Cc3ccccc3)C(=O)N[C@H]3CCS[C@H]4CCC[C@@H](C(=O)OC)N4C3=O)CC(=O)OC(C)(C)C)C(=O)N21]

Methyl (4S,7S,10aS)-4-(2R,5R)-2-benzyl-7-tert-butoxy-5-(((4S,7S,10aS)-7-(methoxycarbonyl)-5-oxooctahydro-7H-pyrido[2,1-b][1,3]thiazepin-4-yl)carbamoyl)-7-oxoheptanoyl)amino)-5-oxooctahydro-7H-pyrido[2,1-b][1,3]thiazepine-7-carboxylate was synthesized as described in General Procedure F using Intermediate 46 (33 mg, 0.094 mmol) and (4S,7S,10aS)-methyl 4-amino-5-oxooctahydro-2H-pyrido[2,1-b][1,3]thiazepine-7-carboxylate (60.8 mg, 0.235 mmol) to give a white solid (34 mg, 43% yield). Anal. Calcd. for $C_{41}H_{58}N_4O_{10}S_2$ m/z 830.7. found: 831.4 (M+H)$^+$; $^1$H NMR (400 MHz, CDCl$_3$) δ ppm 7.41 (1H, d, J=6.6 Hz), 7.28-7.21 (2H, m), 7.19-7.09 (4H, m), 5.39 (1H, t, J=4.7 Hz), 5.33 (1H, t, J=4.4 Hz), 5.21-5.16 (1H, m), 5.13 (1H, d, J=6.0 Hz), 5.08 (1H, t, J=6.9 Hz), 5.01 (1H, t, J=6.9 Hz), 3.74-3.71 (3H, m), 3.69 (3H, s), 3.29-3.09 (2H, m), 2.96-2.88 (1H, m), 2.88-2.78 (2H, m), 2.76-2.68 (1H, m), 2.66-2.52 (2H, m), 2.48-2.36 (3H, m), 2.32-2.18 (2H, m), 2.09-1.95 (4H, m), 1.84 (1H, dt, J=14.3, 3.3 Hz), 1.75-1.44 (12H, m), 1.42 (9H, s).

Example 28

Methyl (4S,7S,10aS)-4-(((2R,5R)-5-benzyl-6-(((4S,7S,10aS)-7-(methoxycarbonyl)-5-oxooctahydro-7H-pyrido[2,1-b][1,3]thiazepin-4-yl)amino)-2-(2-methoxy-2-oxoethyl)-6-oxohexanoyl)amino)-5-oxooctahydro-7H-pyrido[2,1-b][1,3]thiazepine-7-carboxylate

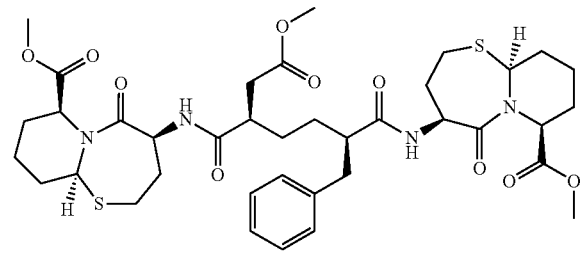 [SMILES: COC(=O)C[C@@H](CC[C@H](Cc1ccccc1)C(=O)N[C@H]1CCS[C@H]2CCC[C@@H](C(=O)OC)N2C1=O)C(=O)N[C@H]1CCS[C@H]2CCC[C@@H](C(=O)OC)N2C1=O]

A: (3R,6R)-6-Benzyl-7-((4S,7S,10aS)-7-(methoxycarbonyl)-5-oxooctahydro-2H-pyrido[2,1-b][1,3]thiazepin-4-ylamino)-3-((4S,7S,10aS)-7-(methoxycarbonyl)-5-oxooctahydro-2H-pyrido[2,1-b][1,3]thiazepin-4-ylcarbamoyl)-7-oxoheptanoic acid

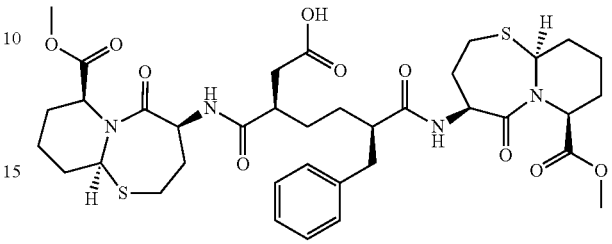

Trifluoroacetic acid (0.1 mL) was added to a 0° C. solution of Example 27 (33 mg, 0.040 mmol) in DCM (0.1 mL). The reaction mixture was then stirred at rt for 1 hr. The reaction mixture was concentrated. The crude product was purified by RP prep-HPLC (Method A) to give (3R,6R)-6-benzyl-7-((4S,7S,10aS)-7-(methoxycarbonyl)-5-oxooctahydro-2H-pyrido[2,1-b][1,3]thiazepin-4-ylamino)-3-((4S,7S,10aS)-7-(methoxycarbonyl)-5-oxooctahydro-2H-pyrido[2,1-b][1,3]thiazepin-4-ylcarbamoyl)-7-oxoheptanoic acid (21 mg, 0.027 mmol, 68% yield). Anal. Calcd. for $C_{37}H_{50}N_4O_{10}S_2$ m/z 774.7. found: 775.2 (M+H)$^+$; $^1$H NMR (400 MHz, CDCl$_3$) δ ppm 7.70 (1H, d, J=6.6 Hz), 7.32-7.10 (6H, m), 5.39 (1H, t, J=4.4 Hz), 5.35 (1H, t, J=4.4 Hz), 5.20-5.14 (1H, m), 5.14-5.00 (3H, m), 3.71 (3H, s), 3.69 (3H, s), 3.22 (1H, t, J=11.5 Hz), 3.12 (1H, t, J=11.3 Hz), 2.97-2.88 (1H, m), 2.87-2.78 (2H, m), 2.77-2.67 (3H, m), 2.57-2.35 (4H, m), 2.22 (1H, ddd, J=14.2, 3.2, 3.0 Hz), 2.10-1.93 (5H, m), 1.82-1.46 (12H, m).

B: Methyl (4S,7S,10aS)-4-(((2R,5R)-5-benzyl-6-(((4S,7S,10aS)-7-(methoxycarbonyl)-5-oxooctahydro-7H-pyrido[2,1-b][1,3]thiazepin-4-yl)amino)-2-(2-methoxy-2-oxoethyl)-6-oxohexanoyl)amino)-5-oxooctahydro-7H-pyrido[2,1-b][1,3]thiazepine-7-carboxylate

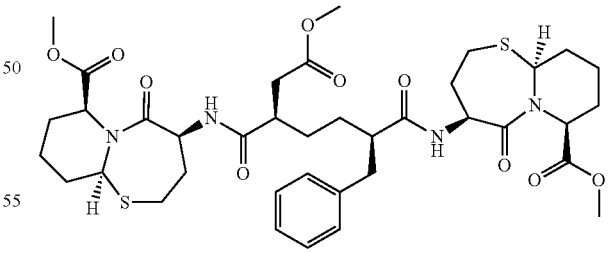

TMS-diazomethane (2.0 M in ether, 0.0061 mL, 0.012 mmol) was added to a solution of (3R,6R)-6-benzyl-7-((4S,7S,10aS)-7-(methoxycarbonyl)-5-oxooctahydro-2H-pyrido[2,1-b][1,3]thiazepin-4-ylamino)-3-((4S,7S,10aS)-7-(methoxycarbonyl)-5-oxooctahydro-2H-pyrido[2,1-b][1,3]thiazepin-4-ylcarbamoyl)-7-oxoheptanoic acid (5.4 mg, 7.0 mmol) in DCM (0.06 mL) and MeOH (0.0062 mL). Gas evolution occurred. The reaction was stirred at rt for 1 hr. The reaction mixture was concentrated and triturated with hexanes. The solid was dried over vacuum to give methyl (4S, 7S,10aS)-4-(((2R,5R)-5-benzyl-6-(((4S,7S,10aS)-7-(methoxycarbonyl)-5-oxooctahydro-7H-pyrido[2,1-b][1,3]thiazepin-4-yl)amino)-2-(2-methoxy-2-oxoethyl)-6-oxohexanoyl)amino)-5-oxooctahydro-7H-pyrido[2,1-b][1,3]thiazepine-7-carboxylate (5.0 mg, 0.0063 mmol, 91% yield) as a white solid. Anal. Calcd. for $C_{38}H_{52}N_4O_{10}S_2$ m/z 788.7. found: 789.2 (M+H)$^+$; $^1$H NMR (400 MHz, CDCl$_3$) δ ppm 7.32 (1H, d), 7.25-7.21 (2H, m), 7.19-7.11 (3H, m), 7.00 (1H, d), 5.39 (1H, t, J=4.7 Hz), 5.36 (1H, t, J=4.7 Hz), 5.21-5.16 (1H, m), 5.16-5.12 (1H, m), 5.10-4.98 (2H, m), 3.72 (3H, s), 3.69 (3H, s), 3.65 (3H, s), 3.28-3.10 (2H, m), 2.98-2.81 (3H, m), 2.77-2.62 (3H, m), 2.47-2.37 (3H, m), 2.34 (1H, dd, J=15.7, 3.6 Hz), 2.27-2.19 (1H, m), 2.08-1.95 (4H, m), 1.88 (1H, ddd, J=10.9, 7.0, 3.6 Hz), 1.76-1.47 (12H, m).

Example 29

Methyl (4S,7S,10aS)-4-(((2R,5R)-7-amino-2-benzyl-5-(((4S,7S,10aS)-7-(methoxycarbonyl)-5-oxooctahydro-7H-pyrido[2,1-b][1,3]thiazepin-4-yl)carbamoyl)-7-oxoheptanoyl)amino)-5-oxooctahydro-7H-pyrido[2,1-b][1,3]thiazepine-7-carboxylate

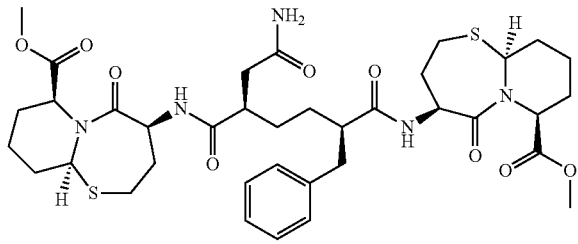 [SMILES: COC(=O)[C@@H]1CCC[C@@H]2SCC[C@H](NC(=O)[C@H](CC[C@H](Cc3ccccc3)C(=O)N[C@H]3CCS[C@H]4CCC[C@@H](C(=O)OC)N4C3=O)CC(N)=O)C(=O)N21]

Isobutyl chloroformate (3.0 mg, 0.022 mmol) was added to a 0° C. solution of (3R,6R)-6-benzyl-7-((4S,7S,10aS)-7-(methoxycarbonyl)-5-oxooctahydro-2H-pyrido[2,1-b][1,3]thiazepin-4-ylamino)-3-((4S,7S,10aS)-7-(methoxycarbonyl)-5-oxooctahydro-2H-pyrido[2,1-b][1,3]thiazepin-4-ylcarbamoyl)-7-oxoheptanoic acid (16 mg, 0.021 mmol) and NMM (2.5 mg, 0.025 mmol) in DCM (0.1 mL). After 30 min at 0° C., NH$_4$OH (1.5 mg, 0.041 mmol) was added. The ice bath was removed and the reaction mixture was stirred at rt for 1 hr. The reaction mixture was concentrated. The residue was purified by RP prep-HPLC (Method A) to give methyl (4S, 7S,10aS)-4-(((2R,5R)-7-amino-2-benzyl-5-(((4S,7S,10aS)-7-(methoxycarbonyl)-5-oxooctahydro-7H-pyrido[2,1-b][1,3]thiazepin-4-yl)carbamoyl)-7-oxoheptanoyl)amino)-5-oxooctahydro-7H-pyrido[2,1-b][1,3]thiazepine-7-carboxylate (8.5 mg, 0.010 mmol, 53% yield) as a colorless oil. Anal. Calcd. for $C_{37}H_{51}N_5O_9S_2$ m/z 773.7. found: 7749.2 (M+H)$^+$; $^1$H NMR (400 MHz, CDCl$_3$) δ ppm 7.53 (1H, d, J=6.6 Hz), 7.28-7.11 (6H, m), 6.38 (1H, br. s.), 6.18 (1H, br. s.), 5.43-5.36 (2H, m), 5.20-5.14 (1H, m), 5.14-5.00 (3H, m), 4.03-3.80 (2H, m), 3.72 (3H, s), 3.69 (3H, s), 3.25-3.08 (2H, m), 2.97-2.89 (1H, m), 2.89-2.80 (2H, m), 2.79-2.66 (2H, m), 2.61-2.36 (4H, m), 2.32 (1H, dd, J=14.8, 4.9 Hz), 2.24-2.15 (1H, m), 2.08-1.94 (4H, m), 1.86-1.76 (1H, m), 1.74-1.57 (8H, m), 1.57-1.46 (2H, m).

Example 30

(4S,7S,10aS)-Methyl 4-((2R,5R)-2,5-dibenzyl-6-oxo-6-((4S,10aS)-5-oxooctahydro-2H-pyrido[2,1-b][1,3]thiazepin-4-ylamino)hexanamido)-5-oxooctahydro-2H-pyrido[2,1-b][1,3]thiazepine-7-carboxylate

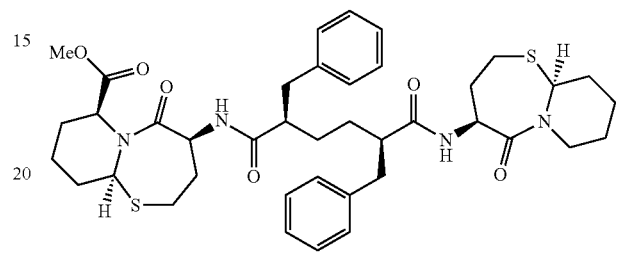

(4S,7S,10aS)-Methyl 4-((2R,5R)-2,5-dibenzyl-6-oxo-6-((4S,10aS)-5-oxooctahydro-2H-pyrido[2,1-b][1,3]thiazepin-4-ylamino)hexanamido)-5-oxooctahydro-2H-pyrido[2,1-b][1,3]thiazepine-7-carboxylate was synthesized as described in General Procedure H using Intermediate 23 (20 mg, 0.035 mmol) and Intermediate 40 (11 mg, 0.053 mmol) to give a white solid (17 mg, 66% yield). Anal. Calcd. for $C_{40}H_{52}N_4O_6S_2$ m/z 748.7. found: 749.6 (M+H)$^+$; $^1$H NMR (400 MHz, CDCl$_3$) δ ppm 7.36-7.07 (m, 10H), 6.93 (d, J=6.7 Hz, 1H), 6.90 (d, J=6.8 Hz, 1H), 5.33 (t, J=4.6 Hz, 1H), 5.27 (t, J=3.9 Hz, 1H), 5.18-5.11 (m, 1H), 5.04-4.90 (m, 2H), 4.23 (d, J=13.3 Hz, 1H), 3.69 (s, 3H), 3.24-3.03 (m, 2H), 2.99-2.65 (m, 6H), 2.57 (ddd, J=14.4, 6.1, 2.9 Hz, 1H), 2.47-2.30 (m, 3H), 2.19-1.39 (m, 17H), 1.32-1.18 (m, 2H).

Example 31

Dimethyl (4S,7S,10aS,4'S,7'S,10a'S)-4,4'-(((2R,5R)-2-benzyl-5-(4-fluorobenzyl)-1,6-dioxo-1,6-hexanediyl)diimino)bis(5-oxooctahydro-7H-pyrido[2,1-b][1,3]thiazepine-7-carboxylate)

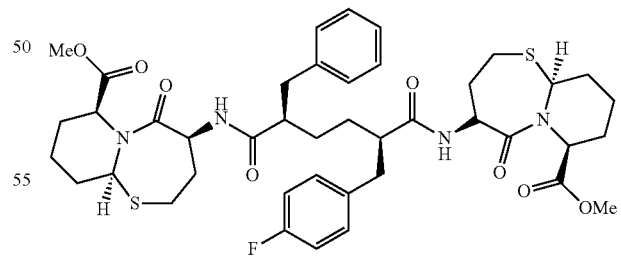

Dimethyl (4S,7S,10aS,4'S,7'S,10a'S)-4,4'-(((2R,5R)-2-benzyl-5-(4-fluorobenzyl)-1,6-dioxo-1,6-hexanediyl)diimino)bis(5-oxooctahydro-7H-pyrido[2,1-b][1,3]thiazepine-7-carboxylate) was synthesized as described in General Procedure F using Intermediate 19 (12 mg, 0.035 mmol) and (4S,7S,10aS)-methyl 4-amino-5-oxooctahydro-2H-pyrido[2,1-b][1,3]thiazepine-7-carboxylate (22 mg, 0.084 mmol) to give a white solid (15 mg, 52% yield). Anal.

Calcd. for $C_{42}H_{53}FN_4O_8S_2$ m/z 824.7. found: 825.6 (M+H)$^+$; $^1$H NMR (400 MHz, DMSO-d$_6$) δ ppm 7.22 (d, J=7.4 Hz, 1H), 7.20-7.06 (m, 5H), 7.01 (d, J=6.8 Hz, 1H), 6.91 (t, J=8.6 Hz, 1H), 5.34 (t, J=4.4 Hz, 2H), 5.17-5.08 (m, 2H), 5.01-4.92 (m, 2H), 3.79-3.63 (m, 5H), 3.21-3.08 (m, 2H), 2.90-2.75 (m, 4H), 2.69 (td, J=13.3, 5.9 Hz, 2H), 2.47-2.28 (m, 4H), 2.03 (d, J=5.1 Hz, 4H), 1.92-1.56 (m, 15H), 1.55-1.43 (m, 2H).

Example 32

Dimethyl (4S,7S,10aS,4'S,7'S,10a'S)-4,4'-(((2R,5R)-2-benzyl-5-(cyanomethyl)-1,6-dioxo-1,6-hexanediyl)diimino)bis(5-oxooctahydro-7H-pyrido[2,1-b][1,3]thiazepine-7-carboxylate)

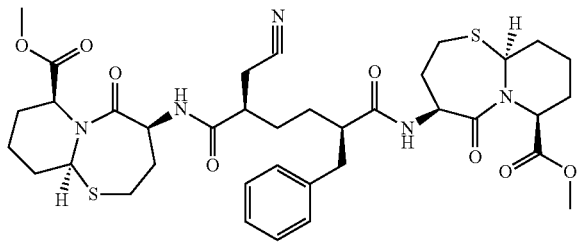 [SMILES: COC(=O)[C@@H]1CCC[C@@H]2SCC[C@H](NC(=O)[C@H](CC[C@H](CC#N)C(=O)N[C@H]3CCS[C@H]4CCC[C@@H](C(=O)OC)N4C3=O)Cc3ccccc3)C(=O)N21]

TFAA (15 mg, 0.069 mmol) was slowly added to a 0° C. solution of Example 29 (27 mg, 0.034 mmol) and TEA (12.2 mg, 0.121 mmol) in DCM (0.25 mL). The reaction mixture was then stirred at rt for 1.5 hr. The reaction mixture was concentrated and the residue was partitioned between EtOAc and 10% aqueous Na$_2$CO$_3$. The organic phase was isolated, washed with saturated aqueous NaCl, dried over MgSO$_4$, filtered and concentrated. The crude product was purified by RP prep-HPLC (Method A) to give dimethyl (4S,7S,10aS, 4'S,7'S,10a'S)-4,4'-(((2R,5R)-2-benzyl-5-(cyanomethyl)-1, 6-dioxo-1,6-hexanediyl)diimino)bis(5-oxooctahydro-7H-pyrido[2,1-b][1,3]thiazepine-7-carboxylate) (13 mg, 0.018 mmol, 51% yield). Anal. Calcd. for $C_{37}H_{49}N_5O_8S_2$ m/z 755.7. found: 756.2 (M+H)$^+$; $^1$H NMR (400 MHz, CDCl$_3$) δ ppm 7.74 (1H, d, J=6.6 Hz), 7.30-7.21 (3H, m), 7.20-7.11 (3H, m), 5.44-5.35 (2H, m), 5.18-5.00 (4H, m), 3.72 (3H, s), 3.69 (3H, s), 3.20 (1H, ddd, J=14.0, 10.7, 2.7 Hz), 3.15-3.01 (3H, m), 2.96 (1H, ddd, J=14.4, 7.0, 2.7 Hz), 2.91-2.82 (2H, m), 2.71 (1H, dd, J=13.2, 6.6 Hz), 2.65-2.55 (2H, m), 2.53-2.35 (4H, m), 2.25 (1H, ddd, J=10.7, 6.9, 3.3 Hz), 2.09-1.96 (4H, m), 1.82 (1H, td, J=7.1, 3.8 Hz), 1.78-1.51 (10H, m).

Example 33

(4S,7S,10aS)-Methyl 4-((2R,5R)-2,5-dibenzyl-6-oxo-6-((S)-2-oxo-1-(pyridin-3-ylmethyl)azepan-3-ylamino)hexanamido)-5-oxooctahydro-2H-pyrido[2,1-b][1,3]thiazepine-7-carboxylate

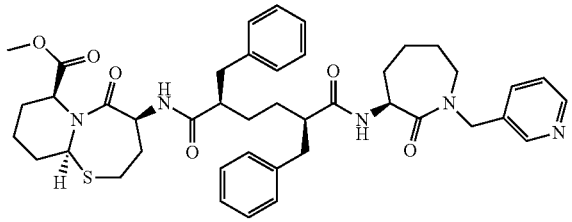

(4S,7S,10aS)-Methyl 4-((2R,5R)-2,5-dibenzyl-6-oxo-6-((S)-2-oxo-1-(pyridin-3-ylmethyl)azepan-3-ylamino)hexanamido)-5-oxooctahydro-2H-pyrido[2,1-b][1,3]thiazepine-7-carboxylate was synthesized as described in General Procedure H using Intermediate 23 (7.0 mg, 0.012 mmol) and Intermediate 41 (4.4 mg, 0.020 mmol) to give a white solid (4.5 mg, 47% yield). Anal. Calcd. for $C_{43}H_{53}N_5O_6S$ m/z 767.7. found: 768.7 (M+H)$^+$; $^1$H NMR (500 MHz, CDCl$_3$) δ ppm 8.79 (br. s., 1H), 8.69 (d, J=4.95 Hz, 1H), 8.11 (d, J=7.70 Hz, 1H), 7.70 (dd, J=7.70, 5.50 Hz, 1H), 7.22 (t, J=7.42 Hz, 4H), 7.19-7.10 (m, 6H), 6.98 (d, J=6.60 Hz, 1H), 6.79 (d, J=6.60 Hz, 1H), 5.35-5.28 (m, 1H), 5.15-5.08 (m, 1H), 4.98 (br. s., 1H), 4.88 (d, J=15.40 Hz, 1H), 4.68-4.57 (m, 1H), 4.44 (d, J=15.40 Hz, 1H), 3.67 (s, 3H), 3.60 (dd, J=15.12, 11.82 Hz, 1H), 3.29-3.10 (m, 2H), 2.84-2.77 (m, 3H), 2.77-2.67 (m, 2H), 2.04-1.97 (m, 2H), 1.90-1.48 (m, 13H), 1.26 (t, J=7.15 Hz, 2H), 1.13 (d, J=13.20 Hz, 2H).

Example 34

(4S,7S,10aS)-Methyl 4-((2R,5R)-2,5-dibenzyl-6-((S)-1-benzyl-2-oxoazepan-3-ylamino)-6-oxohexanamido)-5-oxooctahydro-2H-pyrido[2,1-b][1,3]thiazepine-7-carboxylate

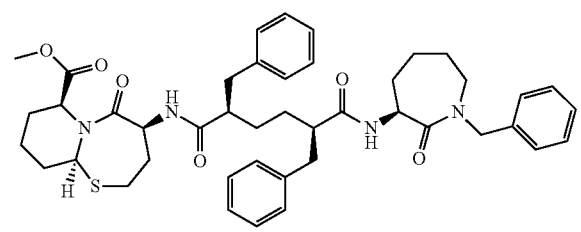 [SMILES: COC(=O)[C@@H]1CCC[C@@H]2SCC[C@H](NC(=O)[C@H](CC[C@H](Cc3ccccc3)C(=O)N[C@H]3CCCCN(Cc4cccnc4)C3=O)Cc3ccccc3)C(=O)N21]

(4S,7S,10aS)-Methyl 4-((2R,5R)-2,5-dibenzyl-6-oxo-6-((S)-2-oxo-1-(pyridin-3-ylmethyl)azepan-3-ylamino)hexanamido)-5-oxooctahydro-2H-pyrido[2,1-b][1,3]thiazepine-7-carboxylate was synthesized as described in General Procedure H using Intermediate 23 (12 mg, 0.021 mmol) and Intermediate 42 (5.1 mg, 0.023 mmol) to give a white solid (14 mg, 83% yield). Anal. Calcd. for $C_{44}H_{54}N_4O_6S$ m/z 767.7. found: 767.5 (M+H)$^+$; $^1$H NMR (500 MHz, CDCl$_3$) δ ppm 7.30 (q, J=7.51 Hz, 3H), 7.25-7.19 (m, 6H), 7.18-7.11 (m, 6H), 6.98 (d, J=6.60 Hz, 2H), 5.33 (t, J=4.40 Hz, 1H), 5.18-5.11 (m, 1H), 5.03-4.93 (m, 1H), 4.66 (d, J=14.85 Hz, 1H), 4.59 (dd, J=10.45, 6.60 Hz, 1H), 4.48 (d, J=14.85 Hz, 1H), 3.67 (s, 3H), 3.45 (dd, J=15.40, 11.55 Hz, 1H), 3.25-3.10 (m, 2H), 2.90-2.77 (m, 3H), 2.73 (ddd, J=13.33, 5.91, 2.75 Hz, 2H), 2.46-2.35 (m, 3H), 2.04-2.00 (m, 3H), 1.90-1.46 (m, 14H).

Example 35

Methyl (4S,7S,10aS)-4-(((2R,5R)-5-benzyl-2-(2-hydroxyethyl)-6-(4S,7S,10aS)-7-(methoxycarbonyl)-5-oxooctahydro-7H-pyrido[2,1-b][1,3]thiazepin-4-yl)amino)-6-oxohexanoyl)amino)-5-oxooctahydro-7H-pyrido[2,1-b][1,3]thiazepine-7-carboxylate

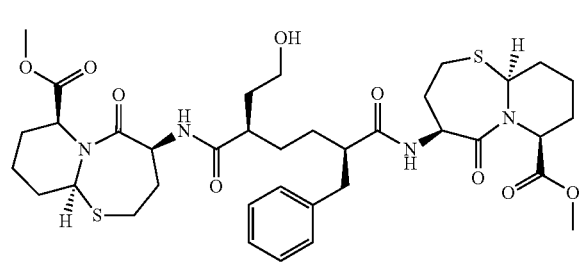 [SMILES: COC(=O)[C@@H]1CCC[C@@H]2SCC[C@H](NC(=O)[C@@H](CCO)CC[C@H](Cc3ccccc3)C(=O)N[C@H]3CCS[C@H]4CCC[C@@H](C(=O)OC)N4C3=O)C(=O)N21]

Borane-THF (1.0 M in THF, 0.128 mL, 0.128 mmol) was added dropwise to a 0° C. solution of (3R,6R)-6-benzyl-7-((4S,7S,10aS)-7-(methoxycarbonyl)-5-oxooctahydro-2H-pyrido[2,1-b][1,3]thiazepin-4-ylamino)-3-((4S,7S,10aS)-7-(methoxycarbonyl)-5-oxooctahydro-2H-pyrido[2,1-b][1,3]thiazepin-4-ylcarbamoyl)-7-oxoheptanoic acid (90 mg, 0.12 mmol) in THF (0.4 mL). After 50 min, LC/MS showed only a trace of product. Another 130 μL of borane-THF solution was added and the reaction mixture was then stirred at rt for an additional 40 min. The reaction mixture was cooled to 0° C. and quenched by dropwise addition of aqueous saturated NH$_4$Cl. The solution was then partitioned between EtOAc and water. The organic phase was isolated, washed with saturated aqueous NaCl, dried over MgSO$_4$, filtered and concentrated. The residue was purified by RP prep-HPLC (Method A) to give methyl (4S,7S,10aS)-4-(((2R,5R)-5-benzyl-2-(2-hydroxyethyl)-6-((4S,7S,10aS)-7-(methoxycarbonyl)-5-oxooctahydro-7H-pyrido[2,1-b][1,3]thiazepin-4-yl)amino)-6-oxohexanoyl)amino)-5-oxooctahydro-7H-pyrido[2,1-b][1,3]thiazepine-7-carboxylate (80 mg, 9.1 mmol, 91% yield) as a white solid. Anal. Calcd. for C$_{37}$H$_{52}$N$_4$O$_9$S$_2$ m/z 760.7. found: 761.2 (M+H)$^+$; $^1$H NMR (400 MHz, CDCl$_3$) δ ppm 7.28-7.09 (7H, m), 5.43-5.31 (2H, m), 5.21-4.98 (4H, m), 3.73 (3H, s), 3.69 (4H, s), 3.59-3.36 (4H, m), 3.24 (1H, t, J=11.8 Hz), 3.11 (1H, t, J=11.0 Hz), 2.98-2.88 (1H, m), 2.83 (2H, dd, J=13.2, 9.3 Hz), 2.77-2.68 (1H, m), 2.56-2.36 (3H, m), 2.27-2.16 (1H, m), 2.11-1.94 (5H, m), 1.89-1.58 (10H, m), 1.56-1.44 (2H, m).

Example 36

(2R,5R)-2,5-Dibenzyl-N1,N6-bis((4S,10aS)-5-oxooctahydro-2H-pyrido[2,1-b][1,3]thiazepin-4-yl)hexanediamide

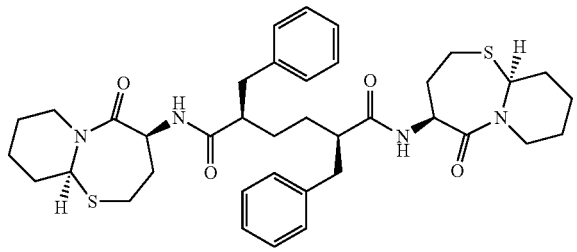 [SMILES: O=C(N[C@H]1CCS[C@H]2CCCCN2C1=O)[C@H](CC[C@H](Cc1ccccc1)C(=O)N[C@H]1CCS[C@H]2CCCCN2C1=O)Cc1ccccc1]

(2R,5R)-2,5-Dibenzyl-N1,N6-bis((4S,10aS)-5-oxooctahydro-2H-pyrido[2,1-b][1,3]thiazepin-4-yl)hexanediamide was synthesized as described in General Procedure F using Intermediate 3 (20 mg, 0.061 mmol) and Intermediate 40 (29.5 mg, 0.147 mmol) to give a white solid (27 mg, 64% yield). Anal. Calcd. for C$_{38}$H$_{50}$N$_4$O$_4$S$_2$ m/z 690.7. found: 691.5 (M+H)$^+$; $^1$H NMR (400 MHz, CDCl$_3$) δ ppm 7.32-7.05 (m, 10H), 6.86 (d, J=6.7 Hz, 2H), 5.28 (t, J=4.0 Hz, 2H), 5.04-4.91 (m, 2H), 4.23 (d, J=13.6 Hz, 2H), 3.12 (ddd, J=13.9, 11.0, 2.6 Hz, 1H), 3.02-2.87 (m, 2H), 2.81 (dd, J=13.4, 9.6 Hz, 2H), 2.71 (dd, J=13.3, 5.7 Hz, 2H), 2.58 (ddd, J=14.3, 6.0, 2.9 Hz, 2H), 2.43-2.31 (m, 2H), 2.11-1.75 (m, 9H), 1.76-1.60 (m, 4H), 1.60-1.38 (m, 6H), 1.33-1.18 (m, 2H).

Example 37

Dimethyl (4S,7S,10aS,4'S,7'S,10a'S)-4,4'-(((2R,5R)-2-benzyl-5-(4-methoxybenzyl)-1,6-dioxo-1,6-hexanediyl)diimino)bis(5-oxooctahydro-7H-pyrido[2,1-b][1,3]thiazepine-7-carboxylate)

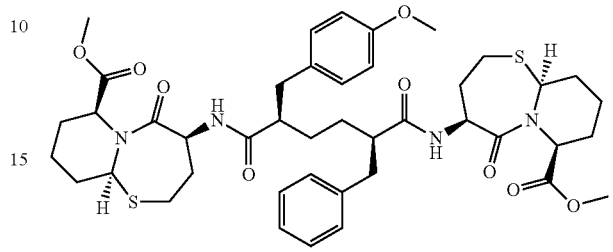

Dimethyl (4S,7S,10aS,4'S,7'S,10a'S)-4,4'-(((2R,5R)-2-benzyl-5-(4-methoxybenzyl)-1,6-dioxo-1,6-hexanediyl)diimino)bis(5-oxooctahydro-7H-pyrido[2,1-b][1,3]thiazepine-7-carboxylate) was synthesized as described in General Procedure F using Intermediate 10 (10 mg, 0.028 mmol) and (4S,7S,10aS)-methyl 4-amino-5-oxooctahydro-2H-pyrido[2,1-b][1,3]thiazepine-7-carboxylate (20 mg, 0.067 mmol) to give a white solid (15 mg, 65% yield). Anal. Calcd. for C$_{43}$H$_{56}$N$_4$O$_9$S$_2$ m/z 836.7. found: 837.2 (M+H)$^+$; $^1$H NMR (400 MHz, DMSO-d$_6$) δ ppm 7.90 (d, J=7.3 Hz, 2H), 7.27-7.09 (m, 3H), 7.05 (d, J=8.6 Hz, 2H), 6.74 (d, J=8.6 Hz, 2H), 5.74-5.52 (m, 2H), 5.09-4.89 (m, 3H), 3.68 (s, 2H), 3.56 (d, J=1.7 Hz, 6H), 3.41-3.24 (m, 2H), 3.08 (dt, J=10.8, 8.0 Hz, 2H), 2.85-2.68 (m, 4H), 2.66-2.42 (m, 7H), 2.19 (d, J=12.9 Hz, 2H), 2.06-1.90 (m, 2H), 1.81 (d, J=14.2 Hz, 2H), 1.76-1.35 (m, 11H), 1.35-1.17 (m, 2H).

Example 38

Dimethyl (4S,7S,10aS,4'S,7'S,10a'S)-4,4'-(((2R,5R)-2-benzyl-5-(4-hydroxybenzyl)-1,6-dioxo-1,6-hexanediyl)diimino)bis(5-oxooctahydro-7H-pyrido[2,1-b][1,3]thiazepine-7-carboxylate)

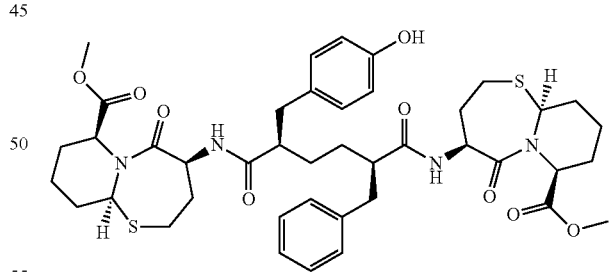

Dimethyl (4S,7S,10aS,4'S,7'S,10a'S)-4,4'-(((2R,5R)-2-benzyl-5-(4-hydroxybenzyl)-1,6-dioxo-1,6-hexanediyl)diimino)bis(5-oxooctahydro-7H-pyrido[2,1-b][1,3]thiazepine-7-carboxylate) was synthesized as described in General Procedure F using Intermediate 11 (8.5 mg, 0.025 mmol) and (4S,7S,10aS)-methyl 4-amino-5-oxooctahydro-2H-pyrido[2,1-b][1,3]thiazepine-7-carboxylate (18 mg, 0.060 mmol) to give a white solid (5.6 mg, 27% yield). Anal. Calcd. for C$_{42}$H$_{54}$N$_4$O$_9$S$_2$ m/z 822.7. found: 823.6 (M+H)$^+$; $^1$H NMR (400 MHz, DMSO-d$_6$) δ ppm 9.04 (s, 1H), 7.87 (dd, J=11.5, 7.3 Hz, 2H), 7.29-7.02 (m, 3H), 6.92 (d, J=8.4 Hz, 2H), 6.56 (d, J=8.3 Hz, 2H), 5.79-5.50 (m, 2H), 5.12-4.86 (m, 3H), 3.55 (d, J=2.7 Hz, 6H), 3.33 (d, J=17.8 Hz, 1H), 3.17-2.96 (m, 3H), 2.84-2.71 (m, 3H), 2.71-2.38 (m, 7H), 2.18 (d, J=13.2 Hz, 2H), 2.06-1.90 (m, 2H), 1.88-1.34 (m, 13H), 1.34-1.17 (m, 2H).

Example 39

(4S,7S,10aS)-Methyl 4-((2R,5R)-2,5-dibenzyl-6-oxo-6-((S)-2-oxo-1-phenethylazepan-3-ylamino)hexanamido)-5-oxooctahydro-2H-pyrido[2,1-b][1,3]thiazepine-7-carboxylate

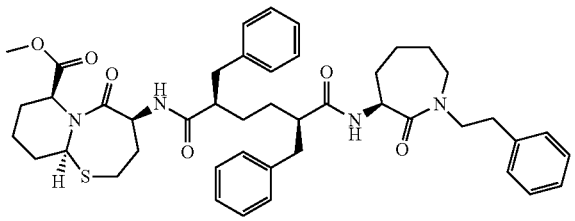 [SMILES: COC(=O)[C@@H]1CCC[C@@H]2SCC[C@H](NC(=O)[C@H](CC[C@H](Cc3ccccc3)C(=O)N[C@H]3CCCCN(CCc4ccccc4)C3=O)Cc3ccccc3)C(=O)N21]

(4S,7S,10aS)-Methyl 4-((2R,5R)-2,5-dibenzyl-6-oxo-6-((S)-2-oxo-1-phenethylazepan-3-ylamino)hexanamido)-5-oxooctahydro-2H-pyrido[2,1-b][1,3]thiazepine-7-carboxylate was synthesized as described in General Procedure H using Intermediate 23 (7.0 mg, 0.012 mmol) and (S)-3-amino-1-phenethylazepan-2-one (2.9 mg, 0.012 mmol) to give a white solid (2.0 mg, 20% yield). Anal. Calcd. for $C_{45}H_{56}N_4O_6S$ m/z 780.7. found: 781.7 (M+H)$^+$; $^1$H NMR (500 MHz, CDCl$_3$) δ ppm 7.31-7.27 (m, 2H), 7.24-7.19 (m, 6H), 7.18-7.10 (m, 7H), 6.91 (d, J=6.60 Hz, 1H), 6.86 (d, J=6.60 Hz, 1H), 5.32 (t, J=4.95 Hz, 1H), 5.19-5.09 (m, 1H), 5.04-4.92 (m, 1H), 4.50 (dd, J=9.89, 6.60 Hz, 1H), 3.73-3.69 (m, 1H), 3.68 (s, 3H), 3.53-3.39 (m, 2H), 3.24-3.03 (m, 2H), 2.86-2.77 (m, 5H), 2.76-2.67 (m, 2H), 2.43-2.32 (m, 3H), 2.06-1.97 (m, 2H), 1.91-1.83 (m, 2H), 1.79-1.47 (m, 13H).

Example 40

Methyl (4S,7S,10aS)-4-(2S,5R)-5-benzyl-6-(((4S,7S,10aS)-7-(methoxycarbonyl)-5-oxooctahydro-7H-pyrido[2,1-b][1,3]thiazepin-4-yl)amino)-6-oxo-2-propylhexanoyl)amino)-5-oxooctahydro-7H-pyrido[2,1-b][1,3]thiazepine-7-carboxylate

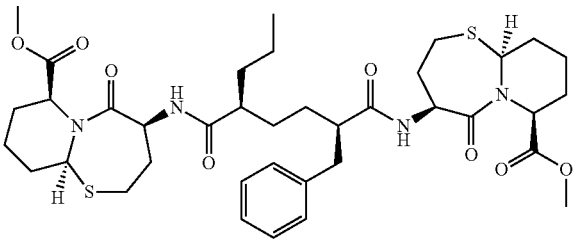 [SMILES: CCC[C@@H](CC[C@H](Cc1ccccc1)C(=O)N[C@H]1CCS[C@H]2CCC[C@@H](C(=O)OC)N2C1=O)C(=O)N[C@H]1CCS[C@H]2CCC[C@@H](C(=O)OC)N2C1=O]

Methyl (4S,7S,10aS)-4-(((2S,5R)-5-benzyl-6-(((4S,7S,10aS)-7-(methoxycarbonyl)-5-oxooctahydro-7H-pyrido[2,1-b][1,3]thiazepin-4-yl)amino)-6-oxo-2-propylhexanoyl)amino)-5-oxooctahydro-7H-pyrido[2,1-b][1,3]thiazepine-7-carboxylate was synthesized as described in General Procedure F using Intermediate 8 (11 mg, 0.040 mmol) and (4S,7S,10aS)-methyl 4-amino-5-oxooctahydro-2H-pyrido[2,1-b][1,3]thiazepine-7-carboxylate (26 mg, 0.099 mmol) to give a white solid (16 mg, 55% yield). Anal. Calcd. for $C_{38}H_{54}N_4O_8S_2$ m/z 758.7. found: 759.3 (M+H)$^+$; $^1$H NMR (400 MHz, CDCl$_3$) δ ppm 7.45 (1H, d, J=6.6 Hz), 7.28-7.20 (2H, m), 7.20-7.09 (4H, m), 5.42-5.36 (1H, m), 5.34-5.29 (1H, m), 5.18 (1H, d, J=5.5 Hz), 5.16-5.07 (2H, m), 4.99 (1H, t, J=7.1 Hz), 3.73 (3H, s), 3.69 (3H, s), 3.27 (1H, t, J=12.4 Hz), 3.15 (1H, t), 2.91 (1H, dd, J=14.0, 5.2 Hz), 2.85-2.70 (3H, m), 2.49-2.35 (3H, m), 2.28-2.19 (1H, m), 2.18-1.92 (6H, m), 1.83-1.30 (14H, m), 1.29-1.19 (2H, m), 0.87 (3H, t, J=7.1 Hz).

Example 41

(4S,7S,10aS)-Methyl 4-((2R,5R)-2,5-dibenzyl-6-((S)-1-(3-methoxybenzyl)-2-oxoazepan-3-ylamino)-6-oxohexanamido)-5-oxooctahydro-2H-pyrido[2,1-b][1,3]thiazepine-7-carboxylate

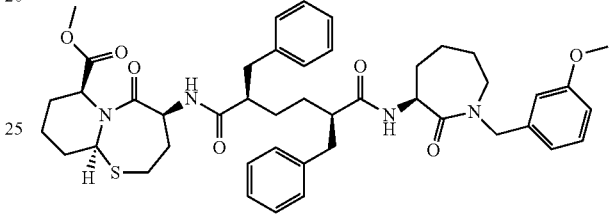

(4S,7S,10aS)-Methyl 4-((2R,5R)-2,5-dibenzyl-6-((S)-1-(3-methoxybenzyl)-2-oxoazepan-3-ylamino)-6-oxohexanamido)-5-oxooctahydro-2H-pyrido[2,1-b][1,3]thiazepine-7-carboxylate was synthesized as described in General Procedure H using Intermediate 23 (7.0 mg, 0.012 mmol) and Intermediate 43 (3.1 mg, 0.012 mmol) to give a white solid (7.1 mg, 70% yield). Anal. Calcd. for $C_{45}H_{56}N_4O_7S$ m/z 796.7. found: 797.7 (M+H)$^+$; $^1$H NMR (500 MHz, CDCl$_3$) δ ppm 7.25-7.19 (m, 5H), 7.19-7.11 (m, 8H), 6.85-6.72 (m, 3H), 5.33 (t, J=4.67 Hz, 1H), 5.12 (d, J=6.60 Hz, 1H), 5.04-4.95 (m, 1H), 4.63-4.43 (m, 3H), 3.78 (s, 3H), 3.67 (s, 3H), 3.46 (dd, J=15.12, 11.82 Hz, 1H), 3.24-3.12 (m, 3H), 2.86-2.70 (m, 5H), 2.46-2.37 (m, 3H), 2.02 (d, J=4.95 Hz, 1H), 1.84-1.49 (m, 11H), 1.28-1.23 (m, 3H).

Example 42

(4S,7S,10aS)-Methyl 4-((2R,5R)-2,5-dibenzyl-6-oxo-6-((S)-2-oxo-1-phenylazepan-3-ylamino)hexanamido)-5-oxooctahydro-2H-pyrido[2,1-b][1,3]thiazepine-7-carboxylate

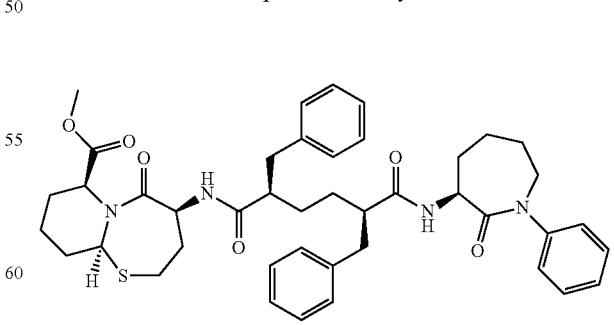

(4S,7S,10aS)-Methyl 4-((2R,5R)-2,5-dibenzyl-6-oxo-6-((S)-2-oxo-1-phenylazepan-3-ylamino)hexanamido)-5-oxooctahydro-2H-pyrido[2,1-b][1,3]thiazepine-7-carboxylate was synthesized as described in General Procedure H using Intermediate 23 (7.0 mg, 0.012 mmol) and Intermediate 25 (3.0 mg, 0.012 mmol) to give a white solid (5.7 mg, 60% yield). Anal. Calcd. for $C_{43}H_{52}N_4O_6S$ m/z 752.7. found: 753.3 (M+H)+; 1H NMR (500 MHz, CDCl3) δ ppm 7.41-7.32 (m, 2H), 7.24-7.18 (m, 5H), 7.17-7.08 (m, 8H), 6.88 (d, J=6.60 Hz, 1H), 6.83 (d, J=6.05 Hz, 1H), 5.31 (t, J=4.67 Hz, 1H), 5.14 (d, J=4.40 Hz, 1H), 5.03-4.91 (m, 1H), 4.75 (dd, J=10.72, 6.87 Hz, 1H), 3.93 (dd, J=15.12, 11.27 Hz, 1H), 3.68 (s, 3H), 3.59 (dd, J=15.40, 4.95 Hz, 1H), 3.14 (t, J=11.55 Hz, 1H), 2.92-2.74 (m, 3H), 2.71 (dd, J=13.20, 5.50 Hz, 2H), 2.47-2.29 (m, 3H), 2.01-1.47 (m, 16H), 1.31 (d, J=12.10 Hz, 1H).

Example 43

Dimethyl (4S,7S,10aS,4'S,7'S,10a'S)-4,4'-(((2R,5R)-2-(3-chlorobenzyl)-5-(cyclohexylmethyl)-1,6-dioxo-1,6-hexanediyl)diimino)bis(5-oxooctahydro-7H-pyrido[2,1-b][1,3]thiazepine-7-carboxylate)

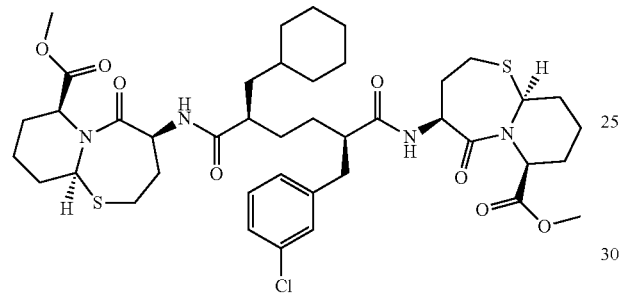

Dimethyl (4S,7S,10aS,4'S,7'S,10a'S)-4,4'-(((2R,5R)-2-(3-chlorobenzyl)-5-(cyclohexylmethyl)-1,6-dioxo-1,6-hexanediyl)diimino)bis(5-oxooctahydro-7H-pyrido[2,1-b][1,3]thiazepine-7-carboxylate) was synthesized as described in General Procedure F using Intermediate 13 (24 mg, 0.065 mmol) and (4S,7S,10aS)-methyl 4-amino-5-oxooctahydro-2H-pyrido[2,1-b][1,3]thiazepine-7-carboxylate (46.3 mg, 0.157 mmol) to give a white solid (16 mg, 27% yield). Anal. Calcd. for $C_{42}H_{59}ClN_4O_8S_2$ m/z 846.7. found: 847.7 (M+H)+; 1H NMR (400 MHz, DMSO-d6) δ ppm 7.41 (d, J=6.6 Hz, 1H), 7.21-7.11 (m, 3H), 7.03 (d, J=7.0 Hz, 1H), 5.40 (t, J=4.5 Hz, 1H), 5.34 (t, J=4.5 Hz, 1H), 5.25-5.16 (m, 1H), 5.16-5.07 (m, 2H), 5.05-4.95 (m, 1H), 3.73 (s, 3H), 3.70 (s, 3H), 3.34-3.13 (m, 2H), 3.01-2.64 (m, 4H), 2.61-2.30 (m, 8H), 2.30-2.17 (m, 2H), 2.13-1.83 (m, 5H), 1.81-1.56 (m, 11H), 1.56-1.34 (m, 3H), 1.31-1.03 (m, 5H), 0.94-0.74 (m, 2H).

Example 44

Dimethyl (4S,7S,10aS,4'S,7'S,10a'S)-4,4'-(((2R,5R)-2-(4-hydroxybenzyl)-5-(4-methoxybenzyl)-1,6-dioxo-1,6-hexanediyl)diimino)bis(5-oxooctahydro-7H-pyrido[2,1-b][1,3]thiazepine-7-carboxylate)

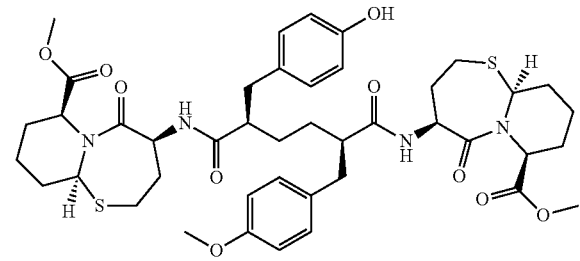 [SMILES: COC(=O)[C@@H]1CCC[C@@H]2SCC[C@H](NC(=O)[C@H](CC[C@H](Cc3ccc(OC)cc3)C(=O)N[C@H]3CCS[C@H]4CCC[C@@H](C(=O)OC)N4C3=O)Cc3ccc(O)cc3)C(=O)N21]

Dimethyl (4S,7S,10aS,4'S,7'S,10a'S)-4,4'-(((2R,5R)-2-(4-hydroxybenzyl)-5-(4-methoxybenzyl)-1,6-dioxo-1,6-hexanediyl)diimino)bis(5-oxooctahydro-7H-pyrido[2,1-b][1,3]thiazepine-7-carboxylate) was synthesized as described in General Procedure F using Intermediate 17 (12 mg, 0.032 mmol) and (4S,7S,10aS)-methyl 4-amino-5-oxooctahydro-2H-pyrido[2,1-b][1,3]thiazepine-7-carboxylate (23 mg, 0.077 mmol) to give a white solid (16 mg, 56% yield). Anal. Calcd. for $C_{43}H_{56}N_4O_{10}S_2$ m/z 852.7. found: 853.4 (M+H)+; 1H NMR (400 MHz, CDCl3)) δ ppm 7.41 (d, J=6.6 Hz, 1H), 7.16 (dd, J=9.7, 6.8 Hz, 2H), 7.03 (d, J=7.0 Hz, 1H), 5.40 (t, J=4.5 Hz, 1H), 5.34 (t, J=4.5 Hz, 1H), 5.23-5.16 (m, 1H), 5.16-5.07 (m, 2H), 5.05-4.95 (m, 1H), 3.73 (s, 3H), 3.70 (s, 2H), 3.34-3.11 (m, 3H), 2.85 (ddd, J=23.6, 21.4, 10.3 Hz, 3H), 2.69 (dd, J=13.3, 5.3 Hz, 1H), 2.63-2.29 (m, 8H), 2.29-2.17 (m, 2H), 1.98 (dd, J=50.2, 26.9 Hz, 5H), 1.80-1.55 (m, 10H), 1.55-1.35 (m, 3H), 1.31-1.04 (m, 4H), 0.95-0.75 (m, 2H).

Example 45

Dimethyl (4S,7S,10aS,4'S,7'S,10a'S)-4,4'-(((2R,5R)-2-(3-chlorobenzyl)-5-(4-methoxybenzyl)-1,6-dioxo-1,6-hexanediyl)diimino)bis(5-oxooctahydro-7H-pyrido[2,1-b][1,3]thiazepine-7-carboxylate)

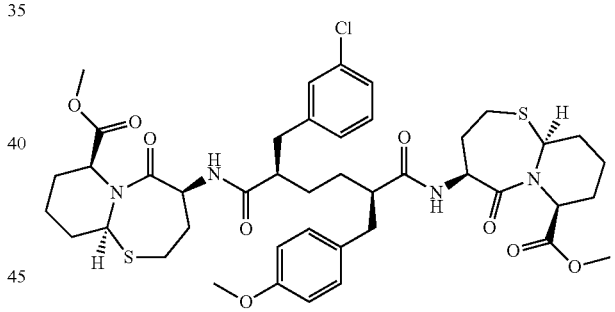

Dimethyl (4S,7S,10aS,4'S,7'S,10a'S)-4,4'-(((2R,5R)-2-(3-chlorobenzyl)-5-(4-methoxybenzyl)-1,6-dioxo-1,6-hexanediyl)diimino)bis(5-oxooctahydro-7H-pyrido[2,1-b][1,3]thiazepine-7-carboxylate) was synthesized as described in General Procedure F using Intermediate 9 (9.0 mg, 0.023 mmol) and (4S,7S,10aS)-methyl 4-amino-5-oxooctahydro-2H-pyrido[2,1-b][1,3]thiazepine-7-carboxylate (16 mg, 0.055 mmol) to give a white solid (9.6 mg, 47% yield). Anal. Calcd. for $C_{43}H_{55}ClN_4O_9S_2$ m/z 870.7. found: 871.2 (M+H)+; 1H NMR (400 MHz, CDCl3) δ ppm 7.36 (t, J=7.0 Hz, 2H), 7.22-7.10 (m, 3H), 7.07-6.98 (m, 2H), 6.78 (d, J=8.6 Hz, 2H), 5.34 (t, J=4.4 Hz, 2H), 5.20-5.07 (m, 2H), 5.05-4.95 (m, 2H), 3.76 (s, 3H), 3.69 (s, 6H), 3.33-3.06 (m, 8H), 2.90-2.62 (m, 5H), 2.48-2.31 (m, 3H), 2.11-1.97 (m, 2H), 1.90-1.56 (m, 11H), 1.56-1.45 (m, 2H).

Example 46

Dimethyl (4S,7S,10aS,4'S,7'S,10a'S)-4,4'-(((2R,5R)-2-(3-chlorobenzyl)-5-(4-hydroxybenzyl)-1,6-dioxo-1,6-hexanediyl)diimino)bis(5-oxooctahydro-7H-pyrido[2,1-b][1,3]thiazepine-7-carboxylate)

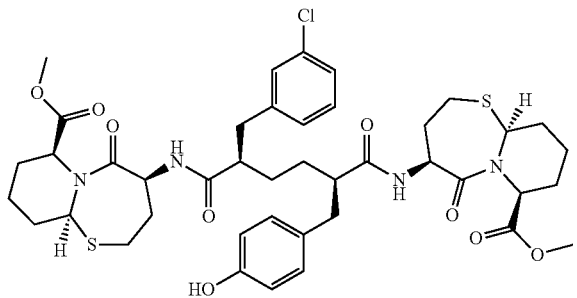 [SMILES: COC(=O)[C@@H]1CCC[C@@H]2SCC[C@H](NC(=O)[C@H](CC[C@H](Cc3cccc(Cl)c3)C(=O)N[C@H]3CCS[C@H]4CCC[C@@H](C(=O)OC)N4C3=O)Cc3ccc(O)cc3)C(=O)N21]

Dimethyl (4S,7S,10aS,4'S,7'S,10a'S)-4,4'-(((2R,5R)-2-(3-chlorobenzyl)-5-(4-hydroxybenzyl)-1,6-dioxo-1,6-hexanediyl)diimino)bis(5-oxooctahydro-7H-pyrido[2,1-b][1,3]thiazepine-7-carboxylate) was synthesized as described in General Procedure F using Intermediate 15 (14 mg, 0.037 mmol) and (4S,7S,10aS)-methyl 4-amino-5-oxooctahydro-2H-pyrido[2,1-b][1,3]thiazepine-7-carboxylate (26 mg, 0.089 mmol) to give a white solid (16 mg, 50% yield). Anal. Calcd. for $C_{42}H_{53}ClN_4O_9S_2$ m/z 856.7. found: 857.2 (M+H)$^+$; $^1$H NMR (400 MHz, CDCl$_3$) δ ppm 7.68 (t, J=7.3 Hz, 1H), 7.21-7.08 (m, 2H), 7.05-6.93 (m, 2H), 6.87-6.62 (m, 5H), 5.39-5.27 (m, 2H), 5.15-4.96 (m, 4H), 3.69 (s, 3H), 3.69 (s, 3H), 3.19-3.02 (m, 2H), 2.90-2.63 (m, 6H), 2.54-2.34 (m, 4H), 2.13-1.97 (m, 4H), 1.84-1.43 (m, 15H).

Example 47

(4S,7S,10aS)-Methyl 4-((2R,5R)-2,5-dibenzyl-6-((S,Z)-1-benzyl-2-oxo-1,2,3,4,7,8-hexahydroazocin-3-ylamino)-6-oxohexanamido)-5-oxooctahydro-2H-pyrido[2,1-b][1,3]thiazepine-7-carboxylate

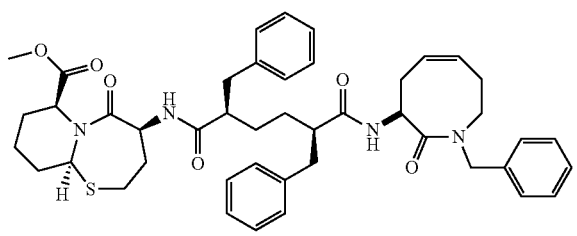

(4S,7S,10aS)-Methyl 4-((2R,5R)-2,5-dibenzyl-6-((S,Z)-1-benzyl-2-oxo-1,2,3,4,7,8-hexahydroazocin-3-ylamino)-6-oxohexanamido)-5-oxooctahydro-2H-pyrido[2,1-b][1,3]thiazepine-7-carboxylate was synthesized as described in General Procedure H using Intermediate 23 (8.0 mg, 0.014 mmol) and Intermediate 44 (6.5 mg, 0.028 mmol) to give a white solid (6.8 mg, 61% yield). Anal. Calcd. for $C_{45}H_{54}N_4O_6S$ m/z 778.7. found: 779.3 (M+H)$^+$; $^1$H NMR (400 MHz, CDCl$_3$) δ ppm 7.40-7.05 (m, 17H), 5.48-5.26 (m, 4H), 5.18-5.06 (m, 1H), 5.05-4.93 (m, 3H), 4.84 (d, J=14.8 Hz, 1H), 4.17 (d, J=14.8 Hz, 1H), 3.92-3.75 (m, 1H), 3.67 (s, 3H), 3.14 (dt, J=14.3, 8.7 Hz, 2H), 2.87-2.66 (m, 5H), 2.61-2.32 (m, 6H), 2.25 (dt, J=16.4, 8.0 Hz, 1H), 2.06-1.97 (m, 2H), 1.86-1.44 (m, 7H).

Example 48

(4S,7S,10aS)-Methyl 4-((2R,5R)-2,5-dibenzyl-6-((S)-1-benzyl-2-oxoazocan-3-ylamino)-6-oxohexanamido)-5-oxooctahydro-2H-pyrido[2,1-b][1,3]thiazepine-7-carboxylate

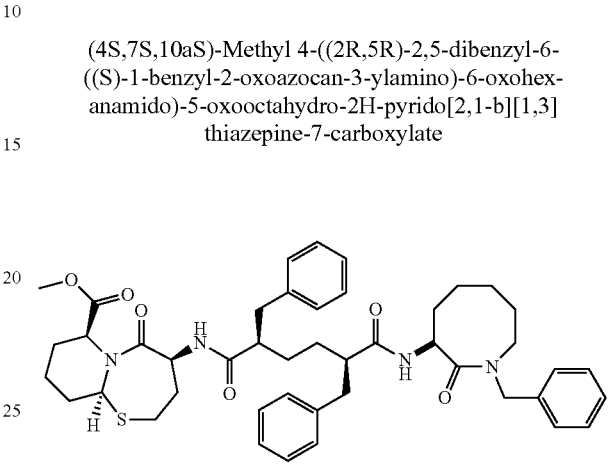

(4S,7S,10aS)-Methyl 4-((2R,5R)-2,5-dibenzyl-6-((S)-1-benzyl-2-oxoazocan-3-ylamino)-6-oxohexanamido)-5-oxooctahydro-2H-pyrido[2,1-b][1,3]thiazepine-7-carboxylate was synthesized as described in General Procedure H using Intermediate 23 (11 mg, 0.019 mmol) and Intermediate 45 (6.3 mg, 0.027 mmol) to give a white solid (9.5 mg, 62% yield). Anal. Calcd. for $C_{45}H_{56}N_4O_6S$ m/z 780.7. found: 781.3 (M+H)$^+$; $^1$H NMR (400 MHz, CDCl$_3$) δ ppm 7.40-7.03 (m, 16H), 6.81 (d, J=7.4 Hz, 1H), 5.34 (t, J=4.6 Hz, 1H), 5.13 (d, J=6.1 Hz, 1H), 5.07 (d, J=14.7 Hz, 1H), 5.03-4.93 (m, 1H), 4.92-4.80 (m, 1H), 4.06 (d, J=14.7 Hz, 1H), 3.77 (t, J=13.2 Hz, 1H), 3.68 (s, 3H), 3.25-3.04 (m, 2H), 2.92-2.64 (m, 5H), 2.47-2.29 (m, 2H), 2.12-1.95 (m, 2H), 1.90-1.09 (m, 18H).

Example 49

(4R,7R)-7-Benzyl-8-((4S,7S,10aS)-7-(methoxycarbonyl)-5-oxooctahydro-2H-pyrido[2,1-b][1,3]thiazepin-4-ylamino)-4-((4S,7S,10aS)-7-(methoxycarbonyl)-5-oxooctahydro-2H-pyrido[2,1-b][1,3]thiazepin-4-ylcarbamoyl)-8-oxooctanoic acid

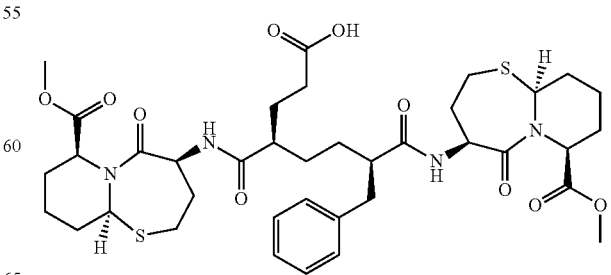

A: Methyl (4S,7S,10aS)-4-(2R,5R)-2-benzyl-8-tert-butoxy-5-(((4S,7S,10aS)-7-(methoxycarbonyl)-5-oxooctahydro-7H-pyrido[2,1-b][1,3]thiazepin-4-yl)carbamoyl)-8-oxooctanoyl)amino)-5-oxooctahydro-7H-pyrido[2,1-b][1,3]thiazepine-7-carboxylate

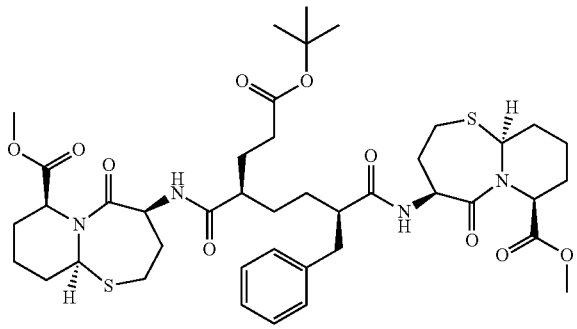 [SMILES: COC(=O)[C@@H]1CCC[C@@H]2SCC[C@H](NC(=O)[C@@H](CCC(=O)OC(C)(C)C)CC[C@H](Cc3ccccc3)C(=O)N[C@H]3CCS[C@H]4CCC[C@@H](C(=O)OC)N4C3=O)C(=O)N21]

Methyl (4S,7S,10aS)-4-(2R,5R)-2-benzyl-8-tert-butoxy-5-(((4S,7S,10aS)-7-(methoxycarbonyl)-5-oxooctahydro-7H-pyrido[2,1-b][1,3]thiazepin-4-yl)carbamoyl)-8-oxooctanoyl)amino)-5-oxooctahydro-7H-pyrido[2,1-b][1,3]thiazepine-7-carboxylate was synthesized as described in General Procedure F using Intermediate 7 (21 mg, 0.056 mmol) and (4S,7S,10aS)-methyl 4-amino-5-oxooctahydro-2H-pyrido[2,1-b][1,3]thiazepine-7-carboxylate (36.3 mg, 0.141 mmol) to give a white solid (45 mg, 95% yield). Anal. Calcd. for $C_{42}H_{60}N_4O_{10}S_2$ m/z 844.7. found: 845.2 (M+H)$^+$.

B: (4R,7R)-7-Benzyl-8-((4S,7S,10aS)-7-(methoxycarbonyl)-5-oxooctahydro-2H-pyrido[2,1-b][1,3]thiazepin-4-ylamino)-4-((4S,7S,10 aS)-7-(methoxycarbonyl)-5-oxooctahydro-2H-pyrido[2,1-b][1,3]thiazepin-4-ylcarbamoyl)-8-oxooctanoic acid

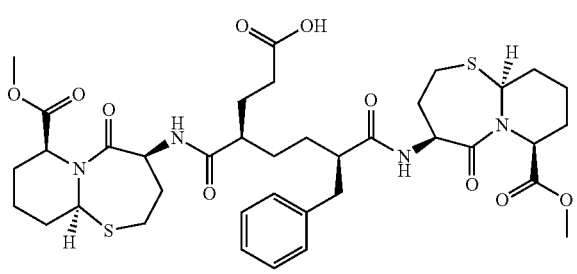 [SMILES: COC(=O)[C@@H]1CCC[C@@H]2SCC[C@H](NC(=O)[C@@H](CCC(=O)O)CC[C@H](Cc3ccccc3)C(=O)N[C@H]3CCS[C@H]4CCC[C@@H](C(=O)OC)N4C3=O)C(=O)N21]

TFA (0.1 mL) was added to a 0° C. solution of methyl (4S,7S,10aS)-4-(((2R,5R)-2-benzyl-8-tert-butoxy-5-(((4S,7S,10aS)-7-(methoxycarbonyl)-5-oxooctahydro-7H-pyrido[2,1-b][1,3]thiazepin-4-yl)carbamoyl)-8-oxooctanoyl)amino)-5-oxooctahydro-7H-pyrido[2,1-b][1,3]thiazepine-7-carboxylate (45 mg, 0.053 mmol) in DCM (0.2 mL). The reaction mixture was then stirred at rt for 4 hr. The reaction mixture was concentrated and dried under vacuum. The residue was purified by RP prep-HPLC to give (4R,7R)-7-benzyl-8-((4S,7S,10aS)-7-(methoxycarbonyl)-5-oxooctahydro-2H-pyrido[2,1-b][1,3]thiazepin-4-ylamino)-4-((4S,7S,10aS)-7-(methoxycarbonyl)-5-oxooctahydro-2H-pyrido[2,1-b][1,3]thiazepin-4-ylcarbamoyl)-8-oxooctanoic acid (8.5 mg, 0.011 mmol, 20% yield) as a white solid. Anal. Calcd. for $C_{38}H_{52}N_4O_{10}S_2$ m/z 788.5. found: 789.0 (M+H)$^+$; $^1$H NMR (400 MHz, CDCl$_3$) δ ppm 7.59 (1H, d, J=5.5 Hz), 7.29-7.10 (6H, m), 5.44-5.29 (2H, m), 5.24-4.96 (6H, m), 3.72 (3H, s), 3.69 (3H, s), 3.30-3.19 (1H, m), 3.18-3.08 (1H, m), 2.97-2.68 (4H, m), 2.50-2.17 (6H, m), 2.10-1.91 (5H, m), 1.90-1.54 (11H, m), 1.53-1.39 (2H, m).

Example 50

(4S,7S,10aS)-Methyl 4-((2R,5R)-2,5-dibenzyl-6-((S)-1-(3-chlorobenzyl)-2-oxoazepan-3-ylamino)-6-oxohexanamido)-5-oxooctahydro-2H-pyrido[2,1-b][1,3]thiazepine-7-carboxylate

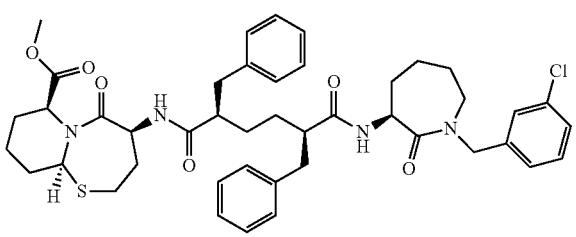 [SMILES: COC(=O)[C@@H]1CCC[C@@H]2SCC[C@H](NC(=O)[C@H](CC[C@H](Cc3ccccc3)C(=O)N[C@H]3CCCCN(Cc4cccc(Cl)c4)C3=O)Cc3ccccc3)C(=O)N21]

(4S,7S,10aS)-Methyl 4-((2R,5R)-2,5-dibenzyl-6-((S)-1-(3-chlorobenzyl)-2-oxoazepan-3-ylamino)-6-oxohexanamido)-5-oxooctahydro-2H-pyrido[2,1-b][1,3]thiazepine-7-carboxylate was synthesized as described in General Procedure H using Intermediate 23 (7.0 mg, 0.012 mmol) and Intermediate 47 (3.6 mg, 0.012 mmol) to give a white solid (7.0 mg, 69% yield). Anal. Calcd. for $C_{44}H_{53}ClN_4O_6S$ m/z 800.4. found: 801.4 (M+H)$^+$; $^1$H NMR (500 MHz, CDCl$_3$) δ ppm 7.25-7.19 (m, 7H), 7.18-7.12 (m, 6H), 7.10 (d, J=4.40 Hz, 1H), 6.96 (d, J=6.60 Hz, 1H), 6.92 (d, J=6.60 Hz, 1H), 5.33 (t, J=4.67 Hz, 1H), 5.17-5.12 (m, 1H), 5.03-4.93 (m, 1H), 4.64 (d, J=14.85 Hz, 1H), 4.59 (dd, J=10.45, 6.60 Hz, 1H), 4.42 (d, J=14.85 Hz, 1H), 3.67 (s, 3H), 3.49 (dd, J=15.40, 11.55 Hz, 1H), 3.24-3.09 (m, 2H), 2.90-2.78 (m, 3H), 2.77-2.68 (m, 2H), 2.45-2.34 (m, 3H), 2.02 (d, J=5.50 Hz, 2H), 1.90-1.79 (m, 2H), 1.72 (br. s., 4H), 1.68-1.49 (m, 8H).

Example 51

Methyl (4S,7S,10aS)-4-(((2R,5R)-5-benzyl-6-(((4S,7S,10aS)-7-(methoxycarbonyl)-5-oxooctahydro-7H-pyrido[2,1-b][1,3]thiazepin-4-yl)amino)-2-(3-methoxy-3-oxopropyl)-6-oxohexanoyl)amino)-5-oxooctahydro-7H-pyrido[2,1-b][1,3]thiazepine-7-carboxylate

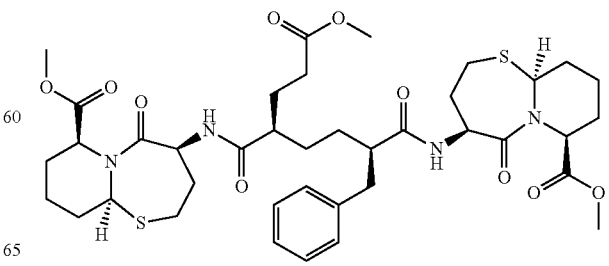

Methyl (4S,7S,10aS)-4-(((2R,5R)-5-benzyl-6-(((4S,7S,10aS)-7-(methoxycarbonyl)-5-oxooctahydro-7H-pyrido[2,1-b][1,3]thiazepin-4-yl)amino)-2-(3-methoxy-3-oxopropyl)-6-oxohexanoyl)amino)-5-oxooctahydro-7H-pyrido[2,1-b][1,3]thiazepine-7-carboxylate (1.8 mg, 0.0022 mmol) was synthesized as described for the preparation of Example 28 using (4R,7R)-7-benzyl-8-((4S,7S,10aS)-7-(methoxycarbonyl)-5-oxooctahydro-2H-pyrido[2,1-b][1,3]thiazepin-4-ylamino)-4-((4S,7S,10aS)-7-(methoxycarbonyl)-5-oxooctahydro-2H-pyrido[2,1-b][1,3]thiazepin-4-ylcarbamoyl)-8-oxooctanoic acid. Anal. Calcd. for $C_{39}H_{54}N_4O_{10}S_2$ m/z 802.4. found: 803.0 (M+H)$^+$; $^1$H NMR (400 MHz, CDCl$_3$) δ ppm 7.33-7.28 (1H, m), 7.28-7.21 (2H, m), 7.19-7.11 (3H, m), 6.99 (1H, d, J=5.5 Hz), 5.39 (1H, t, J=4.7 Hz), 5.34 (1H, t, J=4.7 Hz), 5.21-5.17 (1H, m), 5.16-5.12 (1H, m), 5.11-5.05 (1H, m), 5.02-4.95 (1H, m), 3.73 (3H, s), 3.69 (3H, s), 3.66 (3H, s), 3.32-3.22 (1H, m), 3.21-3.11 (1H, m), 2.97-2.88 (1H, m), 2.87-2.78 (2H, m), 2.75-2.68 (1H, m), 2.48-2.32 (3H, m), 2.32-2.14 (3H, m), 2.09-1.80 (9H, m), 1.80-1.56 (9H, m), 1.54-1.37 (2H, m).

Example 52

Methyl (4S,7S,10aS)-4-(((2R,5R)-8-amino-2-benzyl-5-(((4S,7S,10aS)-7-(methoxycarbonyl)-5-oxooctahydro-7H-pyrido[2,1-b][1,3]thiazepin-4-yl)carbamoyl)-8-oxooctanoyl)amino)-5-oxooctahydro-7H-pyrido[2,1-b][1,3]thiazepine-7-carboxylate

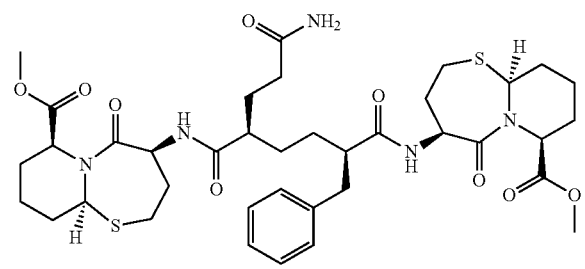 [SMILES: COC(=O)[C@@H]1CCC[C@@H]2SCC[C@H](NC(=O)[C@@H](CCC(N)=O)CC[C@H](Cc3ccccc3)C(=O)N[C@H]3CCS[C@H]4CCC[C@@H](C(=O)OC)N4C3=O)C(=O)N21]

Methyl (4S,7S,10aS)-4-(((2R,5R)-8-amino-2-benzyl-5-(((4S,7S,10aS)-7-(methoxycarbonyl)-5-oxooctahydro-7H-pyrido[2,1-b][1,3]thiazepin-4-yl)carbamoyl)-8-oxooctanoyl)amino)-5-oxooctahydro-7H-pyrido[2,1-b][1,3]thiazepine-7-carboxylate (5.0 mg, 0.0064 mmol) was synthesized as described for the preparation of Example 29 using (4R,7R)-7-benzyl-8-((4S,7S,10 aS)-7-(methoxycarbonyl)-5-oxooctahydro-2H-pyrido[2,1-b][1,3]thiazepin-4-ylamino)-4-((4S,7S,10aS)-7-(methoxycarbonyl)-5-oxooctahydro-2H-pyrido[2,1-b][1,3]thiazepin-4-ylcarbamoyl)-8-oxooctanoic acid. Anal. Calcd. for $C_{38}H_{53}N_5O_9S_2$ m/z 787.4. found: 788.3 (M+H)$^+$; $^1$H NMR (400 MHz, CDCl$_3$) δ ppm 7.59 (1H, d, J=6.6 Hz), 7.26-6.98 (7H, m), 6.57 (1H, br. s.), 5.38-5.21 (2H, m), 5.16-4.78 (6H, m), 3.65 (3H, s), 3.62 (3H, s), 3.21-3.10 (1H, m), 3.07-2.97 (1H, m), 2.90-2.81 (1H, m), 2.78-2.63 (2H, m), 2.49-2.16 (5H, m), 2.15-2.06 (1H, m), 2.04-1.86 (6H, m), 1.86-1.71 (1H, m), 1.71-1.49 (8H, m), 1.48-1.36 (1H, m), 1.31-1.15 (3H, m).

Example 53

Dimethyl (4S,7S,10aS,4'S,7'S,10a'S)-4,4'-(((2R,5R)-2-benzyl-5-(cyclohexylmethyl)-1,6-dioxo-1,6-hexanediyl)diimino)bis(5-oxooctahydro-7H-pyrido[2,1-b][1,3]thiazepine-7-carboxylate)

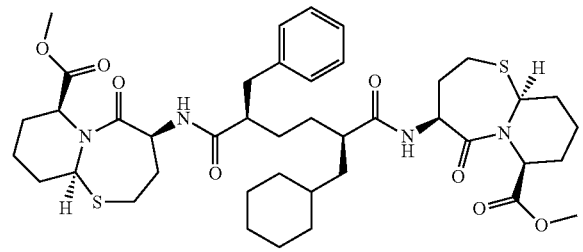 [SMILES: COC(=O)[C@@H]1CCC[C@@H]2SCC[C@H](NC(=O)[C@H](CC[C@H](CC3CCCCC3)C(=O)N[C@H]3CCS[C@H]4CCC[C@@H](C(=O)OC)N4C3=O)Cc3ccccc3)C(=O)N21]

Dimethyl (4S,7S,10aS,4'S,7'S,10a'S)-4,4'-(((2R,5R)-2-benzyl-5-(cyclohexylmethyl)-1,6-dioxo-1,6-hexanediyl)diimino)bis(5-oxooctahydro-7H-pyrido[2,1-b][1,3]thiazepine-7-carboxylate) was synthesized as described in General Procedure F using Intermediate 14 (6.8 mg, 0.020 mmol) and (4S,7S,10aS)-methyl 4-amino-5-oxooctahydro-2H-pyrido[2,1-b][1,3]thiazepine-7-carboxylate (18.09 mg, 0.061 mmol) to give a white solid (12 mg, 70.7% yield). Anal. Calcd. for $C_{42}H_{60}N_4O_8S_2$ m/z 812.7. found: 813.2 (M+H)$^+$; $^1$H NMR (400 MHz, DMSO-d$_6$) δ ppm 7.33 (dd, J=24.8, 6.3 Hz, 1H), 7.28-7.20 (m, 2H), 7.20-7.05 (m, 2H), 5.48-5.27 (m, 2H), 5.19 (d, J=4.3 Hz, 1H), 5.16-4.93 (m, 2H), 3.74 (s, 3H), 3.49 (d, J=160.4 Hz, 8H), 3.20-3.09 (m, 1H), 3.00-2.66 (m, 4H), 2.52-2.34 (m, 2H), 2.24 (d, J=5.1 Hz, 2H), 2.16-1.90 (m, 4H), 1.90-1.33 (m, 15H), 1.31-1.06 (m, 6H), 0.84 (dd, J=24.2, 11.9 Hz, 2H), 0.06-0.04 (m, 3H).

Example 54

(4S,7S,10aS)-Methyl 4-((2R,5R)-2,5-dibenzyl-6-((S)-1-(2-chlorobenzyl)-2-oxoazepan-3-ylamino)-6-oxohexanamido)-5-oxooctahydro-2H-pyrido[2,1-b][1,3]thiazepine-7-carboxylate

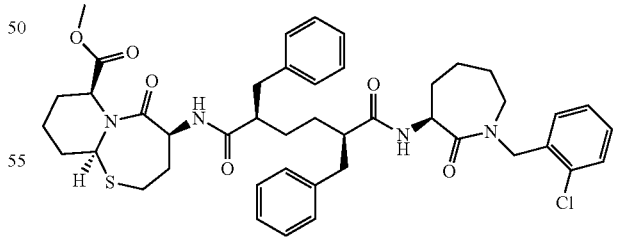

(4S,7S,10aS)-Methyl 4-((2R,5R)-2,5-dibenzyl-6-((S)-1-(2-chlorobenzyl)-2-oxoazepan-3-ylamino)-6-oxohexanamido)-5-oxooctahydro-2H-pyrido[2,1-b][1,3]thiazepine-7-carboxylate was synthesized as described in General Procedure H using Intermediate 23 (7.0 mg, 0.012 mmol) and Intermediate 48 (3.6 mg, 0.012 mmol) to give a white solid (7.0 mg, 69% yield). Anal. Calcd. for $C_{44}H_{53}ClN_4O_6S$ m/z 800.4. found: 801.4 (M+H)$^+$; $^1$H NMR (500 MHz, CDCl$_3$) δ ppm 7.39-7.32 (m, 1H), 7.25-7.17 (m, 7H), 7.18-7.11 (m, 6H), 6.92 (t, J=7.70 Hz, 2H), 5.32 (t, J=4.67 Hz, 1H), 5.17-5.10 (m, 1H), 4.97 (t, J=6.87 Hz, 1H), 4.81 (d, J=15.40 Hz, 1H), 4.68-4.63 (m, 1H), 4.63-4.57 (m, 1H), 3.68 (s, 3H), 3.50 (dd, J=15.40, 11.55 Hz, 1H), 3.29-3.11 (m, 2H), 2.92-2.75 (m, 3H), 2.75-2.66 (m, 2H), 2.46-2.30 (m, 3H), 2.03-1.99 (m, 2H), 1.89-1.79 (m, 2H), 1.77-1.45 (m, 13H).

Example 55

(4S,7S,10aS)-Methyl 4-((2R,5R)-2,5-dibenzyl-6-((S)-1-(3-chlorophenyl)-2-oxoazepan-3-ylamino)-6-oxohexanamido)-5-oxooctahydro-2H-pyrido[2,1-b][1,3]thiazepine-7-carboxylate

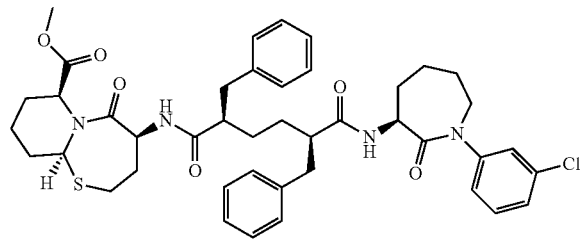 [SMILES: COC(=O)[C@@H]1CCC[C@@H]2SCC[C@H](NC(=O)[C@H](CC[C@H](Cc3ccccc3)C(=O)N[C@H]3CCCCN(c4cccc(Cl)c4)C3=O)Cc3ccccc3)C(=O)N21]

(4S,7S,10aS)-Methyl 4-((2R,5R)-2,5-dibenzyl-6-((S)-1-(3-chlorophenyl)-2-oxoazepan-3-ylamino)-6-oxohexanamido)-5-oxooctahydro-2H-pyrido[2,1-b][1,3]thiazepine-7-carboxylate was synthesized as described in General Procedure H using Intermediate 23 (7.0 mg, 0.012 mmol) and Intermediate 49 (3.4 mg, 0.012 mmol) to give a white solid (5.1 mg, 51% yield). Anal. Calcd. for $C_{43}H_{51}ClN_4O_6S$ m/z 786.4. found: 787.5 (M+H)$^+$; $^1$H NMR (500 MHz, CDCl$_3$) δ ppm 7.29 (d, J=8.25 Hz, 1H), 7.25-7.18 (m, 5H), 7.18-7.10 (m, 7H), 7.03 (d, J=7.70 Hz, 1H), 6.89 (d, J=6.60 Hz, 1H), 6.79 (d, J=6.60 Hz, 1H), 5.32 (t, J=4.40 Hz, 1H), 5.17-5.12 (m, 1H), 5.03-4.93 (m, 1H), 4.75 (dd, J=9.90, 7.15 Hz, 1H), 3.93 (dd, J=15.40, 11.55 Hz, 1H), 3.68 (s, 3H), 3.58 (dd, J=15.12, 4.67 Hz, 1H), 3.21-3.09 (m, 1H), 2.90-2.76 (m, 3H), 2.76-2.67 (m, 2H), 2.44-2.27 (m, 3H), 2.02-1.97 (m, 2H), 1.97-1.90 (m, 1H), 1.90-1.77 (m, 3H), 1.76-1.46 (m, 11H).

Example 56

(4S,7S,10aS)-Methyl 4-((2R,5R)-2,5-dibenzyl-6-((S)-1-(4-chlorophenyl)-2-oxoazepan-3-ylamino)-6-oxohexanamido)-5-oxooctahydro-2H-pyrido[2,1-b][1,3]thiazepine-7-carboxylate

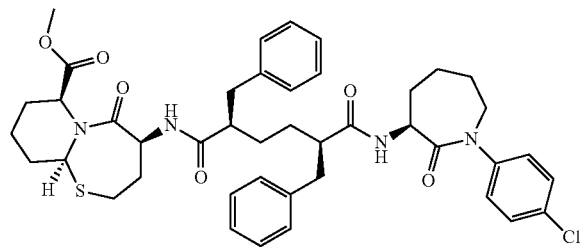 [SMILES: COC(=O)[C@@H]1CCC[C@@H]2SCC[C@H](NC(=O)[C@H](CC[C@H](Cc3ccccc3)C(=O)N[C@H]3CCCCN(c4ccc(Cl)cc4)C3=O)Cc3ccccc3)C(=O)N21]

(4S,7S,10aS)-Methyl 4-((2R,5R)-2,5-dibenzyl-6-((S)-1-(4-chlorophenyl)-2-oxoazepan-3-ylamino)-6-oxohexanamido)-5-oxooctahydro-2H-pyrido[2,1-b][1,3]thiazepine-7-carboxylate was synthesized as described in General Procedure H using Intermediate 23 (7.0 mg, 0.012 mmol) and Intermediate 50 (3.4 mg, 0.012 mmol) to give a white solid (6.8 mg, 69% yield). Anal. Calcd. for $C_{43}H_{51}ClN_4O_6S$ m/z 786.4. found: 787.4 (M+H)$^+$; $^1$H NMR (500 MHz, CDCl$_3$) δ ppm 7.33 (d, J=8.25 Hz, 2H), 7.22 (q, J=7.15 Hz, 4H), 7.19-7.10 (m, 6H), 7.11-7.04 (m, 2H), 6.89 (br. s., 1H), 6.85-6.73 (m, 1H), 5.31 (br. s., 1H), 5.14 (br. s., 1H), 4.98 (br. s., 1H), 4.78 (br. s., 1H), 3.92 (br. s., 1H), 3.68 (s, 3H), 3.61-3.52 (m, 1H), 3.24-3.08 (m, 1H), 2.92-2.75 (m, 3H), 2.76-2.65 (m, 2H), 2.46-2.26 (m, 3H), 2.09-1.43 (m, 17H).

Example 57

(4S,7S,10aS)-Methyl 4-((2R,5R)-2,5-dibenzyl-6-((S,Z)-1-benzyl-2-oxo-2,3,4,7-tetrahydro-1H-azepin-3-ylamino)-6-oxohexanamido)-5-oxooctahydro-2H-pyrido[2,1-b][1,3]thiazepine-7-carboxylate

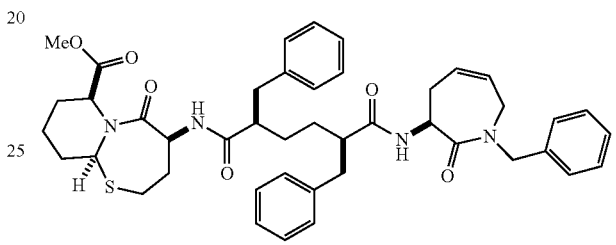

(4S,7S,10aS)-Methyl 4-((2R,5R)-2,5-dibenzyl-6-((S,Z)-1-benzyl-2-oxo-2,3,4,7-tetrahydro-1H-azepin-3-ylamino)-6-oxohexanamido)-5-oxooctahydro-2H-pyrido[2,1-b][1,3]thiazepine-7-carboxylate was synthesized as described in General Procedure H using Intermediate 23 (11 mg, 0.019 mmol) and Intermediate 51 (5.9 mg, 0.027 mmol) to give a white solid (10 mg, 68% yield). Anal. Calcd. for $C_{44}H_{52}N_4O_6S$ m/z 764.4. found: 765.2 (M+H)$^+$; $^1$H NMR (400 MHz, CDCl$_3$) δ ppm 7.41-7.06 (m, 16H), 6.96 (d, J=7.1 Hz, 1H), 5.67-5.48 (m, 2H), 5.34 (t, J=4.6 Hz, 1H), 5.18-5.06 (m, 2H), 5.05-4.93 (m, 1H), 4.61 (dd, J=51.2, 15.0 Hz, 2H), 4.34 (d, J=17.6 Hz, 1H), 3.67 (s, 3H), 3.33 (dd, J=17.6, 6.8 Hz, 1H), 3.14 (t, J=11.4 Hz, 1H), 2.91-2.64 (m, 4H), 2.51-2.14 (m, 6H), 2.02 (d, J=4.4 Hz, 2H), 1.89-1.44 (m, 9H).

Example 58

(4S,7S,10aS)-Methyl 4-((2R,5R)-2,5-dibenzyl-6-oxo-6-((S,Z)-2-oxo-1-phenyl-2,3,4,7-tetrahydro-1H-azepin-3-ylamino)hexanamido)-5-oxooctahydro-2H-pyrido[2,1-b][1,3]thiazepine-7-carboxylate

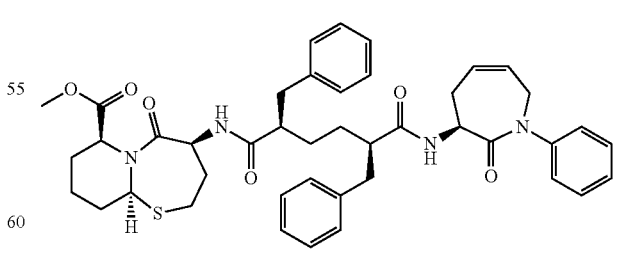

(4S,7S,10aS)-Methyl 4-((2R,5R)-2,5-dibenzyl-6-oxo-6-((S,Z)-2-oxo-1-phenyl-2,3,4,7-tetrahydro-1H-azepin-3-ylamino)hexanamido)-5-oxooctahydro-2H-pyrido[2,1-b][1,3]thiazepine-7-carboxylate was synthesized as described in General Procedure H using Intermediate 23 (30 mg, 0.053 mmol) and Intermediate 52 (20 mg, 0.064 mmol) to give a white solid (26 mg, 65% yield). Anal. Calcd. for $C_{43}H_{50}N_4O_6S$ m/z 750.4. found: 751.4 (M+H)$^+$; $^1$H NMR (400 MHz, DMSO-d$_6$) δ ppm 7.86 (dd, J=36.0, 7.3 Hz, 2H), 7.34 (t, J=7.8 Hz, 2H), 7.26-7.06 (m, 11H), 6.02-5.84 (m, 1H), 5.79-5.66 (m, 1H), 5.65-5.56 (m, 1H), 5.28-5.12 (m, 1H), 5.01 (d, J=4.4 Hz, 2H), 4.82 (d, J=17.7 Hz, 1H), 3.78 (dd, J=17.8, 7.9 Hz, 1H), 3.17-2.93 (m, 2H), 2.93-2.36 (m, 11H), 2.25-2.04 (m, 2H), 2.04-1.87 (m, 2H), 1.87-1.73 (m, 1H), 1.72-1.38 (m, 7H), 1.32 (d, J=6.2 Hz, 2H).

Example 59

(2R,5R)-2,5-Dibenzyl-N1-((S)-2-oxo-1-phenylazepan-3-yl)-N6-((4S,10aS)-5-oxooctahydro-2H-pyrido[2,1-b][1,3]thiazepin-4-yl)hexanediamide

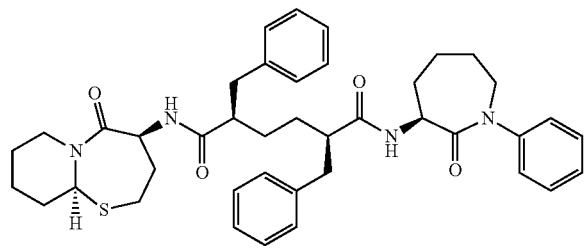 [SMILES: O=C(N[C@H]1CCCCN(c2ccccc2)C1=O)[C@H](CC[C@H](Cc1ccccc1)C(=O)N[C@H]1CCS[C@H]2CCCCN2C1=O)Cc1ccccc1]

(2R,5R)-2,5-Dibenzyl-N1-((S)-2-oxo-1-phenylazepan-3-yl)-N6-((4S,10aS)-5-oxooctahydro-2H-pyrido[2,1-b][1,3]thiazepin-4-yl)hexanediamide was synthesized as described in General Procedure H using Intermediate 24 (20 mg, 0.039 mmol) and Intermediate 40 (10 mg, 0.051 mmol) to give a white solid (16 mg, 58% yield). Anal. Calcd. for $C_{41}H_{50}N_4O_4S$ m/z 694.4. found: 695.3 (M+H)$^+$; $^1$H NMR (400 MHz, DMSO-d$_6$) δ ppm 7.76 (dd, J=18.7, 7.1 Hz, 2H), 7.35 (t, J=7.8 Hz, 2H), 7.29-7.03 (m, 11H), 5.60 (s, 1H), 5.04-4.85 (m, 1H), 4.76-4.59 (m, 1H), 4.08 (d, J=13.2 Hz, 1H), 3.95 (dd, J=15.3, 11.5 Hz, 1H), 3.52 (d, J=15.9 Hz, 1H), 3.07 (t, J=11.3 Hz, 1H), 2.87-2.35 (m, 11H), 2.08-1.01 (m, 17H).

Example 60

(4S,7S,10aS)-Methyl 4-((2R,5R)-2,5-dibenzyl-6-oxo-6-((7S,10aR,Z)-6-oxo-1,2,3,4,6,7,8,10a-octahydropyrido[1,2-a]azepin-7-ylamino)hexanamido)-5-oxooctahydro-2H-pyrido[2,1-b][1,3]thiazepine-7-carboxylate

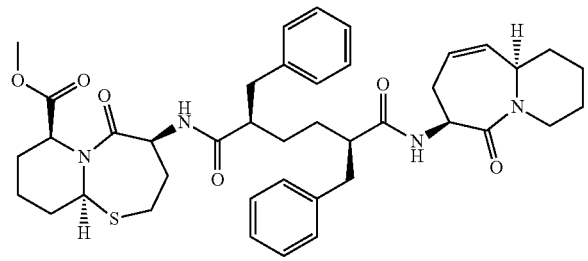 [SMILES: COC(=O)[C@@H]1CCC[C@@H]2SCC[C@H](NC(=O)[C@H](CC[C@H](Cc3ccccc3)C(=O)N[C@H]3CCC[C@H]4CCCCN4C3=O)Cc3ccccc3)C(=O)N21]

(4S,7S,10aS)-Methyl 4-((2R,5R)-2,5-dibenzyl-6-oxo-6-((7S,10aR,Z)-6-oxo-1,2,3,4,6,7,8,10a-octahydropyrido[1,2- a]azepin-7-ylamino)hexanamido)-5-oxooctahydro-2H-pyrido[2,1-b][1,3]thiazepine-7-carboxylate was synthesized as described in General Procedure H using Intermediate 23 (11 mg, 0.019 mmol) and Intermediate 53 (4.6 mg, 0.021 mmol) to give a white solid (12 mg, 90% yield). Anal. Calcd. for $C_{41}H_{52}N_4O_6S$ m/z 728.4. found: 729.3 (M+H)$^+$; $^1$H NMR (400 MHz, CDCl$_3$) δ ppm 7.29-7.10 (11H, m), 7.05 (1H, d, J=7.1 Hz), 5.63-5.48 (2H, m), 5.39-5.30 (2H, m), 5.14-5.09 (1H, m), 5.04-4.96 (1H, m), 4.80-4.71 (1H, m), 4.02-3.93 (1H, m), 3.68 (3H, s), 3.21-3.10 (1H, m), 3.05-2.94 (1H, m), 2.87-2.69 (6H, m), 2.50-2.36 (3H, m), 2.31-2.18 (1H, m), 2.07-1.99 (2H, m), 1.89-1.45 (15H, m).

Example 61

(4S,7S,10aS)-Methyl 4-((2R,5R)-2,5-dibenzyl-6-oxo-6-((7S,10aR)-6-oxodecahydropyrido[1,2-a]azepin-7-ylamino)hexanamido)-5-oxooctahydro-2H-pyrido[2,1-b][1,3]thiazepine-7-carboxylate

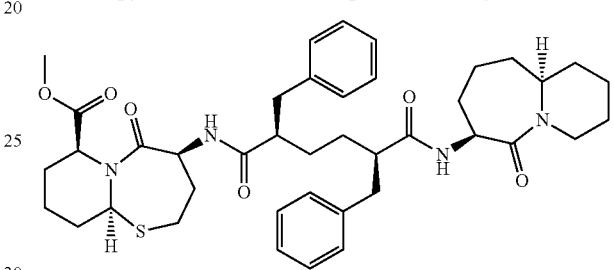

(4S,7S,10aS)-Methyl 4-((2R,5R)-2,5-dibenzyl-6-oxo-6-((7S,10aR)-6-oxodecahydropyrido[1,2-a]azepin-7-ylamino)hexanamido)-5-oxooctahydro-2H-pyrido[2,1-b][1,3]thiazepine-7-carboxylate was synthesized as described in General Procedure H using Intermediate 23 (11 mg, 0.019 mmol) and Intermediate 54 (4.7 mg, 0.021 mmol) to give a white solid (12 mg, 91% yield). Anal. Calcd. for $C_{41}H_{54}N_4O_6S$ m/z 730.4. found: 731.3 (M+H)$^+$; $^1$H NMR (400 MHz, CDCl$_3$) δ ppm 7.32-7.07 (12H, m), 5.33 (1H, t, J=4.7 Hz), 5.15-5.08 (1H, m), 5.05-4.95 (1H, m), 4.83-4.72 (1H, m), 4.15 (1H, d, J=11.5 Hz), 3.88-3.77 (1H, m), 3.68 (3H, s), 3.15 (1H, ddd, J=14.2, 11.1, 2.7 Hz), 2.90-2.68 (6H, m), 2.51-2.35 (3H, m), 2.08-1.99 (2H, m), 1.85-1.42 (20H, m), 1.06-0.90 (1H, m).

Example 62

(4S,7S,10aS)-Methyl 4-((2R,5R)-2,5-dibenzyl-6-oxo-6-((7S,11aR,Z)-6-oxo-2,3,4,6,7,8,9,11a-octahydro-1H-pyrido[1,2-a]azocin-7-ylamino)hexanamido)-5-oxooctahydro-2H-pyrido[2,1-b][1,3]thiazepine-7-carboxylate

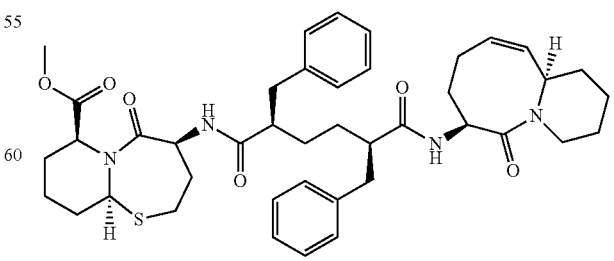

(4S,7S,10aS)-Methyl 4-((2R,5R)-2,5-dibenzyl-6-oxo-6-((7S,11aR,Z)-6-oxo-2,3,4,6,7,8,9,11a-octahydro-1H-pyrido

[1,2-a]azocin-7-ylamino)hexanamido)-5-oxooctahydro-2H-pyrido[2,1-b][1,3]thiazepine-7-carboxylate was synthesized as described in General Procedure H using Intermediate 23 (11 mg, 0.019 mmol) and Intermediate 55 (4.9 mg, 0.021 mmol) to give a white solid (10 mg, 74% yield). Anal. Calcd. for $C_{42}H_{54}N_4O_6S$ m/z 742.4. found: 743.3 (M+H)$^+$; $^1$H NMR (400 MHz, CDCl$_3$) δ ppm 7.28-7.08 (12H, m), 5.94 (1H, t, J=9.3 Hz), 5.81-5.71 (1H, m), 5.33 (1H, t, J=4.7 Hz), 5.15-5.10 (1H, m), 5.04-4.95 (1H, m), 4.92-4.84 (1H, m), 4.73-4.65 (1H, m), 4.21 (1H, d, J=13.2 Hz), 3.68 (3H, s), 3.16 (1H, ddd, J=14.2, 11.1, 2.7 Hz), 2.87-2.65 (6H, m), 2.48-2.30 (4H, m), 2.18-2.07 (1H, m), 2.07-2.00 (2H, m), 1.91-1.42 (16H, m), 1.11-0.98 (1H, m).

Example 63

(4S,7S,10aS)-Methyl 4-((2R,5R)-2,5-dibenzyl-6-oxo-6-((7S,11aS)-6-oxodecahydro-1H-pyrido[1,2-a]azocin-7-ylamino)hexanamido)-5-oxooctahydro-2H-pyrido[2,1-b][1,3]thiazepine-7-carboxylate

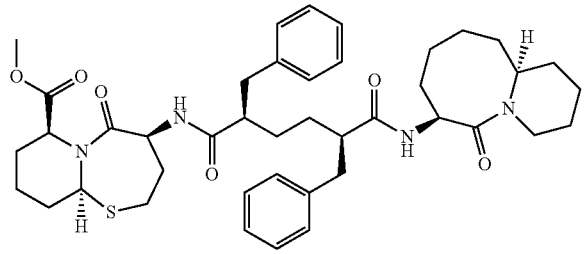 [SMILES: COC(=O)[C@@H]1CCC[C@@H]2SCC[C@H](NC(=O)[C@H](CC[C@H](Cc3ccccc3)C(=O)N[C@H]3CCCC[C@H]4CCCCN4C3=O)Cc3ccccc3)C(=O)N21]

(4S,7S,10aS)-Methyl 4-((2R,5R)-2,5-dibenzyl-6-oxo-6-((7S,11aS)-6-oxodecahydro-1H-pyrido[1,2-a]azocin-7-ylamino)hexanamido)-5-oxooctahydro-2H-pyrido[2,1-b][1,3]thiazepine-7-carboxylate was synthesized as described in General Procedure H using Intermediate 23 (11 mg, 0.019 mmol) and Intermediate 56 (5.0 mg, 0.021 mmol) to give a white solid (11 mg, 80% yield). Anal. Calcd. for $C_{42}H_{56}N_4O_6S$ m/z 744.4. found: 745.3 (M+H)$^+$; $^1$H NMR (400 MHz, CDCl$_3$) δ ppm 7.28-7.08 (11H, m), 7.05 (1H, d, J=7.1 Hz), 5.33 (1H, t, J=4.7 Hz), 5.15-5.09 (1H, m), 5.04-4.95 (1H, m), 4.82-4.73 (1H, m), 4.39 (1H, d, J=13.2 Hz), 4.16 (1H, d, J=12.6 Hz), 3.68 (3H, s), 3.16 (1H, t, J=11.5 Hz), 2.87-2.69 (5H, m), 2.52 (1H, td, J=13.2, 2.7 Hz), 2.46-2.34 (3H, m), 2.15 (1H, t, J=13.5 Hz), 2.07-1.99 (2H, m), 1.94-1.77 (2H, m), 1.76-1.37 (16H, m), 1.36-1.19 (2H, m), 1.08-0.94 (1H, m), 0.89-0.76 (1H, m).

Example 64

(4S,7S,10aS)-methyl 4-((2R,5R)-2,5-dibenzyl-6-oxo-6-((4S,8S,10aS)-5-oxo-8-(trifluoromethyl)octahydro-2H-pyrido[2,1-b][1,3]thiazepin-4-ylamino)hexanamido)-5-oxooctahydro-2H-pyrido[2,1-b][1,3]thiazepine-7-carboxylate

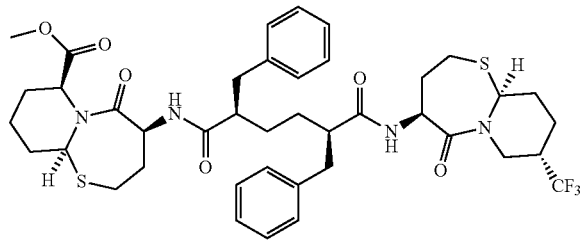 [SMILES: COC(=O)[C@@H]1CCC[C@@H]2SCC[C@H](NC(=O)[C@H](CC[C@H](Cc3ccccc3)C(=O)N[C@H]3CCS[C@H]4CC[C@H](C(F)(F)F)CN4C3=O)Cc3ccccc3)C(=O)N21]

(4S,7S,10aS)-Methyl 4-((2R,5R)-2,5-dibenzyl-6-oxo-6-((4S,8S,10aS)-5-oxo-8-(trifluoromethyl)octahydro-2H-pyrido[2,1-b][1,3]thiazepin-4-ylamino)hexanamido)-5-oxooctahydro-2H-pyrido[2,1-b][1,3]thiazepine-7-carboxylate was synthesized as described in General Procedure H using Intermediate 23 (11 mg, 0.019 mmol) and Intermediate 60 (6.3 mg, 0.023 mmol) to give a white solid (10 mg, 65% yield). Anal. Calcd. for $C_{41}H_{51}F_3N_4O_6S_2$ m/z 816.4. found: 817.3 (M+H)$^+$; $^1$H NMR (400 MHz, CDCl$_3$) δ ppm 7.34-7.05 (m, 10H), 6.87 (d, J=6.3 Hz, 2H), 5.33 (t, J=4.6 Hz, 1H), 5.22-5.07 (m, 2H), 5.05-4.93 (m, 1H), 4.84-4.71 (m, 1H), 4.37 (d, J=14.8 Hz, 1H), 3.69 (s, 3H), 3.33-3.10 (m, 3H), 2.92-2.51 (m, 7H), 2.48-2.20 (m, 4H), 2.12-1.92 (m, 3H), 1.93-1.76 (m, 2H), 1.77-1.19 (m, 11H).

Example 65

(4S,7S,10aS)-Methyl 4-((2R,5R)-2,5-dibenzyl-6-oxo-6-((4S,8R,10aS)-5-oxo-8-(trifluoromethyl)octahydro-2H-pyrido[2,1-b][1,3]thiazepin-4-ylamino)hexanamido)-5-oxooctahydro-2H-pyrido[2,1-b][1,3]thiazepine-7-carboxylate

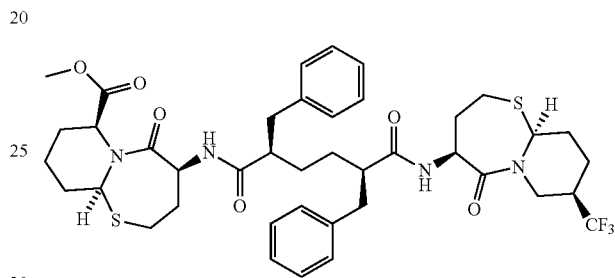

(4S,7S,10aS)-Methyl 4-((2R,5R)-2,5-dibenzyl-6-oxo-6-((4S,8R,10aS)-5-oxo-8-(trifluoromethyl)octahydro-2H-pyrido[2,1-b][1,3]thiazepin-4-ylamino)hexanamido)-5-oxooctahydro-2H-pyrido[2,1-b][1,3]thiazepine-7-carboxylate was synthesized as described in General Procedure H using Intermediate 23 (15 mg, 0.026 mmol) and Intermediate 61 (8.5 mg, 0.032 mmol) to give a white solid (16 mg, 73% yield). Anal. Calcd. for $C_{41}H_{51}F_3N_4O_6S_2$ m/z 816.4. found: 817.3 (M+H)$^+$; $^1$H NMR (400 MHz, CDCl$_3$) δ ppm 7.43 (d, J=7.0 Hz, 1H), 7.36 (d, J=7.0 Hz, 1H), 7.30-7.06 (m, 10H), 5.33 (t, J=4.5 Hz, 1H), 5.26 (t, 1H), 5.12-5.06 (m, 1H), 5.00 (qd, J=10.2, 3.2 Hz, 2H), 4.47 (dd, J=13.4, 4.5 Hz, 1H), 3.68 (s, 3H), 3.17-3.03 (m, 2H), 2.89 (dd, J=15.3, 10.4 Hz, 2H), 2.84-2.70 (m, 5H), 2.55 (ddd, J=14.5, 5.9, 2.9 Hz, 1H), 2.49-2.38 (m, 3H), 2.38-2.24 (m, 1H), 2.16-1.99 (m, 4H), 1.99-1.86 (m, 1H), 1.83-1.45 (m, 11H), 1.22 (td, J=11.0, 8.0 Hz, 1H).

Example 66

(2R,5R)-2,5-Dibenzyl-N1-((S)-2-oxo-1-phenylazepan-3-yl)-N6-((4S,8R,10aS)-5-oxo-8-(trifluoromethyl)octahydro-2H-pyrido[2,1-b][1,3]thiazepin-4-yl)hexanediamide

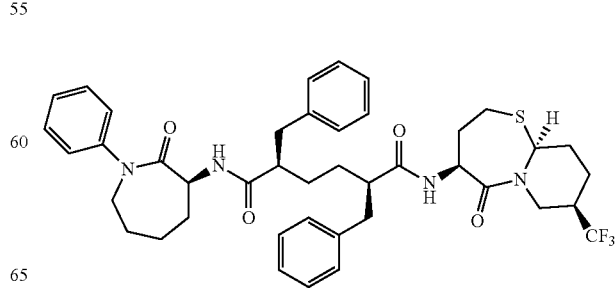

(2R,5R)-2,5-Dibenzyl-N1-((S)-2-oxo-1-phenylazepan-3-yl)-N6-((4S,8R,10aS)-5-oxo-8-(trifluoromethyl)octahydro-2H-pyrido[2,1-b][1,3]thiazepin-4-yl)hexanediamide was synthesized as described in General Procedure H using Intermediate 24 (15 mg, 0.029 mmol) and Intermediate 61 (9.4 mg, 0.035 mmol) to give a white solid (14 mg, 63% yield). Anal. Calcd. for $C_{42}H_{49}F_3N_4O_4S$ m/z 762.4. found: 763.3 (M+H)$^+$; $^1$H NMR (400 MHz, CDCl$_3$) δ ppm 7.45-7.02 (m, 15H), 5.24 (t, 1H), 5.02-4.90 (m, 1H), 4.79 (dd, J=9.4, 7.0 Hz, 1H), 4.48 (dd, J=13.3, 4.4 Hz, 1H), 3.94 (dd, J=16.1, 12.3 Hz, 1H), 3.60 (d, J=15.1 Hz, 1H), 3.11-3.00 (m, 1H), 2.93-2.68 (m, 5H), 2.52 (ddd, J=14.4, 6.0, 2.9 Hz, 1H), 2.48-2.21 (m, 4H), 2.17-1.46 (m, 13H), 1.42-1.09 (m, 4H).

Example 67

(2R,5R)-2,5-Dibenzyl-N1,N6-bis((4S,8R,10aS)-5-oxo-8-(trifluoromethyl)octahydro-2H-pyrido[2,1-b][1,3]thiazepin-4-yl)hexanediamide

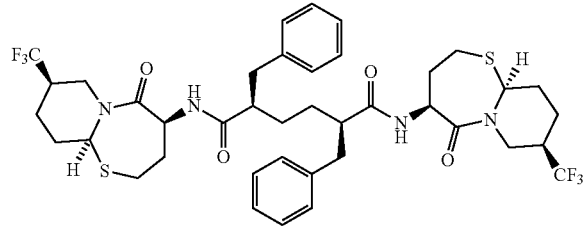 [SMILES: O=C(N[C@H]1CCS[C@H]2CC[C@@H](C(F)(F)F)CN2C1=O)[C@H](CC[C@H](Cc1ccccc1)C(=O)N[C@H]1CCS[C@H]2CC[C@@H](C(F)(F)F)CN2C1=O)Cc1ccccc1]

(2R,5R)-2,5-Dibenzyl-N1,N6-bis((4S,8R,10aS)-5-oxo-8-(trifluoromethyl)octahydro-2H-pyrido[2,1-b][1,3]thiazepin-4-yl)hexanediamide was synthesized as described in General Procedure F using Intermediate 3 (10 mg, 0.031 mmol) and Intermediate 61 (19 mg, 0.070 mmol) to give a white solid (16 mg, 62% yield). Anal. Calcd. for $C_{40}H_{48}F_6N_4O_4S_2$ m/z 826.4. found: 827.3 (M+H)$^+$; $^1$H NMR (400 MHz, CDCl$_3$) δ ppm 7.33-7.04 (m, 8H), 6.82 (d, J=7.0 Hz, 2H), 5.34-5.21 (m, 1H), 5.08-4.88 (m, 2H), 4.50 (dd, J=13.3, 4.4 Hz, 1H), 3.22-3.03 (m, 2H), 2.89 (t, J=12.8 Hz, 2H), 2.76 (ddd, J=19.0, 13.3, 7.8 Hz, 4H), 2.59 (ddd, J=14.4, 5.9, 2.9 Hz, 2H), 2.44-2.21 (m, 6H), 2.19-1.42 (m, 16H), 1.37-1.17 (m, 2H).

Example 68

(4S,7S,10aS)-Methyl 4-((2R,5R)-2,5-dibenzyl-6-((S)-1-(2-methoxyphenyl)-2-oxoazepan-3-ylamino)-6-oxohexanamido)-5-oxooctahydro-2H-pyrido[2,1-b][1,3]thiazepine-7-carboxylate

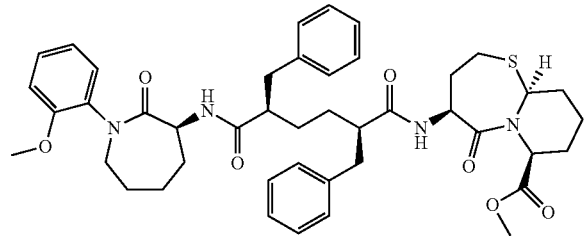 [SMILES: COC(=O)[C@@H]1CCC[C@@H]2SCC[C@H](NC(=O)[C@H](CC[C@H](Cc3ccccc3)C(=O)N[C@H]3CCCCN(c4ccccc4OC)C3=O)Cc3ccccc3)C(=O)N21]

(4S,7S,10aS)-Methyl 4-((2R,5R)-2,5-dibenzyl-6-((S)-1-(2-methoxyphenyl)-2-oxoazepan-3-ylamino)-6-oxohexanamido)-5-oxooctahydro-2H-pyrido[2,1-b][1,3]thiazepine-7-carboxylate was synthesized as described in General Procedure H using Intermediate 23 (23 mg, 0.040 mmol) and Intermediate 62 (14 mg, 0.040 mmol) to give a white solid (10 mg, 31% yield). Anal. Calcd. for $C_{44}H_{54}N_4O_7S$ m/z 782.4. found: 783.3 (M+H)$^+$; $^1$H NMR (400 MHz, chloroform-d) δ ppm 7.08-7.33 (10H, m), 6.98-7.08 (2H, m), 6.91-6.98 (2H, m), 5.31 (1H, t, J=4.67 Hz), 5.08-5.18 (1H, m), 4.91-5.02 (1H, m), 4.76 (1H, dd, J=10.17, 6.32 Hz), 4.03-4.35 (4H, m), 3.84-3.96 (1H, m), 3.80 (3H, s), 3.68 (3H, s), 3.29-3.46 (1H, m), 3.04-3.23 (2H, m), 2.65-2.91 (5H, m), 2.30-2.49 (3H, m), 1.90-2.05 (3H, m), 1.57-1.90 (8H, m), 1.41-1.56 (3H, m).

Example 69

(4S,7S,10aS)-Methyl 4-((2R,5R)-2,5-dibenzyl-6-oxo-6-((S,Z)-2-oxo-1-phenyl-1,2,3,4,5,8-hexahydroazocin-3-ylamino)hexanamido)-5-oxooctahydro-2H-pyrido[2,1-b][1,3]thiazepine-7-carboxylate

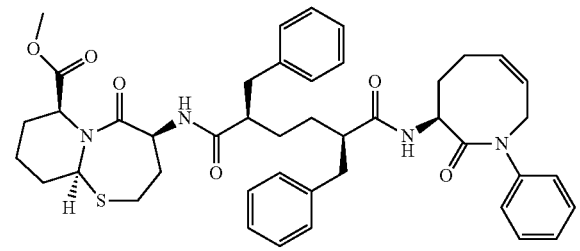 [SMILES: COC(=O)[C@@H]1CCC[C@@H]2SCC[C@H](NC(=O)[C@H](CC[C@H](Cc3ccccc3)C(=O)N[C@H]3CC/C=C\CN(c4ccccc4)C3=O)Cc3ccccc3)C(=O)N21]

(4S,7S,10aS)-Methyl 4-((2R,5R)-2,5-dibenzyl-6-oxo-6-((S,Z)-2-oxo-1-phenyl-1,2,3,4,5,8-hexahydroazocin-3-ylamino)hexanamido)-5-oxooctahydro-2H-pyrido[2,1-b][1,3]thiazepine-7-carboxylate was synthesized as described in General Procedure H using Intermediate 23 (11 mg, 0.019 mmol) and Intermediate 63 (5.6 mg, 0.022 mmol) to give a white solid (3.5 mg, 25% yield). Anal. Calcd. for $C_{44}H_{52}N_4O_6S$ m/z 764.4. found: 765.4 (M+H)$^+$; $^1$H NMR (400 MHz, CDCl$_3$) δ ppm 7.40-7.09 (16H, m), 7.00 (1H, d, J=7.1 Hz), 5.98-5.87 (1H, m), 5.60 (1H, d, J=11.5 Hz), 5.34 (1H, t, J=4.7 Hz), 5.11-5.05 (1H, m), 5.04-4.84 (3H, m), 4.06-3.97 (1H, m), 3.66 (3H, s), 3.08-2.99 (1H, m), 2.87-2.70 (5H, m), 2.49-2.33 (4H, m), 2.13-1.96 (3H, m), 1.88-1.73 (3H, m), 1.71-1.51 (7H, m), 1.38-1.28 (1H, m).

Example 70

(4S,7S,10aS)-Methyl 4-((2R,5R)-2,5-dibenzyl-6-oxo-6-((S)-2-oxo-1-phenylazocan-3-ylamino)hexanamido)-5-oxooctahydro-2H-pyrido[2,1-b][1,3]thiazepine-7-carboxylate

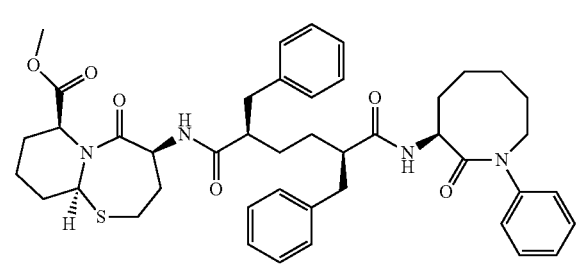 [SMILES: COC(=O)[C@@H]1CCC[C@@H]2SCC[C@H](NC(=O)[C@H](CC[C@H](Cc3ccccc3)C(=O)N[C@H]3CCCCCN(c4ccccc4)C3=O)Cc3ccccc3)C(=O)N21]

(4S,7S,10aS)-Methyl 4-((2R,5R)-2,5-dibenzyl-6-oxo-6-((S)-2-oxo-1-phenylazocan-3-ylamino)hexanamido)-5-oxooctahydro-2H-pyrido[2,1-b][1,3]thiazepine-7-carboxylate was synthesized as described in General Procedure H using Intermediate 23 (11 mg, 0.019 mmol) and Intermediate 64 (5.7 mg, 0.022 mmol) to give a white solid (6.6 mg, 46% yield). Anal. Calcd. for $C_{44}H_{54}N_4O_6S$ m/z 766.5. found: 767.5 (M+H)⁺; ¹H NMR (400 MHz, CDCl₃) δ ppm 7.41-7.34 (2H, m), 7.31-7.03 (14H, m), 6.84 (1H, d, J=7.7 Hz), 5.32 (1H, t, J=4.7 Hz), 5.14-5.09 (1H, m), 5.06-4.98 (1H, m), 4.97-4.90 (1H, m), 4.19 (1H, t, J=14.0 Hz), 3.67 (3H, s), 3.53 (1H, d, J=14.3 Hz), 3.07 (1H, ddd, J=14.2, 11.1, 2.7 Hz), 2.87-2.67 (5H, m), 2.43-2.26 (3H, m), 2.04-1.95 (2H, m), 1.82-1.45 (16H, m), 1.34-1.24 (1H, m).

mmol) to give a white solid (8.0 mg, 57% yield). Anal. Calcd. for $C_{42}H_{49}N_5O_4S$ m/z 719.7. found: 720.7 (M+H)⁺; ¹H NMR (400 MHz, CDCl₃) δ ppm 7.40-7.32 (2H, m), 7.29-7.05 (13H, m), 7.00-6.91 (2H, m), 5.39-5.34 (1H, m), 5.31-5.25 (1H, m), 5.02-4.93 (1H, m), 4.85-4.76 (1H, m), 3.99-3.89 (1H, m), 3.63-3.54 (1H, m), 3.00-2.90 (1H, m), 2.89-2.68 (4H, m), 2.66-2.57 (1H, m), 2.45-2.31 (2H, m), 2.20-2.08 (2H, m), 2.03-1.62 (11H, m), 1.62-1.47 (3H, m), 1.43-1.26 (2H, m).

Example 71

(4S,7S,10aS)-Methyl 4-((2R,5R)-2,5-dibenzyl-6-((S)-1-(3-methoxyphenyl)-2-oxoazepan-3-ylamino)-6-oxohexanamido)-5-oxooctahydro-2H-pyrido[2,1-b][1,3]thiazepine-7-carboxylate

Example 73

(2R,5R)—N1-((4S,7S,10aS)-7-(1,3,4-Oxadiazol-2-yl)-5-oxooctahydro-2H-pyrido[2,1-b][1,3]thiazepin-4-yl)-2,5-dibenzyl-N6-((S)-2-oxo-1-phenylazepan-3-yl)hexanediamide

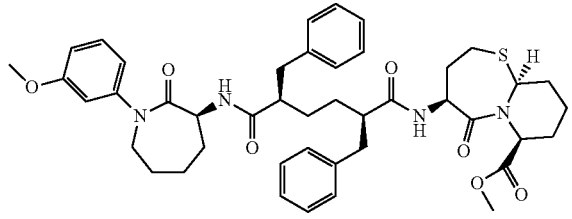 [SMILES: COC(=O)[C@@H]1CCC[C@@H]2SCC[C@H](NC(=O)[C@H](CC[C@H](Cc3ccccc3)C(=O)N[C@H]3CCCCN(c4cccc(OC)c4)C3=O)Cc3ccccc3)C(=O)N21]

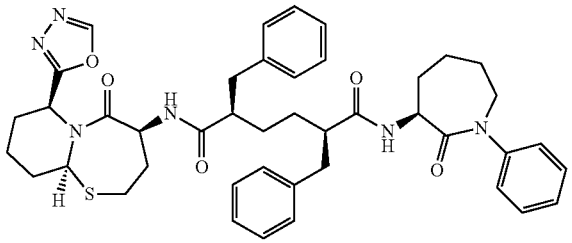

(4S,7S,10aS)-Methyl 4-((2R,5R)-2,5-dibenzyl-6-((S)-1-(3-methoxyphenyl)-2-oxoazepan-3-ylamino)-6-oxohexanamido)-5-oxooctahydro-2H-pyrido[2,1-b][1,3]thiazepine-7-carboxylate was synthesized as described in General Procedure H using Intermediate 23 (24 mg, 0.042 mmol) and Intermediate 65 (19 mg, 0.055 mmol) to give a white solid (21 mg, 62% yield). Anal. Calcd. for $C_{44}H_{54}N_4O_7S$ m/z 782.7. found: 783.7 (M+H)⁺; ¹H NMR (400 MHz, CDCl₃) δ ppm 7.36-7.02 (m, 11H), 6.83 (dd, J=8.2, 2.1 Hz, 1H), 6.69 (dt, J=4.2, 1.6 Hz, 2H), 6.42 (s, 2H), 5.32 (t, J=4.6 Hz, 1H), 5.17-5.07 (m, 1H), 5.04-4.91 (m, 1H), 4.76 (dd, J=9.7, 6.9 Hz, 1H), 3.98 and 3.78 (2s, 3H), 3.93 (dd, J=15.4, 11.6 Hz, 1H), 3.68 (s, 3H), 3.63-3.54 (m, 1H), 3.16-3.06 (m, 1H), 2.90-2.67 (m, 5H), 2.53-2.32 (m, 3H), 2.07-1.79 (m, 5H), 1.79-1.43 (m, 11H), 1.40-1.23 (m, 1H).

(2R,5R)—N1-((4S,7S,10aS)-7-(1,3,4-Oxadiazol-2-yl)-5-oxooctahydro-2H-pyrido[2,1-b][1,3]thiazepin-4-yl)-2,5-dibenzyl-N6-((S)-2-oxo-1-phenylazepan-3-yl)hexanediamide was synthesized as described in General Procedure H using Intermediate 24 (10 mg, 0.020 mmol) and Intermediate 35 (7.1 mg, 0.023 mmol) to give a white solid (3.5 mg, 24% yield). Anal. Calcd. for $C_{43}H_{50}N_6O_5S$ m/z 762.7. found: 763.3 (M+H)⁺; ¹H NMR (400 MHz, CDCl₃) δ ppm 8.31 (1H, s), 7.40-7.32 (2H, m), 7.31-7.07 (13H, m), 7.02-6.90 (2H, m), 5.91 (1H, d, J=4.9 Hz), 5.27 (1H, t, J=4.4 Hz), 5.05-4.97 (1H, m), 4.78 (1H, dd, J=9.3, 6.6 Hz), 3.93 (1H, dd, J=15.1, 11.3 Hz), 3.59 (1H, dd, J=14.8, 4.9 Hz), 3.18-3.07 (1H, m), 2.90-2.68 (6H, m), 2.55 (1H, ddd, J=14.3, 5.5, 2.7 Hz), 2.46-2.33 (2H, m), 2.14-1.80 (8H, m), 1.77-1.65 (4H, m), 1.64-1.25 (4H, m).

Example 72

(2R,5R)-2,5-Dibenzyl-N1-((4S,7S,10aS)-7-cyano-5-oxooctahydro-2H-pyrido[2,1-b][1,3]thiazepin-4-yl)-N6-((S)-2-oxo-1-phenylazepan-3-yl)hexanediamide

Example 74

(2R,5R)-2,5-Dibenzyl-N1-((4S,7S,10aS)-7-(methoxymethyl)-5-oxooctahydro-2H-pyrido[2,1-b][1,3]thiazepin-4-yl)-N6-((S)-2-oxo-1-phenylazepan-3-yl)hexanediamide

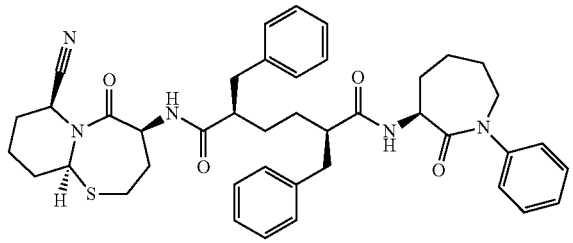 [SMILES: N#C[C@@H]1CCC[C@@H]2SCC[C@H](NC(=O)[C@H](CC[C@H](Cc3ccccc3)C(=O)N[C@H]3CCCCN(c4ccccc4)C3=O)Cc3ccccc3)C(=O)N12]

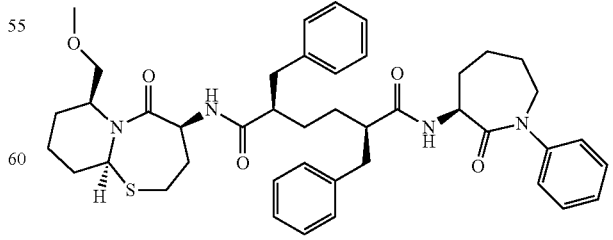

(2R,5R)-2,5-Dibenzyl-N1-((4S,7S,10aS)-7-cyano-5-oxooctahydro-2H-pyrido[2,1-b][1,3]thiazepin-4-yl)-N6-((S)-2-oxo-1-phenylazepan-3-yl)hexanediamide was synthesized as described in General Procedure H using Intermediate 24 (10 mg, 0.020 mmol) and Intermediate 36 (6.1 mg, 0.023

(2R,5R)-2,5-Dibenzyl-N1-((4S,7S,10aS)-7-(methoxymethyl)-5-oxooctahydro-2H-pyrido[2,1-b][1,3]thiazepin-4-yl)-N6-((S)-2-oxo-1-phenylazepan-3-yl)hexanediamide was synthesized as described in General Procedure H using Intermediate 24 (10 mg, 0.020 mmol) and Intermediate 66 (6.6 mg, 0.023 mmol) to give a white solid (7.6 mg, 53% yield). Anal. Calcd. for $C_{43}H_{54}N_4O_5S$ m/z 738.7. found: 739.3 (M+H)$^+$; $^1$H NMR (400 MHz, CDCl$_3$) δ ppm 7.38 (2H, t, J=7.8 Hz), 7.30-7.18 (3H, m), 7.18-7.09 (8H, m), 6.91 (1H, d, J=6.4 Hz), 6.83 (1H, d, J=6.4 Hz), 5.29-5.19 (1H, m), 4.96-4.87 (1H, m), 4.76 (1H, dd, J=9.9, 6.6 Hz), 4.71-4.64 (1H, m), 3.95 (1H, dd, J=15.1, 11.9 Hz), 3.70 (1H, t, J=9.4 Hz), 3.60 (1H, dd, J=15.1, 4.6 Hz), 3.40-3.31 (4H, m), 3.22-3.12 (1H, m), 2.90-2.78 (2H, m), 2.75-2.60 (3H, m), 2.40-2.30 (2H, m), 2.06-1.92 (4H, m), 1.91-1.79 (3H, m), 1.79-1.43 (9H, m), 1.36-1.24 (2H, m).

Example 75

(2R,5R)-2,5-Dibenzyl-N1,N6-bis((7S,10aR,Z)-6-oxo-1,2,3,4,6,7,8,10a-octahydropyrido[1,2-a]azepin-7-yl)hexanediamide

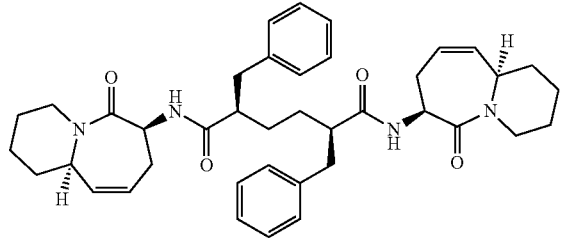 [SMILES: O=C(N[C@H]1CC=C[C@H]2CCCCN2C1=O)[C@H](CC[C@H](Cc1ccccc1)C(=O)N[C@H]1CC=C[C@H]2CCCCN2C1=O)Cc1ccccc1]

(2R,5R)-2,5-Dibenzyl-N1,N6-bis((7S,10aR,Z)-6-oxo-1,2,3,4,6,7,8,10a-octahydropyrido[1,2-a]azepin-7-yl)hexanediamide was synthesized as described in General Procedure F using Intermediate 3 (10 mg, 0.031 mmol) and Intermediate 53 (15 mg, 0.069 mmol) to give a white solid (7.6 mg, 38% yield). Anal. Calcd. for $C_{40}H_{48}F_6N_4O_4S_2$ m/z 650.4. found: 655.0 (M+H)$^+$; $^1$H NMR (400 MHz, CDCl$_3$) δ ppm 7.25-7.10 (10H, m), 6.97 (2H, d, J=7.1 Hz), 5.62-5.49 (4H, m), 5.41-5.31 (2H, m), 4.79-4.72 (2H, m), 4.22-3.77 (4H, m), 3.05-2.94 (2H, m), 2.87-2.67 (6H, m), 2.48-2.37 (2H, m), 2.29 (2H, dd, J=18.4, 4.1 Hz), 1.87-1.44 (14H, m).

Example 76

(4S,7S,10aS)-Methyl 4-((2R,5R)-2,5-dibenzyl-6-oxo-6-((S)-2-oxo-1-(pyridin-3-yl)azepan-3-ylamino)hexanamido)-5-oxooctahydro-2H-pyrido[2,1-b][1,3]thiazepine-7-carboxylate

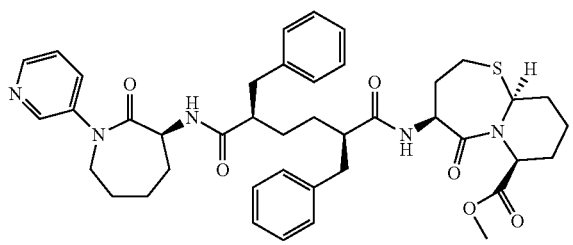 [SMILES: COC(=O)[C@@H]1CCC[C@@H]2SCC[C@H](NC(=O)[C@H](CC[C@H](Cc3ccccc3)C(=O)N[C@H]3CCCCN(c4cccnc4)C3=O)Cc3ccccc3)C(=O)N21]

(4S,7S,10aS)-Methyl 4-((2R,5R)-2,5-dibenzyl-6-oxo-6-((S)-2-oxo-1-(pyridin-3-yl)azepan-3-ylamino)hexanamido)-5-oxooctahydro-2H-pyrido[2,1-b][1,3]thiazepine-7-carboxylate was synthesized as described in General Procedure H using Intermediate 23 (34 mg, 0.061 mmol) and Intermediate 67 (24 mg, 0.055 mmol) to give a white solid (17 mg, 35% yield). Anal. Calcd. for $C_{42}H_{51}N_5O_6S$ m/z 753.7. found: 754.3 (M+H)$^+$; $^1$H NMR (400 MHz, CDCl$_3$) δ ppm 10.68 (s, 1H), 8.90 (d, J=1.9 Hz, 1H), 8.68 (d, J=5.4 Hz, 1H), 8.20 (d, J=8.5 Hz, 1H), 7.82 (dd, J=8.4, 5.5 Hz, 1H), 7.28-7.08 (m, 9H), 7.02 (d, J=6.9 Hz, 1H), 5.31 (t, J=4.5 Hz, 1H), 5.21-5.04 (m, 1H), 5.03-4.93 (m, 1H), 4.92-4.79 (m, 1H), 4.08 (dd, J=15.6, 11.6 Hz, 1H), 3.83-3.71 (m, 1H), 3.68 (s, 3H), 3.22-3.04 (m, 1H), 2.91-2.68 (m, 5H), 2.55-2.33 (m, 3H), 2.16-1.90 (m, 4H), 1.91-1.43 (m, 13H), 1.41-1.21 (m, 1H).

Example 77

(4S,7S,10aS)-Methyl 4-((2R,5R)-2,5-dibenzyl-6-oxo-6-((S,Z)-2-oxo-1-o-tolyl-2,3,4,7-tetrahydro-1H-azepin-3-ylamino)hexanamido)-5-oxooctahydro-2H-pyrido[2,1-b][1,3]thiazepine-7-carboxylate

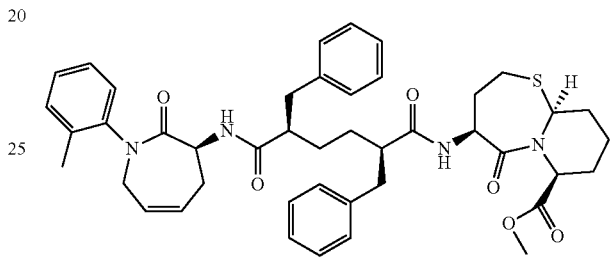

(4S,7S,10aS)-Methyl 4-((2R,5R)-2,5-dibenzyl-6-oxo-6-((S,Z)-2-oxo-1-o-tolyl-2,3,4,7-tetrahydro-1H-azepin-3-ylamino)hexanamido)-5-oxooctahydro-2H-pyrido[2,1-b][1,3]thiazepine-7-carboxylate was synthesized as described in General Procedure H using Intermediate 23 (29 mg, 0.051 mmol) and Intermediate 68 (17 mg, 0.051 mmol) to give a white solid (24 mg, 61% yield). Anal. Calcd. for $C_{44}H_{52}N_4O_6S$ m/z 764.7. found: 765.3 (M+H)$^+$; $^1$H NMR (400 MHz, CDCl$_3$) δ ppm 7.45-6.98 (m, 12H), 6.98-6.84 (m, 2H), 5.89-5.70 (m, 2H), 5.39-5.21 (m, 2H), 5.11 (d, J=5.4 Hz, 1H), 5.04-4.91 (m, 1H), 4.81 (t, J=19.2 Hz, 1H), 4.45 (s, 2H), 3.98 (s, 1H), 3.67 (d, J=3.2 Hz, 3H), 3.63-3.43 (m, 1H), 3.09 (dd, J=25.8, 13.3 Hz, 1H), 2.95-2.62 (m, 5H), 2.54-2.21 (m, 4H), 2.16 and 2.12 (2s, 3H), 2.07-1.89 (m, 3H), 1.87-1.40 (m, 8H).

Example 78

(4S,7S,10aS)-Methyl 4-((2R,5R)-2,5-dibenzyl-6-oxo-6-((S)-2-oxo-1-o-tolylazepan-3-ylamino)hexanamido)-5-oxooctahydro-2H-pyrido[2,1-b][1,3]thiazepine-7-carboxylate

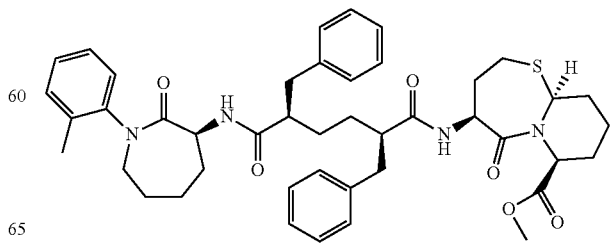

(4S,7S,10aS)-Methyl 4-((2R,5R)-2,5-dibenzyl-6-oxo-6-((S)-2-oxo-1-o-tolylazepan-3-ylamino)hexanamido)-5-oxooctahydro-2H-pyrido[2,1-b][1,3]thiazepine-7-carboxylate was synthesized as described in General Procedure H using Intermediate 23 (45 mg, 0.080 mmol) and Intermediate 69 (27 mg, 0.080 mmol) to give a white solid (35 mg, 57% yield). Anal. Calcd. for $C_{44}H_{54}N_4O_6S$ m/z 766.7. found: 767.4 (M+H)$^+$; $^1$H NMR (400 MHz, CDCl$_3$) δ ppm 7.38-6.86 (m, 14H), 5.38-5.23 (m, 1H), 5.19-5.07 (m, 1H), 5.04-4.90 (m, 1H), 4.82-4.66 (m, 1H), 4.14 (s, 3H), 4.04-3.83 (m, 1H), 3.68 (s, 3H), 3.59-3.46 (m, 1H), 3.31 (dd, J=15.0, 4.9 Hz, 1H), 3.10 (dd, J=24.7, 11.2 Hz, 1H), 2.95-2.63 (m, 4H), 2.53-2.26 (m, 3H), 2.19 and 2.13 (2s, 3H), 2.07-1.92 (m, 3H), 1.91-1.42 (m, 12H), 1.44-1.27 (m, 1H).

Example 79

(2R,5R)-2,5-Dibenzyl-N1-((S)-1-(2-methoxyphenyl)-2-oxoazepan-3-yl)-N6-((4S,7S,10aS)-5-oxo-7-(trifluoromethyl)octahydro-2H-pyrido[2,1-b][1,3]thiazepin-4-yl)hexanediamide

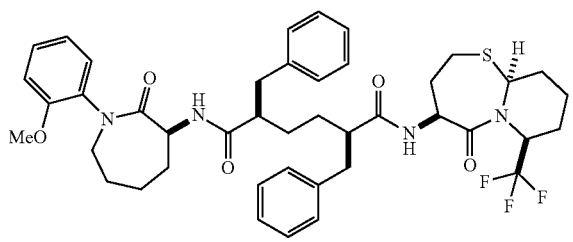

(2R,5R)-2,5-Dibenzyl-N1-((S)-1-(2-methoxyphenyl)-2-oxoazepan-3-yl)-N6-((4S,7S,10aS)-5-oxo-7-(trifluoromethyl)octahydro-2H-pyrido[2,1-b][1,3]thiazepin-4-yl)hexanediamide was synthesized as described in General Procedure H using Intermediate 70 (19 mg, 0.035 mmol) and Intermediate 77 (9.0 mg, 0.034 mmol) to give a white solid (25 mg, 90% yield). Anal. Calcd. for $C_{43}H_{51}F_3N_4O_5S$ m/z 792.7. found: 793.3 (M+H)$^+$; $^1$H NMR (400 MHz, CDCl$_3$) δ ppm 7.40-6.82 (m, 16H), 5.21 (t, J=6.7 Hz, 2H), 4.97-4.84 (m, 2H), 4.76 (t, 1H), 3.98-3.82 (m, 1H), 3.79 (s, 3H), 3.46-3.30 (m, 1H), 3.25-3.08 (m, 1H), 2.93-2.75 (m, 2H), 2.75-2.53 (m, 3H), 2.44-2.29 (m, 3H), 2.21-1.28 (m, 16H).

Example 80

(2R,5R)-2,5-Dibenzyl-N1-((S)-1-(2-methoxyphenyl)-2-oxoazepan-3-yl)-N6-((4S,7R,10aS)-5-oxo-7-(trifluoromethyl)octahydro-2H-pyrido[2,1-b][1,3]thiazepin-4-yl)hexanediamide

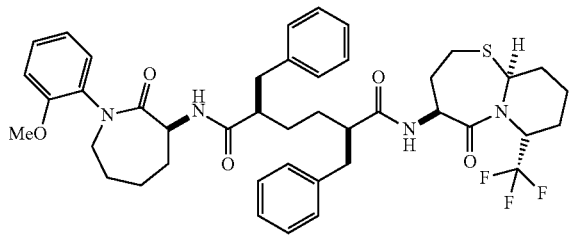

(2R,5R)-2,5-Dibenzyl-N1-((S)-1-(2-methoxyphenyl)-2-oxoazepan-3-yl)-N6-((4S,7R,10aS)-5-oxo-7-(trifluoromethyl)octahydro-2H-pyrido[2,1-b][1,3]thiazepin-4-yl)hexanediamide was synthesized as described in General Procedure H using Intermediate 70 (21 mg, 0.039 mmol) and Intermediate 78 (10 mg, 0.037 mmol) to give a white solid (26 mg, 83% yield). Anal. Calcd. for $C_{43}H_{51}F_3N_4O_5S$ m/z 792.7. found: 793.4 (M+H)$^+$; $^1$H NMR (400 MHz, CDCl$_3$) δ ppm 7.37-6.99 (m, 12H), 6.99-6.86 (m, 3H), 6.77 (s, 1H), 5.27 (t, 1H), 5.02-4.80 (m, 2H), 4.75 (dd, J=10.2, 6.6 Hz, 1H), 3.96-3.81 (m, 1H), 3.80 (s, 3H), 3.38 (s, 1H), 3.24-3.07 (m, 1H), 2.91-2.46 (m, 7H), 2.36 (dd, J=12.8, 8.4 Hz, 4H), 2.14-1.58 (m, 9H), 1.58-1.20 (m, 5H).

Example 81

(2R,5R)-2,5-Dibenzyl-N1-((S)-2-oxo-1-o-tolylazepan-3-yl)-N6-((4S,7S,10aS)-5-oxo-7-(trifluoromethyl)octahydro-2H-pyrido[2,1-b][1,3]thiazepin-4-yl)hexanediamide

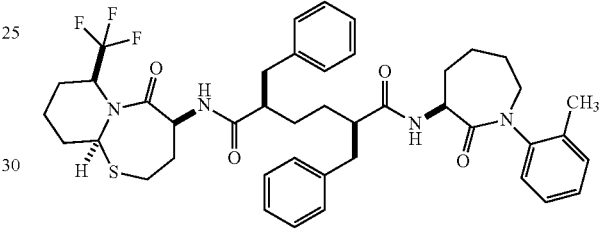

(2R,5R)-2,5-Dibenzyl-N1-((S)-2-oxo-1-o-tolylazepan-3-yl)-N6-((4S,7S,10aS)-5-oxo-7-(trifluoromethyl)octahydro-2H-pyrido[2,1-b][1,3]thiazepin-4-yl)hexanediamide was synthesized as described in General Procedure H using Intermediate 71 (25 mg, 0.047 mmol) and Intermediate 61 (13 mg, 0.047 mmol) to give a white solid (24. mg, 65% yield). Anal. Calcd. for $C_{43}H_{51}F_3N_4O_4S$ m/z 776.7. found: 777.5 (M+H)$^+$; $^1$H NMR (400 MHz, CDCl$_3$) δ ppm 7.36-6.86 (m, 14H), 5.59 (d, 3H), 5.21 (t, J=6.7 Hz, 2H), 4.90 (dd, J=17.2, 7.6 Hz, 1H), 4.83-4.71 (m, 1H), 4.09-3.82 (m, 2H), 3.62-3.44 (m, 1H), 3.32 (dd, J=15.1, 4.9 Hz, 1H), 3.21-3.01 (m, 2H), 2.91-2.53 (m, 5H), 2.50-2.33 (m, 2H), 2.15 (d, J=10.3 Hz, 3H), 2.23-2.04 (m, 1H), 2.06-1.28 (m, 13H).

Example 82

(2R,5R)-2,5-Dibenzyl-N1-((4S,7R,10aS)-7-methyl-5-oxooctahydro-2H-pyrido[2,1-b][1,3]thiazepin-4-yl)-N6-((S)-2-oxo-1-o-tolylazepan-3-yl)hexanediamide

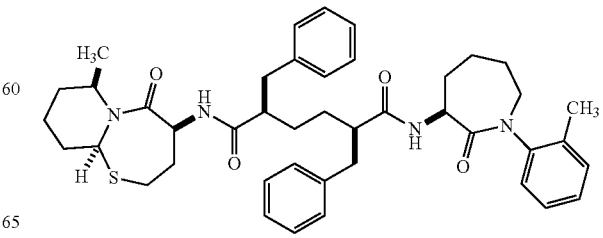

(2R,5R)-2,5-Dibenzyl-N1-((4S,7R,10aS)-7-methyl-5-oxooctahydro-2H-pyrido[2,1-b][1,3]thiazepin-4-yl)-N6-((S)-2-oxo-1-o-tolylazepan-3-yl)hexanediamide was synthesized as described in General Procedure H using Intermediate 71 (17 mg, 0.031 mmol) and Intermediate 72 (7.5 mg, 0.035 mmol) to give a white solid (18 mg, 69% yield). Anal. Calcd. for $C_{43}H_{54}N_4O_4S$ m/z 722.7. found: 723.5 (M+H)$^+$; $^1$H NMR (400 MHz, CDCl$_3$) δ ppm 7.37-6.88 (m, 14H), 5.28 (d, J=5.2 Hz, 1H), 4.99-4.85 (m, 1H), 4.83-4.70 (m, 1H), 4.66-4.56 (m, 1H), 4.09-3.83 (m, 2H), 3.53 (d, J=14.5 Hz, 1H), 3.31 (dd, J=15.0, 5.0 Hz, 1H), 3.15-2.93 (m, 4H), 2.90-2.64 (m, 4H), 2.63-2.49 (m, 2H), 2.48-2.30 (m, 3H), 2.19 and 2.13 (s, 3H), 2.09-1.43 (m, 11H), 1.32 (d, J=6.9 Hz, 3H), 1.44-1.16 (m, 2H).

Example 83

(2R,5R)-2,5-Dibenzyl-N1-((S)-1-(2-methoxyphenyl)-2-oxoazepan-3-yl)-N6-((4S,7R,10aS)-7-methyl-5-oxooctahydro-2H-pyrido[2,1-b][1,3]thiazepin-4-yl)hexanediamide

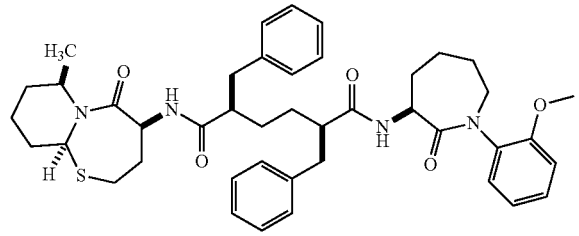

(2R,5R)-2,5-Dibenzyl-N1-((S)-1-(2-methoxyphenyl)-2-oxoazepan-3-yl)-N6-((4S,7R,10aS)-7-methyl-5-oxooctahydro-2H-pyrido[2,1-b][1,3]thiazepin-4-yl)hexanediamide was synthesized as described in General Procedure H using Intermediate 70 (13 mg, 0.024 mmol) and Intermediate 72 (5.7 mg, 0.026 mmol) to give a white solid (14 mg, 77% yield). Anal. Calcd. for $C_{43}H_{54}N_4O_5S$ m/z 738.7. found: 739.6 (M+H)$^+$; $^1$H NMR (400 MHz, CDCl$_3$) δ ppm 7.35-6.88 (m, 14H), 5.28 (d, J=4.5 Hz, 1H), 4.97-4.89 (m, 1H), 4.85-4.73 (m, 1H), 4.66-4.54 (m, 1H), 3.98 and 3.79 (s, 3H), 3.96-3.83 (m, 1H), 3.54-3.29 (m, 2H), 3.14-2.90 (m, 2H), 2.88-2.66 (m, 4H), 2.64-2.36 (m, 3H), 2.12-1.40 (m, 16H), 1.32 (d, J=6.9 Hz, 3H), 1.30-1.13 (m, 2H).

Example 84

(4S,7S,10aS)-Methyl 4-((2R,5R)-2,5-dibenzyl-6-((4S,7R,10aS)-7-methyl-5-oxooctahydro-2H-pyrido[2,1-b][1,3]thiazepin-4-ylamino)-6-oxohexanamido)-5-oxooctahydro-2H-pyrido[2,1-b][1,3]thiazepine-7-carboxylate

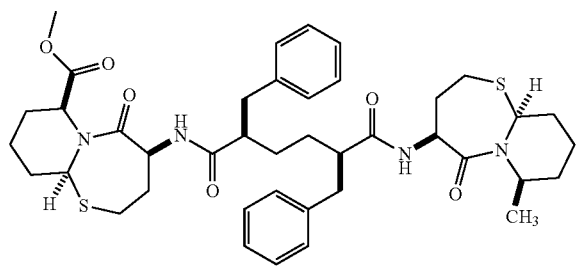

(4S,7S,10aS)-Methyl 4-((2R,5R)-2,5-dibenzyl-6-((4S,7R,10aS)-7-methyl-5-oxooctahydro-2H-pyrido[2,1-b][1,3]thiazepin-4-ylamino)-6-oxohexanamido)-5-oxooctahydro-2H-pyrido[2,1-b][1,3]thiazepine-7-carboxylate was synthesized as described in General Procedure H using Intermediate 23 (22 mg, 0.037 mmol) and Intermediate 72 (8.0 mg, 0.037 mmol) to give a white solid (21 mg, 70% yield). Anal. Calcd. for $C_{41}H_{54}N_4O_6S_2$ m/z 762.7. found: 763.5 (M+H)$^+$; $^1$H NMR (400 MHz, CDCl$_3$) δ ppm 7.38-7.02 (m, 10H), 5.44-5.24 (m, 2H), 5.20-5.07 (m, 1H), 5.08-4.85 (m, 2H), 4.71-4.50 (m, 1H), 3.69 (s, 3H), 3.25-2.95 (m, 3H), 2.93-2.66 (m, 4H), 2.61 (ddd, J=14.4, 6.9, 2.7 Hz, 1H), 2.49-2.19 (m, 10H), 2.16-1.41 (m, 13H), 1.32 (d, J=6.9 Hz, 3H), 1.43-1.21 (m, 1H).

Example 85

(2R,5R)-2,5-Dibenzyl-N1-((S)-1-(2-methoxyphenyl)-2-oxoazepan-3-yl)-N6-((4S,7S,10aS)-5-oxo-7-vinyloctahydro-2H-pyrido[2,1-b][1,3]thiazepin-4-yl)hexanediamide

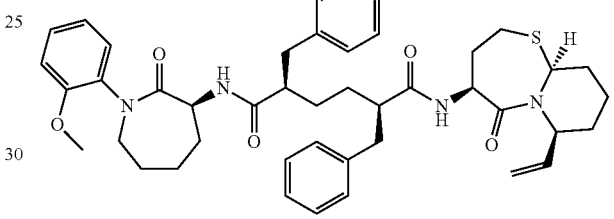

(2R,5R)-2,5-Dibenzyl-N1-((S)-1-(2-methoxyphenyl)-2-oxoazepan-3-yl)-N6-((4S,7S,10aS)-5-oxo-7-vinyloctahydro-2H-pyrido[2,1-b][1,3]thiazepin-4-yl)hexanediamide was synthesized as described in General Procedure H using Intermediate 70 (36 mg, 0.067 mmol) and Intermediate 73 (23 mg, 0.067 mmol) to give a white solid (30 mg, 59% yield). Anal. Calcd. for $C_{44}H_{54}N_4O_5S$ m/z 750.7. found: 751.5 (M+H)$^+$; $^1$H NMR (400 MHz, CDCl$_3$) δ ppm 7.29-7.07 (m, 11H), 7.07-6.89 (m, 3H), 6.36-6.18 (m, 1H), 5.33 (s, 1H), 5.23 (d, J=17.1 Hz, 1H), 5.12 (d, J=10.3 Hz, 1H), 5.06-4.90 (m, 2H), 4.84-4.70 (m, 1H), 4.02-3.84 (m, 1H), 3.79 (s, 3H), 3.47-3.29 (m, 1H), 3.04-2.89 (m, 1H), 2.89-2.75 (m, 2H), 2.75-2.64 (m, 1H), 2.61-2.47 (m, 1H), 2.46-2.23 (m, 8H), 2.10-1.55 (m, 11H), 1.54-1.42 (m, 2H), 1.39-1.15 (m, 2H).

Example 86

(2R,5R)-2,5-Dibenzyl-N1-((4S,7R,10aS)-7-ethyl-5-oxooctahydro-2H-pyrido[2,1-b][1,3]thiazepin-4-yl)-N6-((S)-2-oxo-1-o-tolylazepan-3-yl)hexanediamide

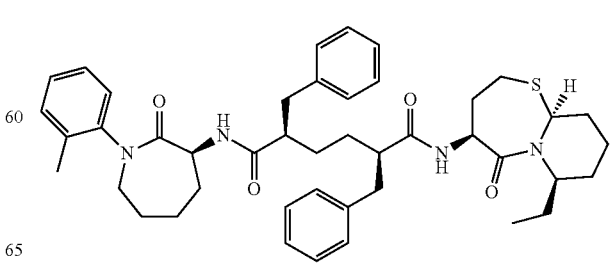

(2R,5R)-2,5-Dibenzyl-N1-((4S,7R,10aS)-7-ethyl-5-oxooctahydro-2H-pyrido[2,1-b][1,3]thiazepin-4-yl)-N6-((S)-2-oxo-1-o-tolylazepan-3-yl)hexanediamide was synthesized as described in General Procedure H using Intermediate 72 (35 mg, 0.067 mmol) and Intermediate 74 (23 mg, 0.067 mmol) to give a white solid (29 mg, 58% yield). Anal. Calcd. for $C_{44}H_{56}N_4O_4S$ m/z 736.7. found: 737.6 (M+H)$^+$; $^1$H NMR (400 MHz, CDCl$_3$) δ ppm 7.30-7.07 (m, 11H), 7.06-6.90 (m, 3H), 5.24 (d, J=4.7 Hz, 1H), 4.97-4.84 (m, 1H), 4.82-4.70 (m, 1H), 4.40-4.28 (m, 1H), 4.08-3.84 (m, 2H), 3.61-3.46 (m, 1H), 3.30 (d, J=15.5 Hz, 1H), 3.20-3.02 (m, 2H), 2.96-2.55 (m, 5H), 2.49-2.28 (m, 3H), 2.20 and 2.14 (2s, 3H), 1.83 (d, J=13.6 Hz, 5H), 1.78-1.44 (m, 10H), 1.43-1.22 (m, 3H), 0.89 (t, J=7.4 Hz, 3H).

Example 87

(2R,5R)-2,5-Dibenzyl-N1-((4S,7R,10aS)-7-ethyl-5-oxooctahydro-2H-pyrido[2,1-b][1,3]thiazepin-4-yl)-N6-((S)-1-(2-methoxyphenyl)-2-oxoazepan-3-yl)hexanediamide

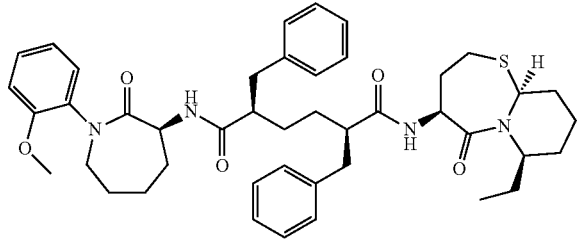 [SMILES: CC[C@@H]1CCC[C@@H]2SCC[C@H](NC(=O)[C@H](CC[C@H](Cc3ccccc3)C(=O)N[C@H]3CCCCN(c4ccccc4OC)C3=O)Cc3ccccc3)C(=O)N12]

(2R,5R)-2,5-Dibenzyl-N1-((4S,7R,10aS)-7-ethyl-5-oxooctahydro-2H-pyrido[2,1-b][1,3]thiazepin-4-yl)-N6-((S)-1-(2-methoxyphenyl)-2-oxoazepan-3-yl)hexanediamide was synthesized as described in General Procedure H using Intermediate 70 (36 mg, 0.067 mmol) and Intermediate 74 (23 mg, 0.067 mmol) to give a white solid (25 mg, 49% yield). Anal. Calcd. for $C_{44}H_{56}N_4O_5S$ m/z 752.7. found: 753.6 (M+H)$^+$; $^1$H NMR (400 MHz, CDCl$_3$) δ ppm 7.41-7.07 (m, 11H), 7.07-6.87 (m, 3H), 5.24 (s, 1H), 5.00-4.84 (m, 1H), 4.81-4.69 (m, 1H), 4.38-4.26 (m, 1H), 4.09-3.83 (m, 1H), 3.79 (d, J=3.5 Hz, 3H), 3.47-3.27 (m, 1H), 3.22-3.03 (m, 1H), 2.90-2.54 (m, 5H), 2.45-2.28 (m, 2H), 2.23-1.94 (m, 11H), 1.93-1.76 (m, 3H), 1.77-1.59 (m, 4H), 1.50 (d, J=29.0 Hz, 3H), 1.39-1.22 (m, 1H), 0.97-0.82 (m, 3H).

Example 88

(2R,5R)-2,5-Dibenzyl-N1-((S)-2-oxo-1-o-tolylazepan-3-yl)-N6-((4S,8S,10aS)-5-oxo-8-(trifluoromethyl)octahydro-2H-pyrido[2,1-b][1,3]thiazepin-4-yl)hexanediamide

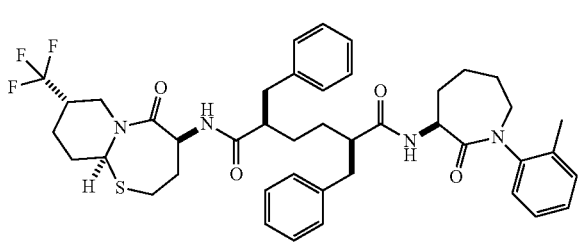

(2R,5R)-2,5-Dibenzyl-N1-((S)-2-oxo-1-o-tolylazepan-3-yl)-N6-((4S,8S,10aS)-5-oxo-8-(trifluoromethyl)octahydro-2H-pyrido[2,1-b][1,3]thiazepin-4-yl)hexanediamide was synthesized as described in General Procedure H using Intermediate 71 (8.2 mg, 0.016 mmol) and Intermediate 60 (3.5 mg, 0.013 mmol) to give a white solid (5.9 mg, 58% yield). Anal. Calcd. for $C_{43}H_{51}F_3N_4O_4S$ m/z 776.7. found: 777.6 (M+H)$^+$; $^1$H NMR (400 MHz, CDCl$_3$) δ ppm 7.42-6.89 (m, 14H), 5.86 (s, 2H), 5.11 (dd, J=14.2, 7.0 Hz, 1H), 4.81 (dd, J=10.6, 6.6 Hz, 2H), 4.38-4.26 (m, 1H), 4.09-3.86 (m, 2H), 3.54 (d, J=16.2 Hz, 1H), 3.40-3.09 (m, 3H), 2.91-2.38 (m, 7H), 2.21 and 2.14 (s, 3H), 2.28-2.07 (m, 1H), 2.07-1.77 (m, 5H), 1.75-1.22 (m, 9H).

Example 89

(2R,5R)-2,5-Dibenzyl-N1-((S)-1-(2-methoxyphenyl)-2-oxoazepan-3-yl)-N6-((4S,8S,10aS)-5-oxo-8-(trifluoromethyl)octahydro-2H-pyrido[2,1-b][1,3]thiazepin-4-yl)hexanediamide

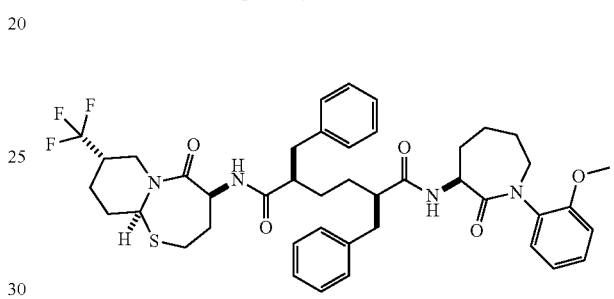

(2R,5R)-2,5-Dibenzyl-N1-((S)-1-(2-methoxyphenyl)-2-oxoazepan-3-yl)-N6-((4S,8S,10aS)-5-oxo-8-(trifluoromethyl)octahydro-2H-pyrido[2,1-b][1,3]thiazepin-4-yl)hexanediamide was synthesized as described in General Procedure H using Intermediate 70 (8.5 mg, 0.016 mmol) and Intermediate 60 (3.5 mg, 0.013 mmol) to give a white solid (7.6 mg, 74% yield). Anal. Calcd. for $C_{43}H_{51}F_3N_4O_5S$ m/z 792.7. found: 793.6 (M+H)$^+$; $^1$H NMR (400 MHz, CDCl$_3$) δ ppm 7.38-7.03 (m, 11H), 7.04-6.82 (m, 3H), 5.12 (t, J=7.3 Hz, 1H), 4.90-4.64 (m, 2H), 4.35 (d, J=14.8 Hz, 1H), 3.98 and 3.82 (2s, 3H), 3.97-3.84 (m, 1H), 3.27 (dd, J=14.8, 6.6 Hz, 6H), 2.95-2.53 (m, 5H), 2.48-2.30 (m, 2H), 2.26-2.14 (m, 1H), 2.04-1.15 (m, 15H).

Example 90

(2R,5R)-2,5-Dibenzyl-N1-((S)-2-oxo-1-o-tolylazepan-3-yl)-N6-((4S,8R,10aS)-5-oxo-8-(trifluoromethyl)octahydro-2H-pyrido[2,1-b][1,3]thiazepin-4-yl)hexanediamide

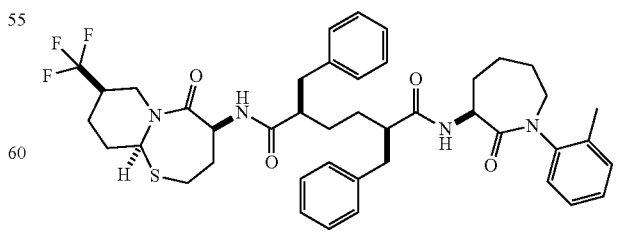

(2R,5R)-2,5-Dibenzyl-N1-((S)-2-oxo-1-o-tolylazepan-3-yl)-N6-((4S,8R,10aS)-5-oxo-8-(trifluoromethyl)octahydro-2H-pyrido[2,1-b][1,3]thiazepin-4-yl)hexanediamide was synthesized as described in General Procedure H using Intermediate 71 (12 mg, 0.022 mmol) and Intermediate 61 (5.0 mg, 0.019 mmol) to give a white solid (5.7 mg, 38% yield). Anal. Calcd. for $C_{43}H_{51}F_3N_4O_4S$ m/z 776.7. found: 777.6 (M+H)+; 1H NMR (400 MHz, CDCl3) δ ppm 7.34-7.03 (m, 11H), 7.04-6.89 (m, 3H), 5.12 (t, J=7.3 Hz, 1H), 4.85-4.67 (m, 2H), 4.35 (d, J=14.8 Hz, 1H), 3.98 and 3.80 (s, 3H), 3.97-3.82 (m, 1H), 3.49-3.08 (m, 8H), 2.93-2.52 (m, 6H), 2.51-2.26 (m, 2H), 2.26-2.13 (m, 1H), 2.05-1.53 (m, 9H), 1.54-1.16 (m, 3H).

Example 91

(2R,5R)-2,5-Dibenzyl-N1-((S)-1-(2-methoxyphenyl)-2-oxoazepan-3-yl)-N6-((4S,8R,10aS)-5-oxo-8-(trifluoromethyl)octahydro-2H-pyrido[2,1-b][1,3]thiazepin-4-yl)hexanediamide

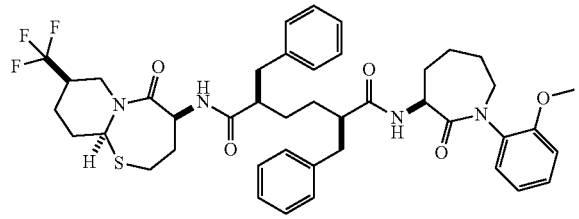

(2R,5R)-2,5-Dibenzyl-N1-((S)-1-(2-methoxyphenyl)-2-oxoazepan-3-yl)-N6-((4S,8R,10aS)-5-oxo-8-(trifluoromethyl)octahydro-2H-pyrido[2,1-b][1,3]thiazepin-4-yl)hexanediamide was synthesized as described in General Procedure H using Intermediate 70 (12 mg, 0.022 mmol) and Intermediate 61 (5.0 mg, 0.019 mmol) to give a white solid (6.5 mg, 43% yield). Anal. Calcd. for $C_{43}H_{51}F_3N_4O_5S$ m/z 792.7. found: 793.6 (M+H)+; 1H NMR (400 MHz, CDCl3) δ ppm 7.44-7.04 (m, 11H), 6.96 (dd, J=17.4, 10.3 Hz, 3H), 5.34-5.13 (m, 2H), 4.89 (d, J=63.4 Hz, 3H), 4.47 (dd, J=13.3, 4.2 Hz, 2H), 3.95 (s, 2H), 3.79 (s, 3H), 3.46 (d, J=42.0 Hz, 2H), 3.05 (s, 2H), 2.98-2.66 (m, 5H), 2.64-2.21 (m, 4H), 2.19-1.87 (m, 4H), 1.87-1.37 (m, 8H).

Example 92

(4S,7S,10aS)-Methyl 4-((2R,5R)-2,5-dibenzyl-6-(((S)-1-(2-methoxyphenyl)-2-oxoazepan-3-yl)(methyl)amino)-6-oxohexanamido)-5-oxooctahydro-2H-pyrido[2,1-b][1,3]thiazepine-7-carboxylate

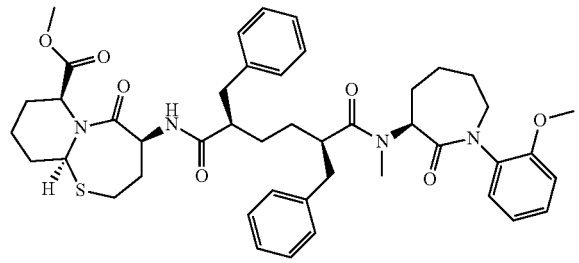 [SMILES: COC(=O)[C@@H]1CCC[C@@H]2SCC[C@H](NC(=O)[C@H](CC[C@H](Cc3ccccc3)C(=O)N(C)[C@H]3CCCCN(c4ccccc4OC)C3=O)Cc3ccccc3)C(=O)N21]

(4S,7S,10aS)-Methyl 4-((2R,5R)-2,5-dibenzyl-6-(((S)-1-(2-methoxyphenyl)-2-oxoazepan-3-yl)(methyl)amino)-6-oxohexanamido)-5-oxooctahydro-2H-pyrido[2,1-b][1,3]thiazepine-7-carboxylate was synthesized as described in General Procedure H using Intermediate 23 (17 mg, 0.029 mmol) and Intermediate 75 (9.1 mg, 0.032 mmol) to give a white solid (12 mg, 52% yield). Anal. Calcd. for $C_{45}H_{56}N_4O_7S$ m/z 796.7. found: 797.3 (M+H)+; 1H NMR (400 MHz, CDCl3) δ ppm 7.45-7.04 (12H, m), 6.96-6.64 (3H, m), 5.71-5.53 (1H, m), 5.34-5.25 (1H, m), 5.14-5.03 (1H, m), 4.94-4.79 (1H, m), 3.99 (1H, dd, J=14.0, 10.7 Hz), 3.76 (3H, s), 3.65 (3H, s), 3.40 (1H, d, J=15.9 Hz), 3.11-2.98 (1H, m), 2.93-2.61 (9H, m), 2.36 (2H, d, J=9.9 Hz), 2.10-1.87 (4H, m), 1.86-1.49 (10H, m), 1.47-1.23 (3H, m).

Example 93

(4S,7S,10aS)-Methyl 4-((2R,5S)-2-(4-fluorobenzyl)-5-((S)-1-(2-methoxyphenyl)-2-oxoazepan-3-ylcarbamoyl)octanamido)-5-oxooctahydro-2H-pyrido[2,1-b][1,3]thiazepine-7-carboxylate

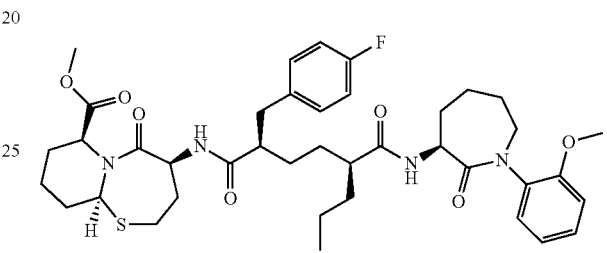

(4S,7S,10aS)-Methyl 4-((2R,5S)-2-(4-fluorobenzyl)-5-((S)-1-(2-methoxyphenyl)-2-oxoazepan-3-ylcarbamoyl)octanamido)-5-oxooctahydro-2H-pyrido[2,1-b][1,3]thiazepine-7-carboxylate was synthesized as described in General Procedure H using Intermediate 76 (10 mg, 0.020 mmol) and (4S,7S,10aS)-methyl 4-amino-5-oxooctahydro-2H-pyrido[2,1-b][1,3]thiazepine-7-carboxylate (5.5 mg, 0.021 mmol) to give a white solid (10 mg, 70% yield). Anal. Calcd. for $C_{40}H_{53}FN_4O_7S$ m/z 752.7. found: 753.3 (M+H)+; 1H NMR (400 MHz, CDCl3) δ ppm 7.53-7.43 (1H, m), 7.31 (1H, t, J=8.0 Hz), 7.28-7.18 (1H, m), 7.14-7.04 (3H, m), 7.01-6.95 (2H, m), 6.88 (2H, t, J=8.8 Hz), 5.35-5.27 (1H, m), 5.15-5.09 (1H, m), 5.04-4.95 (1H, m), 4.94-4.85 (1H, m), 4.05-3.90 (1H, m), 3.82 (3H, s), 3.69 (3H, s), 3.53-3.36 (1H, m), 3.22-3.06 (1H, m), 2.86-2.65 (3H, m), 2.45-2.32 (2H, m), 2.25-2.14 (1H, m), 2.12-1.87 (5H, m), 1.87-1.30 (14H, m), 1.30-1.20 (2H, m), 0.87 (3H, t, J=7.1 Hz).

Example 94

(2R,5S)-2-(4-Fluorobenzyl)-N6-((S)-1-(2-methoxyphenyl)-2-oxoazepan-3-yl)-N1-((4S,7S,10aS)-5-oxo-7-(trifluoromethyl)octahydro-2H-pyrido[2,1-b][1,3]thiazepin-4-yl)-5-propylhexanediamide

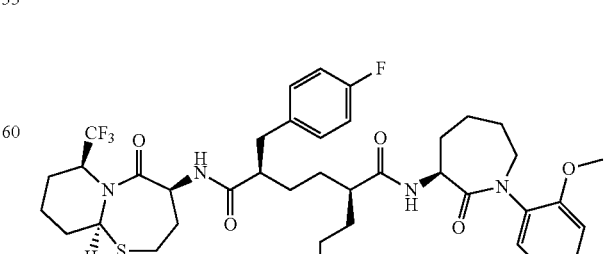

(2R,5S)-2-(4-Fluorobenzyl)-N6-((S)-1-(2-methoxyphenyl)-2-oxoazepan-3-yl)-N1-((4S,7S,10aS)-5-oxo-7-(trifluoromethyl)octahydro-2H-pyrido[2,1-b][1,3]thiazepin-4-yl)-5-propylhexanediamide was synthesized as described in General Procedure H using Intermediate 76 (22 mg, 0.043 mmol) and Intermediate 77 (12 mg, 0.045 mmol) to give a white solid (14 mg, 43% yield). Anal. Calcd. for C$_{39}$H$_{50}$F$_4$N$_4$O$_5$S m/z 762.7. found: 763.3 (M+H)$^+$; $^1$H NMR (400 MHz, CDCl$_3$) δ ppm 7.42-7.22 (3H, m), 7.15-7.02 (3H, m), 7.01-6.94 (2H, m), 6.86 (2H, t, J=8.5 Hz), 5.28-5.15 (2H, m), 4.99-4.83 (2H, m), 4.05-3.88 (1H, m), 3.81 (3H, s), 3.54-3.34 (1H, m), 3.28-3.09 (1H, m), 2.85-2.60 (3H, m), 2.42-2.30 (1H, m), 2.22-1.72 (12H, m), 1.71-1.20 (11H, m), 0.87 (3H, t, J=7.1 Hz).

Example 95

(2R,5R)-2,5-Dibenzyl-N1-((4S,7S,10aS)-7-cyano-5-oxooctahydro-2H-pyrido[2,1-b][1,3]thiazepin-4-yl)-N6-((S)-2-oxo-1-o-tolylazepan-3-yl)hexanediamide

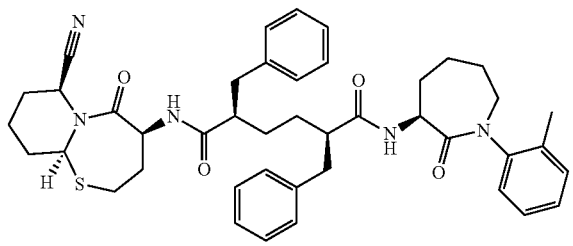 [SMILES: Cc1ccccc1N1CCCC[C@H](NC(=O)[C@H](CC[C@H](Cc2ccccc2)C(=O)N[C@H]2CCS[C@H]3CCC[C@@H](C#N)N3C2=O)Cc2ccccc2)C1=O]

(2R,5R)-2,5-Dibenzyl-N1-((4S,7S,10aS)-7-cyano-5-oxooctahydro-2H-pyrido[2,1-b][1,3]thiazepin-4-yl)-N6-((S)-2-oxo-1-o-tolylazepan-3-yl)hexanediamide was synthesized as described in General Procedure H using Intermediate 71 (10 mg, 0.019 mmol) and Intermediate 36 (5.2 mg, 0.020 mmol) to give a white solid (8.0 mg, 57% yield). Anal. Calcd. for C$_{43}$H$_{51}$N$_5$O$_4$S m/z 733.7. found: 734.3 (M+H)$^+$; $^1$H NMR (400 MHz, CDCl$_3$) (Rotamers) δ ppm 7.39-6.79 (16H, m), 5.35 (1H, d, J=3.8 Hz), 5.24 (1H, d, J=4.9 Hz), 5.02-4.90 (1H, m), 4.87-4.77 (1H, m), 4.07-3.88 (1H, m), 3.58-3.29 (1H, m), 3.02-2.86 (1H, m), 2.85-2.70 (4H, m), 2.66-2.36 (3H, m), 2.21-2.09 (5H, m), 2.05-1.47 (14H, m), 1.46-1.15 (2H, m).

Example 96

(2R,5R)-2,5-Dibenzyl-N1-((4S,7S,10aS)-7-cyano-5-oxooctahydro-2H-pyrido[2,1-b][1,3]thiazepin-4-yl)-N6-((S)-1-(2-methoxyphenyl)-2-oxoazepan-3-yl)hexanediamide

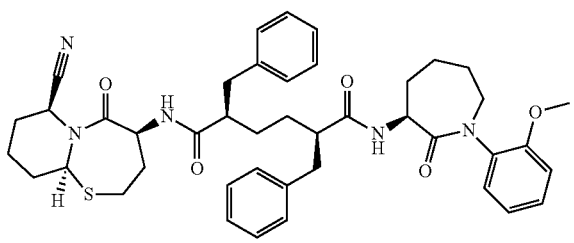 [SMILES: COc1ccccc1N1CCCC[C@H](NC(=O)[C@H](CC[C@H](Cc2ccccc2)C(=O)N[C@H]2CCS[C@H]3CCC[C@@H](C#N)N3C2=O)Cc2ccccc2)C1=O]

(2R,5R)-2,5-Dibenzyl-N1-((4S,7S,10aS)-7-cyano-5-oxooctahydro-2H-pyrido[2,1-b][1,3]thiazepin-4-yl)-N6-((S)-1-(2-methoxyphenyl)-2-oxoazepan-3-yl)hexanediamide was synthesized as described in General Procedure H using Intermediate 70 (11 mg, 0.020 mmol) and Intermediate 36 (5.3 mg, 0.020 mmol) to give a white solid (4.7 mg, 31% yield). Anal. Calcd. for C$_{43}$H$_{51}$N$_5$O$_5$S m/z 749.7. found: 750.3 (M+H)$^+$; $^1$H NMR (400 MHz, CDCl$_3$) δ ppm 7.36-7.22 (6H, m), 7.22-7.11 (6H, m), 7.08 (2H, d, J=6.0 Hz), 6.96 (2H, d), 5.36 (1H, d, J=3.8 Hz), 5.24 (1H, d, J=4.9 Hz), 5.07-4.90 (1H, m), 4.89-4.74 (1H, m), 4.02-3.86 (1H, m), 3.79 (3H, s), 3.50-3.32 (1H, m), 3.07-2.60 (5H, m), 2.57-2.35 (2H, m), 2.15 (2H, t, J=13.2 Hz), 2.05-1.87 (3H, m), 1.85-1.62 (8H, m), 1.62-1.06 (6H, m).

Example 97

Methyl (4S,7S,10aS)-4-(2S,5R)-5-(4-fluorobenzyl)-6-(4S,7S,10aS)-7-(methoxycarbonyl)-5-oxooctahydro-7H-pyrido[2,1-b][1,3]thiazepin-4-yl)amino)-6-oxo-2-propylhexanoyl)amino)-5-oxooctahydro-7H-pyrido[2,1-b][1,3]thiazepine-7-carboxylate

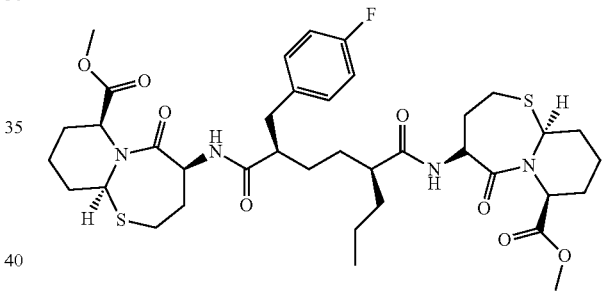

Methyl (4S,7S,10aS)-4-(((2S,5R)-5-(4-fluorobenzyl)-6-(((4S,7S,10aS)-7-(methoxycarbonyl)-5-oxooctahydro-7H-pyrido[2,1-b][1,3]thiazepin-4-yl)amino)-6-oxo-2-propylhexanoyl)amino)-5-oxooctahydro-7H-pyrido[2,1-b][1,3]thiazepine-7-carboxylate was synthesized as described in General Procedure F using Intermediate 20 (6.6 mg, 0.022 mmol) and (4S,7S,10aS)-methyl 4-amino-5-oxooctahydro-2H-pyrido[2,1-b][1,3]thiazepine-7-carboxylate (19 mg, 0.049 mmol) to give a white solid (10 mg, 58% yield). Anal. Calcd. for C$_{38}$H$_{53}$FN$_4$O$_8$S$_2$ m/z 776.7. found: 777.3 (M+H)$^+$; $^1$H NMR (400 MHz, CDCl$_3$) δ ppm 7.31 (1H, d, J=7.1 Hz), 7.14-7.07 (3H, m), 6.92 (2H, t, J=8.8 Hz), 5.39 (1H, t, J=4.7 Hz), 5.33 (1H, t, J=4.7 Hz), 5.20-5.12 (2H, m), 5.12-5.06 (1H, m), 5.01-4.94 (1H, m), 3.74 (3H, s), 3.70 (3H, s), 3.32-3.22 (1H, m), 3.22-3.12 (1H, m), 2.97-2.88 (1H, m), 2.87-2.75 (2H, m), 2.73-2.65 (1H, m), 2.49-2.38 (2H, m), 2.38-2.29 (1H, m), 2.24 (1H, ddd, J=14.2, 3.2, 3.0 Hz), 2.16-1.93 (6H, m), 1.84 (1H, dt, J=14.3, 3.3 Hz), 1.77-1.30 (13H, m), 1.30-1.19 (2H, m), 0.87 (3H, t, J=7.1 Hz).

Example 98

(2R,5S)—N1-((4S,7S,10aS)-7-Cyano-5-oxooctahydro-2H-pyrido[2,1-b][1,3]thiazepin-4-yl)-2-(4-fluorobenzyl)-N6-((S)-1-(2-methoxyphenyl)-2-oxoazepan-3-yl)-5-propylhexanediamide

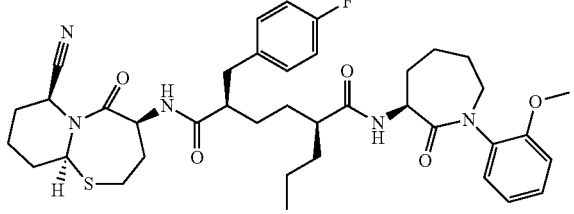

(2R,5S)—N1-((4S,7S,10aS)-7-Cyano-5-oxooctahydro-2H-pyrido[2,1-b][1,3]thiazepin-4-yl)-2-(4-fluorobenzyl)-N6-((S)-1-(2-methoxyphenyl)-2-oxoazepan-3-yl)-5-propylhexanediamide was synthesized as described in General Procedure H using Intermediate 76 (8.5 mg, 0.017 mmol) and Intermediate 36 (5.0 mg, 0.019 mmol) to give a white solid (5.9 mg, 49% yield). Anal. Calcd. for $C_{39}H_{50}FN_5O_5S$ m/z 719.7. found: 720.3 (M+H)$^+$; $^1$H NMR (400 MHz, CDCl$_3$) δ ppm 7.37 (1H, d, J=6.6 Hz), 7.33-7.25 (1H, m), 7.09-7.02 (3H, m), 7.01-6.94 (3H, m), 6.86 (2H, t, J=8.8 Hz), 5.54-5.32 (3H, m), 5.29 (1H, d, J=4.9 Hz), 5.06-4.86 (2H, m), 4.04-3.89 (1H, m), 3.83 (3H, s), 3.54-3.35 (1H, m), 3.10-2.88 (1H, m), 2.80-2.54 (3H, m), 2.41-2.29 (1H, m), 2.21-1.18 (21H, m), 0.93-0.82 (3H, m).

Example 99

Methyl (4S,7S,10aS)-4-(((2S,5R)-5-(4-hydroxybenzyl)-6-(4S,7S,10aS)-7-(methoxycarbonyl)-5-oxooctahydro-7H-pyrido[2,1-b][1,3]thiazepin-4-yl)amino)-6-oxo-2-propylhexanoyl)amino)-5-oxooctahydro-7H-pyrido[2,1-b][1,3]thiazepine-7-carboxylate

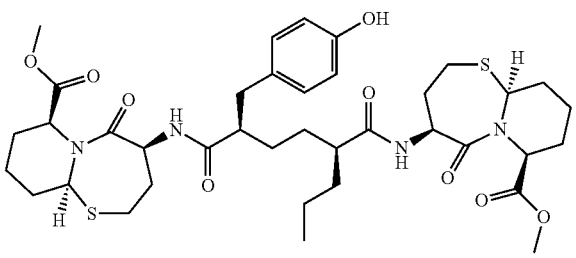 [SMILES: CCC[C@@H](CC[C@H](Cc1ccc(O)cc1)C(=O)N[C@H]1CCS[C@H]2CCC[C@@H](C(=O)OC)N2C1=O)C(=O)N[C@H]1CCS[C@H]2CCC[C@@H](C(=O)OC)N2C1=O]

Methyl (4S,7S,10aS)-4-(((2S,5R)-5-(4-hydroxybenzyl)-6-(4S,7S,10aS)-7-(methoxycarbonyl)-5-oxooctahydro-7H-pyrido[2,1-b][1,3]thiazepin-4-yl)amino)-6-oxo-2-propylhexanoyl)amino)-5-oxooctahydro-7H-pyrido[2,1-b][1,3]thiazepine-7-carboxylate was synthesized as described in General Procedure F using Intermediate 22 (4.9 mg, 0.016 mmol) and (4S,7S,10aS)-methyl 4-amino-5-oxooctahydro-2H-pyrido[2,1-b][1,3]thiazepine-7-carboxylate (9.4 mg, 0.036 mmol) to give a white solid (7.5 mg, 59% yield). Anal. Calcd. for $C_{38}H_{54}N_4O_9S_2$ m/z 774.7. found: 775.3 (M+H)$^+$; $^1$H NMR (400 MHz, CDCl$_3$) δ ppm 7.45 (1H, d, J=6.6 Hz), 7.27-7.21 (1H, m), 6.99 (2H, d, J=8.2 Hz), 6.70 (2H, d, J=8.2 Hz), 5.38 (1H, t, J=4.4 Hz), 5.32 (1H, t, J=4.7 Hz), 5.20-5.05 (3H, m), 5.03-4.95 (1H, m), 3.73 (3H, s), 3.69 (3H, s), 3.30-3.20 (1H, m), 2.85-2.71 (2H, m), 2.69-2.61 (1H, m), 2.46-2.32 (3H, m), 2.26-2.17 (1H, m), 2.17-2.08 (1H, m), 2.08-1.91 (5H, m), 1.90-1.82 (1H, m), 1.74-1.30 (13H, m), 1.29-1.19 (2H, m), 0.86 (3H, t, J=7.1 Hz).

Example 100

Methyl (4S,7S,10aS)-4-(2S,5R)-5-(3-fluorobenzyl)-6-(4S,7S,10aS)-7-(methoxycarbonyl)-5-oxooctahydro-7H-pyrido[2,1-b][1,3]thiazepin-4-yl)amino)-6-oxo-2-propylhexanoyl)amino)-5-oxooctahydro-7H-pyrido[2,1-b][1,3]thiazepine-7-carboxylate

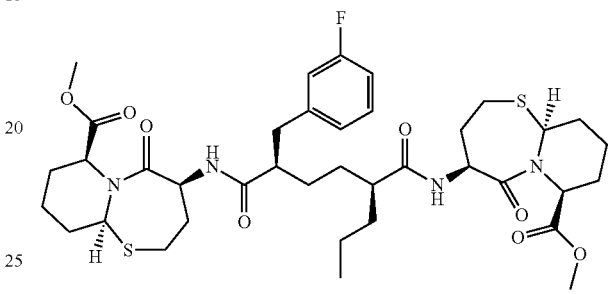

Methyl (4S,7S,10aS)-4-(((2S,5R)-5-(3-fluorobenzyl)-6-(((4S,7S,10aS)-7-(methoxycarbonyl)-5-oxooctahydro-7H-pyrido[2,1-b][1,3]thiazepin-4-yl)amino)-6-oxo-2-propylhexanoyl)amino)-5-oxooctahydro-7H-pyrido[2,1-b][1,3]thiazepine-7-carboxylate was synthesized as described in General Procedure F using Intermediate 21 (20 mg, 0.068 mmol) and (4S,7S,10aS)-methyl 4-amino-5-oxooctahydro-2H-pyrido[2,1-b][1,3]thiazepine-7-carboxylate (58 mg, 0.15 mmol) to give a white solid (24 mg, 46% yield). Anal. Calcd. for $C_{38}H_{53}FN_4O_8S_2$ m/z 776.7. found: 777.3 (M+H)$^+$; $^1$H NMR (400 MHz, CDCl$_3$) δ ppm 7.41 (1H, d, J=6.0 Hz), 7.24-7.16 (2H, m), 6.92 (1H, d, J=7.7 Hz), 6.85 (2H, d, J=8.8 Hz), 5.40 (1H, t, J=4.7 Hz), 5.34 (1H, t, J=4.7 Hz), 5.19 (1H, d, J=6.0 Hz), 5.16-5.08 (2H, m), 5.00 (1H, t, J=6.6 Hz), 3.73 (3H, s), 3.70 (3H, s), 3.27 (1H, t, J=11.5 Hz), 3.17 (1H, t, J=11.3 Hz), 2.97-2.88 (1H, m), 2.88-2.78 (2H, m), 2.77-2.68 (1H, m), 2.49-2.33 (3H, m), 2.24 (1H, ddd, J=14.2, 3.2, 3.0 Hz), 2.18-2.10 (1H, m), 2.09-1.93 (5H, m), 1.86 (1H, ddd, J=14.2, 3.2, 3.0 Hz), 1.76-1.31 (13H, m), 1.30-1.19 (2H, m), 0.87 (3H, t, J=7.1 Hz).

Example 101

(2R,5R)-2,5-Bis(4-fluorobenzyl)-N1-((S)-2-oxo-1-phenylazepan-3-yl)-N6(7S,10aR)-6-oxodecahydropyrido[1,2-a]azepin-7-yl)hexanediamide

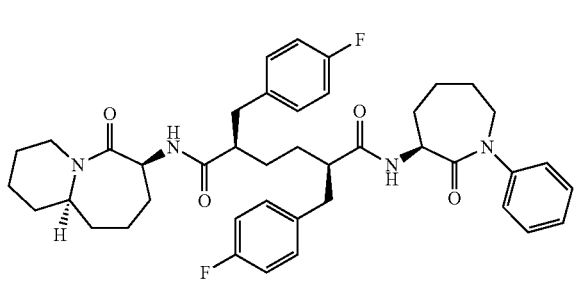 [SMILES: O=C(N[C@H]1CCCCN(c2ccccc2)C1=O)[C@H](CC[C@H](Cc1ccc(F)cc1)C(=O)N[C@H]1CCC[C@H]2CCCCN2C1=O)Cc1ccc(F)cc1]

(2R,5R)-2,5-Bis(4-fluorobenzyl)-N1-((S)-2-oxo-1-phenylazepan-3-yl)-N6-((7S,10aR)-6-oxodecahydropyrido[1,2-a]azepin-7-yl)hexanediamide was synthesized as described in General Procedure H using Intermediate 79 (31 mg, 0.057 mmol) and Intermediate 54 (14 mg, 0.063 mmol) to give a white solid (23 mg, 56% yield). Anal. Calcd. for $C_{42}H_{50}F_2N_4O_4$ m/z 712.7. found: 713.2 (M+H)$^+$; $^1$H NMR (400 MHz, CDCl$_3$) δ ppm 7.38 (2H, t, J=7.7 Hz), 7.31-7.24 (1H, m), 7.23-7.02 (8H, m), 6.96-6.81 (4H, m), 4.82-4.70 (2H, m), 4.16 (1H, d, J=11.5 Hz), 3.96 (1H, dd, J=14.8, 11.5 Hz), 3.82 (1H, d, J=6.0 Hz), 3.61 (1H, dd, J=15.4, 4.9 Hz), 2.89-2.75 (2H, m), 2.74-2.63 (2H, m), 2.39 (2H, d, J=3.3 Hz), 2.01-1.91 (1H, m), 1.90-1.40 (20H, m), 1.41-1.28 (1H, m), 1.03-0.91 (1H, m).

Example 102

(4S,7S)-Methyl 4-((2S,5S)-2,5-dibenzyl-6-((S)-1-isobutyl-2-oxoazepan-3-ylamino)-6-oxohexanamido)-5-oxooctahydro-2H-pyrido[2,1-b][1,3]thiazepine-7-carboxylate

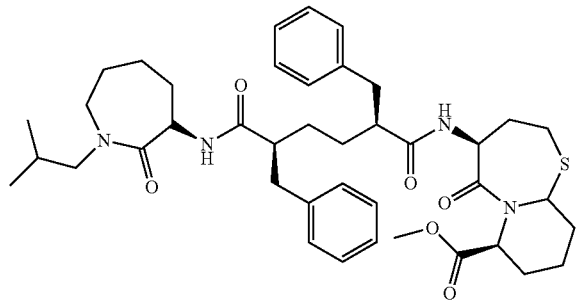

(4S,7S)-Methyl 4-((2S,5S)-2,5-dibenzyl-6-((S)-1-isobutyl-2-oxoazepan-3-ylamino)-6-oxohexanamido)-5-oxooctahydro-2H-pyrido[2,1-b][1,3]thiazepine-7-carboxylate was synthesized as described in General Procedure H using Intermediate 23 (40 mg, 0.070 mmol) and Intermediate 80 (26 mg, 0.088 mmol) to give a white solid (40 mg, 77% yield). Anal. Calcd. for $C_{41}H_{56}N_4O_6S$ m/z 732.4. found: 733.4 (M+H)$^+$; $^1$H NMR (400 MHz, DMSO-d$_6$) δ ppm 7.90 (d, J=7.3 Hz, 2H), 7.67 (d, J=6.8 Hz, 1H), 7.18 (m, 10H), 6.96 (m, 1H), 6.48 (m, 1H), 5.62 (m, 1H), 5.15 (m, 1H), 5.02 (m, 1H), 4.45 (m, 1H), 3.75 (m, 1H), 3.57 (s, 3H), 3.49 (m, 2H), 3.20-3.00 (m, 2H), 2.79 (m, 3H), 2.63 (m, 4H), 2.80-2.57 (m, 4H), 1.82-1.59 (m, 13H), 1.26 (m, 1H), 0.81 (m, 6H).

Example 103

Methyl (4S,7S,10aS)-4-(2R,5S)-2-benzyl-6-(((4S,7S,10aS)-7-(methoxycarbonyl)-5-oxooctahydro-7H-pyrido[2,1-b][1,3]thiazepin-4-yl)amino)-5-methyl-6-oxohexanoyl)amino)-5-oxooctahydro-7H-pyrido[2,1-b][1,3]thiazepine-7-carboxylate

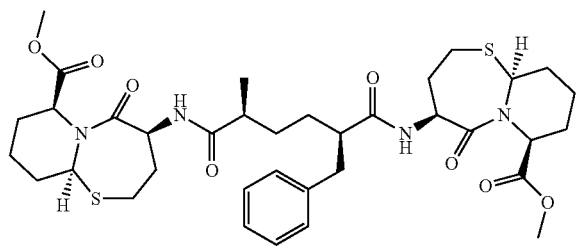 [SMILES: COC(=O)[C@@H]1CCC[C@@H]2SCC[C@H](NC(=O)[C@H](CC[C@H](C)C(=O)N[C@H]3CCS[C@H]4CCC[C@@H](C(=O)OC)N4C3=O)Cc3ccccc3)C(=O)N21]

Methyl (4S,7S,10aS)-4-(((2R,5S)-2-benzyl-6-(((4S,7S,10aS)-7-(methoxycarbonyl)-5- oxooctahydro-7H-pyrido[2, 1-b][1,3]thiazepin-4-yl)amino)-5-methyl-6-oxohexanoyl) amino)-5-oxooctahydro-7H-pyrido[2,1-b][1,3]thiazepine-7-carboxylate was synthesized as described in General Procedure F using Intermediate 81 (20 mg, 0.080 mmol) and (4S,7S,10aS)-methyl 4-amino-5-oxooctahydro-2H-pyrido[2,1-b][1,3]thiazepine-7-carboxylate (54 mg, 0.130 mmol) to give a white solid (20 mg, 34% yield). Anal. Calcd. for $C_{36}H_{50}N_4O_8S_2$ m/z 730.3. found: 731.3 (M+H)$^+$; $^1$H NMR (400 MHz, DMSO-d$_6$) δ ppm 7.98 (d, J=7.2 Hz, 1H), 7.87 (d, J=7.4 Hz, 1H), 7.20 (m, 5H), 5.65 (m, 2H), 5.05 (m, 4H), 3.60 (s, 3H), 3.59 (s, 3H), 3.19-3.05 (m, 3H), 2.89 (m, 1H), 2.83 (m, 1H), 2.65 (m, 2H), 2.60 (m, 1H), 2.38 (m, 1H), 2.21 (m, 2H), 1.99 (m, 4H), 1.85 (m, 5H), 1.65 (m, 3H), 1.58 (m, 7H), 1.25 (m, 2H), 0.94 (d, J=6.7 Hz, 3H).

Example 104

Methyl (4S,7S,10aS)-4-(((2S,5R)-5-benzyl-2-ethyl-6-(((4S,7S,10aS)-7-(methoxycarbonyl)-5-oxooctahydro-7H-pyrido[2,1-b][1,3]thiazepin-4-yl)amino)-6-oxohexanoyl)amino)-5-oxooctahydro-7H-pyrido[2,1-b][1,3]thiazepine-7-carboxylate

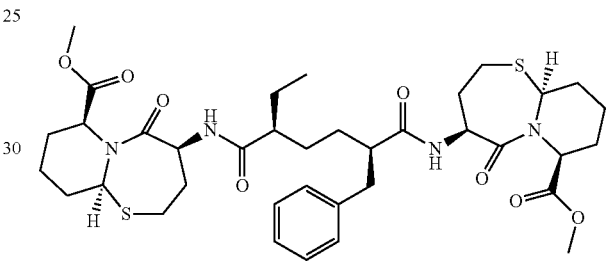

Methyl (4S,7S,10aS)-4-(((2S,5R)-5-benzyl-2-ethyl-6-(((4S,7S,10aS)-7-(methoxycarbonyl)-5-oxooctahydro-7H-pyrido[2,1-b][1,3]thiazepin-4-yl)amino)-6-oxohexanoyl) amino)-5-oxooctahydro-7H-pyrido[2,1-b][1,3]thiazepine-7-carboxylate was synthesized as described in General Procedure F using Intermediate 82 (33 mg, 0.13 mmol) and (4S,7S,10aS)-methyl 4-amino-5-oxooctahydro-2H-pyrido[2,1-b][1,3]thiazepine-7-carboxylate (121 mg, 0.312 mmol) to give a white solid (25 mg, 27% yield). Anal. Calcd. for $C_{37}H_{52}N_4O_8S_2$ m/z 744.3. found: 745.3 (M+H)$^+$; $^1$H NMR (400 MHz, DMSO-d$_6$) δ ppm 7.47 (m, 1H), 7.23-7.13 (m, 5H), 5.40-5.30 (m, 2H), 5.19-5.12 (m, 3H), 4.99 (m, 1H), 3.73 (s, 3H), 3.69 (s, 3H), 3.28-3.12 (m, 2H), 2.92-2.71 (m, 14H), 2.41 (m, 3H), 2.24 (m, 1H), 2.05-1.98 (m, 6H), 1.80-1.44 (m, 14H), 0.86 (t, J=7.4 Hz, 3H).

What is claimed:
1. A compound of formula (A),

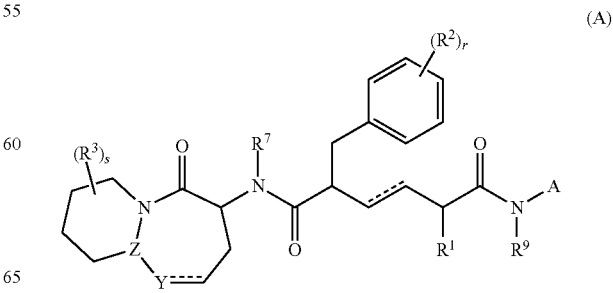

(A)

or a pharmaceutically acceptable salt thereof, wherein:
A is a five- to eight-membered fully or partially saturated monocyclic heterocyclic ring containing from one to two nitrogen atoms and one carbonyl group on the ring; or a nine- to twelve-membered fully saturated or partially saturated bicyclic heterocyclic ring containing one to two nitrogen atoms, optionally one sulfur atom, and one to two carbonyl groups on the ring; wherein when ring A is monocyclic it is optionally substituted with one to two groups $R^{4a}$, and when ring A is bicyclic, it is optionally substituted with one to two groups $R^4$, each independently selected from each other;
each of the bonds denoted as -----, independently of each other, is selected from a single bond and a double bond;
Y is S or $CH_2$ when the bond adjacent Y is a single bond, or Y is CH when the bond adjacent Y (=====) is a double bond;
Z is CH or N, provided that when Z is N, Y is $CH_2$ and the bond adjacent Y is a single bond;
$R^1$ is hydrogen or $(C_1$-$C_6)$alkyl, wherein the alkyl may be substituted with one or more of halogen, OH, $CONH_2$, $CO_2(C_1$-$C_6)$alkyl, $(C_1$-$C_6)$alkoxy, CN, $CF_3$, $CO_2H$, $(C_3$-$C_6)$cycloalkyl, and/or phenyl, wherein the phenyl substituent may be further substituted with one or more of $OCH_3$, OH, and/or halogen;
$R^2$ is at each occurrence selected from $(C_1$-$C_6)$alkoxy, OH, CN, $(C_1$-$C_6)$alkyl, halogen, and $CF_3$;
$R^3$ and $R^4$ are at each occurrence selected independently from CN, $CF_3$, $(C_1$-$C_3)$alkyl, $(C_2$-$C_4)$alkenyl, $(C_1$-$C_4)$alkoxyl, $CO_2(C_1$-$C_6)$alkyl, oxadiazolyl, $CONH(C_1$-$C_4)$alkyl, and CONH-thiozolyl; and $R^{4a}$ is selected from $R^4$ and phenyl, wherein said phenyl is optionally further substituted with halogen, $(C_1$-$C_4)$alkyl, or $(C_1$-$C_4)$alkoxyl;
$R^7$ and $R^9$, at each occurrence taken independently of each other, are selected from hydrogen and $(C_1$-$C_6)$alkyl; and r and s are independently 0, 1, or 2.

2. A compound of claim 1, having the formula:

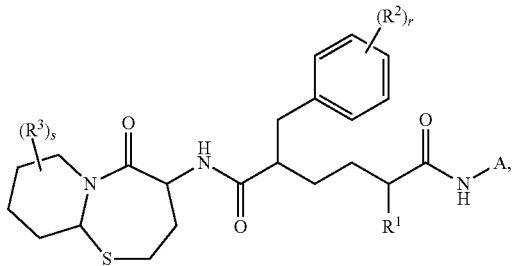

or a pharmaceutically acceptable salt thereof.

3. A compound according to claim 2, having the formula:

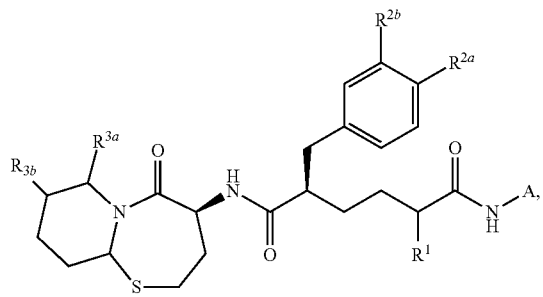

wherein $R^{2a}$ and $R^{2b}$ are selected from hydrogen, halogen, $(C_1$-$C_3)$alkyl, and $(C_1$-$C_4)$alkoxyl, and $R^{3a}$ and $R^{3b}$ are independently selected from hydrogen, CN, $(C_1$-$C_4)$alkyl, $CF_3$, and $CO_2(C_1$-$C_4)$alkyl; or a pharmaceutically acceptable salt thereof.

4. A compound of claim 3, having the formula:

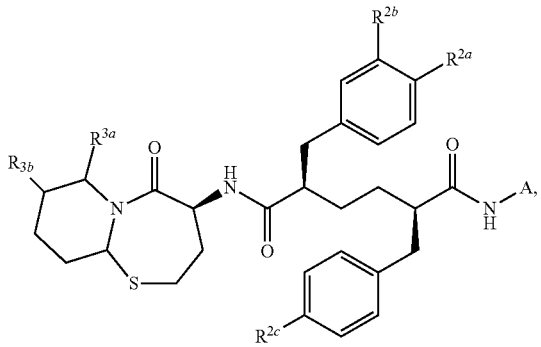

wherein $R^{2c}$ is selected from hydrogen, halogen, $(C_1$-$C_3)$ alkyl, and $(C_1$-$C_4)$alkoxyl.

5. A compound according to claim 1 or 2, wherein ring A is

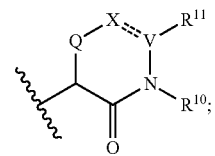

wherein:
Q is —$(CR^5R^6)_m$—$(CH=CH)_o$—$(CH_2)_n$—;
when the bond between X and V is a single bond, X is selected from a bond, S, $CH_2$, or NHC(=O); and when the bond between X and V is a double bond, X is $CR^{12}$;
V is CH or N, provided that when V is N, X is $CH_2$ and the bond between X and V is a single bond; or V can be C, when X is $CR^{12}$ and $R^{11}$ and $R^{12}$ are taken together to form phenyl;
$R^5$ and $R^6$ are independently hydrogen or $(C_1$-$C_6)$alkyl, or $R^5$ and $R^6$ may be taken together to form a $(C_3$-$C_5)$ cycloalkyl;
$R^{10}$ and $R^{11}$ are selected together with V and X, wherein:
(a) $R^{10}$ and $R^{11}$ are taken together with the atoms to which they are attached to form a 5- or 6-membered heterocyclo containing one or two nitrogen atoms, said heterocycle optionally substituted with one or more of $R^4$, wherein V is N or CH, and X is S, a bond, NHC(=O), or $CH_2$; or
(b) $R^{10}$ is selected from hydrogen, $(C_1$-$C_4)$alkyl, $(CH_2)_p$-pyridinyl, or $(CH_2)_q$-phenyl, wherein the alkyl may be substituted with $CO_2(C_1$-$C_2)$alkyl, and the phenyl may be substituted with halogen, $(C_1$-$C_2)$alkyl, or $(C_1$-$C_2)$alkoxyl, and wherein V is CH or N; or
(c) $R^{10}$ is hydrogen, V is C, X is $CR^{12}$, and $R^{11}$ and $R^{12}$ are taken together to form phenyl;
m is 1, 2, 3, or 4;
n is 0 or 1;
o is 0 or 1; provided that m, n and o, taken together, are 1 to 4, and provided further that when the bond between X and V is a double bond, either n is 1 or o is 0; and
p and q are independently 0, 1, 2, or 3.

6. The compound according to claim 5, having formula (A.1),

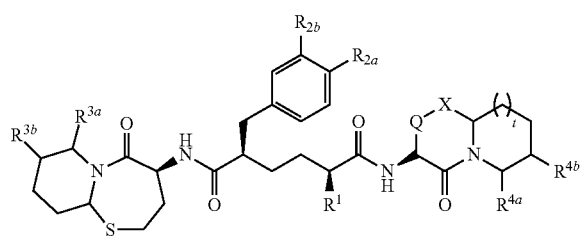

(A.1)

or a pharmaceutically acceptable salt thereof, wherein:
X is a bond, S, or $CH_2$;
$R^{2a}$ and $R^{2b}$ are selected from hydrogen, halogen, $(C_1-C_3)$ alkyl, and $(C_1-C_4)$alkoxyl,
$R^{3a}$, $R^{3b}$, $R^{4a}$, and $R^{4b}$ are each independently selected from hydrogen, CN, $CF_3$, $(C_1-C_3)$alkyl, $(C_2-C_4)$alkenyl, $(C_1-C_3)$alkoxyl, COO$(C_1-C_6)$alkyl, oxadiazolyl, CONH$(C_1-C_4)$alkyl, and C(O)NH-thiozolyl; and
t is 0, 1 or 2.

7. The compound according to claim 6, wherein:
X is S;
Q is $(CR^5R^6)_m$;
$R^1$ is —$CH_2$-phenyl, wherein the phenyl is optionally substituted with halogen, $(C_1-C_3)$alkyl, and $(C_1-C_4)$alkoxyl;
$R^{1a}$ and $R^{4a}$ are independently hydrogen or COOCH$_3$;
$R^{3b}$ and $R^{4b}$ are each either hydrogen or $CF_3$;
$R^5$ and $R^6$ are each hydrogen or $CH_3$;
m is 2; and
t is 1.

8. The compound according to claim 5, having formula (A.2)

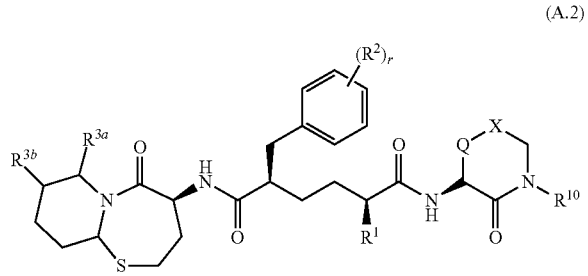

(A.2)

or a pharmaceutically acceptable salt thereof, wherein:
X is a bond or $CH_2$;
$R^2$ is selected from halogen, $(C_1-C_3)$alkyl, and $(C_1-C_4)$alkoxyl;
$R^{3a}$ and $R^{3b}$ are each independently selected from hydrogen, CN, $CF_3$, $(C_1-C_3)$alkyl, $(C_2-C_4)$alkenyl, $(C_1-C_3)$alkoxyl, $CO_2(C_1-C_6)$alkyl, oxadiazolyl, CONH$(C_1-C_4)$alkyl, and C(O)NH-thiozolyl;
$R^{10}$ is selected from hydrogen, $(C_1-C_4)$alkyl, and phenyl, wherein the alkyl optionally may be substituted with $CO_2(C_1-C_2)$alkyl, and the phenyl optionally may be substituted with halogen, $(C_1-C_2)$alkyl, or $(C_1-C_2)$alkoxyl; and
r is 0 or 1.

9. The compound according to claim 8, wherein:
$R^1$ is —$CH_2$-phenyl, wherein the phenyl is optionally substituted with one of halogen, $(C_1-C_3)$alkyl, or $(C_1-C_4)$ alkoxyl;
$R^{3a}$ is independently hydrogen or $CF_3$;
$R^{3b}$ is independently hydrogen or $CF_3$; and
$R^{10}$ is phenyl optionally substituted with —OCH$_3$.

10. The compound according to claim 1 having formula (A.3)

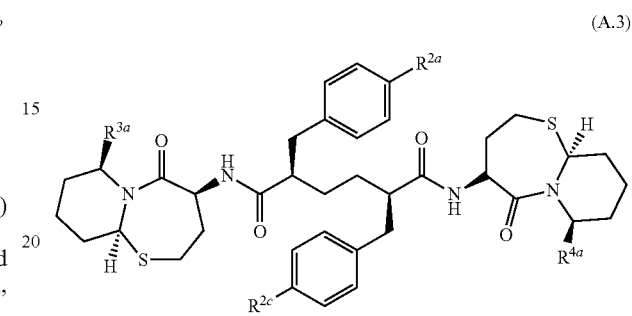

(A.3)

or a pharmaceutically acceptable salt thereof, wherein:
$R^{3a}$ and $R^{4a}$ are each independently hydrogen, CN, $CF_3$, $(C_1-C_3)$alkyl, $(C_2-C_4)$alkenyl, $(C_1-C_3)$alkoxyl, COO $(C_1-C_6)$alkyl, oxadiazolyl, CONH$(C_1-C_4)$alkyl, or C(O) NH-thiozolyl; and
$R^{2a}$ and $R^{2c}$ are each independently hydrogen, OCH$_3$, OH, F, or Cl.

11. The compound according to claim 5 having formula (A.4)

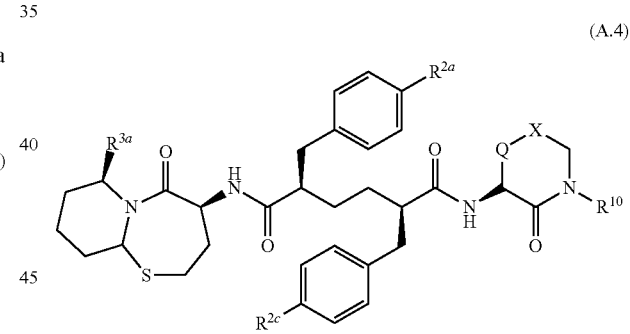

(A.4)

or a pharmaceutically acceptable salt thereof, wherein:
X is a bond or $CH_2$;
$R^{3a}$ is hydrogen, CN, $CF_3$, $(C_1-C_3)$alkyl, $(C_2-C_4)$alkenyl, $(C_1-C_3)$alkoxyl, COO$(C_1-C_6)$alkyl, oxadiazolyl, CONH$(C_1-C_4)$alkyl, or C(O)NH-thiozolyl; and
$R^{2a}$ and $R^{2c}$ are independently hydrogen, OCH$_3$, OH, F, or Cl.

12. The compound according to claim 11, wherein:
$R^{3a}$ is hydrogen, CN, $CF_3$, $CH_3$, $CH_2CH_3$, propylene, or COOCH$_3$; and
$R^{10}$ is isobutyl, phenyl, or benzyl, wherein the phenyl or benzyl optionally are substituted ortho with —CH$_3$ or —OCH$_3$.

13. A pharmaceutical composition comprising one or more compounds according to claim 1, and a pharmaceutically acceptable carrier.

* * * * *